(12) United States Patent
Emerson et al.

(10) Patent No.: US 7,491,731 B2
(45) Date of Patent: Feb. 17, 2009

(54) CRYSTAL STRUCTURE OF LIGANDED CFMS KINASE DOMAIN

(75) Inventors: Holly Kathleen Emerson, Durham, NC (US); David Lee Musso, Durham, NC (US); Stanley Dawes Chamberlain, Durham, NC (US); Gregory Edward Peckham, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 81 days.

(21) Appl. No.: 11/430,342

(22) Filed: May 9, 2006

(65) Prior Publication Data

US 2007/0010540 A1 Jan. 11, 2007

Related U.S. Application Data

(62) Division of application No. 10/391,416, filed on Mar. 18, 2003, now abandoned.

(60) Provisional application No. 60/365,363, filed on Mar. 18, 2002.

(51) Int. Cl.
C07D 239/49 (2006.01)
A61K 31/505 (2006.01)

(52) U.S. Cl. ..................... 514/275; 544/325

(58) Field of Classification Search ................ 544/325; 514/275
See application file for complete search history.

(56) References Cited

OTHER PUBLICATIONS

Vippagunta et al., Crystalline Solids, Advanced Drug Delivery Reviews, 48, pp. 3-26, 2001.*
West, Solid Solutions, Chapter 10, pp. 358 and 365, 1988.*
Ulrich, Crystallization: 4. Crystal Characteristics, Kirk-Othmer Encyclopedia of Chemical Technology, Aug. 2002.*
So et al., Application of Neural Works, J. Med. Chem. vol. 35, No. 17, pp. 3201-3207, 1992.*
Alonso, G., Koegl, M., Mazurenko, N. and Courtneidge, S.A. (1995). Sequence Requirements for Binding of Src Family Tyrosine Kinases To Activated Growth Factor Receptors. *J. Biol. Chem.* 270(17), 9840-9848.
Carlberg, K., Tapley, P., Haystead, C. Rohrschneider, L. (1991).The role kinase activity and the kinase insert region in ligand-induced internalization and degradation of the c-*fms* protein. Eur. Mol. Biol. Org. J. 10(4), 877-883.
Coussens, L., Van Beveren, C., Smith, D., Chen, E., Mitchell, R. L., Isacke, C. M., Verma, I. M., Ullrich, A. (1986). Structural alteration of viral homologue of receptor proto-oncogene *fms* at carboxyl terminus. *Nature* 320, 277-280.
Cox, S., Radzio-Andzelm, E. Taylor, S. S. (1994). Domain movements in protein kinases. *Curr. Opin. Struct. Biol.* 4, 893-901.
Hanks, S. J., Quinn, A. M., Hunter, T. (1988). The Protein Kinase Family: Conserved Features and Deduced Phyogeny of the Catalytic Domains. *Science* 241, 42-52.

Heidaran, et al, Aaronson, S. A. (1991). Deletion or Substitution within the α Platelet-Derived Growth Factor Receptor Kinase Insert Domain: Effects on Functional Coupling with Intracellular Signaling Pathways. *Mol. Cell. Biol.* 11(1), 134-142.
Hubbard, S. R., Wei, L., Ellis, L. Hendrickson, W. A. (1994). Crystal structure of the tyrosine kinase domain of the human insulin receptor. *Nature* 372,746-754.
Hubbard, S. R. (1997). Crystal structure on the activated insulin receptor tyrosine kinase in complex with peptide substrate and ATP analog. *EMBO J.* 16(18), 5572-5581.
Johnson, L. N., Noble, M. E. M., Owen, D. J. (1996). Active and Inactive Protein Kinases: Structural Basis for Regulation. *Cell* 85, 149-158.
Knighton, D. R., et al., Sowadski, J. M. (1991). Crystal Structure of the Catalytic Subunit of Cyclic Adenosine Monophosphate-Dependent Protein Kinase. *Science* 253, 407-414.
McTigue, M. A., et al., Appelt, K. (1999). Crystal structure of the kinase domain of human vascular endothelial growth factor receptor 2: a key enzyme in angiogenesis. *Structure* 7(3), 319-330.
Mohammadi, M., Schlessinger, J., Hubbard, S. R. (1996). Structure of the FGF Receptor Tyrosine Kinase Domain Reveals a Novel Autoinhibitory Mechanism. *Cell* 86, 577-587.
Myles, G. M, Brandt, C. S., Carlsberg, K., Rohrschneider, L. R. (1994). Tyrosine 569 in the c-Fms Juxtamembrane Domain Is Essential for Kinase Activity and Macrophage Colony-Stimulating Factor-Dependent Internalization. *Mol. Cell Biol.* 14(7), 4843-4854.
Pawson, T. (1992). Tyr721 regulates specific binding of the CSF-1 receptor kinase insert to PI 3'-kinase SH2 domains: a model for SH2-mediated receptor—target interactions. *EMBO J.* 11(4), 1365-1372.
Roussel, M. F., Shurtleff, S. A., Downing, J. R., Sherr, C. J. (1990). A point mutation at tyrosine-809 in the human colony-stimulating factor 1 receptor impairs mitogenesis without abrogating tyrosine kinase activity, association with phosphatidylinositol 3-kinase, or induction of c-*fos* and *junB* genes. *Proc. Natl. Acad. Sci. USA* 87, 6738-6742.
Schindler, T., Bornmann, W., Pellicena, P., Miller, W. T., Clarkson, B., Kuriyan, J. (2000). Structural Mechanism for STI-571 Inhibition of Abelson Tyrosine Kinase. *Science* 289, 1938-1942.
Sengupta, A., Liu, W.-K., Yeung, Y. G., Yeung, D. C. Y., Frackelton, Jr., A. R., Stanley, E. R. (1988). Identification and subcellular localization of proteins that are rapidly phosphorylated in tyrosine in response to colony-stimulating factor-1. *Proc. Natl. Acad. Sci. USA* 85, 8062-8066.
Sherr, C. J. (1988). The *fms* oncogene. *Biochim. Biophys. Acta* 948, 225-243.
Sherr, C. J. (1991). Mitogenic response to colony-stimulating factor 1. *Trends Genet.* 7(11-12), 398-402.
Shewchuk, L. M., et al, Moore, J. T. (2000). Structure of the Tie2 RTK Domain: Self-Inhibition by the Nucleotide Binding Loop, Activation Loop and C-Terminal Tail. *Structure* 8, 1105-1113.
Taylor, G. R., Reedijk, M., Rothwell, V., Rohrschneider, L., Pawson, T. (1989). The unique insert of cellular and viral *fms* protein tyrosine kinase domains is dispensable for enzymatic and transforming activities. *EMBO J.* 8(7), 2029-2037.

(Continued)

*Primary Examiner*—Deepak Rao
(74) *Attorney, Agent, or Firm*—Kathryn L. Coulter

(57) ABSTRACT

A crystal structure of the cfms kinase domain, co-crystal structure with a bound small molecule, as well as methods of using the same in the discovery of cfms inhibitors and in the treatment of diseases mediated by inappropriate cfms activity.

4 Claims, 5 Drawing Sheets

OTHER PUBLICATIONS van der Geer, P. and Hunter, T. (1991). Tyrosine 706 and 807 Phosphorylation Site Mutants in the Murine Colony-Stimulating Factor-1 Receptor Are Unaffected in Their Ability To Bind or Phosphorylate Phosphatidylinositol-3 Kinase but Show Differential Defects in Their Ability To Induce Early Response Gene Transcription *Mol. Cell. Biol.* 11(9), 4698-4709.

Wang, Z., Myles, G. M., Brandt., C S., Lioubin, M. N., Rohrschneider, L. (1993). Identification of the Ligand-Binding Regions in the Macrophage Colony-Stimulating Factor Receptor Extracellular Domain. *Mol. Cell. Biol.* 13(9), 5348-5359.

* cited by examiner

CRYSTAL STRUCTURE OF LIGANDED CFMS KINASE DOMAIN

This application is a divisional of U.S. Ser. No. 10/391,416 filed on Mar. 18, 2003 now abandoned, which claims the benefit of U.S. Provisional Application No. 60/365,363 filed Mar. 18, 2002.

BACKGROUND OF THE INVENTION

The present invention relates to the crystal structure of the cfms kinase domain, specifically the cFMS kinase domain in liganded form, methods of using the same in the discovery of cFMS inhibitors and in the treatment of diseases mediated by inappropriate cfms activity, as well as diamino-pyrimidine cFMS inhibitors.

Colony stimulating factor-1 receptor (CSF-1R or CFMS), encoded by the proto oncogene c-fms (Sherr 1985; Woolford 1985), is a cell surface receptor for the macrophage colony-stimulating factor (M-CSF or CSF-1) and a member of the receptor tyrosine kinase (RTK) family of growth factor receptors. CSF-1 (or M-CSF) is a homodimeric growth factor involved in the proliferation, differentiation, and activation of monocytes or macrophages, as well as a proinflammatory cytokine (Tushinski 1982; Metcalf 1986; Becker 1987; Elliott 1989; Young 1990).

cFMS is a hematopoietic growth factor receptor, whose expression is lineage-specific and primarily confined to monocytes, macrophages and their bone marrow progenitors. cFMS is the cellular counterpart of the v-fms oncogene encoded by the genomes of both Susan McDonough and Hardy-Zuckerman five strains of feline sarcoma virus (Coussens 1986; Sherr 1988). The receptor is comprised of an extracellular ligand-binding domain joined through a single membrane-spanning helix to an intracellular protein tyrosine kinase (PTK) domain. It is closely related structurally to the receptors for the platelet-derived growth factor (PDGF), the stem cell factor receptor (the c-kit proto-oncogene product), and flt3/flt2. The extracellular ligand binding domain of these receptors is composed of five immunoglobulin-like loops (Wang 1993), and the PTK domains contain kinase insert (KI) sequences of varying lengths (Sherr, 1991). Binding of CSF-1 to the receptor extracellular ligand-binding domain causes a conformational change and induces a noncovalent dimerization of cFMS, autophosphorylation and activation of the PTK domain, and trans-phosphorylation of specific tyrosine residues in the cytoplasmic domain. These phosphorylated tyrosine residues serve as binding sites for src-homology 2 (SH2) domains contained within cytoplasmic signaling proteins (Sengupta 1988; Reedijk 1992), thereby activating signaling cascades. Both the PI3K-dependent and Ras/mitogen-activated protein kinase-dependent pathways are activated in response to CSF-1 binding to cFMS (Yeung 1998; Kelley, 1999; Kanagasundaram 1999). Following activation of cFMS with CSF-1, the receptor is rapidly internalized via clathrin-coated pits and vesicles and targeted to the lysosome for degradation.

cFMS receptor expression in macrophage populations corresponds to its stage of differentiation and tissue localization. CSF-1/cFMS interaction and signaling is required for the recruitment, development, and maintenance of a subset of macrophages, such as marrow and blood monocytes. Thus, an absence of cFMS is not life-threatening. Deletion of CSF-1, as occurs in the mutant mouse strain op/op and in the mutant rat strain th1/th1, provides an insight into the biology of cFMS/CSF-1 signaling. The op/op mutation renders an osteopetrotic phenotype with severely deficient macrophage populations in the joints, osteoclasts, peritoneal cavity phagocytes, splenic marginal zone metallophils, and lymph node subcapsular sinus macrophages. Other populations reach substantial levels, including bone marrow, phagocytes in the thymic cortex, splenic red pulp, lymph node medulla, intestinal lamina propria, liver (Kupffer cells), lung (alveolar macrophages), and brain (microglia) (Yoshida, H 1990; Wiktor-Jedrzejczak, W. 1991).

Connective tissue macrophages are involved in a number of chronic disease states, such as osteoarthritis, rheumatoid arthritis, osteoporosis, cardiovascular/vessel-wall disease, chronic graft rejection, Alzheimer's, and Lupus-nephritis (Yang 2001; Bischof, 2000; Boyce 1999; Cenci 2000; Campbell 2000; Murphy 2000). These macrophages directly or indirectly influence the production of disease modifiers (MMPs, cathepsins, chemokines, growth and differentiation factors) within the microenvironment (Valledor 2000).

Endogenous CSF-1 critically regulates HIV-1 replication in human monocyte-derived macrophages (MDM). The HIV-1 infected MDM cells produce high levels of CSF-1 by a mechanism that requires active virus replication. This aids the survival of infected macrophages and enhances the spread of infection by increasing macrophage susceptibility to the HIV virus. This suggests that CSF-1 might be a therapeutic target to block HIV-1 replication in human macrophages (Kalter 1991; Bergamini 1994; Gallo 1994; Kutza 2000).

Cancer studies have revealed elevated levels of circulating CSF-1 in patients with acute myeloid leukemia (AML) (Haran-Ghera 1997). It has also been reported that CSF-1 gene transduction into human lung carcinoma cell lines resulted in inhibition of metastic disease to the liver and lymph nodes, but not to the kidney. This suggests that the heterogeneity of organ microenvironments influences the spread of lung carcinoma (Yano 1997). Other evidence suggests that c-Fms activation by CSF-1 induces invasive disease by a urokinase-dependent pathway in breast carcinoma and neoplasms of the female reproductive tract (Kacinski 1997).

Inhibition of the c-fms receptor kinase represents a novel approach in the treatment of chronic disease by modulating proliferation, activation, differentiation, and migration of specific subpopulations of macrophages. It is envisioned that such a treatment would lead to a disease modifying effect—thereby alleviating signs and symptoms. Immunocompetence may be less compromised by this approach than by a more global inflammatory mediator depletion or immune suppressive approaches. Determination of a crystal structure of the cFMS kinase domain would provide a useful tool for indentifying ihibitors of cFMS.

The present inventors have determined the crystal structure of the cFMS kinase domain (cFMSK) alone and complexed with a cFMS inhibitor to 2.7 and 1.8 Å resolution, respectively. The crystal structure contains the non-phosphorylated, catalytic core as well as an N-terminal, juxtamembrane region (NT region). Such a crystal structure is useful in discovering compounds suitable for inhibiting cFMS and for treating diseases characterized by aberrant cfms activity. Also included in the present invention are diamino-pyrimidine cfms inhibitors.

BRIEF SUMMARY OF THE INVENTION

In one aspect of the present invention, there is provided a cFMS kinase domain in liganded crystalline form, comprising the amino acid sequence of SEQ ID NO: 1 or 2 and having the structural coordinates of Table 2.

In a second aspect of the present invention, there is provided a method of CFMS inhibitor design, comprising:

generating a three dimensional computer model which represents a cFMS kinase domain in liganded form, said kinase domain described by the amino acid sequence of SEQ ID NO: 1 or 2 and having the structural coordinates of Table 2;

evaluating compounds as potential cFMS inhibitors using said model; and selecting compounds for further testing based on said evaluation.

In a third aspect of the present invention, there is provided a method of cFMS inhibitor design, comprising:

generating a three dimensional computer model which represents a cFMS kinase domain in liganded form, said kinase domain described by the amino acid sequence of SEQ ID NO: 1 or 2 and having the structural coordinates of Table 2;

evaluating compounds as potential cFMS inhibitors using said model; wherein said evaluation comprises identifying compounds capable of at least one of the following cFMS kinase domain/compound interactions:

(i) one or more interactions with amino acid residues of the CFMS kinase domain hinge region;

(ii) one or more interactions with amino acid residues of the CFMS kinase domain adenine pocket, (iii) one or more interactions with amino acid residues of the cFMS kinase sugar pocket and phosphate region, (iv) one or more interactions with amino acid residues of the cFMS kinase domain back pocket, and (v) one or more interactions with amino acid residues of the cFMS kinase domain solvent interface; and selecting compounds for further testing based on said evaluation.

In a fourth aspect of the present invention, there is provided a method of cFMS inhibitor design, comprising:

generating a three dimensional computer model which represents a cFMS kinase domain in liganded form, said kinase domain described by the amino acid sequence of SEQ ID NO: 1 or 2 and having the structural coordinates of Table 2;

evaluating compounds as potential cFMS inhibitors using said model; wherein said evaluation comprises identifying compounds capable of at least one of the following cFMS kinase domain/compound interactions:

(i) one or more interactions with amino acid residues 663, 664, 665, 666, 667, 668, and 669;

(ii) one or more interactions with amino acid residues 588, 614, 647, and 785, (iii) one or more interactions with amino acid residues 596 and 797 and/or one or more hydrogen bonding interactions with amino acid residue residue 796, (iv) one or more interactions with amino acid residues 550, 640, 646, 769, and 776, and (v) one or more interactions with residues 668 and 672; and selecting compounds for further testing based on said evaluation.

In a fifth aspect of the present invention, there is provided a method of treating a disorder characterized by inappropriate cFMS activity in a mammal, comprising: administering to said mammal a therapeutically effective amount of a compound that can form a complex with a cfms kinase domain thereby resulting in a cFMS kinase domain in liganded form, said kinase domain in liganded form being described by the amino acid sequence of SEQ ID NO: 1 or 2 and the structural coordinates of Table 2, wherein said complex is characterized by at least one of the following cfms kinase domain/compound interactions:

(i) one or more interactions with amino acid residues of the cFMS kinase domain hinge region;

(ii) one or more interactions with amino acid residues of the cFMS kinase domain adenine pocket, (iii) one or more interactions with amino acid residues of the cFMS kinase sugar pocket and phosphate region, (iv) one or more interactions with amino acid residues of the cFMS kinase domain back pocket, and (v) one or more interactions with amino acid residues of the cFMS kinase domain solvent interface.

In a sixth aspect of the present invention, there is provided a method of inhibiting cFMS in a mammal, comprising: administering to said mammal a therapeutically effective amount of a compound that can form a complex with a cfms kinase domain thereby resulting in a cFMS kinase domain in liganded form, said kinase domain in liganded form being described by the amino acid sequence of SEQ ID NO: 1 or 2 and the structural coordinates of Table 2, wherein said complex is characterized by at least one of the following cfms kinase domain/compound interactions:

(i) one or more interactions with amino acid residues of the cFMS kinase domain hinge region;

(ii) one or more interactions with amino acid residues of the cFMS kinase domain adenine pocket, (iii) one or more interactions with amino acid residues of the cFMS kinase sugar pocket and phosphate region, (iv) one or more interactions with amino acid residues of the cFMS kinase domain back pocket, and (v) one or more interactions with amino acid residues of the cFMS kinase domain solvent interface.

In a seventh aspect of the present invention, there is provided a compound of formula (I):

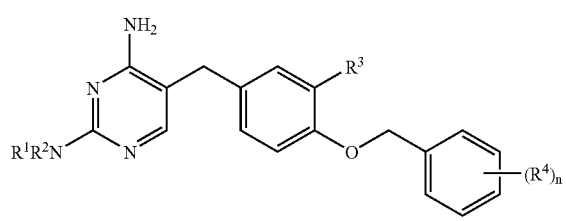

or a salt, solvate, or physiologically functional derivative thereof:

wherein $R^1$ is —H or $C_1$-$C_6$ alkyl;

$R^2$ is —H, $C_1$-$C_6$ alkyl, $C_3$-$C_7$ cycloalkyl, aryl, heterocyclyl, heteroaryl, or —$(CH_2)_p$ $R^6$;

n is 1 or 2;

p is 1, 2, or 3;

$R^3$ is —H or $C_1$-$C_6$ alkoxy;

$R^4$ is $C_1$-$C_6$ alkyl, $C_1$-$C_6$ alkenyl, $C_1$-$C_6$ alkoxy, -halo, $C_1$-$C_6$ haloalkyl, $C_1$-$C_6$ haloalkoxy, aryl, —$SR^5$, or n is 2 and each $R^4$ together with the phenyl ring to which they are attached form the group

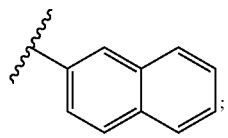

$R^5$ is $C_1$-$C_6$ alkyl; and $R^6$ is $NR^5R^5$, heterocyclyl, aryl, or heteroaryl.

DETAILED DESCRIPTION OF THE INVENTION

Figure 1:
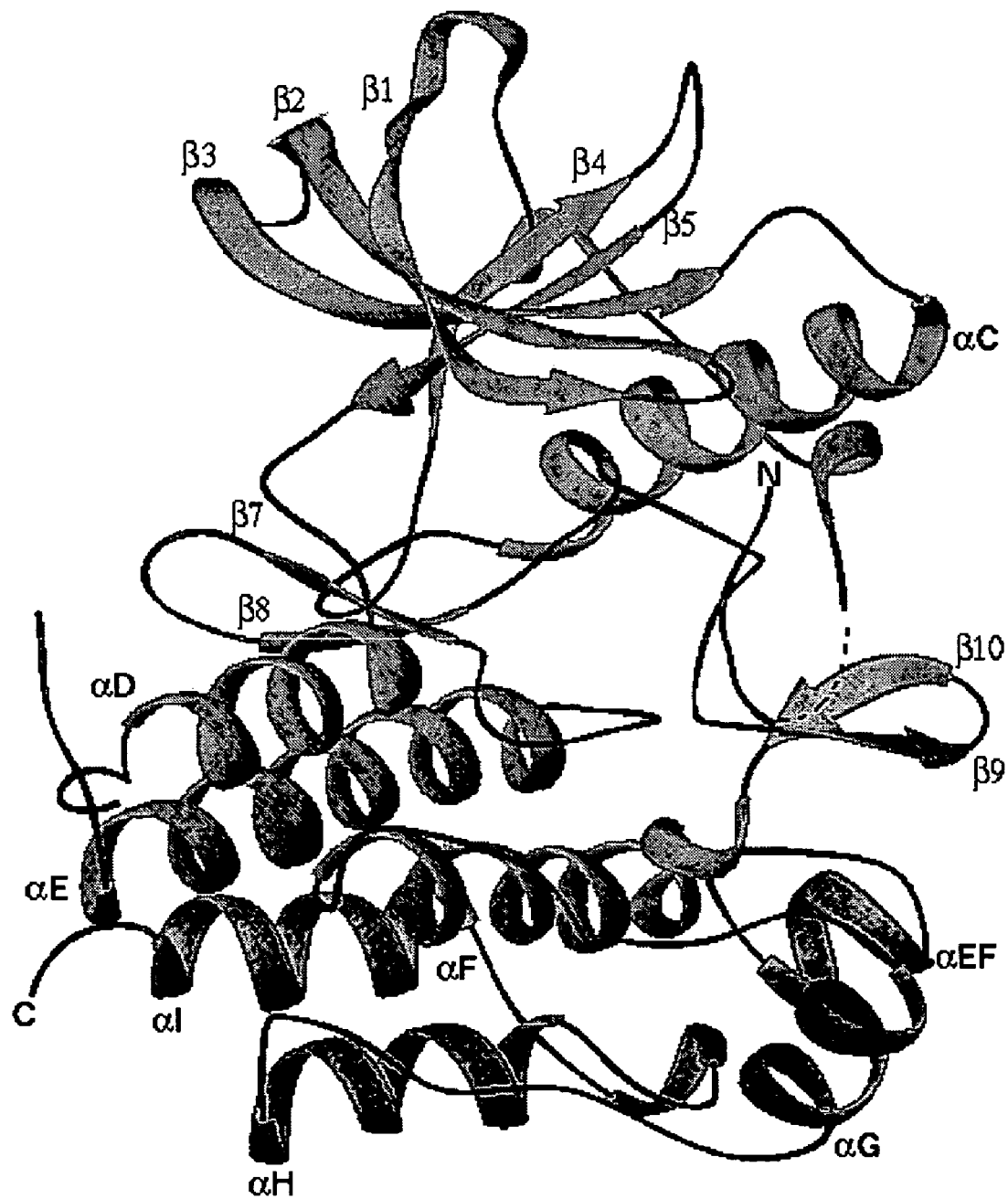
FIG. 1 depicts a ribbon representation, prepared with RIBBONS, of apo cFMSK.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "cFMS" refers to the colony stimulating factor-1 receptor and the term "cFMSK" refers to the colony stimulating factor-1 kinase domain. It is also understood that unless otherwise indicated both terms include within its scope both unactivated and activated forms. That is, the phosphorylated and unphosphorylated forms.

As used herein, the term "mutation" carries its traditional connotation and means a change, inherited, naturally occurring or introduced, in a nucleic acid or polypeptide sequence, and is used in its sense as generally known to those of skill in the art.

As used herein, the term "labeled" means the attachment of a moiety, capable of detection by spectroscopic, radiologic or other methods, to a probe molecule.

As used herein, the term "target cell" refers to a cell, into which it is desired to insert a nucleic acid sequence or polypeptide, or to otherwise effect a modification from conditions known to be standard in the unmodified cell. A nucleic acid sequence introduced into a target cell can be of variable length. Additionally, a nucleic acid sequence can enter a target cell as a component of a plasmid or other vector or as a naked sequence.

As used herein, the term "transcription" means a cellular process involving the interaction of an RNA polymerase with a gene that directs the expression as RNA of the structural information present in the coding sequences of the gene. The process includes, but is not limited to, the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

As used herein, the term "expression" generally refers to the cellular processes by which a biologically active polypeptide is produced from RNA.

As used herein, the term "transcription factor" means a cytoplasmic or nuclear protein which binds to a gene, or binds to an RNA transcript of such gene, or binds to another protein which binds to such gene or such RNA transcript or another protein which in turn binds to such gene or such RNA transcript, so as to thereby modulate expression of the gene. Such modulation can additionally be achieved by other mechanisms; the essence of "transcription factor for a gene" is that the level of transcription of the gene is altered in some way.

As used herein, the term "hybridization" means the binding of a probe molecule, a molecule to which a detectable moiety has been bound, to a target sample.

As used herein, the term "detecting" means confirming the presence of a target entity by observing the occurrence of a detectable signal, such as a radiologic or spectroscopic signal that will appear exclusively in the presence of the target entity.

As used herein, the term "sequencing" means determining the ordered linear sequence of nucleic acids or amino acids of a DNA or protein target sample, using conventional manual or automated laboratory techniques.

As used herein, the term "isolated" means oligonucleotides substantially free of other nucleic acids, proteins, lipids, carbohydrates or other materials with which they can be associated, such association being either in cellular material or in a synthesis medium. The term can also be applied to polypeptides, in which case the polypeptide will be substantially free of nucleic acids, carbohydrates, lipids and other undesired polypeptides.

As used herein, the term "substantially pure" means that the polynucleotide or polypeptide is substantially free of the sequences and molecules with which it is associated in its natural state, and those molecules used in the isolation procedure. The term "substantially free" means that the sample is at least 50%, preferably at least 70%, more preferably 80% and most preferably 90% free of the materials and compounds with which is it associated in nature.

As used herein, the term "primer" means a sequence comprising two or more deoxyribonucleotides or ribonucleotides, preferably more than three, and more preferably more than eight and most preferably at least about 20 nucleotides of an exonic or intronic region. Such oligonucleotides are preferably between ten and thirty bases in length.

As used herein, the term "DNA segment" means a DNA molecule that has been isolated free of total genomic DNA of a particular species. For example, a DNA segment encoding a cFMS or cFMSK polypeptide refers to a DNA segment that encodes SEQ ID NO: 1 or SEQ ID NO: 2, i.e., SEQ ID NO: 3 and SEQ ID NO: 4 respectively, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

As used herein, the phrase "enhancer-promoter" means a composite unit that contains both enhancer and promoter elements. An enhancer-promoter is operatively linked to a coding sequence that encodes at least one gene product.

As used herein, the phrase "operatively linked" means that an enhancer-promoter is connected to a coding sequence in such a way that the transcription of that coding sequence is controlled and regulated by that enhancer-promoter. Techniques for operatively linking an enhancer-promoter to a coding sequence are well known in the art; the precise orientation and location relative to a coding sequence of interest is dependent, inter alia, upon the specific nature of the enhancer-promoter.

As used herein, the term "inhibitor candidate" means a substance that is believed to interact with another moiety, for example a given ligand that is believed to interact to at least partially inhibit the activity of a complete cFMS or cFMS polypeptide, or fragment thereof, and which can be subsequently evaluated for such an interaction and activity inhibition. Representative candidate compounds or substrates include xenobiotics such as drugs and other therapeutic agents, carcinogens and environmental pollutants, natural products and extracts, as well as endobiotics such as steroids, fatty acids and prostaglandins. Other examples of candidate substances that can be investigated using the methods of the present invention include, but are not restricted to, agonists and antagonists of a cFMS or cFMSK polypeptide, toxins and venoms, viral epitopes, hormones (e.g., opioid peptides, steroids, etc.), hormone receptors, peptides, enzymes, enzyme substrates, co-factors, lectins, sugars, oligonucleotides or nucleic acids, oligosaccharides, proteins, small molecules and monoclonal antibodies.

As used herein, the term "modified" means an alteration from an entity's normally occurring state. An entity can be modified by removing discrete chemical units or by adding discrete chemical units. The term "modified" encompasses detectable labels as well as those entities added as aids in purification.

As used herein, the term "interaction" means any relationship between atoms or molecules whereby atomic and/or molecular conditions or forces exist which promote binding equilibrium between such atoms or molecules. Suitable examples include, but are not limited to electrostatic, hydrophobic, hydrophilic, hydrogen, and van der Waals bonding. The nature of such bonding relationships is known in the art and is described for instance in Mathews et al (1990) *Biochemistry*, Chapter 2, pgs 30-54.

As used herein, the terms "structure coordinates" and "structural coordinates" are interchangeable and mean mathematical coordinates derived from mathematical equations related to the patterns obtained on diffraction of a monochromatic beam of X-rays by the atoms (scattering centers) of a cFMSK molecule in crystal form. The diffraction data are used to calculate an electron density map of the repeating unit of the crystal. The electron density maps are used to establish the positions of the individual atoms within the unit cell of the crystal.

Those of skill in the art understand that a set of structure coordinates determined by X-ray crystallography is not without standard error. For the purpose of this invention, any set of structure coordinates for cFMSK or a cFMSK mutant that have a root mean square (RMS) deviation from ideal of no more than 1.5 Å, when superimposed using the polypeptide backbone atoms on the structure coordinates listed in Table 2, shall be considered identical, except that for the activation loop and nucleotide binding loop such deviation from ideal have a RMS of no more than 10 Å.

As used herein, the term "asymmetric unit" means part of a symmetric object from which the whole is built up by repeats. Thus, it is the smallest unit from which the object can be generated by the symmetry operations of its point group.

As used herein, the term "molecular replacement" means a method that involves generating a preliminary model of cFMS or cFMSK mutant crystal whose structure coordinates are unknown, by orienting and positioning a molecule whose structure coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This, in turn, can be subject to any of the several forms of refinement to provide a final, accurate structure of the unknown crystal (Lattman, (1985) in *Methods in Enzymology*, 115: 55-77). Using the structure coordinates of cFMSK and cFMSK in liganded form provided by this invention, molecular replacement can be used to determine the structure coordinates of a crystalline mutant or homologue of cFMSK or of a different crystal form of cFMSK.

As used herein, the terms "β-sheet" and "beta sheet" are interchangeable and mean the conformation of a polypeptide chain stretched into an extended zig-zig conformation. Portions of polypeptide chains that run "parallel" all run in the same direction. Polypeptide chains that are "antiparallel" run in the opposite direction from the parallel chains.

As used herein, the terms "α-helix" and "alpha helix" are interchangeable and mean the conformation of a polypeptide chain wherein the polypeptide backbone is wound around the long axis of the molecule in a left-handed or right-handed direction. The substituent groups of the amino acids protrude outward from the helical backbone, wherein the repeating unit of the structure is a single turn of the helix, which extends about 0.56 nm along the long axis.

As used herein, the term "mutant" means a polypeptide which is obtained by replacing at least one amino acid residue in a native cFMS or cFMSK polypeptide with a different amino acid residue and/or by adding and/or deleting amino acid residues within the native polypeptide or at the N- and/or C-terminus of a polypeptide corresponding to a native cFMS or cFMSK and which has substantially the same three-dimensional structure as the native cFMS or cFMSK from which it is derived. By having substantially the same three-dimensional structure is meant having a set of atomic structure coordinates that have a root mean square deviation (RMS deviation) of less than or equal to about 1.5 Å, (10 Å for the activation loop and nucleotide binding loop) when superimposed with the atomic structure coordinates of the native cFMS or cFMSK from which the mutant is derived when at least about 50% to 100% of the Cα atoms of the native cFMS or cFMSK are included in the superposition. A mutant can have, but need not have, autophosphorylation activity.

As used herein, the term "space group" means a group or array of operations consistent with an infinitely extended regularly repeating pattern. It is the symmetry of a three-dimensional structure, or the arrangement of symmetry elements of a crystal. There are 230 space group symmetries possible; however, there are only 65 space group symmetries available for biological structures.

As used herein, the term "symmetry" means some spatial manipulation of an object resulting in an indistinguishable object. A symmetric object can, therefore, be superimposed on itself by some operation.

As used herein, the term "unit cell" means the fundamental portion of a crystal structure that is repeated infinitely by translation in three dimensions. A unit cell is characterized by three vectors a, b, and c, not located in one plane, which form the edges of a parallelepiped. Angles α, β and γ define the angles between the vectors: angle α is the angle between vectors b and c; angle β is the angle between vectors a and c; and angle γ is the angle between vectors a and b. The entire volume of a crystal can be constructed by regular assembly of unit cells; each unit cell comprises a complete representation of the unit of pattern, the repetition of which builds up the crystal.

As used herein, "monoclinic unit cell" means a unit cell wherein a≠b≠c and α=γ=90° and β≠90°. The vectors a, b and c describe the unit cell edges and the angles α, β, and γ describe the unit cell angles.

As used herein, "orthorhombic unit cell" means a unit cell wherein a≠b≠c; and α=β=γ=90°. The vectors a, b and c describe the unit cell edges and the angles α, β, and γ describe the unit cell angles.

As used herein, the term "crystal lattice" means the array of points defined by the vertices of packed unit cells.

As used herein, the term "active site" means that site in the cFMSK domain where substrate peptide binding, ATP binding and catalysis occur. For cFMS, the active site comprises at least the activation loop and the nucleotide binding loop.

As used herein, the term "activation loop" refers to a loop in tyrosine kinase domains between the conserved Asp-PheGly sequence and the conserved AlaProGlu sequence that is believed to act as a regulatory loop.

As used herein the terms "nucleotide-binding loop" and "glycine-rich loop" are synonomous and mean a loop in an RTK which contains the protein kinase-conserved glycine-rich consensus sequence.

As used herein, the term "autophosphorylation site" means a residue or residues in cFMSK that is phosphorylated by a domain of cFMS itself.

As used herein the term "juxtamembrane region" means that portion of cFMSK located between the transmembrane helix and the tyrosine kinase domain.

As used herein, the terms "kinase insert" and "kinase insert domain" are synonymous and mean an additional domain not found in non-receptor tyrosine kinases or serine/threonine kinases. It is found between helices αD and αE in the C-terminal domain of receptor tyrosine kinases and can vary greatly in sequence and length.

As used herein, the term "C-terminal tail" means that region of an RTK that extends beyond the final helix of the C-terminal domain of the RTK.

As used herein, the term "N-terminal domain" means that region of an RTK that has a defined structure and precedes in sequence the hinge region.

As used herein, the term "modulate" means an increase, decrease, or other alteration of any or all chemical and biological activities or properties of a wild-type or mutant cFMS or cFMSK polypeptide.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight or branched chain hydrocarbon radical having from one to twelve carbon atoms, optionally substituted with substituents selected from the group consisting of $C_1$-$C_6$ alkyl, $C_1$-$C_6$ hydroxyalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aryl, aryloxy, heteroaryl, aminosulfonyl optionally substituted by alkyl, nitro, cyano, halo, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$-$C_6$ alkyl" refers to an alkyl group, as defined above, containing at least 1 and at most 6 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, and n-hexyl.

As used herein, the term "alkylene" refers to a straight or branched chain divalent hydrocarbon radical having from one to ten carbon atoms, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo and $C_1$-$C_6$ perfluoroalkyl, multiple degrees of substitution being allowed. Examples of "alkylene" as used herein include, but are not limited to, methylene, ethylene, n-propylene, n-butylene, and the like.

As used herein, the term "$C_1$-$C_3$ alkylene" refers to an alkylene group, as defined above, which contains at least 1, and at most 3, carbon atoms respectively. Examples of "$C_1$-$C_3$ alkylene" groups useful in the present invention include, but are not limited to, methylene, ethylene, and n-propylene.

As used herein, the term "alkenyl" refers to a hydrocarbon radical having from two to ten carbons and at least one carbon-carbon double bond, optionally substituted with substituents selected from the group which includes $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halo and $C_1$-$C_6$ perfluoroalkyl, multiple degrees of substitution being allowed. Examples of "alkenyl" as used herein include, ethenyl, propenyl, 1-butenyl, 2-butenyl, and isobutenyl.

As used herein, the term "$C_1$-$C_6$ alkenyl" refers to an alkenyl group as defined above containing at least 1, and at most 6, carbon atoms. Examples of "$C_1$-$C_6$ alkyl" groups useful in the present invention include, but are not limited to, ethenyl, propenyl, 1-butenyl, 2-butenyl, and isobutenyl.

As used herein, the term "halogen" refers to fluorine (F), chlorine (Cl), bromine (Br), or iodine (I) and the term "halo" refers to the halogen radicals fluoro (—F), chloro (—Cl), bromo (—Br), and iodo (—I).

As used herein, the term "$C_1$-$C_6$ haloalkyl" refers to an alkyl group as defined above containing at least 1, and at most 6, carbon atoms respectively substituted with at least one halo group, halo being as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo.

As used herein, the term "$C_1$-$C_6$ hydroxyalkyl" refers to an alkyl group as defined above containing at least 1, and at most 6, carbon atoms respectively substituted with at least one hydroxy group, hydroxy being as defined herein. Examples of such branched or straight chained hydroxyalkyl groups useful in the present invention include, but are not limited to, methyl, ethyl, propyl, isopropyl, isobutyl and n-butyl substituted independently with one or more hydroxy groups.

As used herein, the term "cycloalkyl" refers to a non-aromatic cyclic hydrocarbon ring. In a like manner the term "$C_3$-$C_7$ cycloalkyl" refers to a non-aromatic cyclic hydrocarbon ring having from three to seven carbon atoms and which optionally includes a $C_1$-$C_6$ alkyl linker through which it may be attached. The $C_1$-$C_6$ alkyl group is as defined above. Exemplary "$C_3$-$C_7$ cycloalkyl" groups useful in the present invention include, but are not limited to, cyclopropyl, cyclobutyl, cyclopentyl, cyclohexyl and cycloheptyl.

As used herein, the term "heterocyclic" or the term "heterocyclyl" refers to a three to twelve-membered non-aromatic heterocyclic ring, being saturated or having one or more degrees of unsaturation, containing one or more heteroatom substitutions selected from S, S(O), S(O)$_2$, O, or N, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, aryl, heteroaryl, heterocyclyl, nitro, cyano, halo, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyranyl, 1,4-dioxanyl, 1,3-dioxanyl, piperidinyl, piperazinyl, 2,4-piperazinedionyl, pyrrolidinyl, imidazolidinyl, pyrazolidinyl, morpholinyl, thiomorpholinyl, tetrahydrothiopyranyl, tetrahydrothiophenyl, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ alkoxy, $C_1$-$C_6$ haloalkyl, $C_1$-$C_6$ haloalkoxy, $C_1$-$C_6$ hydroxyalkyl, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamide, oxo, hydroxy, mercapto, amino optionally substituted by alkyl or acyl, carboxy, tetrazolyl, carbamoyl optionally substituted by alkyl, aryl, or heteroaryl, aminosulfonyl optionally substituted by alkyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylurea, alkylurea, cycloalkylurea, alkylthiourea, aryloxy, or aralkoxy, multiple degrees of substitution being allowed. Examples of "aryl" groups include, but are not limited to, phenyl, 2-naphthyl, 1-naphthyl, biphenyl, as well as substituted derivatives thereof.

As used herein, the term "aralkyl" refers to an aryl or heteroaryl group, as defined herein, attached through a $C_1$-$C_3$ alkylene linker, wherein the $C_1$-$C_3$ alkylene is as defined herein. Examples of "aralkyl" include, but are not limited to, benzyl, phenylpropyl, 2-pyridylmethyl, 3-isoxazolylmethyl, 5-methyl, 3-isoxazolylmethyl, and 2-imidazoyly ethyl.

As used herein, the term "heteroaryl" refers to a monocyclic five to seven membered aromatic ring, or to a fused bicyclic or tricyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "alkoxy" refers to the group $R_aO$—, where $R_a$ is alkyl as defined above and the term "$C_1$-$C_6$ alkoxy" refers to an alkoxy group as defined herein wherein the alkyl moiety contains at least 1, and at most 6, carbon atoms. Exemplary $C_1$-$C_6$ alkoxy groups useful in the present invention include, but are not limited to, methoxy, ethoxy, n-propoxy, isopropoxy, n-butoxy, and t-butoxy.

As used herein, the term "hydroxy" refers to the group —OH.

As used herein, the term "amino" refers to the group —NH$_2$.

As used herein the term "alkylamino" refers to the group —NHR$_a$ wherein R$_a$ is alkyl as defined above.

As used herein the term "arylamino" refers to the group —NHR$_a$ wherein R$_a$ is aryl as defined above.

As used herein the term "aralkylamino" refers to the group —NHR$_a$ wherein R$_a$ is an aralkyl group as defined above.

As used herein the term "aralkoxy" refers to the group $R_bR_aO$—, where R$_a$ is alkylene and R$_b$ is aryl or heteroaryl all as defined above.

As used herein the term "aryloxy" refers to the group $R_aO$—, where R$_a$ is aryl or heteroaryl both as defined above.

As used herein the term "ureido" refers to the group —NHC(O)NH$_2$.

As used herein, the term "arylurea" refers to the group —NHC(O)NHR$_a$ wherein R$_a$ is aryl as defined above.

As used herein, the term "arylthiourea" refers to the group —NHC(S)NHR$_a$ wherein R$_a$ is aryl as defined above.

As used herein, the term "alkylurea" refers to the group —NHC(O)NHR$_a$ wherein R$_a$ is alkyl as defined above.

As used herein, the term "cycloalkylurea" refers to the group —NHC(O)NHR$_a$ wherein R$_a$ is cycloalkyl as defined above.

As used herein, the term "haloalkoxy" refers to the group $R_aO$—, where R$_a$ is haloalkyl as defined above and the term "$C_1$-$C_6$ haloalkoxy" refers to a haloalkoxy group as defined herein wherein the haloalkyl moiety contains at least 1, and at most 6, carbon atoms. Exemplary $C_1$-$C_6$ haloalkoxy groups useful in the present invention include, but is not limited to, trifluoromethoxy.

As used herein, the term "alkylsulfanyl" refers to the group $R_aS$—, where R$_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "alkylsulfenyl" refers to the group $R_aS(O)$—, where R$_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where R$_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "alkylsulfonylamino" refers to the group —NHS(O)$_2$R$_a$ wherein R$_a$ is alkyl as defined above and the term "$C_1$-$C_6$ alkylsulfonylamino" refers to an alkylsulfonylamino group as defined herein wherein the alkyl moiety contains at least 1, and at most 6, carbon atoms.

As used herein, the term "arylsulfonylamino" refers to the group —NHS(O)$_2$R$_a$ wherein R$_a$ is aryl as defined above.

As used herein, the term "alkylcarboxyamide" refers to the group —NHC(O)$R_a$ wherein $R_a$ is alkyl, amino, or amino substituted with alkyl, aryl or heteroaryl as described above.

As used herein the term "alkylcarboxy" refers to the group —C(O)$R_a$ wherein $R_a$ is alkyl as described above.

As used herein, the term "oxo" refers to the group =O.

As used herein, the term "mercapto" refers to the group —SH.

As used herein, the term "carboxy" refers to the group —C(O)OH.

As used herein, the term "cyano" refers to the group —CN.

As used herein the term "cyanoalkyl" refers to the group —CN$R_a$, wherein $R_a$ is alkyl as defined above. Exemplary "cyanoalkyl" groups useful in the present invention include, but are not limited to, cyanomethyl, cyanoethyl, and cyanoisopropyl.

As used herein, the term "aminosulfonyl" refers to the group —S(O)$_2$NH$_2$.

As used herein, the term "carbamoyl" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group $R_a$C(O)—, where $R_a$ is alkyl, cycloalkyl, or heterocyclyl as defined herein.

As used herein, the term "aroyl" refers to the group $R_a$C(O)—, where $R_a$ is aryl as defined herein.

As used herein, the term "aroylamino" refers to the group $R_a$C(O)NH—, where $R_a$ is aryl as defined herein.

As used herein, the term "heteroaroyl" refers to the group $R_a$C(O)—, where $R_a$ is heteroaryl as defined herein.

As used herein, the term "alkoxycarbonyl" refers to the group $R_a$OC(O)—, where $R_a$ is alkyl as defined herein.

As used herein, the term "acyloxy" refers to the group $R_a$C(O)O—, where $R_a$ is alkyl, cycloalkyl, or heterocyclyl as defined herein.

As used herein, the term "aroyloxy" refers to the group $R_a$C(O)O—, where $R_a$ is aryl as defined herein.

As used herein, the term "heteroaroyloxy" refers to the group $R_a$C(O)O—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted. Also, it is understood that any tautomers and mixtures of tautomers of the compounds of formula (I) are included within the scope of the compounds of formula (I).

Description of APO cFMSK Structure

The overall architecture of cFMSK was analogous to structures reported previously for both serine/threonine and tyrosine protein kinases (Mohammadi 1996 and McTigue 1999). A $C_\alpha$ trace of cFMSK is shown in FIG. 1, where kinase secondary structural elements are labeled according to the convention originally given for cAPK (Knighton & Sowadski, 1991). cFMSK folds into two domains, with catalysis occurring in a cleft between the two domains. Residues in the N-terminal domain are primarily responsible for ligating ATP, while residues in the C-terminal domain are involved in catalysis and substrate binding.

The N-terminal domain (residues 575-669) folds into a twisted β-sheet and one α-helix. The larger C-terminal domain (residues 670-919) contains seven α-helices (αD-αI) and two sets of anti-parallel β-strands (β7/β8 and β9/β10). Strands 7 and 8 are positioned at the interdomain interface adjacent to the N-terminal β-sheet. Like other kinases, cFMSK also contains functionally important loop regions: the glycine-rich nucleotide binding loop (residues 590-594), the catalytic loop (residues 776-783) and the activation loop (residues 796-825), which are described in further detail below.

Activation Loop

Protein kinases contain a large flexible loop, called the activation loop or A-loop, whose conformation is believed to regulate kinase activity. In many kinases, the conformation of the A-loop is controlled by the phosphorylation of specific residues within this region (Johnson 1996). The activation loop generally begins with a conserved AspPheGly sequence (cFMSK 796) and ends at a conserved AlaProGlu (cFMSK 825). In structures of inactive kinases, this loop often blocks either the substrate or ATP binding sites (Hubbard 1994; Mohammadi 1996; and McTigue 1999).

Upon phosphorylation, the A-loop is repositioned to contact residues in the C-terminal domain (Hubbard 1997). The activating phosphate can then interact with a cluster of basic residues, which includes a conserved arginine (cFMSK R777), that precedes the catalytic aspartate (cFMSK D778). The aspartyl residue of the AspPheGly motif ligates a Mg$^{2+}$ ion, which, in turn contacts the β and γ phosphates of ATP.

In cFMSK, the activation loop corresponds to residues 796-825 and contains a single tyrosine at position 809. In the apo cFMSK structure presented here, the A-loop folds under the nucleotide binding loop, partially blocking both the ATP and substrate binding sites. The Phe of the conserved Asp-PheGly motif sits in the ATP binding site and the side chain of cFMSK Phe797 overlays with the ribose of ATP and packs under Val596. Arg801 occupies the beta and gamma phosphate binding site. The carbonyl oxygen of Asp796 forms a hydrogen bond with the epsilon amino group of the catalytic Lys616. Leu799 packs deep into the back of the ATP binding site, packing under the nucleotide binding loop and displacing it upwards relative to its position observed in other kinase structures (Hubbard 1994; Hubburd 1997; Mohammadi 1996; and McYigue 1999).

Nucleotide Binding Loop

The nucleotide binding loop (NB loop) contains residues responsible for binding the triphosphate moiety of ATP in the correct position for catalysis (Johnson 1996 and Cox 1994). This glycine-rich loop is believed to be quite flexible and is often either disordered or has high b-factors in many unliganded kinase structures (Mohammadi 1996 and McTigue 1999). In cFMSK, this loop is well defined and packs against residues in the A-loop. Leu799 of the activation loop, packs deep into the back of the ATP binding site, displacing the NB loop upwards relative to its position observed in other kinase structures (Hubbard 1994; Hubburd 1997; Mohammadi 1996; and McTigue 1999).

Juxtamembrane Region

The cFMSK constructs contains 32 additional residues preceding the conserved catalytic core (residues 542-574). In the apo and inhibitor complex structures, 18 and 28 of these residues are well defined, respectively. In the apo structure, a loop within this region is disordered (residues 555-563). While the function of this juxtamembrane region is unclear, previous studies with murine cFMS suggest that Tyr559 (human Tyr561), is phosphorylated in vivo and interacts with the SH2 domain of Fyn (Alonso 1995). Mutation of this residue to alanine, in the murine protein, eliminates rapid ligand-induced endocytosis of receptor molecules and lose of kinase activity [Myles 1994]. In v-cfms, Tyr544 (human Tyr546) is phosphorylated and interacts with an unidentified 55 kDa protein (Joos 1996). In both the apo and inhibitor complex structures, the NT region is located in close proximity to the ATP binding site. In the inhibitor structure, Tyr561 is located on a solvent exposed loop. The structural or conformational consequences of phosphorylating this residue are not clear.

Catalytic Loop

The catalytic loop of protein kinases lies between αE and β7 and contains an invariant aspartic acid (D778 in cFMS) that serves as the catalytic base in the phosphotransfer reaction (Johnson 1996). The sequence in cFMS is HRDVAARN (residues 776-783). In cFMSK, the backbone and side chain positions of this loop are similar to those in the unliganded FGFR1, Tie2, IRK and VEGFR2 and in the ternary phosphorylated IRK complex structures (Hubbard 1994; Mohammadi 1996; McTigue 1999; and Shewchuk 2000).

Kinase Insert Domain (KID)

Many RTKs contain an insert of variable length and sequence between αD and αE in their C-terminal domain. This insert can be as short as 12 or as long as 97 residues, as in IRK and the platelet-derived growth factor receptor β (PDGFRβ), respectively (Hubbard 1994 and Heideran 1991). Deletion or mutation of this region in other kinases revealed that the KID is not necessary for intrinsic kinase activity (McTigue 1999; Heideran 1991; and Taylor 1989). However, this kinase insert domain may be important for protein-protein interactions involved in signal transduction via phosphorylation of KID residues (Heideran 1991 and Taylor 1989). In cFMS, this region corresponds to residues 668-750 and contains 3 tyrosine, 10 serine and 2 threonine residues. Previous studies with murine cFMS suggested that 3 tyrosine residues within the KID (murine Tyr697, 706 and 721; human Tyr699, 708, 723) were phosphorylated in response to CSF-1 binding to the extracellular domain. Phosphorylated Tyr697, in the murine protein, associates with Grb2, enabling the nucleotide exchange factor Sos1 to activate Ras. Phosphorylated Tyr706 is involved in activation of the STAT1 transcription factor while phosphorylated Tyr721 binds the regulatory p85 subunit of PI-3 kinase. In addition, previous mutational studies suggested that the cFMS KID targets the protein for degradation, following internalization (Carlberg 1991).

The early constructs utilized, that contained the KID, were heterogeneously phosphorylated on 3 serines within the KID (Ser688, Ser713 and Ser733) and yielded poorly diffracting crystals. Therefore, the KID was deleted for structural studies. In both deletion constructs, residues surrounding the deletion were disordered in the crystal structure (residues 687-746). Interestingly helix D, leading into the KID, is nearly twice as long in cFMS than in FGFR1 and VEGFR2.

ATP Binding Site

The ATP binding site (see FIG. 2) can be broken down into several regions: hinge, adenine pocket, sugar pocket, phosphate region, back hydrophobic pocket and solvent interface. ATP is modeled into cfms based on the activated IR structure. The hinge region runs from thr663 to cys667 and would be expected to form hydrogen bonds with the adenine base of ATP. In the orientation shown in the figure, the adenine pocket would be formed by leu588 and ala614 on top, leu785 on the bottom, val647 in the back, and the hinge region on the left side. The sugar pocket would have val596 on top and gly795 on the bottom. The phosphate region would contain gly795, asp796, phe797, arg782, and asn783 on the bottom and right side, and lys616 and glu633 on top. The hydrophobic back pocket in cfms would be formed by thr663, met637, leu640, ile646, leu769, trp550, and his776. A surface at the solvent interface formed by residues gly668 to asn672 could form both hydrophobic and hydrophilic interactions with inhibitors.

Inhibitor/cFMSK Complex Structure

The structure of nonphosphorylated cFMSK was also solved in the presence of a compound of formula (I):

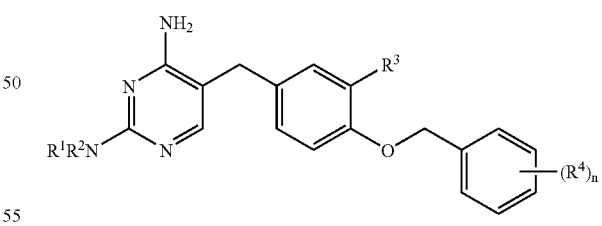

or a salt, solvate, or physiologically functional derivative thereof:

wherein $R^1$ is —H or $C_1$-$C_6$ alkyl;

$R^2$ is —H, $C_1$-$C_6$ alkyl, $C_3$-$C_7$ cycloalkyl, aryl, heterocyclyl, heteroaryl, or —$(CH_2)_p$ $R^6$;

n is 1 or 2;

p is 1, 2, or 3;

$R^3$ is —H or $C_1$-$C_6$ alkoxy;

$R^4$ is $C_1$-$C_6$ alkyl, $C_1$-$C_6$ alkenyl, $C_1$-$C_6$ alkoxy, -halo, $C_1$-$C_6$ haloalkyl, $C_1$-$C_6$ haloalkoxy, aryl, —$SR^5$, or n is 2 and each $R^4$ together with the phenyl ring to which they are attached form the group

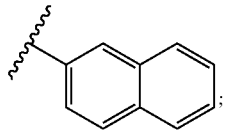

$R^5$ is $C_1$-$C_6$ alkyl; and
$R^6$ is $NR^5R^5$, heterocyclyl, aryl, or heteroaryl.

Specifically, the structure of nonphosphorylated cFMSK was also solved in the presence of a diamino pyrimidine inhibitor of formula (I):

(pIC50=7.5, Formula (Ia)).

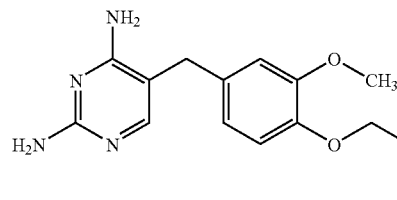

(Ia)

The protein-inhibitor complex was co-crystallized under different conditions and in a different space group then the apo protein (Table 1). While the overall fold was the same for the apo and inhibitor complex structures, differences were observed in the A-loop and NT region.

Figure 3:
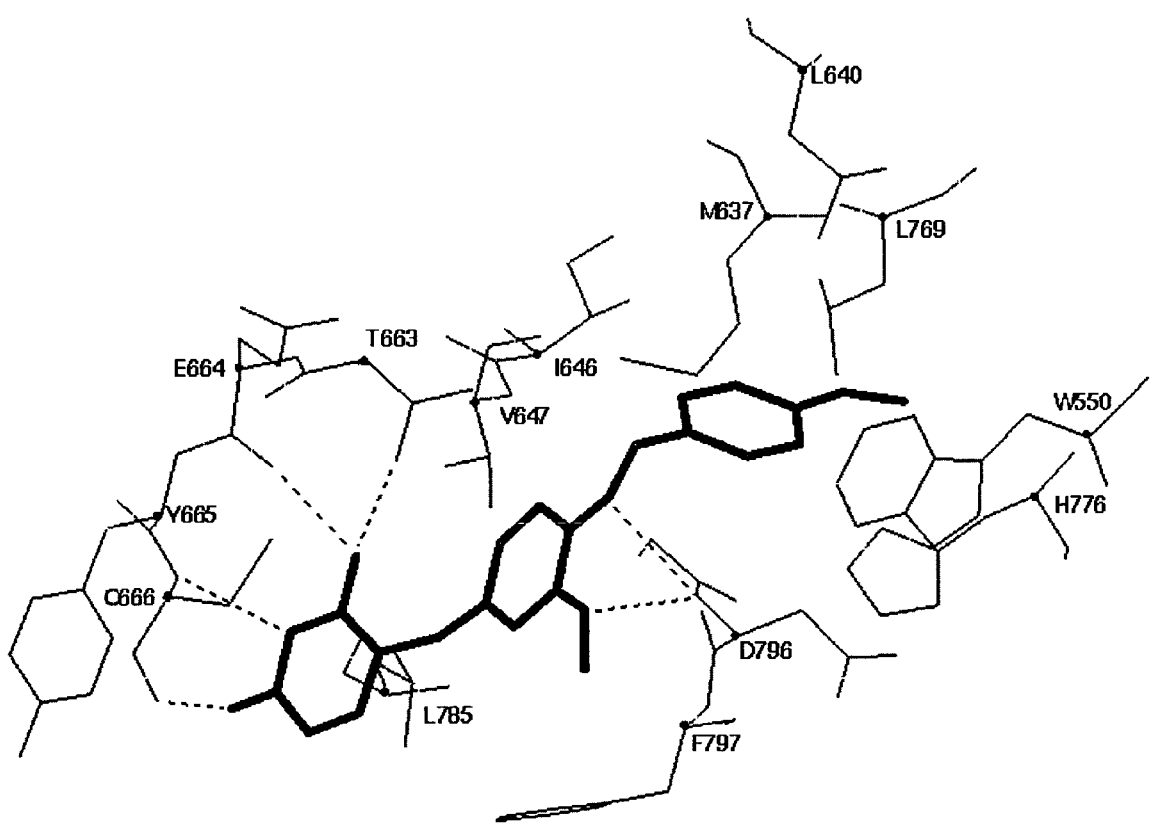
FIG. 3 depicts a representation, created with QUANTA, of the binding of a diamino inhibitor of formula (I) to the ATP binding site of cFMSK.
Figure 5:
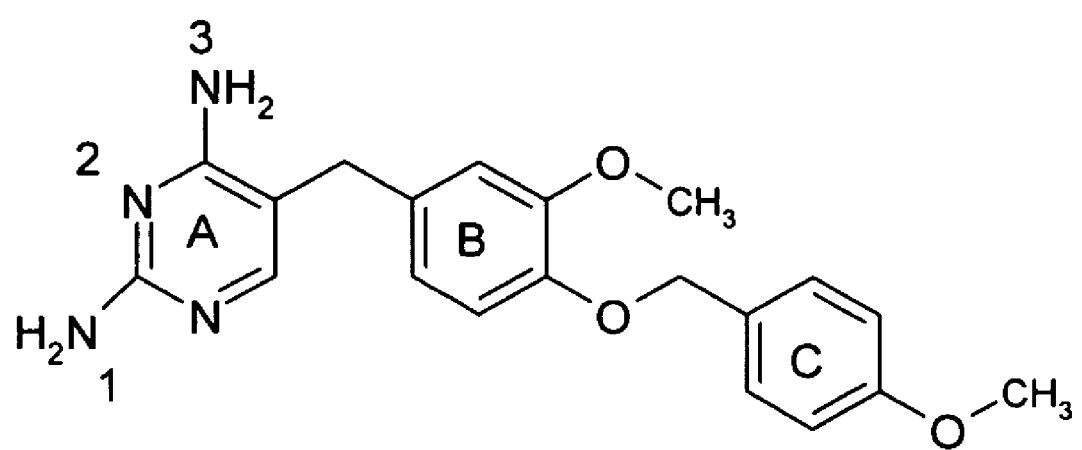
FIG. 5 depicts the various rings (A, B, and C) and nitrogens (1, 2, and 3) of the compound of formula 1(a).

The diamino pyrimidine group hydrogen bonds to the hinge region between the N and C-terminal domains (See FIG. 3). In FIG. 3, the inhibitor is highlighted in bolded lines and the hydrogen bonding is indicated with dashed lines. N1 and N2 (see FIG. 5) of the inhibitor hydrogen bond to the carbonyl and main chain NH of Cys666, respectively. N3 forms a bidentate hydrogen bond to the carbonyl of Glu664 and side chain of Thr663. The B and C rings (see FIG. 5) of the inhibitor lie deep in the back of the ATP binding site, in a pocket not present in the apo structure. The 2 ether oxygens hydrogen bond to the main chain NH of Asp796. The B ring packs against Val647, while the C ring sits in a hydrophobic pocket formed by Ile646, Met637, Leu640, Leu769, Trp550, and H776.

Figure 4:
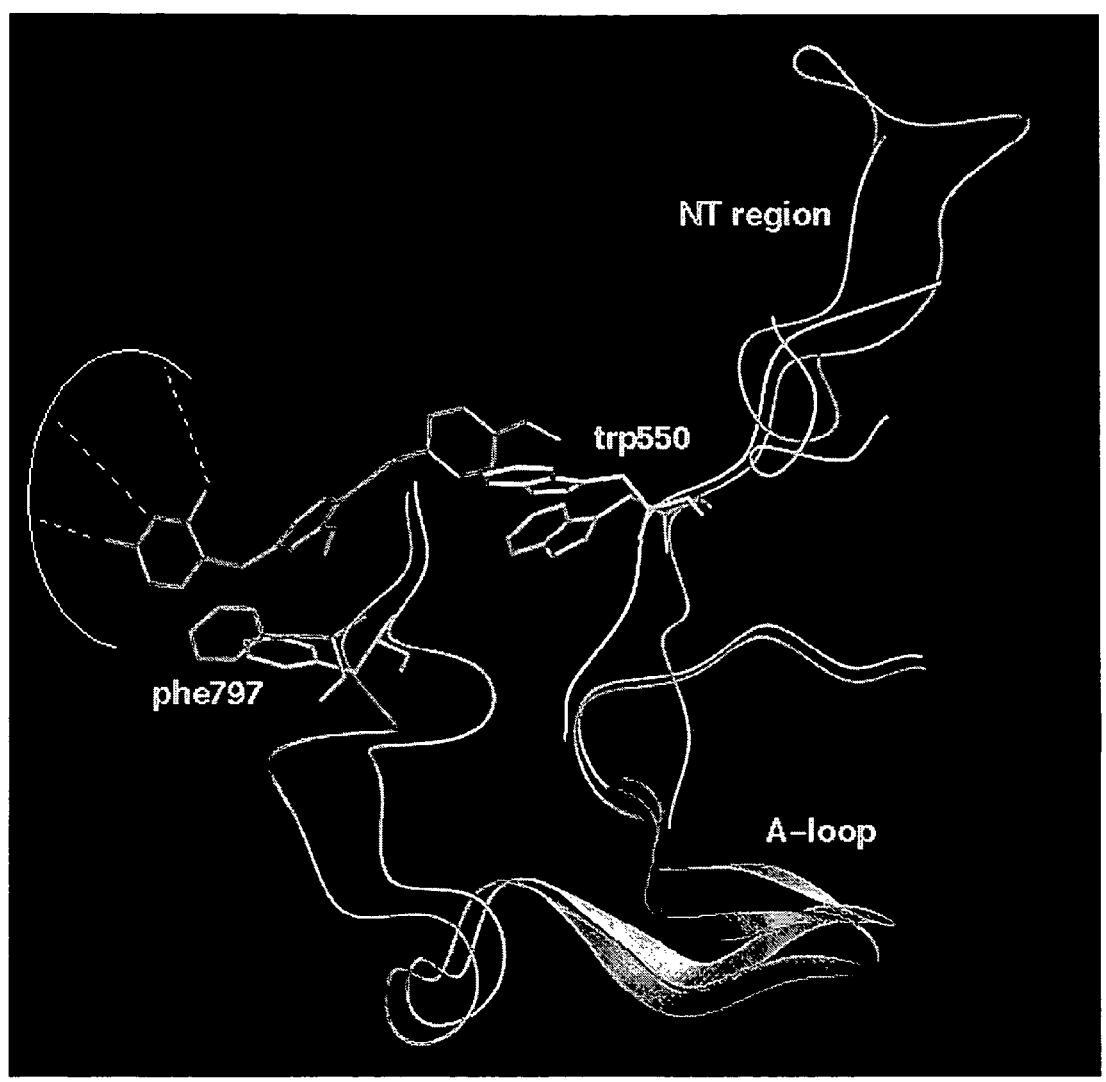
FIG. 4 depicts a superposition, prepared with QUANTA, of the NT region and A-loops in the cFMSK apo and inhibitor structures.

Both the activation loop and NT region move to accommodate inhibitor binding (FIG. 4). In the inhibitor complex structure, the entire NT region is ordered. Residues 546-551 of the NT region, form the back of the inhibitor binding pocket and shift to accommodate the C ring of the inhibitor. Trp 550 makes an edge-to-face interaction with the inhibitor C ring. The end of the inhibitor, corresponding to the C ring of the cFMSK inhibitor, is solvent exposed.

The A-loop in the inhibitor complex is still in an inactive, inhibitory conformation. The first 6 residues of the A-loop shift, relative to their position in the apo structure, to accommodate inhibitor binding. Specifically, Phe797 moves out of the ATP binding site.

While the inhibitor binds to the inactive, nonphosphorylated form of cFMSK in the crystal structure, it presumably also binds to the active, phosphorylated form of the protein. Nonphosphorylated cFMSK will autophosphorylate itself in vitro on Tyr809 in the A-loop, increasing kinase activity ~10 fold. Similar IC50s were observed for the inhibitor on cFMSK whether the inhibitor was added before or after pre-incubation with ATP in an in vitro kinase assay.

Co-crystal structures were also solved using each of the following diaminopyrimidine compounds of formula (Ib), (Ic), and (Id) of the present invention.

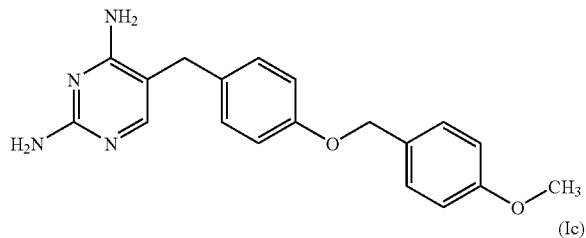

(Ib)

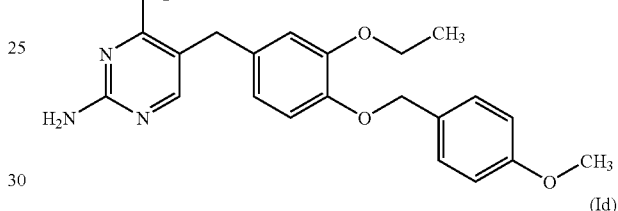

(Ic)

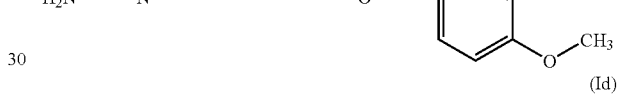

(Id)

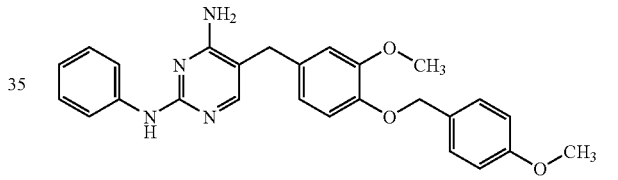

As recited above, the present invention provides a cFMS kinase domain in liganded crystalline form. Such cFMS liganded kinase domain is described by the amino acid sequence of SEQ ID NO: 1 or 2 and the structural coordinates of Table 2. In one embodiment, the SEQ ID is SEQ ID NO: 1. In an alternative embodiment, the SEQ ID is SEQ ID NO: 2. SEQ ID NO: 1 is encoded by the DNA sequence of SEQ ID NO: 3 and SEQ ID NO: 2 is encoded by the DNA sequence of SEQ ID NO: 4. In a further embodiment, is a substantially pure and isolated cFMS kinase domain in liganded crystalline form described by the amino acid sequence of SEQ ID NO: 1 or 2 and the structural coordinates of Table 2. In one embodiment, the SEQ ID is SEQ ID NO: 1. In an alternative embodiment, the SEQ ID is SEQ ID NO: 2.

In one embodiment the liganded cFMS kinase domain in crystalline form has lattice constants of a=80 Å, b=80 Å, c=78 Å, α=90°, β=90°, and γ=90°. In one embodiment, the liganded cFMS kinase domain in crystalline form has a space group of R3. In another embodiment, the liganded cFMS kinase in crystalline form has an entire NT region which is ordered. In still another embodiment, the liganded cFMS kinase in crystalline form has structural coordinates having a deviation from ideal with a RMS of no more than 1.5 Å except that the activation loop and/or a nucleotide binding loop have structural coordinates having a deviation from ideal with a RMS of no more than 10 Å. In a further embodiment, the liganded cFMS kinase in crystalline form has an activation loop and/or a nucleotide binding loop have structural coordinates having a deviation from ideal with a RMS of no more than 10 Å.

In another embodiment, there is provided a cFMS kinase domain/inhibitor complex which includes a cFMS liganded kinase domain described by the amino acid sequence of SEQ ID NO: 1 or 2 and the structural coordinates of Table 2 and a compound capable of at least one of the following interactions with the cFMS kinase domain:

(i) one or more interactions with amino acid residues of the cFMS kinase domain hinge region;

(ii) one or more interactions with amino acid residues of the cFMS kinase domain adenine pocket, (iii) one or more interactions with amino acid residues of the cFMS kinase sugar pocket and phosphate region, (iv) one or more interactions with amino acid residues of the cFMS kinase domain back pocket, and (v) one or more interactions with amino acid residues of the cFMS kinase domain solvent interface;

preferably (i) one or more interactions with amino acid residues 663, 664, 665, 666, 667, 668, and 669;

(ii) one or more interactions with amino acid residues 588, 614, 647, and 785, (iii) one or more interactions with amino acid residues 596 and 797 and/or one or more interactions with amino acid residue 796, (iv) one or more interactions with amino acid residues 550, 640, 646, 769, and 776, and (v) one or more interactions with residues 668 and 672.

More preferred embodiments of interactions (i), (ii), (iii), (iv), and (v) are described following.

Figure 2:
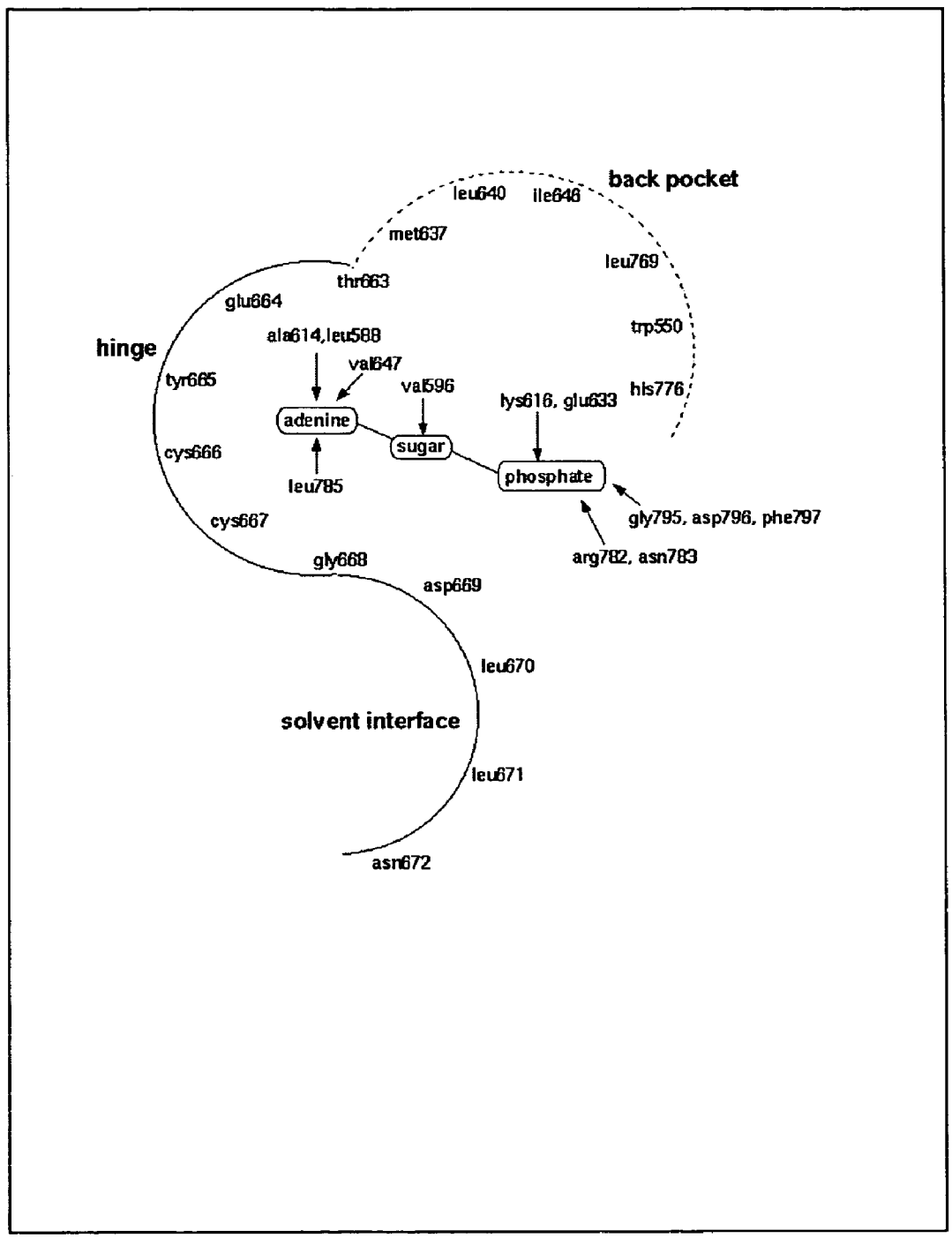
FIG. 2 depicts a representation of the various regions of the ATP binding site of cFMSK.

The amino acid region referred to in the interactions described in (i), which include amino acid residues 663-669, is typically referred to as the hinge region (see FIG. 2). In one embodiment, there are one or more kinase domain/compound hydrogen bonding interactions with at least one of amino acid residues 663 to 669, preferably two or more hydrogen bonding interactions with at least one of amino acid residues 663 to 669, more preferably three or more hydrogen bonding interactions with at least one of amino acid residues 663 to 669, most preferably four or more hydrogen bonding interactions with at least one of amino acid residues 663 to 669.

In one embodiment, there is a kinase domain/compound hydrogen bonding interaction with threonine 663, preferably one hydrogen bonding interaction with the side chain oxygen of threonine 663. Typically, this hydrogen bond is at a distance of 2.7 to 3.7, preferably 2.9 to 3.5, more preferably 3.1 to 3.3 Å. In another embodiment, there is a kinase domain/ compound hydrogen bonding interaction with glutamic acid 664, preferably one hydrogen bonding interaction with a carbonyl oxygen of glutamic acid 664. Typically, this hydrogen bond is at a distance of 2.3 to 3.3, preferably 2.5 to 3.1, more preferably 2.7 to 2.9 Å. In another embodiment, there is a kinase domain/compound hydrogen bonding interaction with cysteine 666, preferably one hydrogen bonding interaction with the carbonyl oxygen of cysteine 666. Typically, this hydrogen bond is at a distance of 2.3 to 3.3, preferably 2.5 to 3.1, more preferably 2.7 to 2.9 Å. In a further embodiment, there is one kinase domain/compound hydrogen bonding interaction with the backbone —N(H)— of cysteine 666. Typically, this hydrogen bond is at a distance of 2.8 to 3.8, preferably 3.0 to 3.6, more preferably 3.2 to 3.4 Å. In one embodiment, there are two kinase domain/compound hydrogen bonding interactions with cysteine 666, preferably one hydrogen bonding interaction with the carbonyl oxygen and one hydrogen bonding interaction with the backbone —N(H)— of cysteine 666.

In a more preferred embodiment, there is one kinase domain/compound hydrogen bonding interaction with each of threonine 663 and glutamic acid 664 and two hydrogen bonding interactions with cysteine 666. In a most preferred embodiment, there are four kinase domain/compound hydrogen bonding interactions: (i) a hydrogen bonding interaction with the side chain oxygen of threonine 663, (ii) a hydrogen bonding interaction with the carbonyl oxygen of glutamic acid 664, (iii) a hydrogen bonding interaction with the carbonyl oxygen of cysteine 666, and (iv) a hydrogen bonding interaction with the backbone —N(H)— of cysteine 666.

The amino acid region referred to in the interactions in (ii) described what is commonly termed the adenine pocket (see FIG. 2), which is formed by residues 588 and 614 on top, residue 785 on the bottom, and residue 647 in the back, with the hinge region, described above, being on the left side of the pocket. In one embodiment, there are one or more kinase domain/compound hydrophobic interactions with at least one of amino acid residues 588, 614, 647, and 785, preferably two or more hydrophobic interactions with at least two of amino acid residues 588, 614, 647, and 785, more preferably three or more hydrophobic interactions with at least three of amino acid residues 588, 614, 647, and 785, most preferably four or more hydrophobic bonding interactions with at least four of amino acid residues 588, 614, 647, and 785.

In one embodiment, there is a kinase domain/compound hydrophobic interaction with leucine 588, preferably a hydrophobic interaction with the side chain of leucine 588. In another embodiment, there is a kinase domain/compound hydrophobic interaction with alanine 614, preferably a hydrophobic bonding interaction with the side chain of alanine 614. In another embodiment, there is a kinase domain/ compound hydrophobic interaction with valine 647, preferably a hydrophobic interaction with the side chain of valine 647. In a further embodiment, there is a kinase domain/compound hydrophobic interaction with leucine 785, preferably a hydrogen bonding interaction with the side chain of leucine 785.

In a more preferred embodiment, there is one kinase domain/compound hydrophobic interaction with each of leucine 588, alanine 614, valine 647, and leucine 785. In a most preferred embodiment, there are four kinase domain/compound hydrophobic bonding interactions: (i) a hydrophobic interaction with the side chain of leucine 588, (ii) a hydrophobic interaction with the side chain of alanine 614, (iii) a hydrophobic interaction with the side chain of valine 647, and (iv) a hydrophobic interaction with the side chain of leucine 785.

The amino acid region referred to in the interactions in (iii) described what is commonly termed the sugar pocket (see FIG. 2), which is formed by residue 596 on top and residue 795 on the bottom and the phosphate region formed by residues 795, 796, 797, 782 and 783 on the bottom and right side and residues 616 and 633 on top. In one embodiment, there are one or more kinase domain/compound hydrophobic interactions with at least one of amino acid residues 596 and 797 and one or more hydrogen bonding interactions with residue 796, preferably two or more hydrophobic interactions with amino acid residues 596 and 797 and two hydrogen bonding interactions with residue 796.

In one embodiment, there is a kinase domain/compound hydrophobic interaction with valine 596, preferably a hydrophobic interaction with the side chain of valine 596. In another embodiment, there is a kinase domain/compound hydrophobic interaction with phenylalanine 797, preferably a hydrophobic interaction with the side chain of phenylalanine 797. In one embodiment, there is one, preferably two hydrogen bonding interactions with aspartic acid 796.

In a more preferred embodiment, there is one kinase domain/compound hydrophobic interaction with each of valine 596 and phenylalanine 797. In a most preferred embodiment, there are two kinase domain/compound hydrophobic bonding interactions: (i) a hydrophobic interaction with the side chain of valine 596 and (ii) a hydrophobic interaction with the side chain of phenylalanine 797, and two hydrogen bonding interactions with the backbone —N(H)— of aspartic acid 796. Typically, one of these hydrogen bonds is at a distance of 2.7 to 3.7, preferably 2.9 to 3.5, more preferably 3.1 to 3.3 Å and the other hydrogen bond is at a distance of 2.2 to 3.2, preferably 2.4 to 3.1, more preferably 3.6 to 2.8 Å.

The amino acid region referred to in the interactions in (iv) described what is commonly termed the back pocket (see FIG. 2), which is formed by residues 663, 637, 640, 646, 769, 550, and 776. In one embodiment, there are one or more kinase domain/compound hydrophobic interactions with at least one of amino acid residues 637, 640, 646, 663, 769, and 776, preferably two or more hydrophobic interactions with at least two of amino acid residues 637, 640, 646, 663, 769, and 776, more preferably three or more hydrophobic interactions with at least three of amino acid residues 637, 640, 646, 663, 769, and 776, still more preferably four or more hydrophobic bonding interactions with at least four of amino acid residues 637, 640, 646, 663, 769, and 776, even more preferably five or more hydrophobic bonding interactions with at least four of amino acid residues 637, 640, 646, 663, 769, and 776, and most preferably six or more hydrophobic bonding interactions with at least four of amino acid residues 637, 640, 646, 663, 769, and 776.

In one embodiment, there is a kinase domain/compound hydrophobic interaction with methionine 637, preferably a hydrophobic interaction with the side chain of methionine 637. In another embodiment, there is a kinase domain/compound hydrophobic interaction with leucine 640, preferably a hydrophobic bonding interaction with the side chain of leucine 640. In another embodiment, there is a kinase domain/compound hydrophobic interaction with isoleucine 646, preferably a hydrophobic interaction with the side chain of isoleucine 646. In a further embodiment, there is a kinase domain/compound hydrophobic interaction with threonine 663, preferably a hydrophobic interaction with the side chain of threonine 663. In another further embodiment, there is a kinase domain/compound hydrophobic interaction with leucine 769, preferably a hydrophobic interaction with the side chain of leucine 769. In another embodiment, there is a kinase domain/compound hydrophobic interaction with histidine 776, preferably a hydrophobic interaction with the side chain of histidine 776.

In a more preferred embodiment, there is one kinase domain/compound hydrophobic interaction with each of methionine 637, leucine 640, isoleucine 646, threonine 663, leucine 769, and histidine 776. In a most preferred embodiment, there are six kinase domain/compound hydrophobic bonding interactions: (i) a hydrophobic interaction with the side chain of methionine 637, (ii) a hydrophobic interaction with the side chain of leucine 640, (iii) a hydrophobic interaction with the side chain of isoleucine 646, (iv) a hydrophobic interaction with the side chain of threonine 663, (v) a hydrophobic interaction with the side chain of leucine 769, and (vi) a hydrophobic interaction with the side chain of histidine 776.

The amino acid region referred to in the interactions in (v) describe what is commonly termed the solvent interface (see FIG. 2), which is formed by residues 668 and 672. In one embodiment, there are one or more kinase domain/compound hydrophobic and/or hydrophilic interactions with at least one of amino acid residues 668 and 672, preferably two or more hydrophobic and/or hydrophilic interactions with at least two of amino acid residues 668 and 672, more preferably three or more hydrophobic and/or hydrophilic interactions with at least two of amino acid residues 668 and 672.

In one embodiment, there is a kinase domain/compound hydrophobic and/or hydrophilic interaction with glycine 668. In another embodiment, there is a kinase domain/compound hydrophobic and/or hydrophilic interaction with asparagine 672.

In a more preferred embodiment, there is one kinase domain/compound hydrophobic and/or hydrophilic interaction with each of glycine 668 and asparagine 672. In a most preferred embodiment, there are two kinase domain/compound hydrophobic and/or hydrophilic interactions: (i) a hydrophobic and/or hydrophilic interaction with glycine 668 and (ii) a hydrophobic and/or hydrophilic interaction with asparagine 672.

In another embodiment, residues 546-551 of the NT region of the cfms kinase domain shift to accommodate the compound.

In one embodiment, the compound is a compound of formula (I) a, b, c, or d.

The method of cFMS inhibitor design of the present invention includes as a first step: generating a three dimensional computer model which represents a cFMS kinase domain in liganded form, said kinase domain being described by the amino acid sequence of SEQ ID NO: 1 or 2 and having the structural coordinates of Table 2. Typically, such a computer model of SEQ ID NO: 1 or 2 and the structural coordinates of Table 2 is constructed utilizing a commercially available software program. Software programs for generating three-dimensional graphical representations of molecules or portions thereof from a set of structural coordinates are well known and used in the art. Suitable examples of such computer programs for viewing or otherwise manipulating protein structures include, but are not limited to, the following: Midas (University of California, San Francisco), MidasPlus (University of California, San Francisco), MOIL (Univeristy of Illinois), Yummie (Yale University), Sybyl (Tripos, Inc.), Insight/Discover (Biosym Technologies), MacroModel (Columbia University), Quanta (Molecular Simulations, Inc.), CNS (Molecular Simulations, Inc.), Cerius (Molucular Simulations, Inc.), Alchemy (Tripos, Inc.), LabVision (Tripos, Inc.), Rasmol (Glaxo Research and Development), Ribbon (University of Alabama), NAOMI (Oxford University), Explorer Eyechem (Silicon Graphics, Inc.), Univision (Cray Research), Molscript (Uppsala University), Chem-3D (Cambridge Scientific), Chain (Baylor College of Medicine), O (Uppsala University), GRASP (Columbia University), X-Plor (Molecular Simulations, Inc., Yale University), Spartan (Wavefunction, Inc.), Catalyst (Molecular Simulations, Inc.), Molcadd (Tripos, Inc.), VMD (University of Illinois/Beckman Institute), Sculpt (Interactive Simulations, Inc.), Procheck (Brookhaven National Laboratory), DGEOM (QCPE), RE_VIEW (Brunel University), Modeller (Birbeck College, University of London), Xmol (Minnesota Supercomputing Center), Protein Expert (Cambridge Scientific), HyperChem (Hypercube), MD Display (University of Washington), PKB (National Center for Biotechnology Information, NIH), ChemX (Chemical Design, Ltd.), Cameleon (Oxford Molecular, Inc.), and Iditis (Oxford Molecular, Inc.).

Once the three dimensional model of the cFMS kinase domain is established candidate inhibitor compounds may be evaluated utilizing the model and the selected software application. Initially, it is understood that the term "evaluate" includes within its scope, without limitation, de novo inhibitor molecular design, computer-aided optimization of known candidate inhibitors, as well as computer-based selection of candidate inhibitors. Various computational analysis methods are known in the art for the evaluation of potential binding interactions between a polypeptide binding pocket and a candidate inhibitor molecule. Such methods typically utilize at least one of the software packages recited above and are known in the art. Computational and other evaluation methods are described for instance in U.S. Pat. Nos. 6,251,620 and 6,356,845, such patents being incorporated herein by reference to the extent that they disclose computational and other evaluation methods for drug design, selection and/or optimization.

Examples of protein-inhibitor interactions which are screened for include potential electrostatic, hydrophobic, hydrophilic, van der Waals, and hydrogen bonding between the cFMS kinase molecule and candidate inhibitors as well as favorable candidate inhibitor conformations within the cFMS kinase binding pocket.

In one embodiment, evaluation of compounds as potential cFMS inhibitors using said model comprises identifying compounds capable of at least one of the following cFMS kinase domain/compound interactions:

(i) one or more interactions with amino acid residues of the cFMS kinase domain hinge region;

(ii) one or more interactions with amino acid residues of the cFMS kinase domain adenine pocket, (iii) one or more interactions with amino acid residues of the cFMS kinase sugar pocket and phosphate region, (iv) one or more interactions with amino acid residues of the cFMS kinase domain back pocket, and (vi) one or more interactions with amino acid residues of the cFMS kinase domain solvent interface;

preferably (i) one or more interactions with amino acid residues 663, 664, 665, 666, 667, 668, and 669;

(ii) one or more interactions with amino acid residues 588, 614, 647, and 785, (iii) one or more interactions with amino acid residues 596 and 797 and/or one or more interactions with amino acid residue residue 796, (iv) one or more interactions with amino acid residues 550, 640, 646, 769, and 776, and (v) one or more interactions with residues 668 and 672.

Further preferred embodiments of the interactions (i), (ii), (iii), (iv), and (v) are as described above.

If evaluation indicates that a compound shows promise as a candidate inhibitor the compounds are selected for further testing based on said evaluation. An inhibitor candidate is generally sought which can exist in a conformation which appears to be structurally compatible with at least a part of the cFMS kinase domain binding pocket. Such conformation will be sterically and energetically compatible with the cFMS kinase domain. Typically, the above listed non-covalent or secondary bonding interactions will be important in the interaction of the candidate inhibitor and the cFMS kinase domain. In addition, other conformational factors include the overall three dimensional structure and orientation of the candidate inhibitor within the protein structure, especially the binding pocket as well as spatial and energetic relationships of the various functional groups of the candidate inhibitor and cFMS kinase domain which have potential for interaction. The further testing done typically is to evaluate the inhibitory effect on the kinase activity of cFMS and may take the form of enzyme or cell based assays as well as other assays known in the art for measuring the inhibitory effect on the kinase activity of cFMS.

The present invention also provides a method of inhibiting cFMS in a mammal, which includes administering to said mammal a therapeutically effective amount of a compound that can form a complex with a cFMS kinase domain thereby resulting in a cfms kinase domain in liganded form. Also provided is a method of treating a disorder characterized by inappropriate cFMS activity in a mammal which includes administering to said mammal a therapeutically effective amount of a compound that can form a complex with a cFMS kinase domain thereby resulting in a cFMS kinase domain in liganded form.

Compounds useful in the treatment methods of the present invention include those having interactions (i), (ii), (iii), (iv), and (v) with the cFMS kinase domain. Such interactions are as described above.

The inappropriate cFMS activity referred to herein is any cFMS activity that deviates from the normal cFMS activity expected in a particular mammalian subject. Inappropriate cFMS activity may take the form of, for instance, an abnormal increase in activity, or an aberration in the timing and or control of cFMS activity. Such inappropriate activity may result then, for example, from overexpression or mutation of the protein kinase leading to inappropriate or uncontrolled activation. Furthermore, it is also understood that unwanted cFMS activity may reside in an abnormal source, such as a malignancy. That is, the level of cFMS activity does not have to be abnormal to be considered inappropriate, rather the activity derives from an abnormal source.

While it is possible that, for use in therapy, therapeutically effective amounts of the compounds described in the present invention, as well as salts, solvates and physiologically functional derivatives thereof, may be administered as the raw chemical, it is possible to present the active ingredient as a pharmaceutical composition. Accordingly, the invention further provides pharmaceutical compositions, which include therapeutically effective amounts of the compounds described herein and salts, solvates and physiological functional derivatives thereof, and one or more pharmaceutically acceptable carriers, diluents, or excipients. The compounds of the formula (Ia, b, c, d) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the present invention or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the present invention, depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of the present invention for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of the present invention per se. It is envisaged that similar dosages would be appropriate for treatment of the other conditions referred to above.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

Structure Determination

Initial attempts to crystallize the catalytic core of cFMS (cFMSK) were unsuccessful due to poor expression and solubility of the protein. Limited proteolysis and mass spectroscopic analysis of the entire cytoplasmic region suggested the kinase insert domain (KID) was heterogeneously phosphorylated and not well folded and that the NT region may provide stability. Two new constructs were made based on these studies with different sized deletions of the KID. Construct 1 contained residues 542-919Δ696-741, while construct 2 contains 542-919Δ682-741. Both constructs also contain a 6-histidine tag at the N-terminus for purification purposes. Constructs were expressed in baculovirus-infected insect cells and purified by standard chromatographic procedures. Crystallization screens were initially performed using non-phosphorylated protein alone or complexed with a diaminopyrimidine inhibitor. Three different crystal forms of apo cFMSK were obtained: crystal forms I and II using construct 1 and crystal form III with construct 2 (Table 1). The protein inhibitor complex, using either construct 1 or 2, yielded crystal form IV.

The structure of crystal form I was solved by molecular replacement using the structure of the of fibroblast growth factor receptor 1 (FGFR1) catalytic core (Mohammadi 1996) as a search model. The structure was refined to an R-factor of 20% at 2.7 Å resolution. 5 residues at the N-terminus, 3 residues at the C-terminus and a loop within the NT region (residues 555-563) were disordered and could not be modeled. 16 residues surrounding the kinase insert domain deletion were also disordered (residues 687-696 and 741-746). The structures of crystal forms II and IV were solved by molecular replacement using the structure determined for crystal form I. The structure in crystal form III was not fully refined due to the poor quality of the data and large number of molecules in the asymmetric unit. The overall fold in crystal forms I, II and IV was essentially identical, however significant differences in the activation loop and NT region were observed between the apo and inhibitor complex structures.

Certain embodiments of the present invention will now be illustrated by way of example only.

Materials and Methods

Construct Generation

A combination of limited proteolysis and modeling was used to define the constructs for structural studies. First, the cytoplasmic domain of cFMS was cloned from a human universal library (Clontech, Palo Alto, Calif.) by PCR. The sequence was identical to that reported in GENBANK (X03663). The coding region corresponding to residues 538-972 was fused to a 6×His tag (MKKGHHHHHHG) and subcloned into a pFASTBAC1 (Gibco BRL) expression vector by PCR (construct 1). The N-terminal primer included an EcoRI restriction. The C-terminal primer included a stop codon and a SphI restriction site. The cfms construct was transfected into *Spodoptera frugiperda* (sf-9) cells, single plaques were isolated, and high titer stocks were generated. Construct A was expressed and purified, as described below for the final truncated constructs.

Limited proteolysis was performed on construct A to define a smaller, stable catalytic domain (see below for more details). Proteolysis suggested that both the N- and C-terminus could be truncated and that the kinase insert domain was not well ordered. Therefore, a second construct (construct B) was generated corresponding to residues 542-919 fused to a 6× his tag (MKKGHHHHHHG). The protein was expressed and purified as described below for the final constructs.

Construct B did not yield suitable crystals. Peptide mapping of a tryptic digest of construct 2, by mass spectrometry, indicated that 3 serines were heterogeneously phosphorylated (688, 713 and 733). A third construct (construct C) was generated in which the serines at position 688, 713 and 733 were mutated to alanine, using the following 3 primers—5'ggac-ccagcctggcccccggccaggac 3', 5' gtccgcagggacgctggcttctc-cagc 3', 5'gtctccacttctgcaaatgactccttc 3'. This construct also did not yield suitable crystals.

Two final constructs, 1 and 2, were generated with the same his tag and N and C termini as construct B and C but with different length deletions of the kinase insert domain. Deletions were designed by modeling the kinase domain of cfms using the Tie2, FGFR1, IRK and VEGFR2 crystal structures. Residues 696-741 and 682-741 were deleted in constructs 1 and 2 respectively. The proteins were expressed, purified and crystallized as described below.

Limited Proteolysis

Purified construct A was digested with a panel of 8 proteases in a 96 well plate. 5 ug of cFMS (5 uL at 1 mg/mL) was added to 5 uL of 10 mg/mL protease in 20 uL of reaction buffer (50 mM Tris-HCl, pH 8.0, 100 mM NaCl). Reactions were stopped at 0.75, 2, and 18 hours with 10 uL of 4×SDS-PAGE sample buffer. All digests were analyzed by SDS-PAGE (NuPAGE Novex 10% Bis-Tris gel, MES running buffer). Bands of interest were electroblotted on PVDF membrane and subjected to Edman sequencing.

| Proteases used | Source (Boehringer Mannheim unless otherwise noted) |
| --- | --- |
| 1.) Trypsin | catalogue # 1418475 |
| 2.) Chymotrypsin | catalogue # 1418467 |
| 3.) Lys C | catalogue # 1047825 |
| 4.) Glu C | catalogue # 1047817 |
| 5.) Asp N | catalogue # 1054589 |
| 6.) Arg C | catalogue # 1370529 |
| 7.) Thermolysin | catalogue # 161586 |
| 8.) Subtilisin | catalogue # 572908 (Calbiochem) |

Protein Fermentation/Purification

Four constructs were generated for structural studies. The fermentation and purification was similar for all constructs.

Fermentation: Large-scale (2L) virus preparations for fermentation were made by infecting Sf-9 cells growing in Grace's Supplemented medium (GIBCO/Life Technologies)+0.1% capluronic® F-68 (GIBCO/Life Technologies)+ 10% FBS (HyClone Laboratories) at a multiplicity of infection (MOI) of 0.1 in 6L shake flasks at 27.5° C. and 120 RPM. Viral supernatants were harvested at 72 hours post-infection via centrifugation at 2500 RPM for 20 minutes. Viral titers were determined via ELISA. A 36 L stirred bioreactor (University Research Glassware) was outfitted with external overhead stirrer & water bath and internal dip tubes, heat-transfer coil, paddle-style impeller and $dO_2$ probe. The bioreactor was inoculated with *Trichoplusia ni(T. ni)* cells [kindly obtained from JRH BioSciences (Woodland, Calif.)] at ~$0.5 \times 10^6$/mL. The culture was grown in Ex-Cell™ 405 insect cell medium (JRH BioSciences)+50 µg/mL gentamicin (GIBCO/Life Technologies). The temperature was maintained at 27.5° C. using an external water bath, an internal temperature probe and heat-transfer coil. Agitation was maintained at 30 RPM using an external overhead drive and an internal paddle-type impeller. Dissolved oxygen was maintained at 50% via sparging under the control of an internal $dO_2$ probe. Cells were allowed to double overnight at the above parameters, and the culture was then infected at a density of ~$1 \times 10^6$/mL at MOI=1. The culture was monitored daily for pH, glucose, lactate and glutamine levels as well as cell count and viability via trypan blue exclusion. Infection was allowed to proceed at the above parameters, and cells were harvested at 48 hours post-infection using a Centritech® 100 continuous flow centrifuge (DuPont). Concentrated cells were subsequently centrifuged at 2000 RPM for 20 minutes and washed with protease inhibitor buffer [1× Dulbecco's PBS (GIBCO/Life Technologies), 1 mM EDTA (Sigma), 1 mM p-aminobenzamidine (Sigma), 1 µg/mL aprotinin (Boehringer Mannheim), 1 µg/mL leupeptin (Boehringer Mannheim)]. Cells were centrifuged again at 2000 RPM for 20 minutes. The supernatant was decanted, and the cells were flash frozen in a dry ice/ethanol bath and stored at −80° C. until further purification.

Purification: All operations were carried out at 4° C. 12 L of *T. ni* cells (220 g of wet cell pellet stored −80° C.) was thawed in 1500 mL of lysis buffer. The cells were suspended using a polytron homogenizer twice for 60 seconds each time. The homogenate was centrifuged for 40 minutes at 30,000×g (14,000 rpm) in a Sorvall SLA 1500 rotor. The pelleted material was discarded, and the supernatant was filtered through a 1.2 micron cartridge filter. The lysate was directly loaded onto the first column.

1st Column Step: A 2.6 cm diameter column was packed with a Amersham Pharmacia Ni-Chelating Sepharose FF resin to a 65 mL bed volume. The Chelating Sepharose resin was coupled at a 30 µmol Ni/mL gel (complete Ni/gel saturation). A BioPilot instrument (Amersham Pharmacia) was used as the liquid chromotography operating system and was run at a 20 mL/minute flow rate. Before sample loading, the column was equilibrated with 5 column volumes (CV's) of Ni-Chelating buffer A. After sample loading, the column was washed for 5 CV's with Ni-Chelating buffer A. A non-linear gradient was applied to the column with a 5 CV step, 13% Ni-Chelating buffer B wash step, followed by a 5 CV gradient to 100% Ni-Chelating buffer B. 25 mL fractions were collected. The fractions containing cFMS protein (major absorbance peak after the 13% Ni-Chelating buffer B wash step) were pooled together (200 mL) and EDTA and DTT were added to a final concentration of 1 mM. The pool was diluted to a final volume of 800 mL using Ni-pool dilution buffer. The 800 mL pool was loaded directly onto the next column.

2nd Column Step: A 2.6 cm diameter column was packed with a Poros HS (Perceptive) cation exchange resin to a 40 mL bed volume. A BioPilot instrument was used as the LC operating system and was run at a 25 mL/minute flow rate. After loading the 800 mL Ni-Chelating pool, the column was washed with cation buffer A for 5 CV. The column was step eluted with a series of increasing 100 mM NaCl steps. A single fraction was collected during the 300 mM NaCl step. The 300 mM NaCl cation eluate was concentrated using a 10,000 KDa molecular weight cut off (MWCO) membrane to a final volume of 12 mL. The concentrated retentate was directly loaded onto the next column.

3rd Column Step: Size exclusion chromatography. The retentate was loaded onto a pre-packed S-75 Superdex size exclusion column (Amersham Pharmacia XK 2.6 column, 320 mL CV). The operating system was a FPLC (Amersham Pharmacia) instrument that was run at a 3 mL/minute flow rate. 4 mL fractions were collected. The fractions from the top 75-80% of the major peak eluting from the column were combined into a single pool. The pool was concentrated using a 10K MWCO membrane to a final volume of 9 mL.

Buffers:
1. Ni-Chelating buffer A: 25 mM HEPES (pH 7), 200 mM NaCl, 40 mM imidazole.
2. Ni-Chelating buffer B: 25 mM HEPES (pH 7), 200 mM NaCl, 400 mM imidazole.
3. Ni-pool dilution buffer: 20 mM HEPES (pH 7), 1 mM DTT, 1 mM EDTA, 5% (v/v) glycerol.
4. Cation buffer A: 25 mM HEPES (pH 7), 1 mM DTT.
5. Cation buffer B: 25 mM HEPES (pH 7), 1 mM DTT, 1000 mM NaCl.
6. SEC buffer: 20 mM HEPES (pH 7), 100 mM NaCl, 5 mM DTT.

Protein Digestion for Mass Spectrometry

Trypsin digestions of 200-1000 picomoles of cFMS were carried out in 50 mM Tris pH 8.5, 1 mM $CaCl_2$, and 10% acetonitrile. In some instances, cFMS was reduced and alkylated with DTT and 4-vinylpyridine prior to digestion. Digestion proceeded at 37° C. for 12-18 hours.

Mass Spectrometry: LCMS

Mass measurements of intact protein were determined using liquid chromatography mass spectrometry (LCMS). Protein samples were initially desalted on a Poros R2/H column (Perceptive Biosystems; Framingham, Mass.). Effluent from the desalting column was directed to a SCIEX API III mass spectrometer (PE Sciex, Concord, ON, Canada), and spectra were acquired in positive ion mode with electrospray ionization. Intact protein mass values were obtained from the reconstructed mass spectra that were generated from the processed data. Assignment of phosphorylation states were made by identifying masses that were multiples of 80 Da higher than the expected mass of cFMS.

Mass Spectrometry: nanoES MS

Nanoelectrospray ionization (nanoES) MS on a Q-TOF instrument from Micromass (UK) was used to map phosphorylation sites after trypsin digestion. Sample was introduced to the MS with either static nanoES using a pulled capillary tip (Mann) or capillary LCMS/MS. The LC system was from LC Packings and consisted of the Famos autosampler and the Ultimate solvent delivery pump. Separation was carried out on a 75 µm I.D. C.18 PepMap column (LC Packings). The Q-TOF is capable of data dependent ion selection for collision induced fragmentation.

Two sample preparation approaches were used to map the phosphorylation sites. In the first approach, phosphorylated peptides were isolated from non-phosphorylated peptides using Ga(III) immobilized metal affinity chromatography (IMAC). Briefly, an aliquot of the trypsin digest was acidified and loaded onto an IMAC microcolumn charged with Ga(III). The column was then washed with 0.1% acetic acid/30% acetonitrile to remove non-phosphorylated peptides. Retained peptides were then eluted with 0.2 M sodium phosphate, pH 8.2 and directly applied to a microcolumn packed with Poros R2/H reverse phase media. Bound peptides were washed with 0.1% formic acid and then eluted directly into a nanoelectrospray capillary tip. Static nanoESI was used to acquire MS and MS/MS spectra of the purified peptides. Phosphorylated residues were identified from MS/MS data.

In the second approach, the cFMS trypsin digest was analyzed by capillary LCMS/MS with data dependant scanning. This data file was then used to conduct a Mascot protein database search that compared uninterpreted MS/MS data to theoretical MS/MS spectra of user specified proteolytic peptides. The spectra were interpreted manually to confirm the assignment.

Preparation of Inhibitor Candidate Compounds

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| µL (microliters); | psi (pounds per square inch); |
| M (molar); | mM (millimolar); |
| mol (moles); | mmol (millimoles); |

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

HPLC were recorded on a Gilson HPLC or Shimazu HPLC system by the following conditions. Column: 50×4.6 mm (id) stainless steel packed with 5 µm Phenomenex Luna C-18; Flow rate: 2.0 mL/min; Mobile phase: A phase=50 mM ammonium acetate (pH 7.4), B phase=acetonitrile, 0-0.5 min (A: 100%, B: 0%), 0.5-3.0 min (A:100-0%, B:0-100%), 3.0-3.5 min (A: 0%, B: 100%), 3.5-3.7 min (A: 0-100%, B: 100-0%), 3.7-4.5 min (A: 100%, B: 0%); Detection:UV 254 nm; Injection volume: 3 µL.

Low-resolution mass spectra (MS) were recorded on a JOEL JMS-AX505HA, JOEL SX-102, or a SCIEX-APIiii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).
Compounds of Formula I can be prepared according to the synthetic sequences illustrated in Schemes 1-4 and further detailed in the Examples section following.
Scheme 1
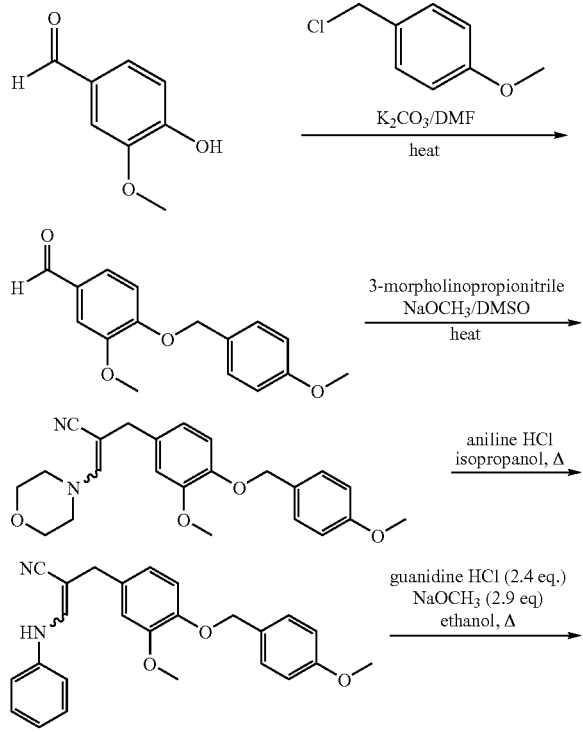
Scheme 2
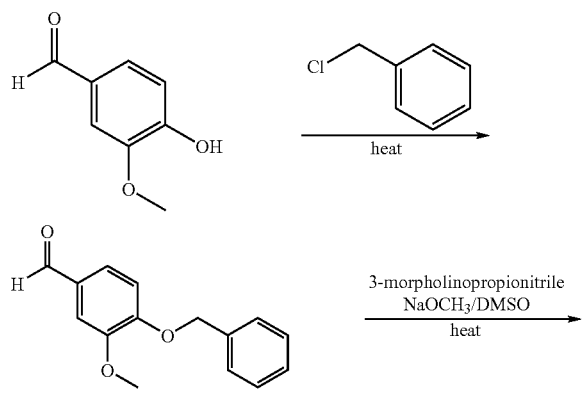
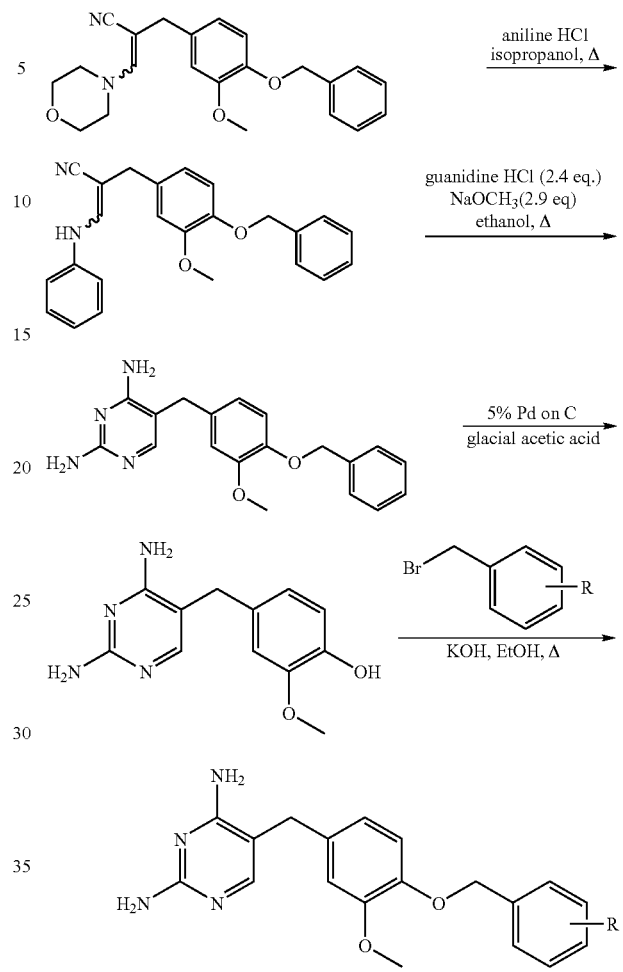
Scheme 3
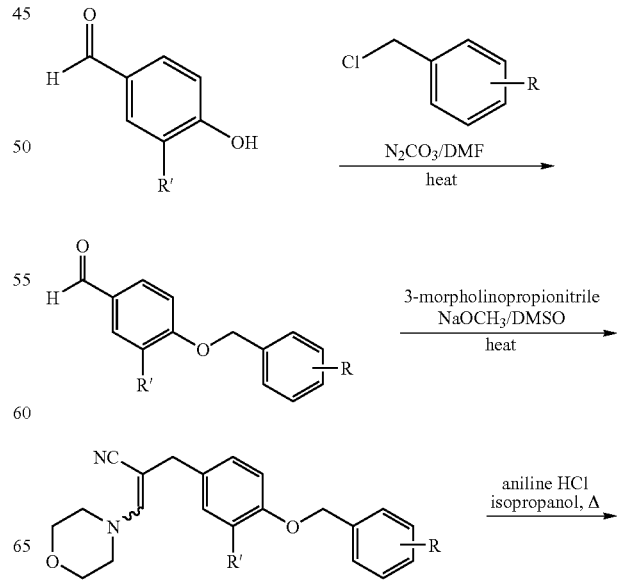

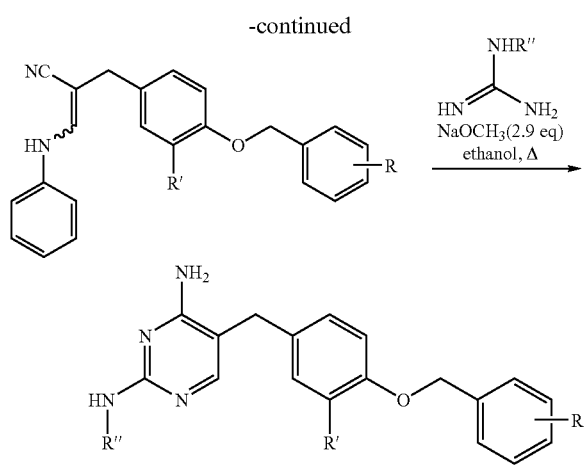

Scheme 4

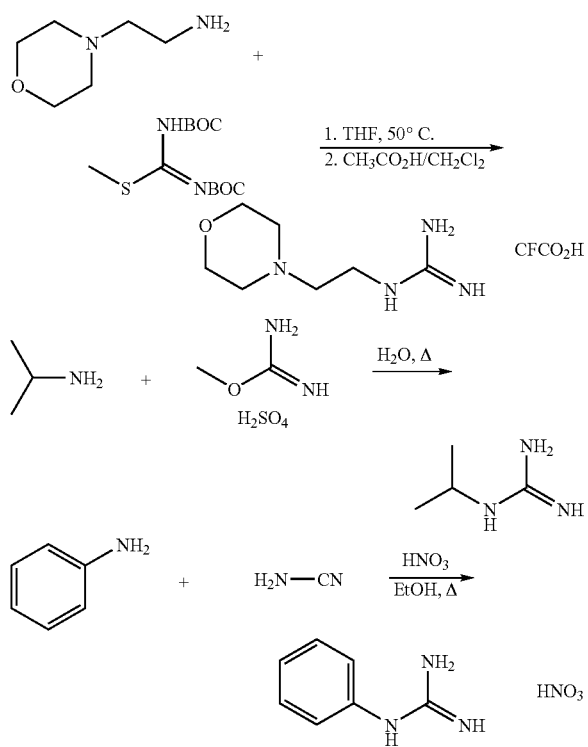

Intermediate Example 1

3-anilino-2-{3-methoxy-4-[(4-methoxybenzyl)oxy]benzyl}prop-2-enenitrile

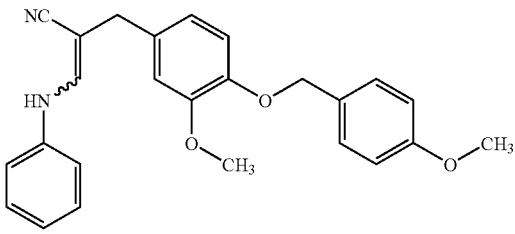

To a homogeneous solution of 2-{3-methoxy-4-[(4-methoxybenzyl)oxy]benzyl}-3-morpholin-4-ylprop-2-enenitrile (14.5 g, 36.7 mmol) in isopropanol (050 mL) was added aniline hydrochloride (4.9 g, 37.5 mmol), and the mixture was stirred at reflux for 20 minutes, combined with 20 mL of water and cooled in an ice bath for 30 minutes. The resulting precipitate was filtered off, washed with water and air dried to give 13.7 g of crude product. This material was recrystalized from methanol/ethanol to afford pure product as a crystalline tan solid (10.5 g, 26.2 mmol). $^1$H NMR (300 MHz, $d_6$-DMSO): δ 9.03 (d, J=12.8 Hz, 1H), 7.59 (d, J=12.8 Hz, 1H), 7.30 (d, J=8.6 Hz, 2H), 7.20 (d, J=7.4 Hz, 2H), 7.16 (m,2H), 6.93 (d, J=8.2 Hz, 1H), 6.88 (d, J=8.4 Hz, 1H), 6.86 (m, 1H), 6.83 (s, 1H), 4.90 (s, 2H), 3.69 (s, 3H), 3.68 (s, 3H), 3.50 (s, 2H), 3.28 (s, 2H). MS (ES-, m/z)=399 (M−H).

Intermediate Example 2

2-{3-methoxy-4-[(4-methoxybenzyl)oxy]benzyl}-3-morpholin-4-ylprop-2-enenitrile

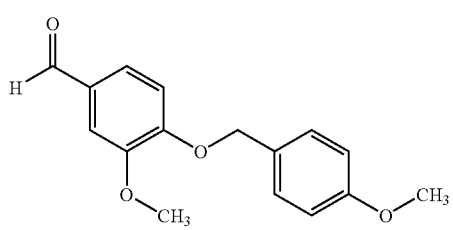

3-Methoxy-4-[(4-methoxybenzyl)oxy]benzaldehyde (20.0 g, 73.4 mmol) and 3-morpholinopropronitrile (Lancaster, 11.0 g, 77.1 mmol) were stirred in DMSO (15 mL) at 65 C until the mixture was homogeneous. The solution was cooled to 40 C and sodium methoxide (0.79 g, 14.7 mmol) was added. The mixture was stirred at 75 C for 15 minutes, then cooled to room temperature and diluted with dichloromethane (150 mL) and water (200 mL). 1N HCl (25 mL) was added and the two layers were seperated. The organics were combined and dried (magnesium sulfate), filtered and concentrated to a red oil (29.5 g, 73 mmol) that was used directly in the synthesis of 3-anilino-2-{3-methoxy-4-[(4-methoxybenzyl)oxy]benzyl}prop-2-enenitrile. $^1$H NMR (300 MHz, $d_6$-DMSO): δ 7.38 (d, 2H), 7.03-6.95 (m,3H), 6.84 (t, J=13.5 Hz, 2H), 6.73 (d, J=8.2 Hz, 1H), 4.98 (s, 3H), 3.78 (s, 3H), 3.76 (s, 3H), 3.66-3.60 (m, 2H), 3.55-3.50 (m, 3H), 3.46-3.43 (m, 2H), 3.36 (s, 1H), 3.33-3.29 (m, 2H). MS (ES+, m/z)=395 (M+H).

Intermediate Example 3

3-Methoxy-4-[(4-methoxybenzyl)oxy]benzaldehyde

A mixture of 4-hydroxy-3-methoxybenzaldehyde (22.6 g, 149 mmol), 4-methoxybenzyl chloride (23.3 g, 149 mmol) and potassium carbonate (30.8 g, 223 mmol) was stirred in N,N-dimethylformamide (DMF) (150 mL) at 90 C for 2 hours. The solution was filtered hot, and cooled to room temperature. The filtrate was concentrated and dissolved ethyl acetate (300 mL) and extracted with aqueous sodium bicarbonate and water. The organics were dried with magnesium sulfate, filtered and concentrated. The crude product was recrystalized with ethyl acetate and hexanes to give product as an off-white solid (34.2 g, 126 mmol). $^1$H NMR (300 MHz, d$_6$-DMSO): δ 9.86 (s, 1H), 7.58 (d, J=8.2 Hz, 1H), 7.44-7.40 (m, 3H), 7.30 (d, J=8.4 Hz, 1H), 6.98 (d, J=8.7 Hz, 2H), 5.15 (s, 2H), 3.84 (s, 3H), 3.78 (s, 3H). MS (ES+, m/z)=273 (M+H).

Intermediate Example 4

N-Phenyl-guanidine nitrate

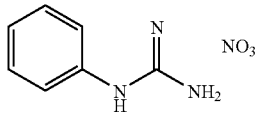

To a solution of aniline (1.28 ml, 14 mmol) in ethanol (14 ml) was added cyanamide (1.25 ml, 16.1 mmol) and nitric acid (1 ml, 14 mmol), and the reaction was heated to reflux. After 16 hours, the reaction was cooled to room temperature and poured into diethyl ether. The resulting precipitate was filtered and dried to afford the title compound as a gray solid (2.50 g, 13 mmol, 90%). NMR (300 MHz, CD$_3$OD): δ 7.47 (m, 2H), 7.36 (m, 1H), 7.30 (m, 2H).

Example 1

5-{3-methoxy-4-[(4-methoxybenzyl)oxy]benzyl}pyrimidine-2,4-diamine

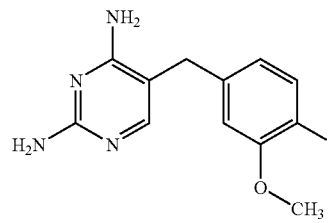

A suspension of 3-anilino-2-{3-methoxy-4-[(4-methoxy-benzyl) oxy]benzyl}prop-2-enenitrile (300 mg, 0.75 mmol) and guanidine hydrochloride (108 mg, 1.13 mmol) in ethanol (5 mL) was stirred at room temperature while sodium methoxide was added. The mixture was stirred at reflux overnight. The solution was cooled 5 C and 2N sodium hydroxide (2 mL) was added. After 15 minutes, a white precipitate was filtered off and washed with water then hexane to give product as a white solid (199 mg, 0.54 mmol). $^1$H NMR (300 MHz, d$_6$-DMSO): δ 7.45 (s, 1H), 7.32 (d, J=8.6 Hz, 2H), 6.93-6.85 (m, 4H), 6.66 (dd, J=8.3 and 1.5 Hz, 1H), 6.02 (s, 2H), 5.65 (s, 2H), 4.91 (s, 2H), 3.73 (s, 3H), 3.70 (s, 3H), 3.50 (s, 2H). MS (ES+, m/z)=367 (M+H).

Example 2

5-[3-Methoxy-4-(4-methoxy-benzyloxy)-benzyl]-N$^2$-phenyl-pyrimidine-2,4-diamine

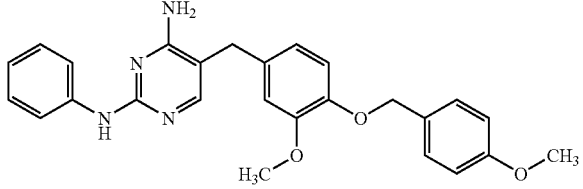

To a solution of 2,3-anilino-2-{3-methoxy-4-[(4-methoxy-benzyl)oxy]benzyl}prop-2-enenitrile (400 mg, 1.0 mmol) and N-phenyl-guanidine nitrate (495 mg, 2.5 mmol) was added a solution of potassium tert-butoxide (1M, 7.5 mmol), and the reaction was heated at 80 C. After 72 hours, the reaction was cooled to room temperature and concentrated. The residue was dissolved in 10% MeOH/CH$_2$Cl$_2$ and passed through a plug of silica gel. The filtrate was concentrated and purified by column chromatography (50% EtOAc/Hexanes) to give the title compound as a yellow foam (172 mg, 0.39 mmol, 39%). $^1$H NMR (300 MHz, d$_6$-DMSO): δ 8.86 (s, 1H), 7.75 (d, J=8.1 Hz, 2H), 7.65 (s, 1H), 7.34 (d, J=8.7 Hz, 3H), 7.19 (t, J=7.8 Hz, 2H), 6.92 (d, J=8.4 Hz, 4H), 6.83 (m, 1H), 6.71 (dd, J=8.1 and 1.8 Hz, 1H), 6.47 (br s, 2H), 4.93 (s, 2H), 3.74 (s, 3H), 3.72 (s, 3H), 3.60 (s, 2H). MS (ES+, m/z)=468 (M+H).

The following compounds of Examples 3-30 of Formula I' were prepared according to the procedure of Schemes 1 and 2 and Example 1 and were characterized as being the indicated compound.

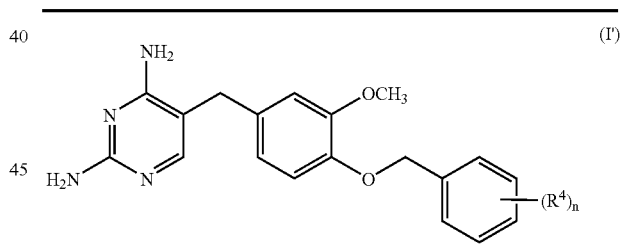

(I')

| Example | N | R$^4$ | Location* |
|---|---|---|---|
| 3 | 1 | —Cl | Para |
| 4 | 1 | —F | Para |
| 5 | 1 | —OCH3 | Para |
| 6 | 1 | —CF3 | Para |
| 7 | 1 | —Br | Para |
| 8 | 1 | —CH3 | Meta |
| 9 | 1 | —OCH3 | Meta |
| 10 | 1 | —Cl | Meta |
| 11 | 1 | —CF3 | Meta |
| 12 | 1 | —Br | Meta |
| 13 | 2 | —Cl, —Cl | Meta, Para |
| 14 | 1 | —OCF3 | Para |
| 15 | 1 | —C(CH3)3 | Para |
| 16 | 1 | —CH2CH3 | Para |
| 17 | 1 | —CH(CH3)2 | Para |
| 18 | 1 | —CH═CH2 | Para |
| 19 | 2 | —Cl, —CH3 | Meta, Para |
| 20 | 2 | —Br, —Br | Meta, Meta |
| 21 | 2 | —CH3, —CH3 | Meta, Para |
| 22 | 2 | —F, —CH3 | Meta, Para |

-continued

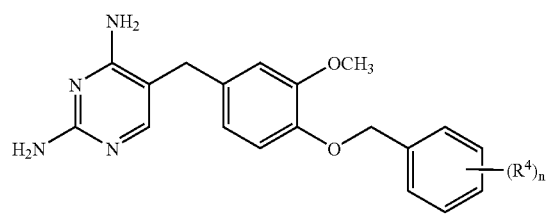
(I')

| Example | N | R⁴ | Location* |
|---|---|---|---|
| 23 | 2 | —CH3, —F | Meta, Para |
| 24 | 2 | —CF3, —Cl | Meta, Para |
| 25 | 2 | —Cl, —OCF3 | Meta, Para |
| 26 | 1 |  (CN, ortho) | Para |
| 27 | 2 | —Cl, —Cl | Ortho, Para |
| 28 | 1 | —I | Para |
| 29 | 1 | —SCH3 | Para |
| 30 | 2 | 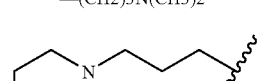 | Fused to Phenyl |

*Location is in reference to the attachment to the CH2 group of the benzyloxy moiety.

The following compounds of Examples 31-56 of Formula I" were prepared according to the procedure of Schemes 1-4 and Examples 1 and 2 and were characterized as being the indicated compound.

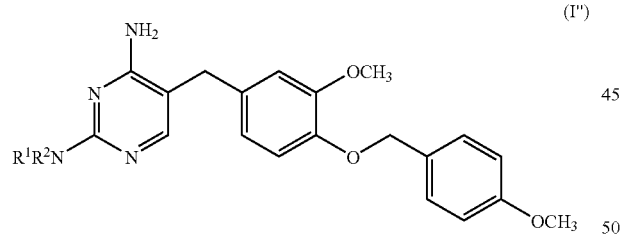
(I")

| Example | R¹ | R² |
|---|---|---|
| 31 | —H |  (cyclopropyl) |
| 32 | —H | —(CH2)3N(CH3)2 |
| 33 | —H | 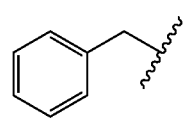 |
| 34 | —H | —CH3 |
| 35 | —H | —CH2CH3 |
| 36 | —CH3 | —CH3 |

-continued

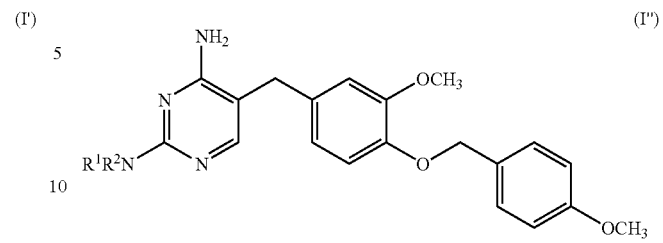
(I")

| Example | R¹ | R² |
|---|---|---|
| 37 | —H | 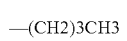 (benzyl) |
| 38 | —H | —(CH2)3CH3 |
| 39 | —H | 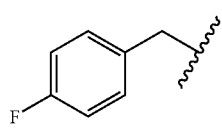 |
| 40 | —H | 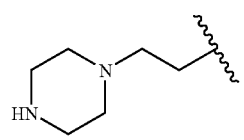 |
| 41 | —H | 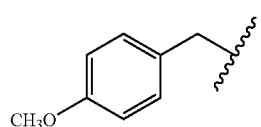 |
| 42 | —H | 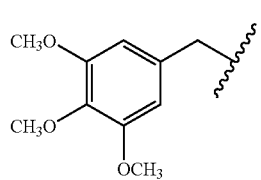 |
| 43 | —H | 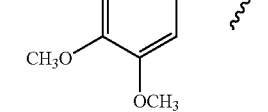 |
| 44 | —H | 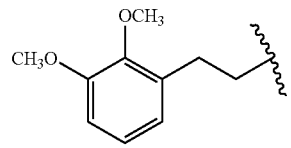 |
| 45 | —H | 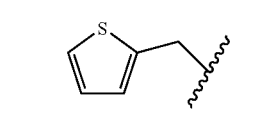 |
| 46 | —H | 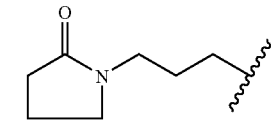 |

(I'')

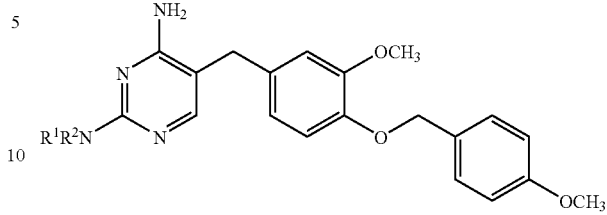

| Example | R¹ | R² |
|---|---|---|
| 47 | —H | 3-cyanophenyl |
| 48 | —H | 3,5-dimethoxyphenyl |
| 49 | —H | 4-(2-hydroxyethyl)phenyl |
| 50 | —H | 3-benzylpyrrolidin-2-yl |
| 51 | —H | benzo[1,3]dioxol-5-yl |
| 52 | —H | 4-methoxyphenyl |
| 53 | —H | 4-morpholinophenyl |
| 54 | —H | 3,4-dimethoxyphenyl |
| 55 | —H | 2-phenylethyl |
| 56 | —H | —CH(CH3)2 |

The following compounds of Examples 57-75 of Formula I''' were prepared according to the procedure of Schemes 1-4 and Examples 1 and 2 and were characterized as being the indicated compound.

(I''')

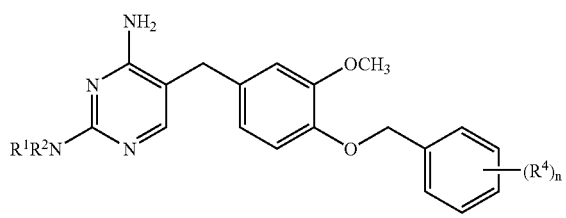

| Example | R¹ | R² | R⁴ | n and Location* |
|---|---|---|---|---|
| 57 | —H | 4-(2-oxopyrrolidin-1-yl)butyl | —CF3 | 1: Para |

-continued

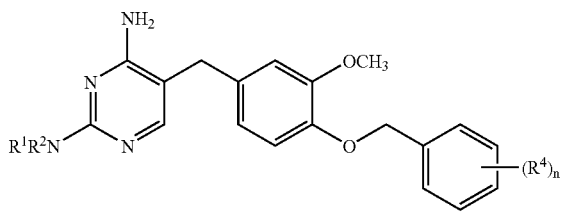

(I''')

| Example | R¹ | R² | R⁴ | n and Location* |
|---|---|---|---|---|
| 58 | —H | cyclopropylmethyl | —CF3 | 1: Para |
| 59 | —H | morpholinopropyl | —CF3 | 1: Para |
| 60 | —H | morpholinopropyl | —C(CH3)3 | 1: Para |
| 61 | —H | morpholinopropyl | —OCF3; —Cl | 2: Para, Meta |
| 62 | —H | cyclopropylmethyl | —C(CH3)3 | 1: Para |
| 63 | —H | cyclopropylmethyl | —Cl, —OCF3 | 2: Meta, Para |
| 64 | —H | (2-oxopyrrolidin-1-yl)propyl | —C(CH3)3 | 1: Para |
| 65 | —H | (2-oxopyrrolidin-1-yl)propyl | —Cl, —OCF3 | 2: Meta, Para |
| 66 | —H | 2-(4-hydroxyethyl)phenyl | —CF3 | Para |
| 67 | —H | 2-(4-hydroxyethyl)phenyl | —C(CH3)3 | Para |

-continued

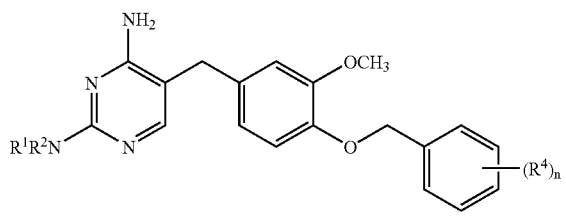

(I''')

| Example | R¹ | R² | R⁴ | n and Location* |
|---------|----|----|----|------------------|
| 68 | —H | HO-CH₂CH₂-(4-phenyl)- | —Cl, —OCF3 | 2: Meta, Para |
| 69 | —H | morpholino-propyl- | —Br | 1: Para |
| 70 | —H | cyclopropylmethyl- | —Br | 1: Para |
| 71 | —H | 2-oxopyrrolidin-1-yl-propyl- | —Br | 1: Para |
| 72 | —H | 2-oxopyrrolidin-1-yl-propyl- | | Fused to Phenyl |
| 73 | —H | 2-oxopyrrolidin-1-yl-propyl- | —CH(CH3)2 | 1: Para |
| 74 | —H | 3,4-dimethoxyphenyl-ethyl- | —Br | 1: Para |
| 75 | —H | 3,4-dimethoxyphenyl-ethyl- | | Fused to Pheyl |

*Location is in reference to the attachment to the CH2 group of the benzyloxy moiety.

The following compounds of Examples 76-77 of Formula I'''' were prepared according to the procedure of Schemes 1-4 and Examples 1-2 and were characterized as being the indicated compound.

(I'''')

[Structure: pyrimidine with NH2 and H2N groups, connected via CH2 to a benzene ring bearing substituent R, linked through O-CH2 to a para-methoxyphenyl group]

| Example | R |
|---------|------|
| 76 | —H |
| 77 | —OCH3 | cFMS Assay: Filter Binding Substrate Phosphorylation Assay

The candidate inhibitor compounds of the present invention were tested for cFMS protein tyrosine kinase inhibitory activity in substrate phosphorylation assays. This assay examines the ability of small molecule organic compounds to inhibit the tyrosine phosphorylation of a peptide substrate.

The substrate phosphorylation assays use the cFMS intracellular domain, expressed in SF-9 insect cells as an aminoterminal GST tagged fusion protein. DNA encoding this recombinant protein was subcloned into the pAcGHLT-A baculovirus vector (Life Technologies, Gibco BRL). The sequence used was derived from GenBank entry X03663. The encoded sequence of the catalytic domain included amino acids 547-980.

The method measures the ability of the isolated enzyme to catalyse the transfer of the g-phosphate from ATP onto tyrosine residues in a biotinylated synthetic peptide (biotin-Ahx-EEEEYFELVAKKK-amide). Substrate phosphorylation was detected by the following procedure:

cFMS kinase was "pre-activated" for 2 hours at room temperature in the presence of 100 uM ATP and 10 mM MgCl2. (It was experimentally determined that under these conditions the rate of catalysis is increased). The enzyme was subsequently diluted and incubated for 30 minutes, at room temperature, in an assay volume of 45 ul containing 10 mM MgCl$_2$, 15 uM ATP, 5 mM DTT, 50 mM NaCl, 20 uM peptide, 0.5 mCi [g-$^{33}$P] ATP/well, 50 mM MOPS, pH 7.5 and 1 ul of test compound in 100% DMSO. The reaction was stopped by the addition of an equal volume of 0.5% phosphoric acid (stop solution). 80 ul of sample was transferred to a phosphocellulose (MAPH) 96-well filter plate (Millipore Corp., Bedford, Mass.) previously pre-wet with 100 ul of stop solution. The plate was washed three times, dried and 40 ul of Optiphase SuperMix scintillation liquid (Wallac Corp., Turku, Finland) was added. The plate was sealed and counted in a Packard Topcount Microplate Scintillation Counter (Packard Instrument Co., Meriden, Conn.).

The data for dose responses were plotted as % Control calculated with the data reduction formula $100*(U1-C2)/(C_1-C_2)$ versus concentration of compound and fitted to the curve described by:

$$y=((V_{max}*x)/(K+x))$$

where $V_{max}$ is the upper asymptote and K is the IC$_{50}$.

The compounds of Examples 1-77 of Formula (I) showed inhibitory activity towards cFMS with a PIC50 of greater than 6.5.

Crystallization and Data Collection

Crystals were obtained with both construct 1 and 2 by the hanging drop vapor diffusion method. Construct 1 yielded crystal form I and II while construct 2 gave crystal forms III. Crystal form IV was obtained with both construct 1 and 2 in the presence of a diaminopyrimidine inhibitor. In all cases, protein (6 mg/ml in 20 mM HEPES pH 7.5, 300 mM NaCl, 5 mM DTT) was mixed with an equal volume of reservoir and incubated at 4° C. The reservoir solutions for the 4 crystal forms were:

Crystal form I: 50-100 mM MES pH 6.5, 50-230 mM (NH$_4$)$_2$SO$_4$, 8-17% PEG 5K MME.
Crystal form II: 100-200 mM Mg$_2$SO$_4$, 18-24% PEG 3350
Crystal form III: 25% PEG 3350, 0.2 M (NH$_4$)$_2$SO$_4$
Crystal form IV: 50-100 mM MES pH 6.5, 50-230 mM (NH$_4$)$_2$SO$_4$, 8-17% PEG 5K MME Prior to data collection, glycerol and PEG 400 were added to a final concentration of 25% and 5%, respectively, and the crystals were flash frozen in liquid N$_2$. Data for all 4 crystal forms were collected at beamline 17-ID on a MAR-CCD detector in the facilities of the Industrial Macromolecular Crystallography Association Collaborative Access Team (IMCA-CAT) at the Advanced Photon Source, Argonne National Laboratory. These facilities are supported by the companies of the Industrial Macromolecular Crystallography Association through a contract with Illinois Institute of Technology (IIT), executed through the IIT's Center for Synchrotron Radiation Research and Instrumentation. The data were processed using HKL2000.

Structure Determination and Refinement

The structure of crystal form I was solved first and subsequently used to solve the other three crystal forms. The structure was solved by molecular replacement using CNS and FGFR1 as a search model (molecule 1 of PDB entry 1FGK). The search model contained FGFR1 residues 464-485, 491-500, 506-578, 592-647 and 651-761. Residues not conserved between FGFR1 and cFMS were truncated to alanine in the model. The correct solution was the top peak in both the rotation and translation functions. Rigid body refinement gave a R-factor of 49%. Multiple rounds of model building and refinement were carried out with QUANTA and CNS. The overall structure was confirmed by a composite omit map calculated with CNS. Analysis of the structure with PROCHECK indicated that all main chain torsions fall within the allowed regions of the Ramachandran plot.

The results are depicted in Tables 1 and 2.

(1) Amino acid sequence: construct 1

(SEQ ID NO: 1)
MKKGHHHHHHGQKPKYQVRWKIIESYEGNSYTFIDPTQLPYNEKWEFPRNNLQFGKTLG

AGAFGKVVEATAFGLGKEDAVLKVAVKMLKSTAHADEKEALMSELKIMSHLGQHENIVN

LLGACTHGGPVLVITEYCCYGDLLNFLRRKAEAMLGPSLAPGQDPEGLDKEDGRPLELR

-continued

DLLHFSSQVAQGMAFLASKNCIHRDVAARNVLLTNGHVAKIGDFGLARDIMNDSNYIVK

GNARLPVKWMAPESIFDCVYTVQSDVWSYGILLWEIFSLGLNPYPGILVNSKFYKLVKD

GYQMAQPAFAPKNIYSIMQACWALEPTHRPTFQQICSFLQEQAQEDRR (2) Amino acid sequence: construct 2
(SEQ ID NO: 2)
MKKGHHHHHHGQKPKYQVRWKIIESYEGNSYTFIDPTQLPYNEKWEFPRNNLQFGKTLG

AGAFGKVVEATAFGLGKEDAVLKVAVKMLKSTAHADEKEALMSELKIMSHLGQHENIVN

LLGACTHGGPVLVLTEYCCYGDLLNFLRRKAEALDKEDGRPLELRDLLHFSSQVAQGMA

FLASKNCIHRDVAARNVLLTNGHVAKIGDFGLARDIMNDSNYIVKGNARLPVKWMAPES

IFDCVYTVQSDVWSYGILLWEIFSLGLNPYPGILVNSKFYKLVKDGYQMAQPAFAPKNI

YSIMQACWALEPTHRPTFQQICSFLQEQAQEDRR

DNA sequence Construct 1 (residues 542-919Δ696-741)
(SEQ ID NO: 3)
```
   1 ATGAAAAAAG GTCATCATCA TCATCATCAT GGTCAGAAGC CCAAGTACCA
  51 GGTCCGCTGG AAGATCATCG AGAGCTATGA GGGCAACAGT TATACTTTCA
 101 TCGACCCCAC GCAGCTGCCT TACAACGAGA AGTGGGAGTT CCCCCGGAAC
 151 AACCTGCAGT TTGGTAAGAC CCTCGGAGCT GGAGCCTTTG GAAGGTGGT
 201 GGAGGCCACG GCCTTTGGTC TGGGCAAGGA GGATGCTGTC CTGAAGGTGG
 251 CTGTGAAGAT GCTGAAGTCC ACGGCCCATG CTGATGAGAA GGAGGCCCTC
 301 ATGTCCGAGC TGAAGATCAT GAGCCACCTG GCCAGCACG AGAACATCGT
 351 CAACCTTCTG GGAGCCTGTA CCCATGGAGG CCCTGTACTG GTCATCACGG
 401 AGTACTGTTG CTATGGCGAC CTGCTCAACT TTCTGCGAAG GAAGGCTGAG
 451 GCCATGCTGG GACCCAGCCT GGCCCCCGGC CAGGACCCCG AGGGACTGGA
 501 CAAGGAGGAT GGACGGCCCC TGGAGCTCCG GGACCTGCTT CACTTCTCCA
 551 GCCAAGTAGC CCAGGGCATG GCCTTCCTCG CTTCCAAGAA TTGCATCCAC
 601 CGGGACGTGG CAGCGCGTAA CGTGCTGTTG ACCAATGGTC ATGTGGCGAA
 651 GATTGGGGAC TTCGGGCTGG CTAGGGACAT CATGAATGAC TCCAACTACA
 701 TTGTCAAGGG CAATGCCCGC TGCCTGTGA AGTGGATGGC CCCAGAGAGC
 751 ATCTTTGACT GTGTCTACAC GGTTCAGAGC GACGTCTGGT CCTATGGCAT
 801 CCTCCTCTGG GAGATCTTCT CACTTGGGCT GAATGCCTAC CCTGGCATCC
 851 TGGTGAACAG CAAGTTCTAT AAACTGGTGA AGGATGGATA CCAAATGGCC
 901 CAGCCTGCAT TTGCCCCAAA GAATATATAC AGCATCATGC AGGCCTGCTG
 951 GGCCTTGGAG CCCACCCACA GACCCACCTT GCAGCAGATC TGCTGCTTCC
1001 TTCAGGAGCA GGCCCAAGAG GACAGGAGAT AATAA
```

DNA sequence Construct 2 (residues 542-919Δ682-741)
(SEQ ID NO: 4)
```
   1 ATGAAAAAAG GTCATCATCA TCATCATCAT GGTCAGAAGC CCAAGTACCA
  51 GGTCCGCTGG AAGATCATCG AGAGCTATGA GGGCAAGAGT TATACTTTCA
 101 TCGACCCCAC GCAGCTGCCT TACAACGAGA AGTGGGAGTT CCCCCGGAAC
 151 AACCTGCAGT TTGGTAAGAC CCTCGGAGCT GGAGCCTTTG GAAGGTGGT
 201 GGAGGCCACG GCCTTTGGTC TGGGCAAGGA GGATGCTGTC CTGAAGGTGG
 251 CTGTGAAGAT GCTGAAGTCC ACGGCCCATG CTGATGAGAA GGAGGCCCTC
 301 ATGTCCGAGC TGAAGATCAT GAGCCACCTG GCCAGCACG AGAACATCGT
```

-continued

```
351 CAACCTTCTG GGAGCCTGTA CCCATGGAGG CCCTGTACTG GTCATCACGG

401 AGTACTGTTG CTATGGCGAC CTGCTCAACT TTCTGCGAAG GAAGGCTGAG

451 GCCCTGGACA AGGAGGATGG ACGGCCCCTG GAGCTCCGGG ACCTGCTTCA

501 CTTCTCCAGC CAAGTAGCCC AGGGCATGGC CTTCCTCGCT TCCAAGAATT

551 GCATCCACCG GGACGTGGCA GCGCGTAACG TGCTGTTGAC CAATGGTCAT

601 GTGGCCAAGA TTGGGGACTT CGGGCTGGCT AGGGACATCA TGAATGACTC

651 CAACTACATT GTCAAGGGCA ATGCCCGCCT GCCTGTGAAG TGGATGGCCC

701 CAGAGAGGAT CTTTGACTGT GTCTACACGG TTCAGAGCGA CGTCTGGTCC

751 TATGGCATCC TCCTCTGGGA GATCTTCTCA CTTGGGCTGA ATCCCTACCC

801 TGGCATCCTG GTGAACAGCA AGTTCTATAA ACTGGTGAAG GATGGATACC

851 AAATGGCCCA GCCTGCATTT GCCCCAAAGA ATATATACAG CATCATGCAG

901 GCCTGCTGGG CCTTGGAGCC CACCCACAGA CCCACCTTCC AGCAGATCTG

951 CTCCTTCCTT CAGGAGCAGG CCCAAGAGGA CAGGAGATAA TAA
```

TABLE 1

Crystal and Data Statistics

| Crystal form | I | II | III | IV |
|---|---|---|---|---|
| Space Group | P4₃2₁2 | I222 | P2₁2₁2₁ | R3 |
| Unit cell a (Å) | 62 | 64 | 65 | 80 |
| Unit cell b (Å) | 62 | 92 | 185 | 80 |
| Unit cell c (Å) | 183 | 134 | 195 | 78 |
| Mol/asu | 1 | 1 | 6 | 1 |
| Resolution (Å) | 2.7 | 2.9 | 3.0 | 1.8 |
| $R_{sym}^{ab}$ (%) | 7.5 | 7.9 | 11 | 7.8 |
| Completeness[b] (%) | 83 | 99 | 98 | 98 |

TABLE 1-continued

Crystal and Data Statistics

| $R_{cryst}^{c}$ (%) | 20 | — | 20 | 19 |
|---|---|---|---|---|
| $R_{free}^{d}$ (%) | 25 | — | 25 | 23 |

[a] $R_{sym} = \Sigma_{hkl} | I - \langle I \rangle | / \Sigma I$, where I is the observed intensity and $\langle I \rangle$ is the average intensity from observations of symmetry-related reflections.
[b] Value in parentheses is for the highest resolution shell.
[c] $R_{cryst} = \Sigma_{hkl} || F_{obs} | - | F_{calc} || / \Sigma | F_{obs} |$, where $F_{obs}$ and $F_{calc}$ are the observed and calculated structure factor amplitudes, respectively, for the hkl reflections.
[d] $R_{free}$ is calculated for a set of reflections that were not included in atomic The application of which this description and claim(s) forms part may be used as a basis for priority in respect of any subsequent application.

TABLE 2 cFMS - Formula (Ia) compound co-crystal
resolution: 500.0-1.8 Å
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1 | N | ALA | A | 544 | 80.225 | −70.486 | 87.710 | 1.00 | 37.13 |
|---|---|---|---|---|---|---|---|---|---|---|
| ATOM | 2 | CA | ALA | A | 544 | 81.411 | −69.923 | 86.998 | 1.00 | 37.13 |
| ATOM | 3 | C | ALA | A | 544 | 81.220 | −70.004 | 85.486 | 1.00 | 37.06 |
| ATOM | 4 | O | ALA | A | 544 | 80.845 | −71.052 | 84.957 | 1.00 | 37.09 |
| ATOM | 5 | CB | ALA | A | 544 | 82.672 | −70.685 | 87.407 | 1.00 | 37.16 |
| ATOM | 6 | N | ALA | A | 545 | 81.475 | −68.895 | 84.796 | 1.00 | 36.95 |
| ATOM | 7 | CA | ALA | A | 545 | 81.342 | −68.838 | 83.339 | 1.00 | 36.78 |
| ATOM | 8 | C | ALA | A | 545 | 82.731 | −68.829 | 82.695 | 1.00 | 36.63 |
| ATOM | 9 | O | ALA | A | 545 | 83.720 | −69.190 | 83.339 | 1.00 | 36.68 |
| ATOM | 10 | CB | ALA | A | 545 | 80.562 | −67.588 | 82.936 | 1.00 | 36.81 |
| ATOM | 11 | N | TYR | A | 546 | 82.804 | −68.424 | 81.427 | 1.00 | 36.33 |
| ATOM | 12 | CA | TYR | A | 546 | 84.085 | −68.369 | 80.720 | 1.00 | 35.95 |
| ATOM | 13 | C | TYR | A | 546 | 84.823 | −67.050 | 80.913 | 1.00 | 35.66 |
| ATOM | 14 | O | TYR | A | 546 | 84.218 | −65.978 | 80.917 | 1.00 | 35.60 |
| ATOM | 15 | CB | TYR | A | 546 | 83.895 | −68.607 | 79.216 | 1.00 | 35.90 |
| ATOM | 16 | CG | TYR | A | 546 | 85.123 | −68.277 | 78.378 | 1.00 | 35.83 |
| ATOM | 17 | CD1 | TYR | A | 546 | 85.462 | −66.952 | 78.080 | 1.00 | 35.76 |
| ATOM | 18 | CD2 | TYR | A | 546 | 85.952 | −69.289 | 77.894 | 1.00 | 35.82 |
| ATOM | 19 | CE1 | TYR | A | 546 | 86.590 | −66.650 | 77.322 | 1.00 | 35.74 |
| ATOM | 20 | CE2 | TYR | A | 546 | 87.086 | −68.996 | 77.137 | 1.00 | 35.73 |
| ATOM | 21 | CZ | TYR | A | 546 | 87.400 | −67.677 | 76.853 | 1.00 | 35.73 |
| ATOM | 22 | OH | TYR | A | 546 | 88.517 | −67.390 | 76.096 | 1.00 | 35.45 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 23 | N | GLN | A | 547 | 86.143 | −67.153 | 81.042 | 1.00 | 35.34 |
| ATOM | 24 | CA | GLN | A | 547 | 87.023 | −66.001 | 81.211 | 1.00 | 35.00 |
| ATOM | 25 | C | GLN | A | 547 | 88.308 | −66.259 | 80.427 | 1.00 | 34.51 |
| ATOM | 26 | O | GLN | A | 547 | 88.789 | −67.393 | 80.383 | 1.00 | 34.57 |
| ATOM | 27 | CB | GLN | A | 547 | 87.333 | −65.788 | 82.694 | 1.00 | 35.39 |
| ATOM | 28 | CG | GLN | A | 547 | 86.234 | −65.048 | 83.445 | 1.00 | 35.87 |
| ATOM | 29 | CD | GLN | A | 547 | 85.613 | −65.873 | 84.559 | 1.00 | 36.21 |
| ATOM | 30 | OE1 | GLN | A | 547 | 84.756 | −65.385 | 85.305 | 1.00 | 36.47 |
| ATOM | 31 | NE2 | GLN | A | 547 | 86.039 | −67.129 | 84.679 | 1.00 | 36.36 |
| ATOM | 32 | N | VAL | A | 548 | 88.855 | −65.219 | 79.799 | 1.00 | 33.86 |
| ATOM | 33 | CA | VAL | A | 548 | 90.070 | −65.367 | 78.997 | 1.00 | 33.17 |
| ATOM | 34 | C | VAL | A | 548 | 91.278 | −65.781 | 79.832 | 1.00 | 32.69 |
| ATOM | 35 | O | VAL | A | 548 | 91.859 | −64.971 | 80.553 | 1.00 | 32.59 |
| ATOM | 36 | CB | VAL | A | 548 | 90.411 | −64.068 | 78.240 | 1.00 | 33.12 |
| ATOM | 37 | CG1 | VAL | A | 548 | 91.678 | −64.266 | 77.429 | 1.00 | 33.07 |
| ATOM | 38 | CG2 | VAL | A | 548 | 89.258 | −63.682 | 77.316 | 1.00 | 33.11 |
| ATOM | 39 | N | ARG | A | 549 | 91.660 | −67.046 | 79.705 | 1.00 | 32.16 |
| ATOM | 40 | CA | ARG | A | 549 | 92.779 | −67.581 | 80.460 | 1.00 | 31.67 |
| ATOM | 41 | C | ARG | A | 549 | 94.154 | −67.452 | 79.803 | 1.00 | 31.20 |
| ATOM | 42 | O | ARG | A | 549 | 95.162 | −67.623 | 80.484 | 1.00 | 31.08 |
| ATOM | 43 | CB | ARG | A | 549 | 92.525 | −69.051 | 80.820 | 1.00 | 31.84 |
| ATOM | 44 | CG | ARG | A | 549 | 91.484 | −69.285 | 81.922 | 1.00 | 32.11 |
| ATOM | 45 | CD | ARG | A | 549 | 91.822 | −70.557 | 82.710 | 1.00 | 32.33 |
| ATOM | 46 | NE | ARG | A | 549 | 92.105 | −70.271 | 84.118 | 1.00 | 32.88 |
| ATOM | 47 | CZ | ARG | A | 549 | 92.863 | −71.028 | 84.907 | 1.00 | 33.02 |
| ATOM | 48 | NH1 | ARG | A | 549 | 93.432 | −72.130 | 84.436 | 1.00 | 33.01 |
| ATOM | 49 | NH2 | ARG | A | 549 | 93.053 | −70.683 | 86.179 | 1.00 | 33.34 |
| ATOM | 50 | N | TRP | A | 550 | 94.220 | −67.170 | 78.501 | 1.00 | 30.66 |
| ATOM | 51 | CA | TRP | A | 550 | 95.536 | −67.026 | 77.873 | 1.00 | 30.31 |
| ATOM | 52 | C | TRP | A | 550 | 96.177 | −65.812 | 78.528 | 1.00 | 30.33 |
| ATOM | 53 | O | TRP | A | 550 | 95.487 | −64.849 | 78.861 | 1.00 | 30.12 |
| ATOM | 54 | CB | TRP | A | 550 | 95.448 | −66.773 | 76.362 | 1.00 | 29.95 |
| ATOM | 55 | CG | TRP | A | 550 | 94.395 | −67.550 | 75.638 | 1.00 | 29.51 |
| ATOM | 56 | CD1 | TRP | A | 550 | 94.036 | −68.851 | 75.849 | 1.00 | 29.35 |
| ATOM | 57 | CD2 | TRP | A | 550 | 93.553 | −67.064 | 74.589 | 1.00 | 29.27 |
| ATOM | 58 | NE1 | TRP | A | 550 | 93.015 | −69.201 | 75.001 | 1.00 | 29.14 |
| ATOM | 59 | CE2 | TRP | A | 550 | 92.699 | −68.124 | 74.215 | 1.00 | 29.21 |
| ATOM | 60 | CE3 | TRP | A | 550 | 93.436 | −65.835 | 73.928 | 1.00 | 29.22 |
| ATOM | 61 | CZ2 | TRP | A | 550 | 91.736 | −67.992 | 73.207 | 1.00 | 29.14 |
| ATOM | 62 | CZ3 | TRP | A | 550 | 92.477 | −65.703 | 72.922 | 1.00 | 29.20 |
| ATOM | 63 | CH2 | TRP | A | 550 | 91.641 | −66.779 | 72.575 | 1.00 | 29.07 |
| ATOM | 64 | N | LYS | A | 551 | 97.492 | −65.839 | 78.710 | 1.00 | 30.43 |
| ATOM | 65 | CA | LYS | A | 551 | 98.135 | −64.701 | 79.345 | 1.00 | 30.58 |
| ATOM | 66 | C | LYS | A | 551 | 99.603 | −64.500 | 79.006 | 1.00 | 30.62 |
| ATOM | 67 | O | LYS | A | 551 | 100.368 | −65.462 | 78.883 | 1.00 | 30.49 |
| ATOM | 68 | CB | LYS | A | 551 | 97.987 | −64.808 | 80.862 | 1.00 | 30.78 |
| ATOM | 69 | CG | LYS | A | 551 | 98.454 | −63.572 | 81.602 | 1.00 | 31.23 |
| ATOM | 70 | CD | LYS | A | 551 | 98.270 | −63.721 | 83.104 | 1.00 | 31.47 |
| ATOM | 71 | CE | LYS | A | 551 | 98.737 | −62.469 | 83.832 | 1.00 | 31.63 |
| ATOM | 72 | NZ | LYS | A | 551 | 98.647 | −62.635 | 85.313 | 1.00 | 31.99 |
| ATOM | 73 | N | ILE | A | 552 | 99.974 | −63.231 | 78.860 | 1.00 | 30.58 |
| ATOM | 74 | CA | ILE | A | 552 | 101.345 | −62.835 | 78.578 | 1.00 | 30.55 |
| ATOM | 75 | C | ILE | A | 552 | 101.935 | −62.509 | 79.942 | 1.00 | 30.69 |
| ATOM | 76 | O | ILE | A | 552 | 101.557 | −61.517 | 80.564 | 1.00 | 30.57 |
| ATOM | 77 | CB | ILE | A | 552 | 101.401 | −61.574 | 77.703 | 1.00 | 30.52 |
| ATOM | 78 | CG1 | ILE | A | 552 | 100.639 | −61.811 | 76.394 | 1.00 | 30.50 |
| ATOM | 79 | CG2 | ILE | A | 552 | 102.846 | −61.192 | 77.440 | 1.00 | 30.43 |
| ATOM | 80 | CD1 | ILE | A | 552 | 101.105 | −63.022 | 75.609 | 1.00 | 30.42 |
| ATOM | 81 | N | ILE | A | 553 | 102.854 | −63.348 | 80.405 | 1.00 | 30.67 |
| ATOM | 82 | CA | ILE | A | 553 | 103.463 | −63.157 | 81.711 | 1.00 | 30.75 |
| ATOM | 83 | C | ILE | A | 553 | 104.845 | −62.537 | 81.622 | 1.00 | 30.99 |
| ATOM | 84 | O | ILE | A | 553 | 105.433 | −62.438 | 80.549 | 1.00 | 30.74 |
| ATOM | 85 | CB | ILE | A | 553 | 103.593 | −64.496 | 82.471 | 1.00 | 30.72 |
| ATOM | 86 | CG1 | ILE | A | 553 | 104.443 | −65.471 | 81.656 | 1.00 | 30.65 |
| ATOM | 87 | CG2 | ILE | A | 553 | 102.215 | −65.080 | 82.753 | 1.00 | 30.73 |
| ATOM | 88 | CD1 | ILE | A | 553 | 104.636 | −66.816 | 82.334 | 1.00 | 30.60 |
| ATOM | 89 | N | GLU | A | 554 | 105.363 | −62.127 | 82.772 | 1.00 | 31.35 |
| ATOM | 90 | CA | GLU | A | 554 | 106.680 | −61.524 | 82.819 | 1.00 | 31.79 |
| ATOM | 91 | C | GLU | A | 554 | 107.735 | −62.607 | 83.009 | 1.00 | 31.87 |
| ATOM | 92 | O | GLU | A | 554 | 107.477 | −63.644 | 83.626 | 1.00 | 31.77 |
| ATOM | 93 | CB | GLU | A | 554 | 106.730 | −60.489 | 83.942 | 1.00 | 32.19 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 94  | CG  | GLU | A | 554 | 105.620 | −59.454 | 83.807 | 1.00 | 32.84 |
|------|-----|-----|-----|---|-----|---------|---------|--------|------|-------|
| ATOM | 95  | CD  | GLU | A | 554 | 105.917 | −58.154 | 84.530 | 1.00 | 33.28 |
| ATOM | 96  | OE1 | GLU | A | 554 | 105.982 | −58.156 | 85.784 | 1.00 | 33.48 |
| ATOM | 97  | OE2 | GLU | A | 554 | 106.085 | −57.129 | 83.831 | 1.00 | 33.55 |
| ATOM | 98  | N   | SER | A | 555 | 108.915 | −62.365 | 82.447 | 1.00 | 32.04 |
| ATOM | 99  | CA  | SER | A | 555 | 110.029 | −63.305 | 82.519 | 1.00 | 32.22 |
| ATOM | 100 | C   | SER | A | 555 | 111.338 | −62.538 | 82.606 | 1.00 | 32.38 |
| ATOM | 101 | O   | SER | A | 555 | 111.660 | −61.751 | 81.721 | 1.00 | 32.25 |
| ATOM | 102 | CB  | SER | A | 555 | 110.059 | −64.191 | 81.274 | 1.00 | 32.22 |
| ATOM | 103 | OG  | SER | A | 555 | 111.172 | −65.067 | 81.307 | 1.00 | 32.41 |
| ATOM | 104 | N   | TYR | A | 556 | 112.090 | −62.778 | 83.673 | 1.00 | 32.61 |
| ATOM | 105 | CA  | TYR | A | 556 | 113.362 | −62.102 | 83.866 | 1.00 | 32.85 |
| ATOM | 106 | C   | TYR | A | 556 | 114.510 | −63.072 | 83.655 | 1.00 | 33.03 |
| ATOM | 107 | O   | TYR | A | 556 | 114.453 | −64.222 | 84.081 | 1.00 | 33.12 |
| ATOM | 108 | CB  | TYR | A | 556 | 113.416 | −61.488 | 85.264 | 1.00 | 32.87 |
| ATOM | 109 | CG  | TYR | A | 556 | 112.339 | −60.451 | 85.488 | 1.00 | 32.94 |
| ATOM | 110 | CD1 | TYR | A | 556 | 111.442 | −60.567 | 86.544 | 1.00 | 33.02 |
| ATOM | 111 | CD2 | TYR | A | 556 | 112.220 | −59.349 | 84.642 | 1.00 | 33.01 |
| ATOM | 112 | CE1 | TYR | A | 556 | 110.447 | −59.610 | 86.755 | 1.00 | 33.16 |
| ATOM | 113 | CE2 | TYR | A | 556 | 111.237 | −58.388 | 84.842 | 1.00 | 33.10 |
| ATOM | 114 | CZ  | TYR | A | 556 | 110.352 | −58.524 | 85.899 | 1.00 | 33.13 |
| ATOM | 115 | OH  | TYR | A | 556 | 109.361 | −57.588 | 86.088 | 1.00 | 33.31 |
| ATOM | 116 | N   | GLU | A | 557 | 115.545 | −62.595 | 82.976 | 1.00 | 33.23 |
| ATOM | 117 | CA  | GLU | A | 557 | 116.715 | −63.407 | 82.670 | 1.00 | 33.37 |
| ATOM | 118 | C   | GLU | A | 557 | 116.309 | −64.680 | 81.926 | 1.00 | 33.26 |
| ATOM | 119 | O   | GLU | A | 557 | 116.983 | −65.709 | 82.014 | 1.00 | 33.30 |
| ATOM | 120 | CB  | GLU | A | 557 | 117.469 | −63.761 | 83.952 | 1.00 | 33.63 |
| ATOM | 121 | CG  | GLU | A | 557 | 117.861 | −62.554 | 84.787 | 1.00 | 33.96 |
| ATOM | 122 | CD  | GLU | A | 557 | 118.939 | −62.881 | 85.806 | 1.00 | 34.20 |
| ATOM | 123 | OE1 | GLU | A | 557 | 120.138 | −62.794 | 85.450 | 1.00 | 34.41 |
| ATOM | 124 | OE2 | GLU | A | 557 | 118.587 | −63.234 | 86.954 | 1.00 | 34.24 |
| ATOM | 125 | N   | GLY | A | 558 | 115.194 | −64.599 | 81.205 | 1.00 | 33.09 |
| ATOM | 126 | CA  | GLY | A | 558 | 114.717 | −65.733 | 80.432 | 1.00 | 32.70 |
| ATOM | 127 | C   | GLY | A | 558 | 115.098 | −65.478 | 78.986 | 1.00 | 32.41 |
| ATOM | 128 | O   | GLY | A | 558 | 115.759 | −64.477 | 78.700 | 1.00 | 32.48 |
| ATOM | 129 | N   | ASN | A | 559 | 114.701 | −66.363 | 78.075 | 1.00 | 32.06 |
| ATOM | 130 | CA  | ASN | A | 559 | 115.029 | −66.169 | 76.667 | 1.00 | 31.62 |
| ATOM | 131 | C   | ASN | A | 559 | 114.264 | −64.993 | 76.072 | 1.00 | 31.15 |
| ATOM | 132 | O   | ASN | A | 559 | 114.774 | −64.288 | 75.205 | 1.00 | 31.16 |
| ATOM | 133 | CB  | ASN | A | 559 | 114.717 | −67.425 | 75.853 | 1.00 | 31.88 |
| ATOM | 134 | CG  | ASN | A | 559 | 115.551 | −68.615 | 76.273 | 1.00 | 32.17 |
| ATOM | 135 | OD1 | ASN | A | 559 | 116.687 | −68.466 | 76.736 | 1.00 | 32.31 |
| ATOM | 136 | ND2 | ASN | A | 559 | 114.996 | −69.810 | 76.101 | 1.00 | 32.29 |
| ATOM | 137 | N   | SER | A | 560 | 113.037 | −64.784 | 76.537 | 1.00 | 30.57 |
| ATOM | 138 | CA  | SER | A | 560 | 112.216 | −63.696 | 76.018 | 1.00 | 29.96 |
| ATOM | 139 | C   | SER | A | 560 | 111.812 | −62.688 | 77.076 | 1.00 | 29.43 |
| ATOM | 140 | O   | SER | A | 560 | 111.746 | −63.000 | 78.260 | 1.00 | 29.43 |
| ATOM | 141 | CB  | SER | A | 560 | 110.973 | −64.257 | 75.332 | 1.00 | 29.98 |
| ATOM | 142 | OG  | SER | A | 560 | 111.322 | −64.825 | 74.087 | 1.00 | 30.16 |
| ATOM | 143 | N   | TYR | A | 561 | 111.522 | −61.474 | 76.628 | 1.00 | 28.87 |
| ATOM | 144 | CA  | TYR | A | 561 | 111.162 | −60.395 | 77.534 | 1.00 | 28.19 |
| ATOM | 145 | C   | TYR | A | 561 | 109.805 | −59.825 | 77.179 | 1.00 | 27.87 |
| ATOM | 146 | O   | TYR | A | 561 | 109.488 | −59.627 | 76.009 | 1.00 | 27.73 |
| ATOM | 147 | CB  | TYR | A | 561 | 112.229 | −59.298 | 77.457 | 1.00 | 27.98 |
| ATOM | 148 | CG  | TYR | A | 561 | 112.173 | −58.279 | 78.570 | 1.00 | 27.66 |
| ATOM | 149 | CD1 | TYR | A | 561 | 111.344 | −57.162 | 78.489 | 1.00 | 27.52 |
| ATOM | 150 | CD2 | TYR | A | 561 | 112.951 | −58.441 | 79.714 | 1.00 | 27.57 |
| ATOM | 151 | CE1 | TYR | A | 561 | 111.294 | −56.230 | 79.529 | 1.00 | 27.45 |
| ATOM | 152 | CE2 | TYR | A | 561 | 112.909 | −57.524 | 80.753 | 1.00 | 27.46 |
| ATOM | 153 | CZ  | TYR | A | 561 | 112.081 | −56.422 | 80.659 | 1.00 | 27.40 |
| ATOM | 154 | OH  | TYR | A | 561 | 112.040 | −55.529 | 81.703 | 1.00 | 27.25 |
| ATOM | 155 | N   | THR | A | 562 | 109.008 | −59.570 | 78.204 | 1.00 | 27.55 |
| ATOM | 156 | CA  | THR | A | 562 | 107.679 | −59.018 | 78.031 | 1.00 | 27.43 |
| ATOM | 157 | C   | THR | A | 562 | 107.721 | −57.506 | 78.253 | 1.00 | 27.52 |
| ATOM | 158 | O   | THR | A | 562 | 107.795 | −57.045 | 79.391 | 1.00 | 27.46 |
| ATOM | 159 | CB  | THR | A | 562 | 106.708 | −59.659 | 79.032 | 1.00 | 27.33 |
| ATOM | 160 | OG1 | THR | A | 562 | 106.634 | −61.066 | 78.770 | 1.00 | 27.20 |
| ATOM | 161 | CG2 | THR | A | 562 | 105.320 | −59.035 | 78.928 | 1.00 | 27.27 |
| ATOM | 162 | N   | PHE | A | 563 | 107.682 | −56.750 | 77.159 | 1.00 | 27.54 |
| ATOM | 163 | CA  | PHE | A | 563 | 107.710 | −55.292 | 77.218 | 1.00 | 27.78 |
| ATOM | 164 | C   | PHE | A | 563 | 106.324 | −54.712 | 77.454 | 1.00 | 28.04 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 165 | O   | PHE | A | 563 | 106.183 | −53.670 | 78.088 | 1.00 | 27.87 |
|------|-----|-----|-----|---|-----|---------|---------|--------|------|-------|
| ATOM | 166 | CB  | PHE | A | 563 | 108.278 | −54.716 | 75.917 | 1.00 | 27.67 |
| ATOM | 167 | CG  | PHE | A | 563 | 109.762 | −54.874 | 75.780 | 1.00 | 27.56 |
| ATOM | 168 | CD1 | PHE | A | 563 | 110.630 | −54.027 | 76.465 | 1.00 | 27.48 |
| ATOM | 169 | CD2 | PHE | A | 563 | 110.295 | −55.876 | 74.980 | 1.00 | 27.57 |
| ATOM | 170 | CE1 | PHE | A | 563 | 112.007 | −54.174 | 76.356 | 1.00 | 27.42 |
| ATOM | 171 | CE2 | PHE | A | 563 | 111.677 | −56.034 | 74.863 | 1.00 | 27.61 |
| ATOM | 172 | CZ  | PHE | A | 563 | 112.534 | −55.177 | 75.555 | 1.00 | 27.55 |
| ATOM | 173 | N   | ILE | A | 564 | 105.300 | −55.391 | 76.947 | 1.00 | 28.42 |
| ATOM | 174 | CA  | ILE | A | 564 | 103.934 | −54.908 | 77.102 | 1.00 | 28.96 |
| ATOM | 175 | C   | ILE | A | 564 | 102.904 | −55.997 | 77.376 | 1.00 | 29.47 |
| ATOM | 176 | O   | ILE | A | 564 | 103.147 | −57.183 | 77.142 | 1.00 | 29.41 |
| ATOM | 177 | CB  | ILE | A | 564 | 103.477 | −54.168 | 75.838 | 1.00 | 28.90 |
| ATOM | 178 | CG1 | ILE | A | 564 | 103.546 | −55.122 | 74.636 | 1.00 | 28.90 |
| ATOM | 179 | CG2 | ILE | A | 564 | 104.335 | −52.937 | 75.620 | 1.00 | 28.93 |
| ATOM | 180 | CD1 | ILE | A | 564 | 103.064 | −54.532 | 73.332 | 1.00 | 28.90 |
| ATOM | 181 | N   | ASP | A | 565 | 101.747 | −55.572 | 77.871 | 1.00 | 30.06 |
| ATOM | 182 | CA  | ASP | A | 565 | 100.633 | −56.475 | 78.144 | 1.00 | 30.72 |
| ATOM | 183 | C   | ASP | A | 565 |  99.517 | −55.991 | 77.226 | 1.00 | 31.12 |
| ATOM | 184 | O   | ASP | A | 565 |  98.835 | −55.010 | 77.519 | 1.00 | 31.11 |
| ATOM | 185 | CB  | ASP | A | 565 | 100.201 | −56.389 | 79.606 | 1.00 | 30.96 |
| ATOM | 186 | CG  | ASP | A | 565 |  98.998 | −57.264 | 79.908 | 1.00 | 31.26 |
| ATOM | 187 | OD1 | ASP | A | 565 |  98.928 | −58.398 | 79.384 | 1.00 | 31.37 |
| ATOM | 188 | OD2 | ASP | A | 565 |  98.123 | −56.821 | 80.677 | 1.00 | 31.57 |
| ATOM | 189 | N   | PRO | A | 566 |  99.323 | −56.681 | 76.095 | 1.00 | 31.48 |
| ATOM | 190 | CA  | PRO | A | 566 |  98.308 | −56.351 | 75.093 | 1.00 | 31.84 |
| ATOM | 191 | C   | PRO | A | 566 |  96.875 | −56.173 | 75.593 | 1.00 | 32.24 |
| ATOM | 192 | O   | PRO | A | 566 |  96.094 | −55.449 | 74.974 | 1.00 | 32.33 |
| ATOM | 193 | CB  | PRO | A | 566 |  98.442 | −57.492 | 74.085 | 1.00 | 31.75 |
| ATOM | 194 | CG  | PRO | A | 566 |  98.866 | −58.646 | 74.949 | 1.00 | 31.63 |
| ATOM | 195 | CD  | PRO | A | 566 |  99.907 | −58.009 | 75.827 | 1.00 | 31.54 |
| ATOM | 196 | N   | THR | A | 567 |  96.532 | −56.813 | 76.708 | 1.00 | 32.70 |
| ATOM | 197 | CA  | THR | A | 567 |  95.179 | −56.721 | 77.244 | 1.00 | 33.22 |
| ATOM | 198 | C   | THR | A | 567 |  94.922 | −55.428 | 78.003 | 1.00 | 33.59 |
| ATOM | 199 | O   | THR | A | 567 |  93.784 | −55.140 | 78.381 | 1.00 | 33.64 |
| ATOM | 200 | CB  | THR | A | 567 |  94.864 | −57.891 | 78.183 | 1.00 | 33.27 |
| ATOM | 201 | OG1 | THR | A | 567 |  95.633 | −57.760 | 79.384 | 1.00 | 33.40 |
| ATOM | 202 | CG2 | THR | A | 567 |  95.199 | −59.220 | 77.506 | 1.00 | 33.33 |
| ATOM | 203 | N   | GLN | A | 568 |  95.977 | −54.653 | 78.236 | 1.00 | 33.98 |
| ATOM | 204 | CA  | GLN | A | 568 |  95.837 | −53.384 | 78.941 | 1.00 | 34.34 |
| ATOM | 205 | C   | GLN | A | 568 |  96.027 | −52.252 | 77.952 | 1.00 | 34.50 |
| ATOM | 206 | O   | GLN | A | 568 |  95.979 | −51.076 | 78.313 | 1.00 | 34.53 |
| ATOM | 207 | CB  | GLN | A | 568 |  96.870 | −53.266 | 80.063 | 1.00 | 34.56 |
| ATOM | 208 | CG  | GLN | A | 568 |  96.678 | −54.273 | 81.176 | 1.00 | 35.03 |
| ATOM | 209 | CD  | GLN | A | 568 |  95.218 | −54.430 | 81.555 | 1.00 | 35.26 |
| ATOM | 210 | OE1 | GLN | A | 568 |  94.534 | −53.447 | 81.854 | 1.00 | 35.51 |
| ATOM | 211 | NE2 | GLN | A | 568 |  94.729 | −55.670 | 81.538 | 1.00 | 35.42 |
| ATOM | 212 | N   | LEU | A | 569 |  96.246 | −52.621 | 76.698 | 1.00 | 34.60 |
| ATOM | 213 | CA  | LEU | A | 569 |  96.454 | −51.645 | 75.640 | 1.00 | 34.73 |
| ATOM | 214 | C   | LEU | A | 569 |  95.278 | −51.660 | 74.672 | 1.00 | 34.85 |
| ATOM | 215 | O   | LEU | A | 569 |  94.518 | −52.630 | 74.615 | 1.00 | 34.79 |
| ATOM | 216 | CB  | LEU | A | 569 |  97.759 | −51.954 | 74.904 | 1.00 | 34.76 |
| ATOM | 217 | CG  | LEU | A | 569 |  98.986 | −51.939 | 75.824 | 1.00 | 34.76 |
| ATOM | 218 | CD1 | LEU | A | 569 | 100.215 | −52.421 | 75.074 | 1.00 | 34.77 |
| ATOM | 219 | CD2 | LEU | A | 569 |  99.196 | −50.528 | 76.355 | 1.00 | 34.81 |
| ATOM | 220 | N   | PRO | A | 570 |  95.106 | −50.577 | 73.901 | 1.00 | 34.90 |
| ATOM | 221 | CA  | PRO | A | 570 |  93.994 | −50.527 | 72.952 | 1.00 | 34.94 |
| ATOM | 222 | C   | PRO | A | 570 |  94.153 | −51.470 | 71.764 | 1.00 | 35.02 |
| ATOM | 223 | O   | PRO | A | 570 |  95.260 | −51.901 | 71.428 | 1.00 | 34.92 |
| ATOM | 224 | CB  | PRO | A | 570 |  93.973 | −49.059 | 72.527 | 1.00 | 34.99 |
| ATOM | 225 | CG  | PRO | A | 570 |  95.424 | −48.680 | 72.587 | 1.00 | 34.91 |
| ATOM | 226 | CD  | PRO | A | 570 |  95.867 | −49.313 | 73.889 | 1.00 | 34.90 |
| ATOM | 227 | N   | TYR | A | 571 |  93.027 | −51.795 | 71.143 | 1.00 | 35.04 |
| ATOM | 228 | CA  | TYR | A | 571 |  93.012 | −52.653 | 69.972 | 1.00 | 35.17 |
| ATOM | 229 | C   | TYR | A | 571 |  93.806 | −51.948 | 68.875 | 1.00 | 35.30 |
| ATOM | 230 | O   | TYR | A | 571 |  93.682 | −50.735 | 68.687 | 1.00 | 35.24 |
| ATOM | 231 | CB  | TYR | A | 571 |  91.564 | −52.873 | 69.528 | 1.00 | 35.16 |
| ATOM | 232 | CG  | TYR | A | 571 |  91.384 | −53.238 | 68.072 | 1.00 | 35.19 |
| ATOM | 233 | CD1 | TYR | A | 571 |  91.749 | −54.495 | 67.592 | 1.00 | 35.20 |
| ATOM | 234 | CD2 | TYR | A | 571 |  90.822 | −52.327 | 67.176 | 1.00 | 35.23 |
| ATOM | 235 | CE1 | TYR | A | 571 |  91.554 | −54.836 | 66.257 | 1.00 | 35.26 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 236 | CE2 | TYR | A | 571 | 90.624 | −52.657 | 65.844 | 1.00 | 35.24 |
|------|-----|-----|-----|---|-----|--------|---------|--------|------|-------|
| ATOM | 237 | CZ  | TYR | A | 571 | 90.987 | −53.910 | 65.389 | 1.00 | 35.32 |
| ATOM | 238 | OH  | TYR | A | 571 | 90.761 | −54.240 | 64.072 | 1.00 | 35.35 |
| ATOM | 239 | N   | ASN | A | 572 | 94.635 | −52.705 | 68.166 | 1.00 | 35.50 |
| ATOM | 240 | CA  | ASN | A | 572 | 95.440 | −52.151 | 67.085 | 1.00 | 35.78 |
| ATOM | 241 | C   | ASN | A | 572 | 94.583 | −52.024 | 65.827 | 1.00 | 36.01 |
| ATOM | 242 | O   | ASN | A | 572 | 94.344 | −53.015 | 65.134 | 1.00 | 36.05 |
| ATOM | 243 | CB  | ASN | A | 572 | 96.636 | −53.060 | 66.804 | 1.00 | 35.74 |
| ATOM | 244 | CG  | ASN | A | 572 | 97.491 | −52.556 | 65.664 | 1.00 | 35.82 |
| ATOM | 245 | OD1 | ASN | A | 572 | 97.199 | −51.518 | 65.068 | 1.00 | 35.83 |
| ATOM | 246 | ND2 | ASN | A | 572 | 98.557 | −53.286 | 65.352 | 1.00 | 35.84 |
| ATOM | 247 | N   | GLU | A | 573 | 94.135 | −50.803 | 65.538 | 1.00 | 36.26 |
| ATOM | 248 | CA  | GLU | A | 573 | 93.287 | −50.525 | 64.378 | 1.00 | 36.59 |
| ATOM | 249 | C   | GLU | A | 573 | 93.759 | −51.102 | 63.045 | 1.00 | 36.83 |
| ATOM | 250 | O   | GLU | A | 573 | 92.948 | −51.331 | 62.153 | 1.00 | 36.83 |
| ATOM | 251 | CB  | GLU | A | 573 | 93.082 | −49.014 | 64.220 | 1.00 | 36.55 |
| ATOM | 252 | CG  | GLU | A | 573 | 92.232 | −48.354 | 65.301 | 1.00 | 36.64 |
| ATOM | 253 | CD  | GLU | A | 573 | 90.776 | −48.803 | 65.277 | 1.00 | 36.68 |
| ATOM | 254 | OE1 | GLU | A | 573 | 90.206 | −48.931 | 64.168 | 1.00 | 36.71 |
| ATOM | 255 | OE2 | GLU | A | 573 | 90.198 | −49.011 | 66.367 | 1.00 | 36.65 |
| ATOM | 256 | N   | LYS | A | 574 | 95.057 | −51.342 | 62.897 | 1.00 | 37.21 |
| ATOM | 257 | CA  | LYS | A | 574 | 95.563 | −51.893 | 61.640 | 1.00 | 37.65 |
| ATOM | 258 | C   | LYS | A | 574 | 95.011 | −53.275 | 61.283 | 1.00 | 37.86 |
| ATOM | 259 | O   | LYS | A | 574 | 95.363 | −53.841 | 60.247 | 1.00 | 37.85 |
| ATOM | 260 | CB  | LYS | A | 574 | 97.092 | −51.946 | 61.646 | 1.00 | 37.76 |
| ATOM | 261 | CG  | LYS | A | 574 | 97.749 | −50.586 | 61.451 | 1.00 | 37.89 |
| ATOM | 262 | CD  | LYS | A | 574 | 99.184 | −50.725 | 60.965 | 1.00 | 38.01 |
| ATOM | 263 | CE  | LYS | A | 574 | 99.789 | −49.365 | 60.635 | 1.00 | 38.11 |
| ATOM | 264 | NZ  | LYS | A | 574 | 101.209 | −49.482 | 60.195 | 1.00 | 38.17 |
| ATOM | 265 | N   | TRP | A | 575 | 94.153 | −53.820 | 62.139 | 1.00 | 38.15 |
| ATOM | 266 | CA  | TRP | A | 575 | 93.561 | −55.128 | 61.879 | 1.00 | 38.46 |
| ATOM | 267 | C   | TRP | A | 575 | 92.136 | −54.977 | 61.354 | 1.00 | 38.76 |
| ATOM | 268 | O   | TRP | A | 575 | 91.531 | −55.946 | 60.890 | 1.00 | 38.70 |
| ATOM | 269 | CB  | TRP | A | 575 | 93.522 | −55.978 | 63.154 | 1.00 | 38.33 |
| ATOM | 270 | CG  | TRP | A | 575 | 94.849 | −56.468 | 63.647 | 1.00 | 38.19 |
| ATOM | 271 | CD1 | TRP | A | 575 | 95.604 | −55.928 | 64.651 | 1.00 | 38.15 |
| ATOM | 272 | CD2 | TRP | A | 575 | 95.563 | −57.622 | 63.185 | 1.00 | 38.13 |
| ATOM | 273 | NE1 | TRP | A | 575 | 96.742 | −56.678 | 64.845 | 1.00 | 38.09 |
| ATOM | 274 | CE2 | TRP | A | 575 | 96.742 | −57.723 | 63.959 | 1.00 | 38.08 |
| ATOM | 275 | CE3 | TRP | A | 575 | 95.319 | −58.584 | 62.194 | 1.00 | 38.12 |
| ATOM | 276 | CZ2 | TRP | A | 575 | 97.676 | −58.747 | 63.773 | 1.00 | 38.01 |
| ATOM | 277 | CZ3 | TRP | A | 575 | 96.251 | −59.606 | 62.008 | 1.00 | 38.02 |
| ATOM | 278 | CH2 | TRP | A | 575 | 97.415 | −59.677 | 62.797 | 1.00 | 38.06 |
| ATOM | 279 | N   | GLU | A | 576 | 91.610 | −53.759 | 61.429 | 1.00 | 39.16 |
| ATOM | 280 | CA  | GLU | A | 576 | 90.244 | −53.469 | 61.001 | 1.00 | 39.66 |
| ATOM | 281 | C   | GLU | A | 576 | 89.957 | −53.880 | 59.551 | 1.00 | 39.93 |
| ATOM | 282 | O   | GLU | A | 576 | 90.786 | −53.696 | 58.657 | 1.00 | 39.91 |
| ATOM | 283 | CB  | GLU | A | 576 | 89.955 | −51.980 | 61.202 | 1.00 | 39.69 |
| ATOM | 284 | CG  | GLU | A | 576 | 88.481 | −51.610 | 61.252 | 1.00 | 39.89 |
| ATOM | 285 | CD  | GLU | A | 576 | 87.746 | −52.224 | 62.434 | 1.00 | 40.01 |
| ATOM | 286 | OE1 | GLU | A | 576 | 88.327 | −52.311 | 63.541 | 1.00 | 40.02 |
| ATOM | 287 | OE2 | GLU | A | 576 | 86.570 | −52.604 | 62.259 | 1.00 | 40.10 |
| ATOM | 288 | N   | PHE | A | 577 | 88.770 | −54.450 | 59.343 | 1.00 | 40.30 |
| ATOM | 289 | CA  | PHE | A | 577 | 88.323 | −54.926 | 58.033 | 1.00 | 40.66 |
| ATOM | 290 | C   | PHE | A | 577 | 86.880 | −54.457 | 57.829 | 1.00 | 40.93 |
| ATOM | 291 | O   | PHE | A | 577 | 86.107 | −54.387 | 58.784 | 1.00 | 40.94 |
| ATOM | 292 | CB  | PHE | A | 577 | 88.387 | −56.457 | 58.001 | 1.00 | 40.64 |
| ATOM | 293 | CG  | PHE | A | 577 | 88.070 | −57.061 | 56.660 | 1.00 | 40.67 |
| ATOM | 294 | CD1 | PHE | A | 577 | 88.947 | −56.918 | 55.591 | 1.00 | 40.61 |
| ATOM | 295 | CD2 | PHE | A | 577 | 86.896 | −57.786 | 56.470 | 1.00 | 40.67 |
| ATOM | 296 | CE1 | PHE | A | 577 | 88.660 | −57.489 | 54.352 | 1.00 | 40.64 |
| ATOM | 297 | CE2 | PHE | A | 577 | 86.601 | −58.362 | 55.232 | 1.00 | 40.68 |
| ATOM | 298 | CZ  | PHE | A | 577 | 87.486 | −58.213 | 54.172 | 1.00 | 40.61 |
| ATOM | 299 | N   | PRO | A | 578 | 86.499 | −54.126 | 56.581 | 1.00 | 41.28 |
| ATOM | 300 | CA  | PRO | A | 578 | 85.134 | −53.664 | 56.299 | 1.00 | 41.53 |
| ATOM | 301 | C   | PRO | A | 578 | 84.060 | −54.709 | 56.599 | 1.00 | 41.72 |
| ATOM | 302 | O   | PRO | A | 578 | 84.064 | −55.795 | 56.030 | 1.00 | 41.78 |
| ATOM | 303 | CB  | PRO | A | 578 | 85.191 | −53.305 | 54.814 | 1.00 | 41.51 |
| ATOM | 304 | CG  | PRO | A | 578 | 86.630 | −52.923 | 54.607 | 1.00 | 41.47 |
| ATOM | 305 | CD  | PRO | A | 578 | 87.342 | −54.010 | 55.378 | 1.00 | 41.37 |
| ATOM | 306 | N   | ARG | A | 579 | 83.144 | −54.361 | 57.496 | 1.00 | 41.99 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 307 | CA | ARG | A | 579 | 82.051 | −55.237 | 57.897 | 1.00 | 42.27 |
|------|-----|-----|-----|---|-----|--------|---------|--------|------|-------|
| ATOM | 308 | C | ARG | A | 579 | 81.241 | −55.696 | 56.690 | 1.00 | 42.50 |
| ATOM | 309 | O | ARG | A | 579 | 80.960 | −56.885 | 56.531 | 1.00 | 42.58 |
| ATOM | 310 | CB | ARG | A | 579 | 81.145 | −54.490 | 58.875 | 1.00 | 42.34 |
| ATOM | 311 | CG | ARG | A | 579 | 79.929 | −55.253 | 59.348 | 1.00 | 42.36 |
| ATOM | 312 | CD | ARG | A | 579 | 79.144 | −54.381 | 60.301 | 1.00 | 42.48 |
| ATOM | 313 | NE | ARG | A | 579 | 79.999 | −53.895 | 61.380 | 1.00 | 42.58 |
| ATOM | 314 | CZ | ARG | A | 579 | 80.487 | −54.661 | 62.352 | 1.00 | 42.56 |
| ATOM | 315 | NH1 | ARG | A | 579 | 80.202 | −55.956 | 62.390 | 1.00 | 42.52 |
| ATOM | 316 | NH2 | ARG | A | 579 | 81.272 | −54.132 | 63.281 | 1.00 | 42.58 |
| ATOM | 317 | N | ASN | A | 580 | 80.870 | −54.738 | 55.844 | 1.00 | 42.69 |
| ATOM | 318 | CA | ASN | A | 580 | 80.090 | −55.008 | 54.636 | 1.00 | 42.82 |
| ATOM | 319 | C | ASN | A | 580 | 80.803 | −55.935 | 53.659 | 1.00 | 42.76 |
| ATOM | 320 | O | ASN | A | 580 | 80.180 | −56.473 | 52.746 | 1.00 | 42.87 |
| ATOM | 321 | CB | ASN | A | 580 | 79.764 | −53.699 | 53.918 | 1.00 | 43.01 |
| ATOM | 322 | CG | ASN | A | 580 | 78.825 | −52.816 | 54.711 | 1.00 | 43.27 |
| ATOM | 323 | OD1 | ASN | A | 580 | 77.654 | −53.154 | 54.909 | 1.00 | 43.47 |
| ATOM | 324 | ND2 | ASN | A | 580 | 79.333 | −51.677 | 55.173 | 1.00 | 43.40 |
| ATOM | 325 | N | ASN | A | 581 | 82.106 | −56.122 | 53.842 | 1.00 | 42.68 |
| ATOM | 326 | CA | ASN | A | 581 | 82.859 | −56.985 | 52.941 | 1.00 | 42.55 |
| ATOM | 327 | C | ASN | A | 581 | 83.101 | −58.388 | 53.488 | 1.00 | 42.43 |
| ATOM | 328 | O | ASN | A | 581 | 84.174 | −58.953 | 53.319 | 1.00 | 42.39 |
| ATOM | 329 | CB | ASN | A | 581 | 84.193 | −56.332 | 52.575 | 1.00 | 42.62 |
| ATOM | 330 | CG | ASN | A | 581 | 84.011 | −54.973 | 51.921 | 1.00 | 42.71 |
| ATOM | 331 | OD1 | ASN | A | 581 | 82.922 | −54.641 | 51.447 | 1.00 | 42.69 |
| ATOM | 332 | ND2 | ASN | A | 581 | 85.081 | −54.186 | 51.879 | 1.00 | 42.75 |
| ATOM | 333 | N | LEU | A | 582 | 82.098 | −58.938 | 54.163 | 1.00 | 42.31 |
| ATOM | 334 | CA | LEU | A | 582 | 82.190 | −60.291 | 54.699 | 1.00 | 42.14 |
| ATOM | 335 | C | LEU | A | 582 | 80.919 | −61.039 | 54.341 | 1.00 | 41.96 |
| ATOM | 336 | O | LEU | A | 582 | 79.820 | −60.600 | 54.678 | 1.00 | 42.01 |
| ATOM | 337 | CB | LEU | A | 582 | 82.357 | −60.279 | 56.222 | 1.00 | 42.15 |
| ATOM | 338 | CG | LEU | A | 582 | 83.762 | −60.160 | 56.817 | 1.00 | 42.12 |
| ATOM | 339 | CD1 | LEU | A | 582 | 83.670 | −60.331 | 58.333 | 1.00 | 42.12 |
| ATOM | 340 | CD2 | LEU | A | 582 | 84.677 | −61.218 | 56.229 | 1.00 | 42.11 |
| ATOM | 341 | N | GLN | A | 583 | 81.066 | −62.163 | 53.650 | 1.00 | 41.77 |
| ATOM | 342 | CA | GLN | A | 583 | 79.909 | −62.962 | 53.270 | 1.00 | 41.51 |
| ATOM | 343 | C | GLN | A | 583 | 79.894 | −64.255 | 54.067 | 1.00 | 41.09 |
| ATOM | 344 | O | GLN | A | 583 | 80.542 | −65.234 | 53.706 | 1.00 | 41.12 |
| ATOM | 345 | CB | GLN | A | 583 | 79.934 | −63.239 | 51.768 | 1.00 | 41.83 |
| ATOM | 346 | CG | GLN | A | 583 | 79.855 | −61.951 | 50.951 | 1.00 | 42.29 |
| ATOM | 347 | CD | GLN | A | 583 | 79.600 | −62.187 | 49.476 | 1.00 | 42.55 |
| ATOM | 348 | OE1 | GLN | A | 583 | 79.547 | −61.238 | 48.690 | 1.00 | 42.66 |
| ATOM | 349 | NE2 | GLN | A | 583 | 79.437 | −63.453 | 49.090 | 1.00 | 42.69 |
| ATOM | 350 | N | PHE | A | 584 | 79.149 | −64.233 | 55.165 | 1.00 | 40.62 |
| ATOM | 351 | CA | PHE | A | 584 | 79.047 | −65.375 | 56.059 | 1.00 | 40.03 |
| ATOM | 352 | C | PHE | A | 584 | 78.452 | −66.603 | 55.397 | 1.00 | 39.47 |
| ATOM | 353 | O | PHE | A | 584 | 77.542 | −66.506 | 54.571 | 1.00 | 39.50 |
| ATOM | 354 | CB | PHE | A | 584 | 78.222 | −65.003 | 57.297 | 1.00 | 40.28 |
| ATOM | 355 | CG | PHE | A | 584 | 78.763 | −63.818 | 58.053 | 1.00 | 40.48 |
| ATOM | 356 | CD1 | PHE | A | 584 | 80.110 | −63.747 | 58.391 | 1.00 | 40.54 |
| ATOM | 357 | CD2 | PHE | A | 584 | 77.927 | −62.768 | 58.418 | 1.00 | 40.59 |
| ATOM | 358 | CE1 | PHE | A | 584 | 80.618 | −62.647 | 59.078 | 1.00 | 40.58 |
| ATOM | 359 | CE2 | PHE | A | 584 | 78.427 | −61.663 | 59.106 | 1.00 | 40.67 |
| ATOM | 360 | CZ | PHE | A | 584 | 79.775 | −61.604 | 59.435 | 1.00 | 40.62 |
| ATOM | 361 | N | GLY | A | 585 | 78.986 | −67.761 | 55.771 | 1.00 | 38.75 |
| ATOM | 362 | CA | GLY | A | 585 | 78.513 | −69.020 | 55.232 | 1.00 | 37.75 |
| ATOM | 363 | C | GLY | A | 585 | 77.914 | −69.888 | 56.319 | 1.00 | 37.02 |
| ATOM | 364 | O | GLY | A | 585 | 77.185 | −69.400 | 57.182 | 1.00 | 37.08 |
| ATOM | 365 | N | LYS | A | 586 | 78.236 | −71.176 | 56.286 | 1.00 | 36.26 |
| ATOM | 366 | CA | LYS | A | 586 | 77.713 | −72.132 | 57.257 | 1.00 | 35.43 |
| ATOM | 367 | C | LYS | A | 586 | 78.343 | −71.978 | 58.637 | 1.00 | 34.71 |
| ATOM | 368 | O | LYS | A | 586 | 79.456 | −71.473 | 58.775 | 1.00 | 34.59 |
| ATOM | 369 | CB | LYS | A | 586 | 77.955 | −73.563 | 56.761 | 1.00 | 35.62 |
| ATOM | 370 | CG | LYS | A | 586 | 79.429 | −73.960 | 56.748 | 1.00 | 35.80 |
| ATOM | 371 | CD | LYS | A | 586 | 79.662 | −75.363 | 56.203 | 1.00 | 36.01 |
| ATOM | 372 | CE | LYS | A | 586 | 81.151 | −75.692 | 56.215 | 1.00 | 36.22 |
| ATOM | 373 | NZ | LYS | A | 586 | 81.483 | −76.976 | 55.527 | 1.00 | 36.39 |
| ATOM | 374 | N | THR | A | 587 | 77.617 | −72.421 | 59.655 | 1.00 | 33.87 |
| ATOM | 375 | CA | THR | A | 587 | 78.107 | −72.375 | 61.026 | 1.00 | 33.03 |
| ATOM | 376 | C | THR | A | 587 | 79.148 | −73.482 | 61.177 | 1.00 | 32.41 |
| ATOM | 377 | O | THR | A | 587 | 78.978 | −74.579 | 60.639 | 1.00 | 32.36 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 378 | CB | THR | A | 587 | 76.971 | −72.626 | 62.031 | 1.00 | 33.09 |
|---|---|---|---|---|---|---|---|---|---|---|
| ATOM | 379 | OG1 | THR | A | 587 | 76.047 | −71.529 | 61.990 | 1.00 | 33.17 |
| ATOM | 380 | CG2 | THR | A | 587 | 77.528 | −72.775 | 63.443 | 1.00 | 33.00 |
| ATOM | 381 | N | LEU | A | 588 | 80.229 | −73.191 | 61.893 | 1.00 | 31.58 |
| ATOM | 382 | CA | LEU | A | 588 | 81.285 | −74.175 | 62.105 | 1.00 | 30.83 |
| ATOM | 383 | C | LEU | A | 588 | 81.256 | −74.695 | 63.533 | 1.00 | 30.32 |
| ATOM | 384 | O | LEU | A | 588 | 81.690 | −75.807 | 63.805 | 1.00 | 30.19 |
| ATOM | 385 | CB | LEU | A | 588 | 82.658 | −73.558 | 61.811 | 1.00 | 30.72 |
| ATOM | 386 | CG | LEU | A | 588 | 82.930 | −73.119 | 60.368 | 1.00 | 30.61 |
| ATOM | 387 | CD1 | LEU | A | 588 | 84.293 | −72.455 | 60.291 | 1.00 | 30.54 |
| ATOM | 388 | CD2 | LEU | A | 588 | 82.866 | −74.321 | 59.431 | 1.00 | 30.61 |
| ATOM | 389 | N | GLY | A | 589 | 80.741 | −73.881 | 64.445 | 1.00 | 29.92 |
| ATOM | 390 | CA | GLY | A | 589 | 80.671 | −74.291 | 65.834 | 1.00 | 29.41 |
| ATOM | 391 | C | GLY | A | 589 | 80.174 | −73.178 | 66.726 | 1.00 | 29.06 |
| ATOM | 392 | O | GLY | A | 589 | 80.103 | −72.028 | 66.307 | 1.00 | 28.99 |
| ATOM | 393 | N | ALA | A | 590 | 79.833 | −73.516 | 67.963 | 1.00 | 28.79 |
| ATOM | 394 | CA | ALA | A | 590 | 79.340 | −72.523 | 68.906 | 1.00 | 28.53 |
| ATOM | 395 | C | ALA | A | 590 | 79.576 | −73.007 | 70.326 | 1.00 | 28.37 |
| ATOM | 396 | O | ALA | A | 590 | 79.812 | −74.193 | 70.549 | 1.00 | 28.17 |
| ATOM | 397 | CB | ALA | A | 590 | 77.851 | −72.263 | 68.670 | 1.00 | 28.38 |
| ATOM | 398 | N | GLY | A | 591 | 79.519 | −72.083 | 71.280 | 1.00 | 28.34 |
| ATOM | 399 | CA | GLY | A | 591 | 79.743 | −72.441 | 72.668 | 1.00 | 28.47 |
| ATOM | 400 | C | GLY | A | 591 | 79.073 | −71.538 | 73.692 | 1.00 | 28.59 |
| ATOM | 401 | O | GLY | A | 591 | 78.004 | −70.971 | 73.444 | 1.00 | 28.58 |
| ATOM | 402 | N | ALA | A | 592 | 79.717 | −71.403 | 74.849 | 1.00 | 28.63 |
| ATOM | 403 | CA | ALA | A | 592 | 79.198 | −70.598 | 75.954 | 1.00 | 28.71 |
| ATOM | 404 | C | ALA | A | 592 | 78.799 | −69.173 | 75.596 | 1.00 | 28.79 |
| ATOM | 405 | O | ALA | A | 592 | 77.666 | −68.767 | 75.854 | 1.00 | 28.71 |
| ATOM | 406 | CB | ALA | A | 592 | 80.208 | −70.575 | 77.096 | 1.00 | 28.67 |
| ATOM | 407 | N | PHE | A | 593 | 79.722 | −68.417 | 75.007 | 1.00 | 28.96 |
| ATOM | 408 | CA | PHE | A | 593 | 79.452 | −67.022 | 74.652 | 1.00 | 29.22 |
| ATOM | 409 | C | PHE | A | 593 | 79.387 | −66.680 | 73.174 | 1.00 | 29.29 |
| ATOM | 410 | O | PHE | A | 593 | 78.704 | −65.731 | 72.791 | 1.00 | 29.31 |
| ATOM | 411 | CB | PHE | A | 593 | 80.494 | −66.097 | 75.282 | 1.00 | 29.43 |
| ATOM | 412 | CG | PHE | A | 593 | 80.440 | −66.044 | 76.774 | 1.00 | 29.75 |
| ATOM | 413 | CD1 | PHE | A | 593 | 79.358 | −66.576 | 77.469 | 1.00 | 29.79 |
| ATOM | 414 | CD2 | PHE | A | 593 | 81.473 | −65.450 | 77.490 | 1.00 | 29.88 |
| ATOM | 415 | CE1 | PHE | A | 593 | 79.304 | −66.520 | 78.855 | 1.00 | 30.00 |
| ATOM | 416 | CE2 | PHE | A | 593 | 81.430 | −65.387 | 78.881 | 1.00 | 29.97 |
| ATOM | 417 | CZ | PHE | A | 593 | 80.343 | −65.924 | 79.563 | 1.00 | 30.03 |
| ATOM | 418 | N | GLY | A | 594 | 80.102 | −67.430 | 72.344 | 1.00 | 29.41 |
| ATOM | 419 | CA | GLY | A | 594 | 80.103 | −67.113 | 70.930 | 1.00 | 29.52 |
| ATOM | 420 | C | GLY | A | 594 | 79.863 | −68.241 | 69.953 | 1.00 | 29.74 |
| ATOM | 421 | O | GLY | A | 594 | 79.682 | −69.402 | 70.328 | 1.00 | 29.64 |
| ATOM | 422 | N | LYS | A | 595 | 79.877 | −67.876 | 68.678 | 1.00 | 29.95 |
| ATOM | 423 | CA | LYS | A | 595 | 79.664 | −68.814 | 67.587 | 1.00 | 30.31 |
| ATOM | 424 | C | LYS | A | 595 | 80.718 | −68.521 | 66.521 | 1.00 | 30.44 |
| ATOM | 425 | O | LYS | A | 595 | 81.239 | −67.403 | 66.439 | 1.00 | 30.34 |
| ATOM | 426 | CB | LYS | A | 595 | 78.258 | −68.620 | 67.011 | 1.00 | 30.51 |
| ATOM | 427 | CG | LYS | A | 595 | 78.026 | −67.201 | 66.506 | 1.00 | 30.82 |
| ATOM | 428 | CD | LYS | A | 595 | 76.582 | −66.734 | 66.674 | 1.00 | 31.02 |
| ATOM | 429 | CE | LYS | A | 595 | 75.640 | −67.346 | 65.663 | 1.00 | 31.21 |
| ATOM | 430 | NZ | LYS | A | 595 | 74.275 | −66.732 | 65.777 | 1.00 | 31.33 |
| ATOM | 431 | N | VAL | A | 596 | 81.042 | −69.529 | 65.720 | 1.00 | 30.59 |
| ATOM | 432 | CA | VAL | A | 596 | 82.022 | −69.373 | 64.657 | 1.00 | 30.88 |
| ATOM | 433 | C | VAL | A | 596 | 81.364 | −69.750 | 63.337 | 1.00 | 31.30 |
| ATOM | 434 | O | VAL | A | 596 | 80.774 | −70.829 | 63.206 | 1.00 | 31.13 |
| ATOM | 435 | CB | VAL | A | 596 | 83.257 | −70.274 | 64.888 | 1.00 | 30.78 |
| ATOM | 436 | CG1 | VAL | A | 596 | 84.292 | −70.032 | 63.798 | 1.00 | 30.74 |
| ATOM | 437 | CG2 | VAL | A | 596 | 83.858 | −69.991 | 66.251 | 1.00 | 30.68 |
| ATOM | 438 | N | VAL | A | 597 | 81.461 | −68.856 | 62.362 | 1.00 | 31.82 |
| ATOM | 439 | CA | VAL | A | 597 | 80.863 | −69.098 | 61.059 | 1.00 | 32.51 |
| ATOM | 440 | C | VAL | A | 597 | 81.899 | −69.018 | 59.946 | 1.00 | 33.15 |
| ATOM | 441 | O | VAL | A | 597 | 82.909 | −68.324 | 60.060 | 1.00 | 33.04 |
| ATOM | 442 | CB | VAL | A | 597 | 79.744 | −68.071 | 60.753 | 1.00 | 32.44 |
| ATOM | 443 | CG1 | VAL | A | 597 | 78.744 | −68.028 | 61.895 | 1.00 | 32.25 |
| ATOM | 444 | CG2 | VAL | A | 597 | 80.347 | −66.701 | 60.518 | 1.00 | 32.40 |
| ATOM | 445 | N | GLU | A | 598 | 81.644 | −69.746 | 58.869 | 1.00 | 33.94 |
| ATOM | 446 | CA | GLU | A | 598 | 82.543 | −69.739 | 57.732 | 1.00 | 34.87 |
| ATOM | 447 | C | GLU | A | 598 | 82.148 | −68.523 | 56.908 | 1.00 | 35.39 |
| ATOM | 448 | O | GLU | A | 598 | 81.043 | −68.007 | 57.051 | 1.00 | 35.36 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 449 | CB | GLU | A | 598 | 82.360 | −71.012 | 56.904 | 1.00 | 35.00 |
| ATOM | 450 | CG | GLU | A | 598 | 83.528 | −71.336 | 55.992 | 1.00 | 35.35 |
| ATOM | 451 | CD | GLU | A | 598 | 83.194 | −72.435 | 54.996 | 1.00 | 35.55 |
| ATOM | 452 | OE1 | GLU | A | 598 | 82.464 | −72.150 | 54.020 | 1.00 | 35.67 |
| ATOM | 453 | OE2 | GLU | A | 598 | 83.652 | −73.580 | 55.189 | 1.00 | 35.63 |
| ATOM | 454 | N | ALA | A | 599 | 83.058 | −68.054 | 56.066 | 1.00 | 36.17 |
| ATOM | 455 | CA | ALA | A | 599 | 82.787 | −66.907 | 55.215 | 1.00 | 37.00 |
| ATOM | 456 | C | ALA | A | 599 | 83.974 | −66.706 | 54.295 | 1.00 | 37.65 |
| ATOM | 457 | O | ALA | A | 599 | 85.050 | −67.251 | 54.530 | 1.00 | 37.69 |
| ATOM | 458 | CB | ALA | A | 599 | 82.556 | −65.662 | 56.061 | 1.00 | 36.91 |
| ATOM | 459 | N | THR | A | 600 | 83.770 | −65.944 | 53.230 | 1.00 | 38.50 |
| ATOM | 460 | CA | THR | A | 600 | 84.848 | −65.664 | 52.294 | 1.00 | 39.39 |
| ATOM | 461 | C | THR | A | 600 | 85.191 | −64.189 | 52.438 | 1.00 | 39.97 |
| ATOM | 462 | O | THR | A | 600 | 84.303 | −63.338 | 52.501 | 1.00 | 39.98 |
| ATOM | 463 | CB | THR | A | 600 | 84.436 | −65.969 | 50.833 | 1.00 | 39.39 |
| ATOM | 464 | OG1 | THR | A | 600 | 83.192 | −65.323 | 50.540 | 1.00 | 39.58 |
| ATOM | 465 | CG2 | THR | A | 600 | 84.292 | −67.474 | 50.620 | 1.00 | 39.42 |
| ATOM | 466 | N | ALA | A | 601 | 86.484 | −63.899 | 52.512 | 1.00 | 40.75 |
| ATOM | 467 | CA | ALA | A | 601 | 86.955 | −62.529 | 52.670 | 1.00 | 41.63 |
| ATOM | 468 | C | ALA | A | 601 | 87.458 | −61.922 | 51.358 | 1.00 | 42.22 |
| ATOM | 469 | O | ALA | A | 601 | 88.433 | −62.397 | 50.774 | 1.00 | 42.29 |
| ATOM | 470 | CB | ALA | A | 601 | 88.058 | −62.482 | 53.721 | 1.00 | 41.53 |
| ATOM | 471 | N | PHE | A | 602 | 86.783 | −60.864 | 50.917 | 1.00 | 42.96 |
| ATOM | 472 | CA | PHE | A | 602 | 87.135 | −60.150 | 49.691 | 1.00 | 43.78 |
| ATOM | 473 | C | PHE | A | 602 | 87.840 | −58.841 | 50.025 | 1.00 | 44.20 |
| ATOM | 474 | O | PHE | A | 602 | 87.269 | −57.973 | 50.684 | 1.00 | 44.26 |
| ATOM | 475 | CB | PHE | A | 602 | 85.888 | −59.811 | 48.871 | 1.00 | 43.97 |
| ATOM | 476 | CG | PHE | A | 602 | 85.094 | −61.006 | 48.446 | 1.00 | 44.28 |
| ATOM | 477 | CD1 | PHE | A | 602 | 83.981 | −61.411 | 49.175 | 1.00 | 44.40 |
| ATOM | 478 | CD2 | PHE | A | 602 | 85.455 | −61.725 | 47.311 | 1.00 | 44.38 |
| ATOM | 479 | CE1 | PHE | A | 602 | 83.234 | −62.516 | 48.782 | 1.00 | 44.49 |
| ATOM | 480 | CE2 | PHE | A | 602 | 84.715 | −62.834 | 46.909 | 1.00 | 44.51 |
| ATOM | 481 | CZ | PHE | A | 602 | 83.601 | −63.226 | 47.648 | 1.00 | 44.52 |
| ATOM | 482 | N | GLY | A | 603 | 89.073 | −58.696 | 49.557 | 1.00 | 44.71 |
| ATOM | 483 | CA | GLY | A | 603 | 89.806 | −57.472 | 49.816 | 1.00 | 45.42 |
| ATOM | 484 | C | GLY | A | 603 | 90.488 | −57.472 | 51.167 | 1.00 | 45.88 |
| ATOM | 485 | O | GLY | A | 603 | 90.668 | −56.420 | 51.781 | 1.00 | 45.94 |
| ATOM | 486 | N | LEU | A | 604 | 90.858 | −58.660 | 51.631 | 1.00 | 46.38 |
| ATOM | 487 | CA | LEU | A | 604 | 91.539 | −58.819 | 52.908 | 1.00 | 46.85 |
| ATOM | 488 | C | LEU | A | 604 | 92.974 | −59.240 | 52.621 | 1.00 | 47.15 |
| ATOM | 489 | O | LEU | A | 604 | 93.213 | −60.272 | 51.989 | 1.00 | 47.20 |
| ATOM | 490 | CB | LEU | A | 604 | 90.837 | −59.888 | 53.754 | 1.00 | 46.90 |
| ATOM | 491 | CG | LEU | A | 604 | 91.311 | −60.096 | 55.197 | 1.00 | 46.97 |
| ATOM | 492 | CD1 | LEU | A | 604 | 90.336 | −61.012 | 55.916 | 1.00 | 47.02 |
| ATOM | 493 | CD2 | LEU | A | 604 | 92.710 | −60.686 | 55.218 | 1.00 | 47.03 |
| ATOM | 494 | N | GLY | A | 605 | 93.925 | −58.436 | 53.085 | 1.00 | 47.50 |
| ATOM | 495 | CA | GLY | A | 605 | 95.326 | −58.742 | 52.861 | 1.00 | 47.91 |
| ATOM | 496 | C | GLY | A | 605 | 95.911 | −57.958 | 51.701 | 1.00 | 48.18 |
| ATOM | 497 | O | GLY | A | 605 | 97.130 | −57.820 | 51.593 | 1.00 | 48.23 |
| ATOM | 498 | N | LYS | A | 606 | 95.046 | −57.445 | 50.829 | 1.00 | 48.43 |
| ATOM | 499 | CA | LYS | A | 606 | 95.492 | −56.673 | 49.673 | 1.00 | 48.69 |
| ATOM | 500 | C | LYS | A | 606 | 94.328 | −56.114 | 48.856 | 1.00 | 48.80 |
| ATOM | 501 | O | LYS | A | 606 | 93.220 | −55.942 | 49.365 | 1.00 | 48.89 |
| ATOM | 502 | CB | LYS | A | 606 | 96.378 | −57.534 | 48.766 | 1.00 | 48.78 |
| ATOM | 503 | CG | LYS | A | 606 | 95.736 | −58.841 | 48.335 | 1.00 | 48.86 |
| ATOM | 504 | CD | LYS | A | 606 | 96.431 | −59.426 | 47.118 | 1.00 | 48.96 |
| ATOM | 505 | CE | LYS | A | 606 | 96.162 | −58.585 | 45.877 | 1.00 | 49.07 |
| ATOM | 506 | NZ | LYS | A | 606 | 96.764 | −59.174 | 44.645 | 1.00 | 49.13 |
| ATOM | 507 | N | ALA | A | 607 | 94.590 | −55.835 | 47.582 | 1.00 | 48.89 |
| ATOM | 508 | CA | ALA | A | 607 | 93.578 | −55.289 | 46.683 | 1.00 | 48.92 |
| ATOM | 509 | C | ALA | A | 607 | 92.264 | −56.061 | 46.763 | 1.00 | 48.92 |
| ATOM | 510 | O | ALA | A | 607 | 91.190 | −55.467 | 46.902 | 1.00 | 48.97 |
| ATOM | 511 | CB | ALA | A | 607 | 94.101 | −55.298 | 45.243 | 1.00 | 48.97 |
| ATOM | 512 | N | ASP | A | 608 | 92.358 | −57.385 | 46.674 | 1.00 | 48.81 |
| ATOM | 513 | CA | ASP | A | 608 | 91.183 | −58.250 | 46.725 | 1.00 | 48.66 |
| ATOM | 514 | C | ASP | A | 608 | 91.639 | −59.702 | 46.549 | 1.00 | 48.40 |
| ATOM | 515 | O | ASP | A | 608 | 91.367 | −60.328 | 45.526 | 1.00 | 48.44 |
| ATOM | 516 | CB | ASP | A | 608 | 90.206 | −57.842 | 45.612 | 1.00 | 48.87 |
| ATOM | 517 | CG | ASP | A | 608 | 88.871 | −58.562 | 45.700 | 1.00 | 49.01 |
| ATOM | 518 | OD1 | ASP | A | 608 | 88.838 | −59.775 | 45.427 | 1.00 | 49.14 |
| ATOM | 519 | OD2 | ASP | A | 608 | 87.854 | −57.913 | 46.038 | 1.00 | 49.13 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 520 | N | ALA | A | 609 | 92.333 | −60.219 | 47.564 | 1.00 | 48.01 |
|---|---|---|---|---|---|---|---|---|---|---|
| ATOM | 521 | CA | ALA | A | 609 | 92.871 | −61.583 | 47.562 | 1.00 | 47.59 |
| ATOM | 522 | C | ALA | A | 609 | 91.829 | −62.704 | 47.527 | 1.00 | 47.24 |
| ATOM | 523 | O | ALA | A | 609 | 92.071 | −63.758 | 46.942 | 1.00 | 47.24 |
| ATOM | 524 | CB | ALA | A | 609 | 93.790 | −61.773 | 48.766 | 1.00 | 47.63 |
| ATOM | 525 | N | VAL | A | 610 | 90.684 | −62.487 | 48.164 | 1.00 | 46.80 |
| ATOM | 526 | CA | VAL | A | 610 | 89.613 | −63.488 | 48.182 | 1.00 | 46.25 |
| ATOM | 527 | C | VAL | A | 610 | 90.038 | −64.836 | 48.769 | 1.00 | 45.79 |
| ATOM | 528 | O | VAL | A | 610 | 90.797 | −65.586 | 48.151 | 1.00 | 45.80 |
| ATOM | 529 | CB | VAL | A | 610 | 89.075 | −63.761 | 46.764 | 1.00 | 46.31 |
| ATOM | 530 | CG1 | VAL | A | 610 | 87.715 | −64.435 | 46.846 | 1.00 | 46.35 |
| ATOM | 531 | CG2 | VAL | A | 610 | 88.986 | −62.476 | 45.986 | 1.00 | 46.32 |
| ATOM | 532 | N | LEU | A | 611 | 89.539 | −65.142 | 49.963 | 1.00 | 45.17 |
| ATOM | 533 | CA | LEU | A | 611 | 89.843 | −66.407 | 50.625 | 1.00 | 44.44 |
| ATOM | 534 | C | LEU | A | 611 | 88.762 | −66.765 | 51.634 | 1.00 | 43.81 |
| ATOM | 535 | O | LEU | A | 611 | 87.967 | −65.917 | 52.036 | 1.00 | 43.73 |
| ATOM | 536 | CB | LEU | A | 611 | 91.210 | −66.346 | 51.317 | 1.00 | 44.56 |
| ATOM | 537 | CG | LEU | A | 611 | 91.612 | −65.047 | 52.019 | 1.00 | 44.66 |
| ATOM | 538 | CD1 | LEU | A | 611 | 90.583 | −64.666 | 53.058 | 1.00 | 44.66 |
| ATOM | 539 | CD2 | LEU | A | 611 | 92.985 | −65.226 | 52.662 | 1.00 | 44.71 |
| ATOM | 540 | N | LYS | A | 612 | 88.723 | −68.031 | 52.030 | 1.00 | 43.05 |
| ATOM | 541 | CA | LYS | A | 612 | 87.728 | −68.466 | 52.995 | 1.00 | 42.19 |
| ATOM | 542 | C | LYS | A | 612 | 88.330 | −68.318 | 54.382 | 1.00 | 41.42 |
| ATOM | 543 | O | LYS | A | 612 | 89.493 | −68.643 | 54.603 | 1.00 | 41.31 |
| ATOM | 544 | CB | LYS | A | 612 | 87.310 | −69.917 | 52.728 | 1.00 | 42.35 |
| ATOM | 545 | CG | LYS | A | 612 | 86.143 | −70.368 | 53.594 | 1.00 | 42.49 |
| ATOM | 546 | CD | LYS | A | 612 | 85.360 | −71.510 | 52.967 | 1.00 | 42.66 |
| ATOM | 547 | CE | LYS | A | 612 | 86.176 | −72.791 | 52.871 | 1.00 | 42.77 |
| ATOM | 548 | NZ | LYS | A | 612 | 85.352 | −73.920 | 52.340 | 1.00 | 42.77 |
| ATOM | 549 | N | VAL | A | 613 | 87.530 | −67.808 | 55.310 | 1.00 | 40.59 |
| ATOM | 550 | CA | VAL | A | 613 | 87.988 | −67.585 | 56.673 | 1.00 | 39.70 |
| ATOM | 551 | C | VAL | A | 613 | 86.958 | −68.012 | 57.715 | 1.00 | 39.11 |
| ATOM | 552 | O | VAL | A | 613 | 85.838 | −68.403 | 57.383 | 1.00 | 38.96 |
| ATOM | 553 | CB | VAL | A | 613 | 88.299 | −66.092 | 56.897 | 1.00 | 39.66 |
| ATOM | 554 | CG1 | VAL | A | 613 | 89.397 | −65.641 | 55.963 | 1.00 | 39.57 |
| ATOM | 555 | CG2 | VAL | A | 613 | 87.045 | −65.265 | 56.669 | 1.00 | 39.56 |
| ATOM | 556 | N | ALA | A | 614 | 87.362 | −67.929 | 58.978 | 1.00 | 38.40 |
| ATOM | 557 | CA | ALA | A | 614 | 86.499 | −68.267 | 60.101 | 1.00 | 37.73 |
| ATOM | 558 | C | ALA | A | 614 | 86.249 | −66.981 | 60.874 | 1.00 | 37.28 |
| ATOM | 559 | O | ALA | A | 614 | 87.185 | −66.245 | 61.177 | 1.00 | 37.13 |
| ATOM | 560 | CB | ALA | A | 614 | 87.176 | −69.289 | 60.994 | 1.00 | 37.69 |
| ATOM | 561 | N | VAL | A | 615 | 84.989 | −66.706 | 61.188 | 1.00 | 36.75 |
| ATOM | 562 | CA | VAL | A | 615 | 84.643 | −65.496 | 61.919 | 1.00 | 36.29 |
| ATOM | 563 | C | VAL | A | 615 | 83.986 | −65.815 | 63.254 | 1.00 | 36.10 |
| ATOM | 564 | O | VAL | A | 615 | 82.931 | −66.450 | 63.300 | 1.00 | 35.95 |
| ATOM | 565 | CB | VAL | A | 615 | 83.673 | −64.606 | 61.105 | 1.00 | 36.20 |
| ATOM | 566 | CG1 | VAL | A | 615 | 83.362 | −63.337 | 61.878 | 1.00 | 36.07 |
| ATOM | 567 | CG2 | VAL | A | 615 | 84.275 | −64.271 | 59.751 | 1.00 | 36.14 |
| ATOM | 568 | N | LYS | A | 616 | 84.615 | −65.382 | 64.342 | 1.00 | 35.89 |
| ATOM | 569 | CA | LYS | A | 616 | 84.052 | −65.608 | 65.664 | 1.00 | 35.73 |
| ATOM | 570 | C | LYS | A | 616 | 83.322 | −64.345 | 66.095 | 1.00 | 35.68 |
| ATOM | 571 | O | LYS | A | 616 | 83.802 | −63.235 | 65.875 | 1.00 | 35.68 |
| ATOM | 572 | CB | LYS | A | 616 | 85.142 | −65.968 | 66.685 | 1.00 | 35.66 |
| ATOM | 573 | CG | LYS | A | 616 | 84.612 | −66.018 | 68.123 | 1.00 | 35.65 |
| ATOM | 574 | CD | LYS | A | 616 | 85.302 | −67.054 | 69.016 | 1.00 | 35.54 |
| ATOM | 575 | CE | LYS | A | 616 | 86.754 | −66.736 | 69.272 | 1.00 | 35.58 |
| ATOM | 576 | NZ | LYS | A | 616 | 87.297 | −67.521 | 70.419 | 1.00 | 35.32 |
| ATOM | 577 | N | MET | A | 617 | 82.154 | −64.524 | 66.699 | 1.00 | 35.61 |
| ATOM | 578 | CA | MET | A | 617 | 81.336 | −63.407 | 67.158 | 1.00 | 35.66 |
| ATOM | 579 | C | MET | A | 617 | 80.531 | −63.849 | 68.372 | 1.00 | 35.74 |
| ATOM | 580 | O | MET | A | 617 | 80.343 | −65.042 | 68.596 | 1.00 | 35.63 |
| ATOM | 581 | CB | MET | A | 617 | 80.379 | −62.978 | 66.044 | 1.00 | 35.56 |
| ATOM | 582 | CG | MET | A | 617 | 79.450 | −64.104 | 65.588 | 1.00 | 35.42 |
| ATOM | 583 | SD | MET | A | 617 | 78.592 | −63.742 | 64.053 | 1.00 | 35.28 |
| ATOM | 584 | CE | MET | A | 617 | 79.884 | −64.074 | 62.855 | 1.00 | 35.30 |
| ATOM | 585 | N | LEU | A | 618 | 80.059 | −62.891 | 69.158 | 1.00 | 35.91 |
| ATOM | 586 | CA | LEU | A | 618 | 79.258 | −63.224 | 70.327 | 1.00 | 36.21 |
| ATOM | 587 | C | LEU | A | 618 | 77.873 | −63.660 | 69.868 | 1.00 | 36.48 |
| ATOM | 588 | O | LEU | A | 618 | 77.430 | −63.291 | 68.783 | 1.00 | 36.44 |
| ATOM | 589 | CB | LEU | A | 618 | 79.122 | −62.017 | 71.258 | 1.00 | 36.04 |
| ATOM | 590 | CG | LEU | A | 618 | 80.370 | −61.524 | 71.988 | 1.00 | 35.97 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 591 | CD1 | LEU | A | 618 | 79.995 | −60.378 | 72.920 | 1.00 | 35.87 |
|---|---|---|---|---|---|---|---|---|---|---|
| ATOM | 592 | CD2 | LEU | A | 618 | 80.987 | −62.665 | 72.775 | 1.00 | 35.81 |
| ATOM | 593 | N | LYS | A | 619 | 77.201 | −64.462 | 70.684 | 1.00 | 36.88 |
| ATOM | 594 | CA | LYS | A | 619 | 75.853 | −64.894 | 70.350 | 1.00 | 37.35 |
| ATOM | 595 | C | LYS | A | 619 | 74.933 | −63.746 | 70.750 | 1.00 | 37.68 |
| ATOM | 596 | O | LYS | A | 619 | 73.955 | −63.458 | 70.066 | 1.00 | 37.71 |
| ATOM | 597 | CB | LYS | A | 619 | 75.480 | −66.172 | 71.110 | 1.00 | 37.25 |
| ATOM | 598 | CG | LYS | A | 619 | 76.358 | −67.358 | 70.766 | 1.00 | 37.25 |
| ATOM | 599 | CD | LYS | A | 619 | 75.641 | −68.685 | 70.973 | 1.00 | 37.26 |
| ATOM | 600 | CE | LYS | A | 619 | 75.331 | −68.942 | 72.431 | 1.00 | 37.23 |
| ATOM | 601 | NZ | LYS | A | 619 | 74.619 | −70.240 | 72.600 | 1.00 | 37.22 |
| ATOM | 602 | N | SER | A | 620 | 75.273 | −63.086 | 71.857 | 1.00 | 38.19 |
| ATOM | 603 | CA | SER | A | 620 | 74.509 | −61.945 | 72.370 | 1.00 | 38.68 |
| ATOM | 604 | C | SER | A | 620 | 75.422 | −60.853 | 72.934 | 1.00 | 39.01 |
| ATOM | 605 | O | SER | A | 620 | 76.350 | −61.139 | 73.697 | 1.00 | 39.06 |
| ATOM | 606 | CB | SER | A | 620 | 73.542 | −62.394 | 73.465 | 1.00 | 38.72 |
| ATOM | 607 | OG | SER | A | 620 | 72.982 | −61.271 | 74.127 | 1.00 | 38.83 |
| ATOM | 608 | N | THR | A | 621 | 75.157 | −59.601 | 72.561 | 1.00 | 39.36 |
| ATOM | 609 | CA | THR | A | 621 | 75.960 | −58.479 | 73.045 | 1.00 | 39.68 |
| ATOM | 610 | C | THR | A | 621 | 75.351 | −57.884 | 74.316 | 1.00 | 39.81 |
| ATOM | 611 | O | THR | A | 621 | 75.638 | −56.744 | 74.685 | 1.00 | 39.89 |
| ATOM | 612 | CB | THR | A | 621 | 76.085 | −57.364 | 71.973 | 1.00 | 39.76 |
| ATOM | 613 | OG1 | THR | A | 621 | 74.806 | −56.751 | 71.750 | 1.00 | 39.92 |
| ATOM | 614 | CG2 | THR | A | 621 | 76.593 | −57.947 | 70.660 | 1.00 | 39.84 |
| ATOM | 615 | N | ALA | A | 622 | 74.520 | −58.672 | 74.992 | 1.00 | 39.92 |
| ATOM | 616 | CA | ALA | A | 622 | 73.866 | −58.224 | 76.214 | 1.00 | 39.99 |
| ATOM | 617 | C | ALA | A | 622 | 74.837 | −57.938 | 77.357 | 1.00 | 40.09 |
| ATOM | 618 | O | ALA | A | 622 | 74.811 | −56.854 | 77.945 | 1.00 | 40.12 |
| ATOM | 619 | CB | ALA | A | 622 | 72.850 | −59.256 | 76.658 | 1.00 | 40.04 |
| ATOM | 620 | N | HIS | A | 623 | 75.696 | −58.906 | 77.666 | 1.00 | 40.12 |
| ATOM | 621 | CA | HIS | A | 623 | 76.646 | −58.758 | 78.766 | 1.00 | 40.11 |
| ATOM | 622 | C | HIS | A | 623 | 77.975 | −58.114 | 78.384 | 1.00 | 39.94 |
| ATOM | 623 | O | HIS | A | 623 | 78.738 | −58.651 | 77.581 | 1.00 | 39.94 |
| ATOM | 624 | CB | HIS | A | 623 | 76.893 | −60.122 | 79.414 | 1.00 | 40.37 |
| ATOM | 625 | CG | HIS | A | 623 | 75.657 | −60.748 | 79.982 | 1.00 | 40.65 |
| ATOM | 626 | ND1 | HIS | A | 623 | 74.515 | −60.946 | 79.236 | 1.00 | 40.76 |
| ATOM | 627 | CD2 | HIS | A | 623 | 75.382 | −61.217 | 81.223 | 1.00 | 40.78 |
| ATOM | 628 | CE1 | HIS | A | 623 | 73.590 | −61.511 | 79.992 | 1.00 | 40.83 |
| ATOM | 629 | NE2 | HIS | A | 623 | 74.090 | −61.686 | 81.202 | 1.00 | 40.86 |
| ATOM | 630 | N | ALA | A | 624 | 78.249 | −56.958 | 78.982 | 1.00 | 39.68 |
| ATOM | 631 | CA | ALA | A | 624 | 79.481 | −56.228 | 78.709 | 1.00 | 39.39 |
| ATOM | 632 | C | ALA | A | 624 | 80.727 | −57.065 | 78.986 | 1.00 | 39.13 |
| ATOM | 633 | O | ALA | A | 624 | 81.736 | −56.938 | 78.291 | 1.00 | 39.14 |
| ATOM | 634 | CB | ALA | A | 624 | 79.518 | −54.946 | 79.533 | 1.00 | 39.46 |
| ATOM | 635 | N | ASP | A | 625 | 80.663 | −57.918 | 80.000 | 1.00 | 38.80 |
| ATOM | 636 | CA | ASP | A | 625 | 81.808 | −58.751 | 80.333 | 1.00 | 38.44 |
| ATOM | 637 | C | ASP | A | 625 | 82.092 | −59.730 | 79.193 | 1.00 | 38.04 |
| ATOM | 638 | O | ASP | A | 625 | 83.245 | −60.063 | 78.928 | 1.00 | 38.01 |
| ATOM | 639 | CB | ASP | A | 625 | 81.566 | −59.499 | 81.654 | 1.00 | 38.63 |
| ATOM | 640 | CG | ASP | A | 625 | 80.518 | −60.588 | 81.536 | 1.00 | 38.79 |
| ATOM | 641 | OD1 | ASP | A | 625 | 79.395 | −60.304 | 81.066 | 1.00 | 39.01 |
| ATOM | 642 | OD2 | ASP | A | 625 | 80.820 | −61.733 | 81.930 | 1.00 | 38.94 |
| ATOM | 643 | N | GLU | A | 626 | 81.039 | −60.178 | 78.514 | 1.00 | 37.56 |
| ATOM | 644 | CA | GLU | A | 626 | 81.197 | −61.094 | 77.391 | 1.00 | 36.99 |
| ATOM | 645 | C | GLU | A | 626 | 81.783 | −60.336 | 76.201 | 1.00 | 36.51 |
| ATOM | 646 | O | GLU | A | 626 | 82.567 | −60.886 | 75.425 | 1.00 | 36.42 |
| ATOM | 647 | CB | GLU | A | 626 | 79.850 | −61.712 | 77.009 | 1.00 | 37.10 |
| ATOM | 648 | CG | GLU | A | 626 | 79.208 | −62.507 | 78.137 | 1.00 | 37.26 |
| ATOM | 649 | CD | GLU | A | 626 | 77.945 | −63.232 | 77.716 | 1.00 | 37.33 |
| ATOM | 650 | OE1 | GLU | A | 626 | 77.290 | −63.832 | 78.596 | 1.00 | 37.34 |
| ATOM | 651 | OE2 | GLU | A | 626 | 77.610 | −63.206 | 76.512 | 1.00 | 37.39 |
| ATOM | 652 | N | LYS | A | 627 | 81.399 | −59.068 | 76.064 | 1.00 | 35.85 |
| ATOM | 653 | CA | LYS | A | 627 | 81.900 | −58.239 | 74.973 | 1.00 | 35.17 |
| ATOM | 654 | C | LYS | A | 627 | 83.372 | −57.920 | 75.191 | 1.00 | 34.62 |
| ATOM | 655 | O | LYS | A | 627 | 84.148 | −57.872 | 74.239 | 1.00 | 34.55 |
| ATOM | 656 | CB | LYS | A | 627 | 81.097 | −56.936 | 74.868 | 1.00 | 35.33 |
| ATOM | 657 | CG | LYS | A | 627 | 79.686 | −57.125 | 74.323 | 1.00 | 35.44 |
| ATOM | 658 | CD | LYS | A | 627 | 78.911 | −55.808 | 74.229 | 1.00 | 35.58 |
| ATOM | 659 | CE | LYS | A | 627 | 78.497 | −55.295 | 75.604 | 1.00 | 35.74 |
| ATOM | 660 | NZ | LYS | A | 627 | 77.567 | −54.122 | 75.516 | 1.00 | 35.91 |
| ATOM | 661 | N | GLU | A | 628 | 83.759 | −57.704 | 76.445 | 1.00 | 33.92 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 662 | CA  | GLU | A | 628 | 85.148 | −57.393 | 76.744 | 1.00 | 33.26 |
|------|-----|-----|-----|---|-----|--------|---------|--------|------|-------|
| ATOM | 663 | C   | GLU | A | 628 | 86.013 | −58.647 | 76.622 | 1.00 | 32.59 |
| ATOM | 664 | O   | GLU | A | 628 | 87.214 | −58.558 | 76.372 | 1.00 | 32.46 |
| ATOM | 665 | CB  | GLU | A | 628 | 85.279 | −56.796 | 78.151 | 1.00 | 33.59 |
| ATOM | 666 | CG  | GLU | A | 628 | 86.697 | −56.316 | 78.484 | 1.00 | 34.00 |
| ATOM | 667 | CD  | GLU | A | 628 | 87.320 | −55.480 | 77.365 | 1.00 | 34.25 |
| ATOM | 668 | OE1 | GLU | A | 628 | 86.697 | −54.478 | 76.941 | 1.00 | 34.34 |
| ATOM | 669 | OE2 | GLU | A | 628 | 88.438 | −55.826 | 76.909 | 1.00 | 34.45 |
| ATOM | 670 | N   | ALA | A | 629 | 85.392 | −59.810 | 76.794 | 1.00 | 31.73 |
| ATOM | 671 | CA  | ALA | A | 629 | 86.105 | −61.079 | 76.686 | 1.00 | 30.91 |
| ATOM | 672 | C   | ALA | A | 629 | 86.567 | −61.271 | 75.245 | 1.00 | 30.32 |
| ATOM | 673 | O   | ALA | A | 629 | 87.712 | −61.662 | 74.993 | 1.00 | 30.23 |
| ATOM | 674 | CB  | ALA | A | 629 | 85.194 | −62.233 | 77.105 | 1.00 | 30.91 |
| ATOM | 675 | N   | LEU | A | 630 | 85.670 | −60.991 | 74.302 | 1.00 | 29.61 |
| ATOM | 676 | CA  | LEU | A | 630 | 85.991 | −61.125 | 72.887 | 1.00 | 28.88 |
| ATOM | 677 | C   | LEU | A | 630 | 87.097 | −60.145 | 72.512 | 1.00 | 28.48 |
| ATOM | 678 | O   | LEU | A | 630 | 87.997 | −60.490 | 71.744 | 1.00 | 28.45 |
| ATOM | 679 | CB  | LEU | A | 630 | 84.750 | −60.874 | 72.022 | 1.00 | 28.73 |
| ATOM | 680 | CG  | LEU | A | 630 | 84.940 | −61.144 | 70.526 | 1.00 | 28.59 |
| ATOM | 681 | CD1 | LEU | A | 630 | 85.321 | −62.603 | 70.316 | 1.00 | 28.58 |
| ATOM | 682 | CD2 | LEU | A | 630 | 83.661 | −60.813 | 69.767 | 1.00 | 28.47 |
| ATOM | 683 | N   | MET | A | 631 | 87.032 | −58.925 | 73.047 | 1.00 | 28.01 |
| ATOM | 684 | CA  | MET | A | 631 | 88.062 | −57.923 | 72.766 | 1.00 | 27.59 |
| ATOM | 685 | C   | MET | A | 631 | 89.417 | −58.370 | 73.314 | 1.00 | 27.25 |
| ATOM | 686 | O   | MET | A | 631 | 90.448 | −58.189 | 72.660 | 1.00 | 27.11 |
| ATOM | 687 | CB  | MET | A | 631 | 87.693 | −56.560 | 73.369 | 1.00 | 27.78 |
| ATOM | 688 | CG  | MET | A | 631 | 86.659 | −55.764 | 72.568 | 1.00 | 27.90 |
| ATOM | 689 | SD  | MET | A | 631 | 87.094 | −55.583 | 70.812 | 1.00 | 28.18 |
| ATOM | 690 | CE  | MET | A | 631 | 88.568 | −54.526 | 70.900 | 1.00 | 28.00 |
| ATOM | 691 | N   | SER | A | 632 | 89.412 | −58.946 | 74.515 | 1.00 | 26.88 |
| ATOM | 692 | CA  | SER | A | 632 | 90.648 | −59.427 | 75.134 | 1.00 | 26.51 |
| ATOM | 693 | C   | SER | A | 632 | 91.263 | −60.536 | 74.289 | 1.00 | 26.00 |
| ATOM | 694 | O   | SER | A | 632 | 92.472 | −60.543 | 74.054 | 1.00 | 25.94 |
| ATOM | 695 | CB  | SER | A | 632 | 90.385 | −59.956 | 76.549 | 1.00 | 26.75 |
| ATOM | 696 | OG  | SER | A | 632 | 90.092 | −58.904 | 77.457 | 1.00 | 27.17 |
| ATOM | 697 | N   | GLU | A | 633 | 90.436 | −61.482 | 73.846 | 1.00 | 25.41 |
| ATOM | 698 | CA  | GLU | A | 633 | 90.932 | −62.569 | 73.010 | 1.00 | 24.84 |
| ATOM | 699 | C   | GLU | A | 633 | 91.583 | −61.963 | 71.780 | 1.00 | 24.56 |
| ATOM | 700 | O   | GLU | A | 633 | 92.680 | −62.350 | 71.389 | 1.00 | 24.29 |
| ATOM | 701 | CB  | GLU | A | 633 | 89.799 | −63.486 | 72.540 | 1.00 | 24.71 |
| ATOM | 702 | CG  | GLU | A | 633 | 89.203 | −64.393 | 73.591 | 1.00 | 24.53 |
| ATOM | 703 | CD  | GLU | A | 633 | 88.283 | −65.429 | 72.969 | 1.00 | 24.42 |
| ATOM | 704 | OE1 | GLU | A | 633 | 87.756 | −66.276 | 73.705 | 1.00 | 24.37 |
| ATOM | 705 | OE2 | GLU | A | 633 | 88.090 | −65.390 | 71.733 | 1.00 | 24.33 |
| ATOM | 706 | N   | LEU | A | 634 | 90.886 | −61.009 | 71.170 | 1.00 | 24.35 |
| ATOM | 707 | CA  | LEU | A | 634 | 91.377 | −60.344 | 69.969 | 1.00 | 24.28 |
| ATOM | 708 | C   | LEU | A | 634 | 92.720 | −59.665 | 70.227 | 1.00 | 24.40 |
| ATOM | 709 | O   | LEU | A | 634 | 93.668 | −59.827 | 69.454 | 1.00 | 24.27 |
| ATOM | 710 | CB  | LEU | A | 634 | 90.350 | −59.305 | 69.488 | 1.00 | 24.00 |
| ATOM | 711 | CG  | LEU | A | 634 | 90.747 | −58.355 | 68.348 | 1.00 | 23.83 |
| ATOM | 712 | CD1 | LEU | A | 634 | 91.180 | −59.129 | 67.124 | 1.00 | 23.56 |
| ATOM | 713 | CD2 | LEU | A | 634 | 89.561 | −57.445 | 68.015 | 1.00 | 23.68 |
| ATOM | 714 | N   | LYS | A | 635 | 92.797 | −58.920 | 71.325 | 1.00 | 24.66 |
| ATOM | 715 | CA  | LYS | A | 635 | 94.027 | −58.199 | 71.667 | 1.00 | 24.96 |
| ATOM | 716 | C   | LYS | A | 635 | 95.236 | −59.111 | 71.835 | 1.00 | 25.03 |
| ATOM | 717 | O   | LYS | A | 635 | 96.346 | −58.775 | 71.412 | 1.00 | 24.99 |
| ATOM | 718 | CB  | LYS | A | 635 | 93.818 | −57.378 | 72.941 | 1.00 | 25.11 |
| ATOM | 719 | CG  | LYS | A | 635 | 92.836 | −56.235 | 72.781 | 1.00 | 25.42 |
| ATOM | 720 | CD  | LYS | A | 635 | 92.764 | −55.419 | 74.056 | 1.00 | 25.79 |
| ATOM | 721 | CE  | LYS | A | 635 | 91.785 | −54.267 | 73.935 | 1.00 | 26.08 |
| ATOM | 722 | NZ  | LYS | A | 635 | 91.693 | −53.535 | 75.237 | 1.00 | 26.35 |
| ATOM | 723 | N   | ILE | A | 636 | 95.025 | −60.263 | 72.460 | 1.00 | 25.15 |
| ATOM | 724 | CA  | ILE | A | 636 | 96.114 | −61.211 | 72.664 | 1.00 | 25.25 |
| ATOM | 725 | C   | ILE | A | 636 | 96.490 | −61.865 | 71.341 | 1.00 | 25.36 |
| ATOM | 726 | O   | ILE | A | 636 | 97.669 | −61.942 | 70.989 | 1.00 | 25.33 |
| ATOM | 727 | CB  | ILE | A | 636 | 95.719 | −62.272 | 73.716 | 1.00 | 25.30 |
| ATOM | 728 | CG1 | ILE | A | 636 | 95.695 | −61.614 | 75.102 | 1.00 | 25.35 |
| ATOM | 729 | CG2 | ILE | A | 636 | 96.703 | −63.440 | 73.691 | 1.00 | 25.29 |
| ATOM | 730 | CD1 | ILE | A | 636 | 95.069 | −62.440 | 76.180 | 1.00 | 25.41 |
| ATOM | 731 | N   | MET | A | 637 | 95.495 | −62.332 | 70.599 | 1.00 | 25.51 |
| ATOM | 732 | CA  | MET | A | 637 | 95.772 | −62.950 | 69.307 | 1.00 | 25.73 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 733 | C | MET | A | 637 | 96.510 | −61.950 | 68.420 | 1.00 | 25.98 |
|---|---|---|---|---|---|---|---|---|---|---|
| ATOM | 734 | O | MET | A | 637 | 97.405 | −62.326 | 67.658 | 1.00 | 26.02 |
| ATOM | 735 | CB | MET | A | 637 | 94.469 | −63.410 | 68.651 | 1.00 | 25.60 |
| ATOM | 736 | CG | MET | A | 637 | 93.868 | −64.626 | 69.325 | 1.00 | 25.35 |
| ATOM | 737 | SD | MET | A | 637 | 92.163 | −64.952 | 68.847 | 1.00 | 25.11 |
| ATOM | 738 | CE | MET | A | 637 | 92.354 | −65.159 | 67.093 | 1.00 | 24.99 |
| ATOM | 739 | N | SER | A | 638 | 96.146 | −60.675 | 68.531 | 1.00 | 26.22 |
| ATOM | 740 | CA | SER | A | 638 | 96.809 | −59.633 | 67.753 | 1.00 | 26.65 |
| ATOM | 741 | C | SER | A | 638 | 98.283 | −59.582 | 68.133 | 1.00 | 26.85 |
| ATOM | 742 | O | SER | A | 638 | 99.166 | −59.618 | 67.278 | 1.00 | 26.84 |
| ATOM | 743 | CB | SER | A | 638 | 96.194 | −58.262 | 68.040 | 1.00 | 26.66 |
| ATOM | 744 | OG | SER | A | 638 | 94.896 | −58.150 | 67.497 | 1.00 | 26.93 |
| ATOM | 745 | N | HIS | A | 639 | 98.525 | −59.493 | 69.434 | 1.00 | 27.16 |
| ATOM | 746 | CA | HIS | A | 639 | 99.871 | −59.421 | 69.989 | 1.00 | 27.52 |
| ATOM | 747 | C | HIS | A | 639 | 100.769 | −60.597 | 69.621 | 1.00 | 27.71 |
| ATOM | 748 | O | HIS | A | 639 | 101.950 | −60.419 | 69.319 | 1.00 | 27.71 |
| ATOM | 749 | CB | HIS | A | 639 | 99.778 | −59.325 | 71.513 | 1.00 | 27.61 |
| ATOM | 750 | CG | HIS | A | 639 | 101.105 | −59.337 | 72.202 | 1.00 | 27.81 |
| ATOM | 751 | ND1 | HIS | A | 639 | 101.955 | −58.252 | 72.198 | 1.00 | 27.83 |
| ATOM | 752 | CD2 | HIS | A | 639 | 101.737 | −60.309 | 72.902 | 1.00 | 27.86 |
| ATOM | 753 | CE1 | HIS | A | 639 | 103.053 | −58.555 | 72.868 | 1.00 | 27.99 |
| ATOM | 754 | NE2 | HIS | A | 639 | 102.946 | −59.797 | 73.305 | 1.00 | 27.88 |
| ATOM | 755 | N | LEU | A | 640 | 100.207 | −61.799 | 69.654 | 1.00 | 27.93 |
| ATOM | 756 | CA | LEU | A | 640 | 100.964 | −63.010 | 69.368 | 1.00 | 28.18 |
| ATOM | 757 | C | LEU | A | 640 | 101.793 | −63.014 | 68.099 | 1.00 | 28.30 |
| ATOM | 758 | O | LEU | A | 640 | 102.939 | −63.452 | 68.109 | 1.00 | 28.37 |
| ATOM | 759 | CB | LEU | A | 640 | 100.030 | −64.222 | 69.362 | 1.00 | 28.19 |
| ATOM | 760 | CG | LEU | A | 640 | 99.553 | −64.674 | 70.744 | 1.00 | 28.24 |
| ATOM | 761 | CD1 | LEU | A | 640 | 98.666 | −65.890 | 70.586 | 1.00 | 28.44 |
| ATOM | 762 | CD2 | LEU | A | 640 | 100.750 | −65.009 | 71.632 | 1.00 | 28.36 |
| ATOM | 763 | N | GLY | A | 641 | 101.218 | −62.536 | 67.004 | 1.00 | 28.48 |
| ATOM | 764 | CA | GLY | A | 641 | 101.947 | −62.534 | 65.753 | 1.00 | 28.59 |
| ATOM | 765 | C | GLY | A | 641 | 101.568 | −63.764 | 64.952 | 1.00 | 28.67 |
| ATOM | 766 | O | GLY | A | 641 | 100.780 | −64.593 | 65.415 | 1.00 | 28.64 |
| ATOM | 767 | N | GLN | A | 642 | 102.133 | −63.889 | 63.756 | 1.00 | 28.67 |
| ATOM | 768 | CA | GLN | A | 642 | 101.837 | −65.015 | 62.885 | 1.00 | 28.62 |
| ATOM | 769 | C | GLN | A | 642 | 102.839 | −66.154 | 63.014 | 1.00 | 28.34 |
| ATOM | 770 | O | GLN | A | 642 | 104.027 | −65.934 | 63.240 | 1.00 | 28.26 |
| ATOM | 771 | CB | GLN | A | 642 | 101.792 | −64.532 | 61.429 | 1.00 | 29.03 |
| ATOM | 772 | CG | GLN | A | 642 | 101.419 | −65.598 | 60.405 | 1.00 | 29.59 |
| ATOM | 773 | CD | GLN | A | 642 | 102.556 | −66.565 | 60.092 | 1.00 | 29.90 |
| ATOM | 774 | OE1 | GLN | A | 642 | 102.320 | −67.696 | 59.649 | 1.00 | 30.04 |
| ATOM | 775 | NE2 | GLN | A | 642 | 103.796 | −66.120 | 60.308 | 1.00 | 30.10 |
| ATOM | 776 | N | HIS | A | 643 | 102.342 | −67.381 | 62.888 | 1.00 | 28.01 |
| ATOM | 777 | CA | HIS | A | 643 | 103.194 | −68.562 | 62.926 | 1.00 | 27.70 |
| ATOM | 778 | C | HIS | A | 643 | 102.492 | −69.708 | 62.220 | 1.00 | 27.57 |
| ATOM | 779 | O | HIS | A | 643 | 101.267 | −69.846 | 62.288 | 1.00 | 27.54 |
| ATOM | 780 | CB | HIS | A | 643 | 103.558 | −68.975 | 64.354 | 1.00 | 27.58 |
| ATOM | 781 | CG | HIS | A | 643 | 104.595 | −70.058 | 64.412 | 1.00 | 27.41 |
| ATOM | 782 | ND1 | HIS | A | 643 | 104.296 | −71.388 | 64.205 | 1.00 | 27.40 |
| ATOM | 783 | CD2 | HIS | A | 643 | 105.938 | −70.000 | 64.589 | 1.00 | 27.35 |
| ATOM | 784 | CE1 | HIS | A | 643 | 105.408 | −72.102 | 64.251 | 1.00 | 27.34 |
| ATOM | 785 | NE2 | HIS | A | 643 | 106.419 | −71.283 | 64.482 | 1.00 | 27.32 |
| ATOM | 786 | N | GLU | A | 644 | 103.290 | −70.523 | 61.548 | 1.00 | 27.34 |
| ATOM | 787 | CA | GLU | A | 644 | 102.809 | −71.654 | 60.771 | 1.00 | 27.29 |
| ATOM | 788 | C | GLU | A | 644 | 102.013 | −72.689 | 61.552 | 1.00 | 26.80 |
| ATOM | 789 | O | GLU | A | 644 | 101.121 | −73.332 | 60.992 | 1.00 | 26.74 |
| ATOM | 790 | CB | GLU | A | 644 | 104.009 | −72.324 | 60.088 | 1.00 | 27.80 |
| ATOM | 791 | CG | GLU | A | 644 | 103.727 | −73.645 | 59.394 | 1.00 | 28.62 |
| ATOM | 792 | CD | GLU | A | 644 | 102.954 | −73.493 | 58.101 | 1.00 | 29.09 |
| ATOM | 793 | OE1 | GLU | A | 644 | 102.806 | −74.515 | 57.384 | 1.00 | 29.45 |
| ATOM | 794 | OE2 | GLU | A | 644 | 102.498 | −72.364 | 57.798 | 1.00 | 29.50 |
| ATOM | 795 | N | ASN | A | 645 | 102.312 | −72.841 | 62.841 | 1.00 | 26.16 |
| ATOM | 796 | CA | ASN | A | 645 | 101.622 | −73.846 | 63.635 | 1.00 | 25.62 |
| ATOM | 797 | C | ASN | A | 645 | 100.643 | −73.389 | 64.721 | 1.00 | 25.27 |
| ATOM | 798 | O | ASN | A | 645 | 100.449 | −74.074 | 65.723 | 1.00 | 25.15 |
| ATOM | 799 | CB | ASN | A | 645 | 102.644 | −74.837 | 64.204 | 1.00 | 25.29 |
| ATOM | 800 | CG | ASN | A | 645 | 103.453 | −75.533 | 63.107 | 1.00 | 25.33 |
| ATOM | 801 | OD1 | ASN | A | 645 | 104.657 | −75.298 | 62.961 | 1.00 | 24.96 |
| ATOM | 802 | ND2 | ASN | A | 645 | 102.788 | −76.390 | 62.326 | 1.00 | 24.99 |
| ATOM | 803 | N | ILE | A | 646 | 100.039 | −72.223 | 64.523 | 1.00 | 25.00 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 804 | CA  | ILE | A | 646 | 99.001  | −71.738 | 65.429 | 1.00 | 24.83 |
|------|-----|-----|-----|---|-----|---------|---------|--------|------|-------|
| ATOM | 805 | C   | ILE | A | 646 | 97.899  | −71.246 | 64.493 | 1.00 | 24.64 |
| ATOM | 806 | O   | ILE | A | 646 | 98.157  | −71.008 | 63.313 | 1.00 | 24.43 |
| ATOM | 807 | CB  | ILE | A | 646 | 99.448  | −70.550 | 66.345 | 1.00 | 24.75 |
| ATOM | 808 | CG1 | ILE | A | 646 | 99.716  | −69.300 | 65.508 | 1.00 | 24.81 |
| ATOM | 809 | CG2 | ILE | A | 646 | 100.677 | −70.941 | 67.162 | 1.00 | 24.69 |
| ATOM | 810 | CD1 | ILE | A | 646 | 99.865  | −68.037 | 66.343 | 1.00 | 24.83 |
| ATOM | 811 | N   | VAL | A | 647 | 96.675  | −71.130 | 65.003 | 1.00 | 24.54 |
| ATOM | 812 | CA  | VAL | A | 647 | 95.563  | −70.636 | 64.194 | 1.00 | 24.69 |
| ATOM | 813 | C   | VAL | A | 647 | 95.704  | −69.117 | 64.204 | 1.00 | 24.69 |
| ATOM | 814 | O   | VAL | A | 647 | 95.538  | −68.482 | 65.248 | 1.00 | 24.60 |
| ATOM | 815 | CB  | VAL | A | 647 | 94.199  | −71.033 | 64.799 | 1.00 | 24.52 |
| ATOM | 816 | CG1 | VAL | A | 647 | 93.072  | −70.487 | 63.942 | 1.00 | 24.55 |
| ATOM | 817 | CG2 | VAL | A | 647 | 94.100  | −72.543 | 64.901 | 1.00 | 24.58 |
| ATOM | 818 | N   | ASN | A | 648 | 96.001  | −68.547 | 63.037 | 1.00 | 24.83 |
| ATOM | 819 | CA  | ASN | A | 648 | 96.244  | −67.113 | 62.906 | 1.00 | 25.05 |
| ATOM | 820 | C   | ASN | A | 648 | 95.082  | −66.146 | 62.743 | 1.00 | 25.13 |
| ATOM | 821 | O   | ASN | A | 648 | 94.064  | −66.449 | 62.123 | 1.00 | 25.12 |
| ATOM | 822 | CB  | ASN | A | 648 | 97.222  | −66.861 | 61.749 | 1.00 | 25.25 |
| ATOM | 823 | CG  | ASN | A | 648 | 98.587  | −67.449 | 62.002 | 1.00 | 25.23 |
| ATOM | 824 | OD1 | ASN | A | 648 | 99.284  | −67.051 | 62.936 | 1.00 | 25.51 |
| ATOM | 825 | ND2 | ASN | A | 648 | 98.980  | −68.404 | 61.176 | 1.00 | 25.36 |
| ATOM | 826 | N   | LEU | A | 649 | 95.270  | −64.961 | 63.314 | 1.00 | 25.21 |
| ATOM | 827 | CA  | LEU | A | 649 | 94.309  | −63.879 | 63.215 | 1.00 | 25.36 |
| ATOM | 828 | C   | LEU | A | 649 | 94.561  | −63.263 | 61.843 | 1.00 | 25.51 |
| ATOM | 829 | O   | LEU | A | 649 | 95.708  | −63.229 | 61.378 | 1.00 | 25.49 |
| ATOM | 830 | CB  | LEU | A | 649 | 94.576  | −62.831 | 64.294 | 1.00 | 25.41 |
| ATOM | 831 | CG  | LEU | A | 649 | 93.784  | −61.523 | 64.208 | 1.00 | 25.38 |
| ATOM | 832 | CD1 | LEU | A | 649 | 92.307  | −61.772 | 64.487 | 1.00 | 25.35 |
| ATOM | 833 | CD2 | LEU | A | 649 | 94.351  | −60.539 | 65.216 | 1.00 | 25.25 |
| ATOM | 834 | N   | LEU | A | 650 | 93.502  | −62.769 | 61.206 | 1.00 | 25.58 |
| ATOM | 835 | CA  | LEU | A | 650 | 93.614  | −62.165 | 59.887 | 1.00 | 25.65 |
| ATOM | 836 | C   | LEU | A | 650 | 93.070  | −60.751 | 59.879 | 1.00 | 25.71 |
| ATOM | 837 | O   | LEU | A | 650 | 93.524  | −59.904 | 59.111 | 1.00 | 25.72 |
| ATOM | 838 | CB  | LEU | A | 650 | 92.861  | −63.008 | 58.849 | 1.00 | 25.75 |
| ATOM | 839 | CG  | LEU | A | 650 | 93.388  | −64.419 | 58.569 | 1.00 | 25.83 |
| ATOM | 840 | CD1 | LEU | A | 650 | 92.438  | −65.136 | 57.611 | 1.00 | 25.92 |
| ATOM | 841 | CD2 | LEU | A | 650 | 94.787  | −64.337 | 57.978 | 1.00 | 25.84 |
| ATOM | 842 | N   | GLY | A | 651 | 92.089  | −60.496 | 60.736 | 1.00 | 25.77 |
| ATOM | 843 | CA  | GLY | A | 651 | 91.508  | −59.171 | 60.804 | 1.00 | 25.94 |
| ATOM | 844 | C   | GLY | A | 651 | 90.369  | −59.125 | 61.793 | 1.00 | 26.06 |
| ATOM | 845 | O   | GLY | A | 651 | 90.100  | −60.110 | 62.477 | 1.00 | 25.99 |
| ATOM | 846 | N   | ALA | A | 652 | 89.696  | −57.984 | 61.869 | 1.00 | 26.26 |
| ATOM | 847 | CA  | ALA | A | 652 | 88.580  | −57.839 | 62.785 | 1.00 | 26.59 |
| ATOM | 848 | C   | ALA | A | 652 | 87.677  | −56.676 | 62.399 | 1.00 | 26.83 |
| ATOM | 849 | O   | ALA | A | 652 | 88.109  | −55.728 | 61.740 | 1.00 | 26.87 |
| ATOM | 850 | CB  | ALA | A | 652 | 89.096  | −57.650 | 64.208 | 1.00 | 26.40 |
| ATOM | 851 | N   | CYS | A | 653 | 86.420  | −56.765 | 62.816 | 1.00 | 27.19 |
| ATOM | 852 | CA  | CYS | A | 653 | 85.438  | −55.722 | 62.551 | 1.00 | 27.64 |
| ATOM | 853 | C   | CYS | A | 653 | 84.960  | −55.235 | 63.915 | 1.00 | 27.98 |
| ATOM | 854 | O   | CYS | A | 653 | 84.154  | −55.894 | 64.572 | 1.00 | 28.00 |
| ATOM | 855 | CB  | CYS | A | 653 | 84.272  | −56.294 | 61.736 | 1.00 | 27.63 |
| ATOM | 856 | SG  | CYS | A | 653 | 84.775  | −57.075 | 60.170 | 1.00 | 27.82 |
| ATOM | 857 | N   | THR | A | 654 | 85.463  | −54.083 | 64.350 | 1.00 | 28.35 |
| ATOM | 858 | CA  | THR | A | 654 | 85.083  | −53.567 | 65.658 | 1.00 | 28.73 |
| ATOM | 859 | C   | THR | A | 654 | 84.234  | −52.304 | 65.595 | 1.00 | 29.01 |
| ATOM | 860 | O   | THR | A | 654 | 83.757  | −51.831 | 66.625 | 1.00 | 29.11 |
| ATOM | 861 | CB  | THR | A | 654 | 86.331  | −53.260 | 66.524 | 1.00 | 28.74 |
| ATOM | 862 | OG1 | THR | A | 654 | 87.022  | −52.126 | 65.987 | 1.00 | 28.85 |
| ATOM | 863 | CG2 | THR | A | 654 | 87.286  | −54.449 | 66.528 | 1.00 | 28.79 |
| ATOM | 864 | N   | HIS | A | 655 | 84.039  | −51.765 | 64.395 | 1.00 | 29.24 |
| ATOM | 865 | CA  | HIS | A | 655 | 83.258  | −50.536 | 64.241 | 1.00 | 29.53 |
| ATOM | 866 | C   | HIS | A | 655 | 81.931  | −50.720 | 63.504 | 1.00 | 29.59 |
| ATOM | 867 | O   | HIS | A | 655 | 81.835  | −51.516 | 62.568 | 1.00 | 29.68 |
| ATOM | 868 | CB  | HIS | A | 655 | 84.088  | −49.477 | 63.502 | 1.00 | 29.59 |
| ATOM | 869 | CG  | HIS | A | 655 | 85.350  | −49.093 | 64.209 | 1.00 | 29.73 |
| ATOM | 870 | ND1 | HIS | A | 655 | 85.357  | −48.524 | 65.464 | 1.00 | 29.88 |
| ATOM | 871 | CD2 | HIS | A | 655 | 86.648  | −49.200 | 63.837 | 1.00 | 29.80 |
| ATOM | 872 | CE1 | HIS | A | 655 | 86.604  | −48.296 | 65.836 | 1.00 | 29.87 |
| ATOM | 873 | NE2 | HIS | A | 655 | 87.408  | −48.697 | 64.866 | 1.00 | 29.88 |
| ATOM | 874 | N   | GLY | A | 656 | 80.922  | −49.969 | 63.943 | 1.00 | 29.64 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 875 | CA  | GLY | A | 656 | 79.607 | −49.998 | 63.327 | 1.00 | 29.65 |
| ATOM | 876 | C   | GLY | A | 656 | 78.804 | −51.276 | 63.433 | 1.00 | 29.63 |
| ATOM | 877 | O   | GLY | A | 656 | 78.024 | −51.590 | 62.535 | 1.00 | 29.68 |
| ATOM | 878 | N   | GLY | A | 657 | 78.976 | −52.005 | 64.531 | 1.00 | 29.60 |
| ATOM | 879 | CA  | GLY | A | 657 | 78.258 | −53.252 | 64.716 | 1.00 | 29.48 |
| ATOM | 880 | C   | GLY | A | 657 | 79.035 | −54.193 | 65.621 | 1.00 | 29.37 |
| ATOM | 881 | O   | GLY | A | 657 | 80.160 | −53.880 | 66.013 | 1.00 | 29.37 |
| ATOM | 882 | N   | PRO | A | 658 | 78.466 | −55.357 | 65.967 | 1.00 | 29.26 |
| ATOM | 883 | CA  | PRO | A | 658 | 79.125 | −56.337 | 66.834 | 1.00 | 29.05 |
| ATOM | 884 | C   | PRO | A | 658 | 80.561 | −56.630 | 66.398 | 1.00 | 28.76 |
| ATOM | 885 | O   | PRO | A | 658 | 80.897 | −56.554 | 65.212 | 1.00 | 28.76 |
| ATOM | 886 | CB  | PRO | A | 658 | 78.229 | −57.567 | 66.705 | 1.00 | 29.15 |
| ATOM | 887 | CG  | PRO | A | 658 | 76.880 | −56.969 | 66.496 | 1.00 | 29.33 |
| ATOM | 888 | CD  | PRO | A | 658 | 77.174 | −55.879 | 65.486 | 1.00 | 29.33 |
| ATOM | 889 | N   | VAL | A | 659 | 81.400 | −56.969 | 67.368 | 1.00 | 28.46 |
| ATOM | 890 | CA  | VAL | A | 659 | 82.800 | −57.283 | 67.108 | 1.00 | 28.17 |
| ATOM | 891 | C   | VAL | A | 659 | 82.955 | −58.634 | 66.415 | 1.00 | 27.80 |
| ATOM | 892 | O   | VAL | A | 659 | 82.440 | −59.647 | 66.885 | 1.00 | 27.81 |
| ATOM | 893 | CB  | VAL | A | 659 | 83.607 | −57.294 | 68.431 | 1.00 | 28.27 |
| ATOM | 894 | CG1 | VAL | A | 659 | 85.027 | −57.798 | 68.186 | 1.00 | 28.30 |
| ATOM | 895 | CG2 | VAL | A | 659 | 83.634 | −55.879 | 69.030 | 1.00 | 28.35 |
| ATOM | 896 | N   | LEU | A | 660 | 83.658 | −58.633 | 65.287 | 1.00 | 27.41 |
| ATOM | 897 | CA  | LEU | A | 660 | 83.902 | −59.852 | 64.526 | 1.00 | 27.06 |
| ATOM | 898 | C   | LEU | A | 660 | 85.404 | −60.097 | 64.493 | 1.00 | 26.83 |
| ATOM | 899 | O   | LEU | A | 660 | 86.180 | −59.187 | 64.201 | 1.00 | 26.77 |
| ATOM | 900 | CB  | LEU | A | 660 | 83.393 | −59.712 | 63.086 | 1.00 | 26.98 |
| ATOM | 901 | CG  | LEU | A | 660 | 81.970 | −59.193 | 62.856 | 1.00 | 26.93 |
| ATOM | 902 | CD1 | LEU | A | 660 | 81.686 | −59.186 | 61.358 | 1.00 | 26.78 |
| ATOM | 903 | CD2 | LEU | A | 660 | 80.962 | −60.058 | 63.587 | 1.00 | 26.89 |
| ATOM | 904 | N   | VAL | A | 661 | 85.809 | −61.327 | 64.799 | 1.00 | 26.48 |
| ATOM | 905 | CA  | VAL | A | 661 | 87.219 | −61.693 | 64.795 | 1.00 | 26.19 |
| ATOM | 906 | C   | VAL | A | 661 | 87.432 | −62.679 | 63.653 | 1.00 | 26.18 |
| ATOM | 907 | O   | VAL | A | 661 | 86.835 | −63.758 | 63.632 | 1.00 | 26.04 |
| ATOM | 908 | CB  | VAL | A | 661 | 87.631 | −62.335 | 66.140 | 1.00 | 26.10 |
| ATOM | 909 | CG1 | VAL | A | 661 | 89.064 | −62.817 | 66.076 | 1.00 | 25.83 |
| ATOM | 910 | CG2 | VAL | A | 661 | 87.464 | −61.323 | 67.261 | 1.00 | 25.92 |
| ATOM | 911 | N   | ILE | A | 662 | 88.293 | −62.296 | 62.712 | 1.00 | 26.11 |
| ATOM | 912 | CA  | ILE | A | 662 | 88.567 | −63.098 | 61.524 | 1.00 | 26.04 |
| ATOM | 913 | C   | ILE | A | 662 | 89.866 | −63.894 | 61.597 | 1.00 | 26.11 |
| ATOM | 914 | O   | ILE | A | 662 | 90.946 | −63.330 | 61.771 | 1.00 | 25.95 |
| ATOM | 915 | CB  | ILE | A | 662 | 88.627 | −62.192 | 60.279 | 1.00 | 26.13 |
| ATOM | 916 | CG1 | ILE | A | 662 | 87.404 | −61.272 | 60.252 | 1.00 | 26.15 |
| ATOM | 917 | CG2 | ILE | A | 662 | 88.707 | −63.040 | 59.018 | 1.00 | 26.07 |
| ATOM | 918 | CD1 | ILE | A | 662 | 87.516 | −60.143 | 59.250 | 1.00 | 26.13 |
| ATOM | 919 | N   | THR | A | 663 | 89.752 | −65.208 | 61.444 | 1.00 | 26.11 |
| ATOM | 920 | CA  | THR | A | 663 | 90.909 | −66.084 | 61.495 | 1.00 | 26.24 |
| ATOM | 921 | C   | THR | A | 663 | 90.982 | −66.949 | 60.251 | 1.00 | 26.38 |
| ATOM | 922 | O   | THR | A | 663 | 90.038 | −67.004 | 59.466 | 1.00 | 26.45 |
| ATOM | 923 | CB  | THR | A | 663 | 90.866 | −67.009 | 62.733 | 1.00 | 26.22 |
| ATOM | 924 | OG1 | THR | A | 663 | 89.637 | −67.748 | 62.741 | 1.00 | 26.28 |
| ATOM | 925 | CG2 | THR | A | 663 | 90.966 | −66.187 | 64.008 | 1.00 | 26.17 |
| ATOM | 926 | N   | GLU | A | 664 | 92.111 | −67.625 | 60.078 | 1.00 | 26.49 |
| ATOM | 927 | CA  | GLU | A | 664 | 92.296 | −68.496 | 58.932 | 1.00 | 26.68 |
| ATOM | 928 | C   | GLU | A | 664 | 91.431 | −69.746 | 59.094 | 1.00 | 26.67 |
| ATOM | 929 | O   | GLU | A | 664 | 91.303 | −70.297 | 60.189 | 1.00 | 26.70 |
| ATOM | 930 | CB  | GLU | A | 664 | 93.767 | −68.891 | 58.800 | 1.00 | 26.81 |
| ATOM | 931 | CG  | GLU | A | 664 | 94.310 | −69.677 | 59.971 | 1.00 | 27.18 |
| ATOM | 932 | CD  | GLU | A | 664 | 95.771 | −70.021 | 59.789 | 1.00 | 27.37 |
| ATOM | 933 | OE1 | GLU | A | 664 | 96.121 | −70.541 | 58.708 | 1.00 | 27.68 |
| ATOM | 934 | OE2 | GLU | A | 664 | 96.568 | −69.781 | 60.718 | 1.00 | 27.40 |
| ATOM | 935 | N   | TYR | A | 665 | 90.832 | −70.185 | 57.997 | 1.00 | 26.56 |
| ATOM | 936 | CA  | TYR | A | 665 | 89.980 | −71.365 | 58.017 | 1.00 | 26.44 |
| ATOM | 937 | C   | TYR | A | 665 | 90.793 | −72.657 | 57.889 | 1.00 | 26.34 |
| ATOM | 938 | O   | TYR | A | 665 | 91.509 | −72.841 | 56.908 | 1.00 | 26.35 |
| ATOM | 939 | CB  | TYR | A | 665 | 88.974 | −71.272 | 56.876 | 1.00 | 26.52 |
| ATOM | 940 | CG  | TYR | A | 665 | 88.123 | −72.507 | 56.721 | 1.00 | 26.57 |
| ATOM | 941 | CD1 | TYR | A | 665 | 87.180 | −72.849 | 57.694 | 1.00 | 26.53 |
| ATOM | 942 | CD2 | TYR | A | 665 | 88.262 | −73.339 | 55.613 | 1.00 | 26.47 |
| ATOM | 943 | CE1 | TYR | A | 665 | 86.397 | −73.987 | 57.565 | 1.00 | 26.47 |
| ATOM | 944 | CE2 | TYR | A | 665 | 87.481 | −74.488 | 55.478 | 1.00 | 26.50 |
| ATOM | 945 | CZ  | TYR | A | 665 | 86.552 | −74.799 | 56.461 | 1.00 | 26.39 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 946  | OH  | TYR | A | 665 | 85.776 | −75.924 | 56.349 | 1.00 | 26.47 |
|------|------|-----|-----|---|-----|--------|---------|--------|------|-------|
| ATOM | 947  | N   | CYS | A | 666 | 90.690 | −73.545 | 58.879 | 1.00 | 26.11 |
| ATOM | 948  | CA  | CYS | A | 666 | 91.417 | −74.824 | 58.853 | 1.00 | 25.93 |
| ATOM | 949  | C   | CYS | A | 666 | 90.438 | −75.925 | 58.425 | 1.00 | 25.97 |
| ATOM | 950  | O   | CYS | A | 666 | 89.757 | −76.522 | 59.251 | 1.00 | 25.96 |
| ATOM | 951  | CB  | CYS | A | 666 | 91.996 | −75.130 | 60.234 | 1.00 | 25.75 |
| ATOM | 952  | SG  | CYS | A | 666 | 93.151 | −73.866 | 60.841 | 1.00 | 25.34 |
| ATOM | 953  | N   | CYS | A | 667 | 90.410 | −76.193 | 57.122 | 1.00 | 25.92 |
| ATOM | 954  | CA  | CYS | A | 667 | 89.483 | −77.142 | 56.510 | 1.00 | 25.87 |
| ATOM | 955  | C   | CYS | A | 667 | 89.189 | −78.523 | 57.102 | 1.00 | 25.67 |
| ATOM | 956  | O   | CYS | A | 667 | 88.085 | −79.032 | 56.913 | 1.00 | 25.73 |
| ATOM | 957  | CB  | CYS | A | 667 | 89.833 | −77.299 | 55.019 | 1.00 | 25.97 |
| ATOM | 958  | SG  | CYS | A | 667 | 91.372 | −78.176 | 54.649 | 1.00 | 26.74 |
| ATOM | 959  | N   | TYR | A | 668 | 90.131 | −79.140 | 57.810 | 1.00 | 25.44 |
| ATOM | 960  | CA  | TYR | A | 668 | 89.875 | −80.472 | 58.356 | 1.00 | 25.14 |
| ATOM | 961  | C   | TYR | A | 668 | 89.352 | −80.537 | 59.794 | 1.00 | 24.89 |
| ATOM | 962  | O   | TYR | A | 668 | 89.169 | −81.626 | 60.345 | 1.00 | 24.75 |
| ATOM | 963  | CB  | TYR | A | 668 | 91.131 | −81.331 | 58.217 | 1.00 | 25.46 |
| ATOM | 964  | CG  | TYR | A | 668 | 91.557 | −81.513 | 56.774 | 1.00 | 25.84 |
| ATOM | 965  | CD1 | TYR | A | 668 | 92.845 | −81.173 | 56.356 | 1.00 | 26.00 |
| ATOM | 966  | CD2 | TYR | A | 668 | 90.660 | −82.003 | 55.821 | 1.00 | 26.09 |
| ATOM | 967  | CE1 | TYR | A | 668 | 93.233 | −81.309 | 55.016 | 1.00 | 26.30 |
| ATOM | 968  | CE2 | TYR | A | 668 | 91.036 | −82.149 | 54.479 | 1.00 | 26.36 |
| ATOM | 969  | CZ  | TYR | A | 668 | 92.323 | −81.797 | 54.084 | 1.00 | 26.44 |
| ATOM | 970  | OH  | TYR | A | 668 | 92.695 | −81.924 | 52.763 | 1.00 | 26.69 |
| ATOM | 971  | N   | GLY | A | 669 | 89.112 | −79.382 | 60.405 | 1.00 | 24.40 |
| ATOM | 972  | CA  | GLY | A | 669 | 88.589 | −79.383 | 61.763 | 1.00 | 24.04 |
| ATOM | 973  | C   | GLY | A | 669 | 89.576 | −79.747 | 62.854 | 1.00 | 23.62 |
| ATOM | 974  | O   | GLY | A | 669 | 90.789 | −79.769 | 62.628 | 1.00 | 23.66 |
| ATOM | 975  | N   | ASP | A | 670 | 89.060 | −80.051 | 64.044 | 1.00 | 23.33 |
| ATOM | 976  | CA  | ASP | A | 670 | 89.919 | −80.376 | 65.180 | 1.00 | 22.85 |
| ATOM | 977  | C   | ASP | A | 670 | 90.591 | −81.741 | 65.107 | 1.00 | 22.68 |
| ATOM | 978  | O   | ASP | A | 670 | 90.050 | −82.706 | 64.561 | 1.00 | 22.44 |
| ATOM | 979  | CB  | ASP | A | 670 | 89.145 | −80.263 | 66.501 | 1.00 | 22.89 |
| ATOM | 980  | CG  | ASP | A | 670 | 88.184 | −81.418 | 66.718 | 1.00 | 22.93 |
| ATOM | 981  | OD1 | ASP | A | 670 | 87.062 | −81.363 | 66.181 | 1.00 | 22.83 |
| ATOM | 982  | OD2 | ASP | A | 670 | 88.562 | −82.386 | 67.417 | 1.00 | 22.92 |
| ATOM | 983  | N   | LEU | A | 671 | 91.782 | −81.803 | 65.688 | 1.00 | 22.48 |
| ATOM | 984  | CA  | LEU | A | 671 | 92.582 | −83.015 | 65.721 | 1.00 | 22.38 |
| ATOM | 985  | C   | LEU | A | 671 | 91.951 | −84.173 | 66.489 | 1.00 | 22.39 |
| ATOM | 986  | O   | LEU | A | 671 | 92.095 | −85.333 | 66.093 | 1.00 | 22.32 |
| ATOM | 987  | CB  | LEU | A | 671 | 93.942 | −82.691 | 66.330 | 1.00 | 22.35 |
| ATOM | 988  | CG  | LEU | A | 671 | 94.862 | −83.870 | 66.601 | 1.00 | 22.33 |
| ATOM | 989  | CD1 | LEU | A | 671 | 95.220 | −84.550 | 65.288 | 1.00 | 22.22 |
| ATOM | 990  | CD2 | LEU | A | 671 | 96.111 | −83.358 | 67.322 | 1.00 | 22.20 |
| ATOM | 991  | N   | LEU | A | 672 | 91.259 | −83.875 | 67.585 | 1.00 | 22.37 |
| ATOM | 992  | CA  | LEU | A | 672 | 90.648 | −84.934 | 68.382 | 1.00 | 22.60 |
| ATOM | 993  | C   | LEU | A | 672 | 89.662 | −85.785 | 67.581 | 1.00 | 22.68 |
| ATOM | 994  | O   | LEU | A | 672 | 89.799 | −87.003 | 67.538 | 1.00 | 22.56 |
| ATOM | 995  | CB  | LEU | A | 672 | 89.951 | −84.355 | 69.619 | 1.00 | 22.59 |
| ATOM | 996  | CG  | LEU | A | 672 | 89.357 | −85.399 | 70.573 | 1.00 | 22.64 |
| ATOM | 997  | CD1 | LEU | A | 672 | 90.456 | −86.325 | 71.075 | 1.00 | 22.52 |
| ATOM | 998  | CD2 | LEU | A | 672 | 88.678 | −84.707 | 71.746 | 1.00 | 22.64 |
| ATOM | 999  | N   | ASN | A | 673 | 88.674 | −85.143 | 66.960 | 1.00 | 22.90 |
| ATOM | 1000 | CA  | ASN | A | 673 | 87.673 | −85.845 | 66.144 | 1.00 | 23.27 |
| ATOM | 1001 | C   | ASN | A | 673 | 88.387 | −86.631 | 65.043 | 1.00 | 23.22 |
| ATOM | 1002 | O   | ASN | A | 673 | 88.028 | −87.769 | 64.731 | 1.00 | 23.07 |
| ATOM | 1003 | CB  | ASN | A | 673 | 86.708 | −84.834 | 65.505 | 1.00 | 23.73 |
| ATOM | 1004 | CG  | ASN | A | 673 | 85.607 | −85.502 | 64.687 | 1.00 | 24.38 |
| ATOM | 1005 | OD1 | ASN | A | 673 | 85.879 | −86.279 | 63.757 | 1.00 | 24.96 |
| ATOM | 1006 | ND2 | ASN | A | 673 | 84.353 | −85.199 | 65.024 | 1.00 | 24.57 |
| ATOM | 1007 | N   | PHE | A | 674 | 89.408 | −86.007 | 64.461 | 1.00 | 23.27 |
| ATOM | 1008 | CA  | PHE | A | 674 | 90.186 | −86.635 | 63.400 | 1.00 | 23.31 |
| ATOM | 1009 | C   | PHE | A | 674 | 90.776 | −87.953 | 63.893 | 1.00 | 23.38 |
| ATOM | 1010 | O   | PHE | A | 674 | 90.630 | −88.991 | 63.245 | 1.00 | 23.32 |
| ATOM | 1011 | CB  | PHE | A | 674 | 91.319 | −85.709 | 62.951 | 1.00 | 23.42 |
| ATOM | 1012 | CG  | PHE | A | 674 | 92.158 | −86.281 | 61.843 | 1.00 | 23.48 |
| ATOM | 1013 | CD1 | PHE | A | 674 | 91.731 | −86.205 | 60.522 | 1.00 | 23.60 |
| ATOM | 1014 | CD2 | PHE | A | 674 | 93.346 | −86.941 | 62.128 | 1.00 | 23.46 |
| ATOM | 1015 | CE1 | PHE | A | 674 | 92.481 | −86.783 | 59.491 | 1.00 | 23.67 |
| ATOM | 1016 | CE2 | PHE | A | 674 | 94.100 | −87.520 | 61.116 | 1.00 | 23.66 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1017 | CZ  | PHE | A | 674 | 93.663 | −87.441  | 59.788 | 1.00 | 23.59 |
|------|------|-----|-----|---|-----|--------|----------|--------|------|-------|
| ATOM | 1018 | N   | LEU | A | 675 | 91.440 | −87.903  | 65.043 | 1.00 | 23.43 |
| ATOM | 1019 | CA  | LEU | A | 675 | 92.056 | −89.085  | 65.635 | 1.00 | 23.59 |
| ATOM | 1020 | C   | LEU | A | 675 | 91.028 | −90.174  | 65.920 | 1.00 | 23.92 |
| ATOM | 1021 | O   | LEU | A | 675 | 91.261 | −91.354  | 65.651 | 1.00 | 23.58 |
| ATOM | 1022 | CB  | LEU | A | 675 | 92.763 | −88.703  | 66.938 | 1.00 | 23.57 |
| ATOM | 1023 | CG  | LEU | A | 675 | 93.979 | −87.775  | 66.809 | 1.00 | 23.45 |
| ATOM | 1024 | CD1 | LEU | A | 675 | 94.417 | −87.301  | 68.191 | 1.00 | 23.38 |
| ATOM | 1025 | CD2 | LEU | A | 675 | 95.108 | −88.520  | 66.105 | 1.00 | 23.32 |
| ATOM | 1026 | N   | ARG | A | 676 | 89.883 | −89.772  | 66.463 | 1.00 | 24.39 |
| ATOM | 1027 | CA  | ARG | A | 676 | 88.843 | −90.735  | 66.797 | 1.00 | 25.09 |
| ATOM | 1028 | C   | ARG | A | 676 | 88.274 | −91.432  | 65.568 | 1.00 | 25.70 |
| ATOM | 1029 | O   | ARG | A | 676 | 88.018 | −92.639  | 65.598 | 1.00 | 25.70 |
| ATOM | 1030 | CB  | ARG | A | 676 | 87.751 | −90.054  | 67.624 | 1.00 | 24.72 |
| ATOM | 1031 | CG  | ARG | A | 676 | 88.282 | −89.645  | 68.994 | 1.00 | 24.54 |
| ATOM | 1032 | CD  | ARG | A | 676 | 87.254 | −88.991  | 69.902 | 1.00 | 24.44 |
| ATOM | 1033 | NE  | ARG | A | 676 | 87.762 | −88.941  | 71.270 | 1.00 | 24.27 |
| ATOM | 1034 | CZ  | ARG | A | 676 | 87.134 | −88.381  | 72.297 | 1.00 | 24.38 |
| ATOM | 1035 | NH1 | ARG | A | 676 | 85.954 | −87.801  | 72.122 | 1.00 | 24.25 |
| ATOM | 1036 | NH2 | ARG | A | 676 | 87.685 | −88.412  | 73.507 | 1.00 | 24.23 |
| ATOM | 1037 | N   | ARG | A | 677 | 88.088 | −90.689  | 64.484 | 1.00 | 26.52 |
| ATOM | 1038 | CA  | ARG | A | 677 | 87.574 | −91.300  | 63.267 | 1.00 | 27.47 |
| ATOM | 1039 | C   | ARG | A | 677 | 88.597 | −92.313  | 62.744 | 1.00 | 27.84 |
| ATOM | 1040 | O   | ARG | A | 677 | 88.233 | −93.378  | 62.244 | 1.00 | 27.81 |
| ATOM | 1041 | CB  | ARG | A | 677 | 87.275 | −90.231  | 62.214 | 1.00 | 27.83 |
| ATOM | 1042 | CG  | ARG | A | 677 | 86.213 | −89.233  | 62.653 | 1.00 | 28.52 |
| ATOM | 1043 | CD  | ARG | A | 677 | 85.500 | −88.619  | 61.456 | 1.00 | 29.25 |
| ATOM | 1044 | NE  | ARG | A | 677 | 86.441 | −88.153  | 60.445 | 1.00 | 29.92 |
| ATOM | 1045 | CZ  | ARG | A | 677 | 87.182 | −87.053  | 60.547 | 1.00 | 30.32 |
| ATOM | 1046 | NH1 | ARG | A | 677 | 87.096 | −86.278  | 61.625 | 1.00 | 30.62 |
| ATOM | 1047 | NH2 | ARG | A | 677 | 88.028 | −86.737  | 59.573 | 1.00 | 30.57 |
| ATOM | 1048 | N   | LYS | A | 678 | 89.878 | −91.985  | 62.876 | 1.00 | 28.34 |
| ATOM | 1049 | CA  | LYS | A | 678 | 90.938 | −92.883  | 62.432 | 1.00 | 28.96 |
| ATOM | 1050 | C   | LYS | A | 678 | 90.974 | −94.161  | 63.276 | 1.00 | 29.41 |
| ATOM | 1051 | O   | LYS | A | 678 | 91.218 | −95.252  | 62.762 | 1.00 | 29.35 |
| ATOM | 1052 | CB  | LYS | A | 678 | 92.292 | −92.170  | 62.498 | 1.00 | 28.97 |
| ATOM | 1053 | CG  | LYS | A | 678 | 92.532 | −91.205  | 61.345 | 1.00 | 28.98 |
| ATOM | 1054 | CD  | LYS | A | 678 | 92.445 | −91.943  | 60.017 | 1.00 | 29.14 |
| ATOM | 1055 | CE  | LYS | A | 678 | 92.752 | −91.043  | 58.837 | 1.00 | 29.15 |
| ATOM | 1056 | NZ  | LYS | A | 678 | 92.717 | −91.820  | 57.564 | 1.00 | 29.15 |
| ATOM | 1057 | N   | ALA | A | 679 | 90.726 | −94.019  | 64.572 | 1.00 | 29.95 |
| ATOM | 1058 | CA  | ALA | A | 679 | 90.710 | −95.167  | 65.470 | 1.00 | 30.60 |
| ATOM | 1059 | C   | ALA | A | 679 | 89.584 | −96.112  | 65.055 | 1.00 | 31.06 |
| ATOM | 1060 | O   | ALA | A | 679 | 89.759 | −97.322  | 65.031 | 1.00 | 30.96 |
| ATOM | 1061 | CB  | ALA | A | 679 | 90.499 | −94.706  | 66.910 | 1.00 | 30.44 |
| ATOM | 1062 | N   | GLU | A | 680 | 88.432 | −95.539  | 64.727 | 1.00 | 31.85 |
| ATOM | 1063 | CA  | GLU | A | 680 | 87.267 | −96.313  | 64.313 | 1.00 | 32.66 |
| ATOM | 1064 | C   | GLU | A | 680 | 87.482 | −97.062  | 63.001 | 1.00 | 33.10 |
| ATOM | 1065 | O   | GLU | A | 680 | 86.937 | −98.150  | 62.809 | 1.00 | 33.18 |
| ATOM | 1066 | CB  | GLU | A | 680 | 86.052 | −95.392  | 64.170 | 1.00 | 32.94 |
| ATOM | 1067 | CG  | GLU | A | 680 | 85.546 | −94.833  | 65.484 | 1.00 | 33.55 |
| ATOM | 1068 | CD  | GLU | A | 680 | 84.421 | −93.821  | 65.305 | 1.00 | 33.97 |
| ATOM | 1069 | OE1 | GLU | A | 680 | 83.864 | −93.368  | 66.336 | 1.00 | 34.11 |
| ATOM | 1070 | OE2 | GLU | A | 680 | 84.100 | −93.474  | 64.139 | 1.00 | 34.10 |
| ATOM | 1071 | N   | ALA | A | 681 | 88.271 | −96.476  | 62.105 | 1.00 | 33.60 |
| ATOM | 1072 | CA  | ALA | A | 681 | 88.545 | −97.075  | 60.798 | 1.00 | 34.16 |
| ATOM | 1073 | C   | ALA | A | 681 | 89.727 | −98.036  | 60.841 | 1.00 | 34.62 |
| ATOM | 1074 | O   | ALA | A | 681 | 90.085 | −98.649  | 59.831 | 1.00 | 34.61 |
| ATOM | 1075 | CB  | ALA | A | 681 | 88.807 | −95.980  | 59.777 | 1.00 | 34.09 |
| ATOM | 1076 | N   | MET | A | 682 | 90.329 | −98.160  | 62.015 | 1.00 | 35.13 |
| ATOM | 1077 | CA  | MET | A | 682 | 91.467 | −99.041  | 62.208 | 1.00 | 35.73 |
| ATOM | 1078 | C   | MET | A | 682 | 91.037 | −100.490 | 62.006 | 1.00 | 35.83 |
| ATOM | 1079 | O   | MET | A | 682 | 89.963 | −100.902 | 62.449 | 1.00 | 35.86 |
| ATOM | 1080 | CB  | MET | A | 682 | 92.023 | −98.855  | 63.621 | 1.00 | 36.31 |
| ATOM | 1081 | CG  | MET | A | 682 | 93.404 | −99.429  | 63.839 | 1.00 | 37.06 |
| ATOM | 1082 | SD  | MET | A | 682 | 94.615 | −98.662  | 62.747 | 1.00 | 38.11 |
| ATOM | 1083 | CE  | MET | A | 682 | 94.897 | −97.104  | 63.607 | 1.00 | 37.91 |
| ATOM | 1084 | N   | LEU | A | 683 | 91.876 | −101.255 | 61.322 | 1.00 | 35.95 |
| ATOM | 1085 | CA  | LEU | A | 683 | 91.595 | −102.660 | 61.073 | 1.00 | 36.17 |
| ATOM | 1086 | C   | LEU | A | 683 | 90.290 | −102.813 | 60.288 | 1.00 | 36.32 |
| ATOM | 1087 | O   | LEU | A | 683 | 89.346 | −103.474 | 60.729 | 1.00 | 36.35 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1088 | CB  | LEU | A | 683 | 91.512  | −103.405 | 62.409 | 1.00 | 36.03 |
|------|------|-----|-----|---|-----|---------|----------|--------|------|-------|
| ATOM | 1089 | CG  | LEU | A | 683 | 91.955  | −104.864 | 62.381 | 1.00 | 36.11 |
| ATOM | 1090 | CD1 | LEU | A | 683 | 91.699  | −105.515 | 63.733 | 1.00 | 36.05 |
| ATOM | 1091 | CD2 | LEU | A | 683 | 91.198  | −105.575 | 61.290 | 1.00 | 36.08 |
| ATOM | 1092 | N   | GLY | A | 684 | 90.246  | −102.181 | 59.123 | 1.00 | 36.53 |
| ATOM | 1093 | CA  | GLY | A | 684 | 89.069  | −102.247 | 58.277 | 1.00 | 36.70 |
| ATOM | 1094 | C   | GLY | A | 684 | 89.413  | −102.942 | 56.978 | 1.00 | 36.76 |
| ATOM | 1095 | OT1 | GLY | A | 684 | 88.572  | −103.696 | 56.455 | 1.00 | 36.87 |
| ATOM | 1096 | OT2 | GLY | A | 684 | 90.531  | −102.719 | 56.476 | 1.00 | 36.86 |
| ATOM | 1097 | N   | ALA | A | 746 | 88.595  | −102.096 | 54.093 | 1.00 | 42.36 |
| ATOM | 1098 | CA  | ALA | A | 746 | 89.480  | −101.002 | 53.609 | 1.00 | 42.33 |
| ATOM | 1099 | C   | ALA | A | 746 | 89.659  | −99.952  | 54.694 | 1.00 | 42.32 |
| ATOM | 1100 | O   | ALA | A | 746 | 88.693  | −99.526  | 55.328 | 1.00 | 42.43 |
| ATOM | 1101 | CB  | ALA | A | 746 | 88.891  | −100.360 | 52.361 | 1.00 | 42.39 |
| ATOM | 1102 | N   | GLY | A | 747 | 90.903  | −99.536  | 54.898 | 1.00 | 42.17 |
| ATOM | 1103 | CA  | GLY | A | 747 | 91.197  | −98.535  | 55.903 | 1.00 | 41.91 |
| ATOM | 1104 | C   | GLY | A | 747 | 92.560  | −97.930  | 55.651 | 1.00 | 41.70 |
| ATOM | 1105 | O   | GLY | A | 747 | 93.482  | −98.621  | 55.210 | 1.00 | 41.75 |
| ATOM | 1106 | N   | ARG | A | 748 | 92.686  | −96.635  | 55.925 | 1.00 | 41.39 |
| ATOM | 1107 | CA  | ARG | A | 748 | 93.943  | −95.919  | 55.731 | 1.00 | 41.02 |
| ATOM | 1108 | C   | ARG | A | 748 | 94.390  | −95.354  | 57.081 | 1.00 | 40.55 |
| ATOM | 1109 | O   | ARG | A | 748 | 94.214  | −94.168  | 57.364 | 1.00 | 40.56 |
| ATOM | 1110 | CB  | ARG | A | 748 | 93.734  | −94.805  | 54.702 | 1.00 | 41.29 |
| ATOM | 1111 | CG  | ARG | A | 748 | 93.396  | −95.342  | 53.311 | 1.00 | 41.67 |
| ATOM | 1112 | CD  | ARG | A | 748 | 92.366  | −94.484  | 52.572 | 1.00 | 41.96 |
| ATOM | 1113 | NE  | ARG | A | 748 | 91.029  | −94.589  | 53.161 | 1.00 | 42.31 |
| ATOM | 1114 | CZ  | ARG | A | 748 | 89.929  | −94.063  | 52.627 | 1.00 | 42.44 |
| ATOM | 1115 | NH1 | ARG | A | 748 | 89.995  | −93.389  | 51.483 | 1.00 | 42.56 |
| ATOM | 1116 | NH2 | ARG | A | 748 | 88.759  | −94.210  | 53.234 | 1.00 | 42.52 |
| ATOM | 1117 | N   | PRO | A | 749 | 94.986  | −96.210  | 57.929 | 1.00 | 40.03 |
| ATOM | 1118 | CA  | PRO | A | 749 | 95.474  | −95.862  | 59.269 | 1.00 | 39.51 |
| ATOM | 1119 | C   | PRO | A | 749 | 96.614  | −94.856  | 59.357 | 1.00 | 38.97 |
| ATOM | 1120 | O   | PRO | A | 749 | 97.361  | −94.648  | 58.399 | 1.00 | 38.93 |
| ATOM | 1121 | CB  | PRO | A | 749 | 95.871  | −97.218  | 59.849 | 1.00 | 39.70 |
| ATOM | 1122 | CG  | PRO | A | 749 | 96.371  | −97.945  | 58.647 | 1.00 | 39.84 |
| ATOM | 1123 | CD  | PRO | A | 749 | 95.313  | −97.614  | 57.611 | 1.00 | 39.97 |
| ATOM | 1124 | N   | LEU | A | 750 | 96.736  | −94.237  | 60.528 | 1.00 | 38.23 |
| ATOM | 1125 | CA  | LEU | A | 750 | 97.796  | −93.271  | 60.783 | 1.00 | 37.42 |
| ATOM | 1126 | C   | LEU | A | 750 | 99.033  | −94.032  | 61.256 | 1.00 | 36.85 |
| ATOM | 1127 | O   | LEU | A | 750 | 98.984  | −94.740  | 62.264 | 1.00 | 36.83 |
| ATOM | 1128 | CB  | LEU | A | 750 | 97.362  | −92.273  | 61.863 | 1.00 | 37.41 |
| ATOM | 1129 | CG  | LEU | A | 750 | 96.234  | −91.289  | 61.532 | 1.00 | 37.43 |
| ATOM | 1130 | CD1 | LEU | A | 750 | 95.869  | −90.497  | 62.778 | 1.00 | 37.35 |
| ATOM | 1131 | CD2 | LEU | A | 750 | 96.674  | −90.352  | 60.415 | 1.00 | 37.44 |
| ATOM | 1132 | N   | GLU | A | 751 | 100.138 | −93.896  | 60.529 | 1.00 | 36.08 |
| ATOM | 1133 | CA  | GLU | A | 751 | 101.371 | −94.577  | 60.905 | 1.00 | 35.34 |
| ATOM | 1134 | C   | GLU | A | 751 | 102.196 | −93.670  | 61.809 | 1.00 | 34.78 |
| ATOM | 1135 | O   | GLU | A | 751 | 101.892 | −92.486  | 61.942 | 1.00 | 34.71 |
| ATOM | 1136 | CB  | GLU | A | 751 | 102.181 | −94.950  | 59.661 | 1.00 | 35.39 |
| ATOM | 1137 | CG  | GLU | A | 751 | 101.476 | −95.904  | 58.695 | 1.00 | 35.35 |
| ATOM | 1138 | CD  | GLU | A | 751 | 101.063 | −97.220  | 59.344 | 1.00 | 35.41 |
| ATOM | 1139 | OE1 | GLU | A | 751 | 101.698 | −97.629  | 60.341 | 1.00 | 35.34 |
| ATOM | 1140 | OE2 | GLU | A | 751 | 100.111 | −97.856  | 58.841 | 1.00 | 35.37 |
| ATOM | 1141 | N   | LEU | A | 752 | 103.235 | −94.226  | 62.429 | 1.00 | 34.02 |
| ATOM | 1142 | CA  | LEU | A | 752 | 104.086 | −93.452  | 63.329 | 1.00 | 33.37 |
| ATOM | 1143 | C   | LEU | A | 752 | 104.466 | −92.103  | 62.735 | 1.00 | 32.85 |
| ATOM | 1144 | O   | LEU | A | 752 | 104.450 | −91.086  | 63.426 | 1.00 | 32.87 |
| ATOM | 1145 | CB  | LEU | A | 752 | 105.363 | −94.228  | 63.674 | 1.00 | 33.25 |
| ATOM | 1146 | CG  | LEU | A | 752 | 106.380 | −93.439  | 64.509 | 1.00 | 33.20 |
| ATOM | 1147 | CD1 | LEU | A | 752 | 105.742 | −93.019  | 65.821 | 1.00 | 33.12 |
| ATOM | 1148 | CD2 | LEU | A | 752 | 107.616 | −94.289  | 64.779 | 1.00 | 33.15 |
| ATOM | 1149 | N   | ARG | A | 753 | 104.818 | −92.105  | 61.453 | 1.00 | 32.25 |
| ATOM | 1150 | CA  | ARG | A | 753 | 105.206 | −90.887  | 60.749 | 1.00 | 31.50 |
| ATOM | 1151 | C   | ARG | A | 753 | 104.147 | −89.792  | 60.892 | 1.00 | 30.74 |
| ATOM | 1152 | O   | ARG | A | 753 | 104.465 | −88.641  | 61.194 | 1.00 | 30.57 |
| ATOM | 1153 | CB  | ARG | A | 753 | 105.427 | −91.203  | 59.264 | 1.00 | 32.00 |
| ATOM | 1154 | CG  | ARG | A | 753 | 105.528 | −89.983  | 58.359 | 1.00 | 32.68 |
| ATOM | 1155 | CD  | ARG | A | 753 | 105.459 | −90.388  | 56.884 | 1.00 | 33.29 |
| ATOM | 1156 | NE  | ARG | A | 753 | 105.351 | −89.229  | 55.995 | 1.00 | 33.77 |
| ATOM | 1157 | CZ  | ARG | A | 753 | 106.348 | −88.389  | 55.723 | 1.00 | 34.04 |
| ATOM | 1158 | NH1 | ARG | A | 753 | 106.144 | −87.363  | 54.904 | 1.00 | 34.18 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1159 | NH2 | ARG | A | 753 | 107.551 | −88.577 | 56.262 | 1.00 | 34.17 |
|---|---|---|---|---|---|---|---|---|---|---|
| ATOM | 1160 | N | ASP | A | 754 | 102.890 | −90.159 | 60.676 | 1.00 | 29.72 |
| ATOM | 1161 | CA | ASP | A | 754 | 101.785 | −89.209 | 60.761 | 1.00 | 28.83 |
| ATOM | 1162 | C | ASP | A | 754 | 101.615 | −88.630 | 62.166 | 1.00 | 28.10 |
| ATOM | 1163 | O | ASP | A | 754 | 101.440 | −87.423 | 62.333 | 1.00 | 27.92 |
| ATOM | 1164 | CB | ASP | A | 754 | 100.484 | −89.887 | 60.326 | 1.00 | 28.94 |
| ATOM | 1165 | CG | ASP | A | 754 | 100.585 | −90.503 | 58.943 | 1.00 | 29.03 |
| ATOM | 1166 | OD1 | ASP | A | 754 | 100.822 | −89.753 | 57.975 | 1.00 | 29.08 |
| ATOM | 1167 | OD2 | ASP | A | 754 | 100.430 | −91.735 | 58.828 | 1.00 | 28.98 |
| ATOM | 1168 | N | LEU | A | 755 | 101.667 | −89.499 | 63.168 | 1.00 | 27.28 |
| ATOM | 1169 | CA | LEU | A | 755 | 101.507 | −89.083 | 64.553 | 1.00 | 26.58 |
| ATOM | 1170 | C | LEU | A | 755 | 102.668 | −88.188 | 64.978 | 1.00 | 26.24 |
| ATOM | 1171 | O | LEU | A | 755 | 102.469 | −87.216 | 65.703 | 1.00 | 25.98 |
| ATOM | 1172 | CB | LEU | A | 755 | 101.402 | −90.311 | 65.454 | 1.00 | 26.42 |
| ATOM | 1173 | CG | LEU | A | 755 | 100.218 | −91.220 | 65.080 | 1.00 | 26.21 |
| ATOM | 1174 | CD1 | LEU | A | 755 | 100.196 | −92.441 | 65.972 | 1.00 | 26.14 |
| ATOM | 1175 | CD2 | LEU | A | 755 | 98.906 | −90.446 | 65.205 | 1.00 | 26.14 |
| ATOM | 1176 | N | LEU | A | 756 | 103.874 | −88.518 | 64.514 | 1.00 | 25.81 |
| ATOM | 1177 | CA | LEU | A | 756 | 105.058 | −87.721 | 64.822 | 1.00 | 25.49 |
| ATOM | 1178 | C | LEU | A | 756 | 104.914 | −86.318 | 64.245 | 1.00 | 25.28 |
| ATOM | 1179 | O | LEU | A | 756 | 105.310 | −85.341 | 64.876 | 1.00 | 25.25 |
| ATOM | 1180 | CB | LEU | A | 756 | 106.319 | −88.379 | 64.251 | 1.00 | 25.37 |
| ATOM | 1181 | CG | LEU | A | 756 | 106.804 | −89.652 | 64.961 | 1.00 | 25.29 |
| ATOM | 1182 | CD1 | LEU | A | 756 | 108.041 | −90.196 | 64.260 | 1.00 | 25.29 |
| ATOM | 1183 | CD2 | LEU | A | 756 | 107.119 | −89.340 | 66.416 | 1.00 | 25.25 |
| ATOM | 1184 | N | HIS | A | 757 | 104.360 | −86.221 | 63.038 | 1.00 | 25.08 |
| ATOM | 1185 | CA | HIS | A | 757 | 104.163 | −84.919 | 62.400 | 1.00 | 24.86 |
| ATOM | 1186 | C | HIS | A | 757 | 103.213 | −84.051 | 63.220 | 1.00 | 24.35 |
| ATOM | 1187 | O | HIS | A | 757 | 103.489 | −82.876 | 63.454 | 1.00 | 24.21 |
| ATOM | 1188 | CB | HIS | A | 757 | 103.587 | −85.060 | 60.984 | 1.00 | 25.39 |
| ATOM | 1189 | CG | HIS | A | 757 | 104.554 | −85.605 | 59.982 | 1.00 | 26.00 |
| ATOM | 1190 | ND1 | HIS | A | 757 | 105.913 | −85.379 | 60.059 | 1.00 | 26.34 |
| ATOM | 1191 | CD2 | HIS | A | 757 | 104.356 | −86.325 | 58.850 | 1.00 | 26.28 |
| ATOM | 1192 | CE1 | HIS | A | 757 | 106.510 | −85.937 | 59.020 | 1.00 | 26.44 |
| ATOM | 1193 | NE2 | HIS | A | 757 | 105.587 | −86.517 | 58.270 | 1.00 | 26.38 |
| ATOM | 1194 | N | PHE | A | 758 | 102.086 | −84.621 | 63.639 | 1.00 | 23.77 |
| ATOM | 1195 | CA | PHE | A | 758 | 101.129 | −83.858 | 64.434 | 1.00 | 23.21 |
| ATOM | 1196 | C | PHE | A | 758 | 101.812 | −83.363 | 65.704 | 1.00 | 22.83 |
| ATOM | 1197 | O | PHE | A | 758 | 101.682 | −82.203 | 66.075 | 1.00 | 22.65 |
| ATOM | 1198 | CB | PHE | A | 758 | 99.917 | −84.713 | 64.824 | 1.00 | 23.16 |
| ATOM | 1199 | CG | PHE | A | 758 | 99.043 | −85.116 | 63.670 | 1.00 | 23.16 |
| ATOM | 1200 | CD1 | PHE | A | 758 | 98.776 | −84.227 | 62.628 | 1.00 | 23.07 |
| ATOM | 1201 | CD2 | PHE | A | 758 | 98.450 | −86.376 | 63.646 | 1.00 | 23.18 |
| ATOM | 1202 | CE1 | PHE | A | 758 | 97.930 | −84.588 | 61.577 | 1.00 | 23.15 |
| ATOM | 1203 | CE2 | PHE | A | 758 | 97.600 | −86.751 | 62.602 | 1.00 | 23.18 |
| ATOM | 1204 | CZ | PHE | A | 758 | 97.340 | −85.855 | 61.565 | 1.00 | 23.13 |
| ATOM | 1205 | N | SER | A | 759 | 102.547 | −84.261 | 66.353 | 1.00 | 22.50 |
| ATOM | 1206 | CA | SER | A | 759 | 103.256 | −83.956 | 67.590 | 1.00 | 22.33 |
| ATOM | 1207 | C | SER | A | 759 | 104.296 | −82.853 | 67.402 | 1.00 | 22.28 |
| ATOM | 1208 | O | SER | A | 759 | 104.407 | −81.947 | 68.233 | 1.00 | 22.19 |
| ATOM | 1209 | CB | SER | A | 759 | 103.951 | −85.215 | 68.116 | 1.00 | 22.28 |
| ATOM | 1210 | OG | SER | A | 759 | 103.039 | −86.292 | 68.221 | 1.00 | 22.03 |
| ATOM | 1211 | N | SER | A | 760 | 105.059 | −82.933 | 66.315 | 1.00 | 22.18 |
| ATOM | 1212 | CA | SER | A | 760 | 106.084 | −81.934 | 66.038 | 1.00 | 22.13 |
| ATOM | 1213 | C | SER | A | 760 | 105.454 | −80.593 | 65.700 | 1.00 | 21.99 |
| ATOM | 1214 | O | SER | A | 760 | 105.908 | −79.544 | 66.172 | 1.00 | 21.86 |
| ATOM | 1215 | CB | SER | A | 760 | 106.982 | −82.384 | 64.882 | 1.00 | 22.34 |
| ATOM | 1216 | OG | SER | A | 760 | 107.856 | −83.417 | 65.305 | 1.00 | 22.79 |
| ATOM | 1217 | N | GLN | A | 761 | 104.403 | −80.630 | 64.890 | 1.00 | 21.79 |
| ATOM | 1218 | CA | GLN | A | 761 | 103.721 | −79.408 | 64.502 | 1.00 | 21.62 |
| ATOM | 1219 | C | GLN | A | 761 | 103.163 | −78.658 | 65.707 | 1.00 | 21.42 |
| ATOM | 1220 | O | GLN | A | 761 | 103.353 | −77.441 | 65.829 | 1.00 | 21.42 |
| ATOM | 1221 | CB | GLN | A | 761 | 102.619 | −79.731 | 63.498 | 1.00 | 21.99 |
| ATOM | 1222 | CG | GLN | A | 761 | 103.130 | −79.810 | 62.064 | 1.00 | 22.39 |
| ATOM | 1223 | CD | GLN | A | 761 | 102.384 | −80.830 | 61.222 | 1.00 | 22.67 |
| ATOM | 1224 | OE1 | GLN | A | 761 | 101.190 | −81.073 | 61.419 | 1.00 | 22.81 |
| ATOM | 1225 | NE2 | GLN | A | 761 | 103.085 | −81.418 | 60.261 | 1.00 | 22.94 |
| ATOM | 1226 | N | VAL | A | 762 | 102.487 | −79.366 | 66.606 | 1.00 | 21.02 |
| ATOM | 1227 | CA | VAL | A | 762 | 101.944 | −78.698 | 67.784 | 1.00 | 20.78 |
| ATOM | 1228 | C | VAL | A | 762 | 103.070 | −78.188 | 68.696 | 1.00 | 20.65 |
| ATOM | 1229 | O | VAL | A | 762 | 102.983 | −77.086 | 69.232 | 1.00 | 20.47 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1230 | CB  | VAL | A | 762 | 100.975 | −79.629 | 68.561 | 1.00 | 20.80 |
|------|------|-----|-----|---|-----|---------|---------|--------|------|-------|
| ATOM | 1231 | CG1 | VAL | A | 762 | 100.515 | −78.965 | 69.857 | 1.00 | 20.48 |
| ATOM | 1232 | CG2 | VAL | A | 762 | 99.763  | −79.940 | 67.686 | 1.00 | 20.54 |
| ATOM | 1233 | N   | ALA | A | 763 | 104.133 | −78.975 | 68.851 | 1.00 | 20.65 |
| ATOM | 1234 | CA  | ALA | A | 763 | 105.254 | −78.567 | 69.691 | 1.00 | 20.63 |
| ATOM | 1235 | C   | ALA | A | 763 | 105.881 | −77.281 | 69.154 | 1.00 | 20.67 |
| ATOM | 1236 | O   | ALA | A | 763 | 106.363 | −76.452 | 69.918 | 1.00 | 20.60 |
| ATOM | 1237 | CB  | ALA | A | 763 | 106.305 | −79.672 | 69.745 | 1.00 | 20.64 |
| ATOM | 1238 | N   | GLN | A | 764 | 105.880 | −77.136 | 67.833 | 1.00 | 20.67 |
| ATOM | 1239 | CA  | GLN | A | 764 | 106.439 | −75.961 | 67.185 | 1.00 | 20.73 |
| ATOM | 1240 | C   | GLN | A | 764 | 105.542 | −74.765 | 67.470 | 1.00 | 20.46 |
| ATOM | 1241 | O   | GLN | A | 764 | 106.024 | −73.658 | 67.717 | 1.00 | 20.40 |
| ATOM | 1242 | CB  | GLN | A | 764 | 106.558 | −76.197 | 65.669 | 1.00 | 21.21 |
| ATOM | 1243 | CG  | GLN | A | 764 | 107.552 | −77.295 | 65.282 | 1.00 | 21.99 |
| ATOM | 1244 | CD  | GLN | A | 764 | 107.602 | −77.565 | 63.771 | 1.00 | 22.57 |
| ATOM | 1245 | OE1 | GLN | A | 764 | 108.390 | −78.395 | 63.304 | 1.00 | 22.87 |
| ATOM | 1246 | NE2 | GLN | A | 764 | 106.758 | −76.867 | 63.006 | 1.00 | 22.80 |
| ATOM | 1247 | N   | GLY | A | 765 | 104.232 | −74.992 | 67.439 | 1.00 | 20.17 |
| ATOM | 1248 | CA  | GLY | A | 765 | 103.296 | −73.916 | 67.716 | 1.00 | 19.80 |
| ATOM | 1249 | C   | GLY | A | 765 | 103.424 | −73.453 | 69.160 | 1.00 | 19.63 |
| ATOM | 1250 | O   | GLY | A | 765 | 103.404 | −72.254 | 69.443 | 1.00 | 19.51 |
| ATOM | 1251 | N   | MET | A | 766 | 103.575 | −74.405 | 70.076 | 1.00 | 19.39 |
| ATOM | 1252 | CA  | MET | A | 766 | 103.720 | −74.084 | 71.498 | 1.00 | 19.19 |
| ATOM | 1253 | C   | MET | A | 766 | 105.036 | −73.348 | 71.759 | 1.00 | 19.27 |
| ATOM | 1254 | O   | MET | A | 766 | 105.081 | −72.409 | 72.563 | 1.00 | 19.31 |
| ATOM | 1255 | CB  | MET | A | 766 | 103.678 | −75.357 | 72.352 | 1.00 | 19.00 |
| ATOM | 1256 | CG  | MET | A | 766 | 102.309 | −76.022 | 72.435 | 1.00 | 18.69 |
| ATOM | 1257 | SD  | MET | A | 766 | 101.007 | −74.837 | 72.861 | 1.00 | 18.49 |
| ATOM | 1258 | CE  | MET | A | 766 | 101.445 | −74.404 | 74.562 | 1.00 | 18.39 |
| ATOM | 1259 | N   | ALA | A | 767 | 106.105 | −73.780 | 71.090 | 1.00 | 19.26 |
| ATOM | 1260 | CA  | ALA | A | 767 | 107.405 | −73.131 | 71.247 | 1.00 | 19.27 |
| ATOM | 1261 | C   | ALA | A | 767 | 107.282 | −71.658 | 70.864 | 1.00 | 19.39 |
| ATOM | 1262 | O   | ALA | A | 767 | 107.935 | −70.796 | 71.464 | 1.00 | 19.41 |
| ATOM | 1263 | CB  | ALA | A | 767 | 108.452 | −73.814 | 70.375 | 1.00 | 19.29 |
| ATOM | 1264 | N   | PHE | A | 768 | 106.458 | −71.368 | 69.857 | 1.00 | 19.34 |
| ATOM | 1265 | CA  | PHE | A | 768 | 106.249 | −69.987 | 69.423 | 1.00 | 19.41 |
| ATOM | 1266 | C   | PHE | A | 768 | 105.504 | −69.213 | 70.504 | 1.00 | 19.44 |
| ATOM | 1267 | O   | PHE | A | 768 | 105.840 | −68.058 | 70.807 | 1.00 | 19.35 |
| ATOM | 1268 | CB  | PHE | A | 768 | 105.438 | −69.938 | 68.128 | 1.00 | 19.37 |
| ATOM | 1269 | CG  | PHE | A | 768 | 105.128 | −68.546 | 67.661 | 1.00 | 19.44 |
| ATOM | 1270 | CD1 | PHE | A | 768 | 106.130 | −67.732 | 67.133 | 1.00 | 19.32 |
| ATOM | 1271 | CD2 | PHE | A | 768 | 103.836 | −68.034 | 67.769 | 1.00 | 19.38 |
| ATOM | 1272 | CE1 | PHE | A | 768 | 105.846 | −66.436 | 66.723 | 1.00 | 19.39 |
| ATOM | 1273 | CE2 | PHE | A | 768 | 103.546 | −66.735 | 67.361 | 1.00 | 19.30 |
| ATOM | 1274 | CZ  | PHE | A | 768 | 104.551 | −65.937 | 66.838 | 1.00 | 19.47 |
| ATOM | 1275 | N   | LEU | A | 769 | 104.478 | −69.838 | 71.073 | 1.00 | 19.35 |
| ATOM | 1276 | CA  | LEU | A | 769 | 103.709 | −69.189 | 72.129 | 1.00 | 19.46 |
| ATOM | 1277 | C   | LEU | A | 769 | 104.621 | −68.910 | 73.308 | 1.00 | 19.56 |
| ATOM | 1278 | O   | LEU | A | 769 | 104.569 | −67.829 | 73.909 | 1.00 | 19.53 |
| ATOM | 1279 | CB  | LEU | A | 769 | 102.535 | −70.073 | 72.570 | 1.00 | 19.40 |
| ATOM | 1280 | CG  | LEU | A | 769 | 101.405 | −70.233 | 71.551 | 1.00 | 19.33 |
| ATOM | 1281 | CD1 | LEU | A | 769 | 100.254 | −70.985 | 72.204 | 1.00 | 19.39 |
| ATOM | 1282 | CD2 | LEU | A | 769 | 100.926 | −68.862 | 71.075 | 1.00 | 19.35 |
| ATOM | 1283 | N   | ALA | A | 770 | 105.470 | −69.886 | 73.626 | 1.00 | 19.68 |
| ATOM | 1284 | CA  | ALA | A | 770 | 106.420 | −69.753 | 74.723 | 1.00 | 19.84 |
| ATOM | 1285 | C   | ALA | A | 770 | 107.416 | −68.628 | 74.442 | 1.00 | 20.01 |
| ATOM | 1286 | O   | ALA | A | 770 | 107.835 | −67.932 | 75.359 | 1.00 | 20.07 |
| ATOM | 1287 | CB  | ALA | A | 770 | 107.168 | −71.074 | 74.936 | 1.00 | 19.65 |
| ATOM | 1288 | N   | SER | A | 771 | 107.785 | −68.445 | 73.176 | 1.00 | 20.26 |
| ATOM | 1289 | CA  | SER | A | 771 | 108.735 | −67.400 | 72.813 | 1.00 | 20.48 |
| ATOM | 1290 | C   | SER | A | 771 | 108.124 | −66.010 | 72.998 | 1.00 | 20.72 |
| ATOM | 1291 | O   | SER | A | 771 | 108.835 | −65.006 | 73.005 | 1.00 | 20.73 |
| ATOM | 1292 | CB  | SER | A | 771 | 109.226 | −67.586 | 71.366 | 1.00 | 20.51 |
| ATOM | 1293 | OG  | SER | A | 771 | 108.237 | −67.231 | 70.422 | 1.00 | 20.38 |
| ATOM | 1294 | N   | LYS | A | 772 | 106.806 | −65.948 | 73.162 | 1.00 | 20.92 |
| ATOM | 1295 | CA  | LYS | A | 772 | 106.144 | −64.669 | 73.382 | 1.00 | 21.21 |
| ATOM | 1296 | C   | LYS | A | 772 | 105.717 | −64.543 | 74.844 | 1.00 | 21.13 |
| ATOM | 1297 | O   | LYS | A | 772 | 104.961 | −63.638 | 75.209 | 1.00 | 21.19 |
| ATOM | 1298 | CB  | LYS | A | 772 | 104.929 | −64.533 | 72.464 | 1.00 | 21.62 |
| ATOM | 1299 | CG  | LYS | A | 772 | 105.302 | −64.497 | 70.993 | 1.00 | 22.18 |
| ATOM | 1300 | CD  | LYS | A | 772 | 106.385 | −63.446 | 70.761 | 1.00 | 22.61 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1301 | CE  | LYS | A | 772 | 106.805 | −63.373 | 69.303 | 1.00 | 22.93 |
| ATOM | 1302 | NZ  | LYS | A | 772 | 105.700 | −62.853 | 68.468 | 1.00 | 22.97 |
| ATOM | 1303 | N   | ASN | A | 773 | 106.224 | −65.452 | 75.674 | 1.00 | 21.06 |
| ATOM | 1304 | CA  | ASN | A | 773 | 105.905 | −65.493 | 77.094 | 1.00 | 21.07 |
| ATOM | 1305 | C   | ASN | A | 773 | 104.407 | −65.630 | 77.293 | 1.00 | 21.06 |
| ATOM | 1306 | O   | ASN | A | 773 | 103.831 | −65.052 | 78.209 | 1.00 | 20.96 |
| ATOM | 1307 | CB  | ASN | A | 773 | 106.407 | −64.237 | 77.815 | 1.00 | 21.33 |
| ATOM | 1308 | CG  | ASN | A | 773 | 107.895 | −64.249 | 78.018 | 1.00 | 21.44 |
| ATOM | 1309 | OD1 | ASN | A | 773 | 108.508 | −65.316 | 78.136 | 1.00 | 21.65 |
| ATOM | 1310 | ND2 | ASN | A | 773 | 108.495 | −63.063 | 78.086 | 1.00 | 21.56 |
| ATOM | 1311 | N   | CYS | A | 774 | 103.784 | −66.416 | 76.425 | 1.00 | 21.18 |
| ATOM | 1312 | CA  | CYS | A | 774 | 102.345 | −66.636 | 76.497 | 1.00 | 21.32 |
| ATOM | 1313 | C   | CYS | A | 774 | 102.003 | −68.011 | 77.051 | 1.00 | 21.18 |
| ATOM | 1314 | O   | CYS | A | 774 | 102.476 | −69.025 | 76.541 | 1.00 | 21.28 |
| ATOM | 1315 | CB  | CYS | A | 774 | 101.720 | −66.482 | 75.102 | 1.00 | 21.51 |
| ATOM | 1316 | SG  | CYS | A | 774 | 99.925  | −66.774 | 75.059 | 1.00 | 22.30 |
| ATOM | 1317 | N   | ILE | A | 775 | 101.201 | −68.038 | 78.113 | 1.00 | 20.97 |
| ATOM | 1318 | CA  | ILE | A | 775 | 100.753 | −69.297 | 78.697 | 1.00 | 20.77 |
| ATOM | 1319 | C   | ILE | A | 775 | 99.348  | −69.496 | 78.114 | 1.00 | 20.32 |
| ATOM | 1320 | O   | ILE | A | 775 | 98.530  | −68.572 | 78.120 | 1.00 | 20.46 |
| ATOM | 1321 | CB  | ILE | A | 775 | 100.686 | −69.229 | 80.247 | 1.00 | 21.01 |
| ATOM | 1322 | CG1 | ILE | A | 775 | 99.892  | −67.996 | 80.685 | 1.00 | 21.19 |
| ATOM | 1323 | CG2 | ILE | A | 775 | 102.091 | −69.202 | 80.832 | 1.00 | 21.09 |
| ATOM | 1324 | CD1 | ILE | A | 775 | 99.782  | −67.847 | 82.192 | 1.00 | 21.58 |
| ATOM | 1325 | N   | HIS | A | 776 | 99.099  | −70.692 | 77.594 | 1.00 | 19.70 |
| ATOM | 1326 | CA  | HIS | A | 776 | 97.842  | −71.055 | 76.948 | 1.00 | 19.19 |
| ATOM | 1327 | C   | HIS | A | 776 | 96.757  | −71.483 | 77.943 | 1.00 | 18.74 |
| ATOM | 1328 | O   | HIS | A | 776 | 95.642  | −70.967 | 77.932 | 1.00 | 18.67 |
| ATOM | 1329 | CB  | HIS | A | 776 | 98.149  | −72.180 | 75.956 | 1.00 | 19.07 |
| ATOM | 1330 | CG  | HIS | A | 776 | 97.002  | −72.575 | 75.088 | 1.00 | 18.88 |
| ATOM | 1331 | ND1 | HIS | A | 776 | 95.848  | −73.142 | 75.587 | 1.00 | 18.75 |
| ATOM | 1332 | CD2 | HIS | A | 776 | 96.861  | −72.554 | 73.741 | 1.00 | 18.82 |
| ATOM | 1333 | CE1 | HIS | A | 776 | 95.049  | −73.457 | 74.585 | 1.00 | 18.84 |
| ATOM | 1334 | NE2 | HIS | A | 776 | 95.639  | −73.112 | 73.454 | 1.00 | 18.70 |
| ATOM | 1335 | N   | ARG | A | 777 | 97.105  | −72.452 | 78.778 | 1.00 | 18.38 |
| ATOM | 1336 | CA  | ARG | A | 777 | 96.242  | −72.990 | 79.822 | 1.00 | 18.01 |
| ATOM | 1337 | C   | ARG | A | 777 | 95.101  | −73.913 | 79.412 | 1.00 | 17.59 |
| ATOM | 1338 | O   | ARG | A | 777 | 94.335  | −74.354 | 80.264 | 1.00 | 17.80 |
| ATOM | 1339 | CB  | ARG | A | 777 | 95.738  | −71.861 | 80.724 | 1.00 | 18.26 |
| ATOM | 1340 | CG  | ARG | A | 777 | 96.908  | −71.143 | 81.422 | 1.00 | 18.67 |
| ATOM | 1341 | CD  | ARG | A | 777 | 96.527  | −70.527 | 82.756 | 1.00 | 19.00 |
| ATOM | 1342 | NE  | ARG | A | 777 | 95.817  | −69.266 | 82.589 | 1.00 | 19.53 |
| ATOM | 1343 | CZ  | ARG | A | 777 | 95.352  | −68.524 | 83.593 | 1.00 | 19.85 |
| ATOM | 1344 | NH1 | ARG | A | 777 | 95.515  | −68.907 | 84.859 | 1.00 | 19.85 |
| ATOM | 1345 | NH2 | ARG | A | 777 | 94.725  | −67.391 | 83.328 | 1.00 | 20.06 |
| ATOM | 1346 | N   | ASP | A | 778 | 94.963  | −74.190 | 78.119 | 1.00 | 16.97 |
| ATOM | 1347 | CA  | ASP | A | 778 | 93.957  | −75.162 | 77.692 | 1.00 | 16.55 |
| ATOM | 1348 | C   | ASP | A | 778 | 94.510  | −75.952 | 76.516 | 1.00 | 16.38 |
| ATOM | 1349 | O   | ASP | A | 778 | 93.849  | −76.130 | 75.506 | 1.00 | 16.52 |
| ATOM | 1350 | CB  | ASP | A | 778 | 92.618  | −74.512 | 77.322 | 1.00 | 16.13 |
| ATOM | 1351 | CG  | ASP | A | 778 | 91.493  | −75.540 | 77.225 | 1.00 | 15.88 |
| ATOM | 1352 | OD1 | ASP | A | 778 | 91.743  | −76.727 | 77.529 | 1.00 | 15.51 |
| ATOM | 1353 | OD2 | ASP | A | 778 | 90.364  | −75.169 | 76.850 | 1.00 | 15.68 |
| ATOM | 1354 | N   | VAL | A | 779 | 95.749  | −76.414 | 76.660 | 1.00 | 16.12 |
| ATOM | 1355 | CA  | VAL | A | 779 | 96.397  | −77.193 | 75.623 | 1.00 | 16.00 |
| ATOM | 1356 | C   | VAL | A | 779 | 95.792  | −78.586 | 75.661 | 1.00 | 15.81 |
| ATOM | 1357 | O   | VAL | A | 779 | 95.834  | −79.250 | 76.687 | 1.00 | 15.72 |
| ATOM | 1358 | CB  | VAL | A | 779 | 97.922  | −77.310 | 75.871 | 1.00 | 16.07 |
| ATOM | 1359 | CG1 | VAL | A | 779 | 98.544  | −78.238 | 74.839 | 1.00 | 16.03 |
| ATOM | 1360 | CG2 | VAL | A | 779 | 98.568  | −75.921 | 75.833 | 1.00 | 15.76 |
| ATOM | 1361 | N   | ALA | A | 780 | 95.243  | −79.016 | 74.534 | 1.00 | 15.64 |
| ATOM | 1362 | CA  | ALA | A | 780 | 94.604  | −80.324 | 74.428 | 1.00 | 15.73 |
| ATOM | 1363 | C   | ALA | A | 780 | 94.282  | −80.569 | 72.957 | 1.00 | 15.55 |
| ATOM | 1364 | O   | ALA | A | 780 | 94.194  | −79.624 | 72.180 | 1.00 | 15.59 |
| ATOM | 1365 | CB  | ALA | A | 780 | 93.312  | −80.350 | 75.277 | 1.00 | 15.59 |
| ATOM | 1366 | N   | ALA | A | 781 | 94.092  | −81.833 | 72.581 | 1.00 | 15.63 |
| ATOM | 1367 | CA  | ALA | A | 781 | 93.805  | −82.186 | 71.187 | 1.00 | 15.62 |
| ATOM | 1368 | C   | ALA | A | 781 | 92.598  | −81.456 | 70.601 | 1.00 | 15.71 |
| ATOM | 1369 | O   | ALA | A | 781 | 92.581  | −81.118 | 69.414 | 1.00 | 15.62 |
| ATOM | 1370 | CB  | ALA | A | 781 | 93.604  | −83.701 | 71.065 | 1.00 | 15.74 |
| ATOM | 1371 | N   | ARG | A | 782 | 91.585  | −81.229 | 71.434 | 1.00 | 15.78 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1372 | CA  | ARG | A | 782 | 90.368 | −80.555 | 71.005 | 1.00 | 15.99 |
|------|------|-----|-----|---|-----|--------|---------|--------|------|-------|
| ATOM | 1373 | C   | ARG | A | 782 | 90.608 | −79.106 | 70.573 | 1.00 | 16.25 |
| ATOM | 1374 | O   | ARG | A | 782 | 89.743 | −78.489 | 69.938 | 1.00 | 16.22 |
| ATOM | 1375 | CB  | ARG | A | 782 | 89.325 | −80.580 | 72.134 | 1.00 | 15.86 |
| ATOM | 1376 | CG  | ARG | A | 782 | 89.776 | −79.904 | 73.420 | 1.00 | 15.77 |
| ATOM | 1377 | CD  | ARG | A | 782 | 88.660 | −79.814 | 74.479 | 1.00 | 15.74 |
| ATOM | 1378 | NE  | ARG | A | 782 | 89.198 | −79.262 | 75.728 | 1.00 | 15.69 |
| ATOM | 1379 | CZ  | ARG | A | 782 | 89.844 | −79.981 | 76.643 | 1.00 | 15.79 |
| ATOM | 1380 | NH1 | ARG | A | 782 | 90.015 | −81.289 | 76.469 | 1.00 | 15.61 |
| ATOM | 1381 | NH2 | ARG | A | 782 | 90.382 | −79.382 | 77.705 | 1.00 | 15.71 |
| ATOM | 1382 | N   | ASN | A | 783 | 91.763 | −78.552 | 70.924 | 1.00 | 16.44 |
| ATOM | 1383 | CA  | ASN | A | 783 | 92.042 | −77.170 | 70.546 | 1.00 | 16.82 |
| ATOM | 1384 | C   | ASN | A | 783 | 93.054 | −77.054 | 69.426 | 1.00 | 16.96 |
| ATOM | 1385 | O   | ASN | A | 783 | 93.526 | −75.957 | 69.122 | 1.00 | 16.81 |
| ATOM | 1386 | CB  | ASN | A | 783 | 92.499 | −76.354 | 71.755 | 1.00 | 16.87 |
| ATOM | 1387 | CG  | ASN | A | 783 | 91.331 | −75.849 | 72.586 | 1.00 | 17.03 |
| ATOM | 1388 | OD1 | ASN | A | 783 | 90.336 | −75.354 | 72.039 | 1.00 | 17.26 |
| ATOM | 1389 | ND2 | ASN | A | 783 | 91.452 | −75.948 | 73.912 | 1.00 | 16.77 |
| ATOM | 1390 | N   | VAL | A | 784 | 93.381 | −78.190 | 68.819 | 1.00 | 17.17 |
| ATOM | 1391 | CA  | VAL | A | 784 | 94.313 | −78.205 | 67.701 | 1.00 | 17.56 |
| ATOM | 1392 | C   | VAL | A | 784 | 93.480 | −78.425 | 66.441 | 1.00 | 18.01 |
| ATOM | 1393 | O   | VAL | A | 784 | 92.622 | −79.315 | 66.396 | 1.00 | 17.85 |
| ATOM | 1394 | CB  | VAL | A | 784 | 95.360 | −79.356 | 67.805 | 1.00 | 17.46 |
| ATOM | 1395 | CG1 | VAL | A | 784 | 96.282 | −79.320 | 66.592 | 1.00 | 17.43 |
| ATOM | 1396 | CG2 | VAL | A | 784 | 96.178 | −79.231 | 69.080 | 1.00 | 17.31 |
| ATOM | 1397 | N   | LEU | A | 785 | 93.709 | −77.595 | 65.432 | 1.00 | 18.59 |
| ATOM | 1398 | CA  | LEU | A | 785 | 92.989 | −77.734 | 64.173 | 1.00 | 19.34 |
| ATOM | 1399 | C   | LEU | A | 785 | 93.929 | −78.248 | 63.089 | 1.00 | 19.84 |
| ATOM | 1400 | O   | LEU | A | 785 | 95.145 | −78.078 | 63.179 | 1.00 | 19.93 |
| ATOM | 1401 | CB  | LEU | A | 785 | 92.390 | −76.397 | 63.735 | 1.00 | 19.34 |
| ATOM | 1402 | CG  | LEU | A | 785 | 91.372 | −75.717 | 64.654 | 1.00 | 19.64 |
| ATOM | 1403 | CD1 | LEU | A | 785 | 90.839 | −74.476 | 63.974 | 1.00 | 19.53 |
| ATOM | 1404 | CD2 | LEU | A | 785 | 90.223 | −76.671 | 64.977 | 1.00 | 19.81 |
| ATOM | 1405 | N   | LEU | A | 786 | 93.352 | −78.884 | 62.071 | 1.00 | 20.53 |
| ATOM | 1406 | CA  | LEU | A | 786 | 94.107 | −79.431 | 60.949 | 1.00 | 21.15 |
| ATOM | 1407 | C   | LEU | A | 786 | 93.736 | −78.647 | 59.696 | 1.00 | 21.56 |
| ATOM | 1408 | O   | LEU | A | 786 | 92.562 | −78.529 | 59.351 | 1.00 | 21.51 |
| ATOM | 1409 | CB  | LEU | A | 786 | 93.770 | −80.915 | 60.755 | 1.00 | 21.14 |
| ATOM | 1410 | CG  | LEU | A | 786 | 94.194 | −81.852 | 61.887 | 1.00 | 21.29 |
| ATOM | 1411 | CD1 | LEU | A | 786 | 93.671 | −83.256 | 61.622 | 1.00 | 21.21 |
| ATOM | 1412 | CD2 | LEU | A | 786 | 95.710 | −81.852 | 62.005 | 1.00 | 21.17 |
| ATOM | 1413 | N   | THR | A | 787 | 94.743 | −78.103 | 59.023 | 1.00 | 22.17 |
| ATOM | 1414 | CA  | THR | A | 787 | 94.507 | −77.313 | 57.821 | 1.00 | 22.84 |
| ATOM | 1415 | C   | THR | A | 787 | 94.984 | −78.055 | 56.569 | 1.00 | 23.21 |
| ATOM | 1416 | O   | THR | A | 787 | 95.142 | −79.273 | 56.587 | 1.00 | 23.18 |
| ATOM | 1417 | CB  | THR | A | 787 | 95.228 | −75.950 | 57.923 | 1.00 | 22.80 |
| ATOM | 1418 | OG1 | THR | A | 787 | 94.761 | −75.089 | 56.880 | 1.00 | 23.25 |
| ATOM | 1419 | CG2 | THR | A | 787 | 96.736 | −76.125 | 57.799 | 1.00 | 22.85 |
| ATOM | 1420 | N   | ASN | A | 788 | 95.213 | −77.314 | 55.486 | 1.00 | 23.77 |
| ATOM | 1421 | CA  | ASN | A | 788 | 95.685 | −77.910 | 54.235 | 1.00 | 24.29 |
| ATOM | 1422 | C   | ASN | A | 788 | 96.904 | −78.804 | 54.467 | 1.00 | 24.28 |
| ATOM | 1423 | O   | ASN | A | 788 | 97.840 | −78.424 | 55.170 | 1.00 | 24.37 |
| ATOM | 1424 | CB  | ASN | A | 788 | 96.047 | −76.812 | 53.234 | 1.00 | 24.80 |
| ATOM | 1425 | CG  | ASN | A | 788 | 94.859 | −75.956 | 52.862 | 1.00 | 25.30 |
| ATOM | 1426 | OD1 | ASN | A | 788 | 93.900 | −76.434 | 52.251 | 1.00 | 25.88 |
| ATOM | 1427 | ND2 | ASN | A | 788 | 94.909 | −74.682 | 53.229 | 1.00 | 25.69 |
| ATOM | 1428 | N   | GLY | A | 789 | 96.886 | −79.990 | 53.865 | 1.00 | 24.31 |
| ATOM | 1429 | CA  | GLY | A | 789 | 97.987 | −80.924 | 54.018 | 1.00 | 24.30 |
| ATOM | 1430 | C   | GLY | A | 789 | 97.956 | −81.575 | 55.388 | 1.00 | 24.32 |
| ATOM | 1431 | O   | GLY | A | 789 | 98.909 | −82.236 | 55.795 | 1.00 | 24.41 |
| ATOM | 1432 | N   | HIS | A | 790 | 96.832 | −81.403 | 56.078 | 1.00 | 24.25 |
| ATOM | 1433 | CA  | HIS | A | 790 | 96.624 | −81.918 | 57.424 | 1.00 | 24.08 |
| ATOM | 1434 | C   | HIS | A | 790 | 97.721 | −81.432 | 58.368 | 1.00 | 23.82 |
| ATOM | 1435 | O   | HIS | A | 790 | 98.221 | −82.176 | 59.217 | 1.00 | 23.82 |
| ATOM | 1436 | CB  | HIS | A | 790 | 96.535 | −83.452 | 57.434 | 1.00 | 24.35 |
| ATOM | 1437 | CG  | HIS | A | 790 | 95.231 | −83.985 | 56.916 | 1.00 | 24.71 |
| ATOM | 1438 | ND1 | HIS | A | 790 | 94.933 | −84.056 | 55.570 | 1.00 | 24.82 |
| ATOM | 1439 | CD2 | HIS | A | 790 | 94.133 | −84.443 | 57.567 | 1.00 | 24.89 |
| ATOM | 1440 | CE1 | HIS | A | 790 | 93.709 | −84.536 | 55.416 | 1.00 | 24.86 |
| ATOM | 1441 | NE2 | HIS | A | 790 | 93.201 | −84.777 | 56.611 | 1.00 | 24.85 |
| ATOM | 1442 | N   | VAL | A | 791 | 98.099 | −80.171 | 58.201 | 1.00 | 23.41 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1443 | CA  | VAL | A | 791 | 99.114  | −79.559 | 59.047 | 1.00 | 23.14 |
|------|------|-----|-----|---|-----|---------|---------|--------|------|-------|
| ATOM | 1444 | C   | VAL | A | 791 | 98.430  | −79.119 | 60.340 | 1.00 | 22.73 |
| ATOM | 1445 | O   | VAL | A | 791 | 97.424  | −78.420 | 60.302 | 1.00 | 22.65 |
| ATOM | 1446 | CB  | VAL | A | 791 | 99.729  | −78.315 | 58.374 | 1.00 | 23.28 |
| ATOM | 1447 | CG1 | VAL | A | 791 | 100.668 | −77.611 | 59.348 | 1.00 | 23.39 |
| ATOM | 1448 | CG2 | VAL | A | 791 | 100.477 | −78.723 | 57.112 | 1.00 | 23.45 |
| ATOM | 1449 | N   | ALA | A | 792 | 98.989  | −79.523 | 61.474 | 1.00 | 22.39 |
| ATOM | 1450 | CA  | ALA | A | 792 | 98.422  | −79.191 | 62.773 | 1.00 | 22.01 |
| ATOM | 1451 | C   | ALA | A | 792 | 98.757  | −77.780 | 63.250 | 1.00 | 21.71 |
| ATOM | 1452 | O   | ALA | A | 792 | 99.890  | −77.305 | 63.101 | 1.00 | 21.62 |
| ATOM | 1453 | CB  | ALA | A | 792 | 98.885  | −80.210 | 63.809 | 1.00 | 22.06 |
| ATOM | 1454 | N   | LYS | A | 793 | 97.753  | −77.129 | 63.830 | 1.00 | 21.15 |
| ATOM | 1455 | CA  | LYS | A | 793 | 97.879  | −75.781 | 64.373 | 1.00 | 20.68 |
| ATOM | 1456 | C   | LYS | A | 793 | 97.227  | −75.710 | 65.763 | 1.00 | 20.31 |
| ATOM | 1457 | O   | LYS | A | 793 | 96.073  | −76.108 | 65.936 | 1.00 | 20.14 |
| ATOM | 1458 | CB  | LYS | A | 793 | 97.187  | −74.770 | 63.451 | 1.00 | 20.80 |
| ATOM | 1459 | CG  | LYS | A | 793 | 97.919  | −74.477 | 62.143 | 1.00 | 20.74 |
| ATOM | 1460 | CD  | LYS | A | 793 | 97.058  | −73.580 | 61.240 | 1.00 | 20.74 |
| ATOM | 1461 | CE  | LYS | A | 793 | 97.871  | −72.988 | 60.088 | 1.00 | 20.72 |
| ATOM | 1462 | NZ  | LYS | A | 793 | 98.714  | −71.841 | 60.544 | 1.00 | 20.67 |
| ATOM | 1463 | N   | ILE | A | 794 | 97.962  | −75.206 | 66.747 | 1.00 | 19.86 |
| ATOM | 1464 | CA  | ILE | A | 794 | 97.409  | −75.070 | 68.085 | 1.00 | 19.48 |
| ATOM | 1465 | C   | ILE | A | 794 | 96.645  | −73.748 | 68.164 | 1.00 | 19.44 |
| ATOM | 1466 | O   | ILE | A | 794 | 97.091  | −72.720 | 67.649 | 1.00 | 19.47 |
| ATOM | 1467 | CB  | ILE | A | 794 | 98.511  | −75.101 | 69.183 | 1.00 | 19.20 |
| ATOM | 1468 | CG1 | ILE | A | 794 | 97.886  | −74.955 | 70.580 | 1.00 | 19.08 |
| ATOM | 1469 | CG2 | ILE | A | 794 | 99.516  | −73.970 | 68.961 | 1.00 | 19.16 |
| ATOM | 1470 | CD1 | ILE | A | 794 | 96.852  | −76.011 | 70.929 | 1.00 | 18.76 |
| ATOM | 1471 | N   | GLY | A | 795 | 95.470  | −73.796 | 68.774 | 1.00 | 19.30 |
| ATOM | 1472 | CA  | GLY | A | 795 | 94.676  | −72.597 | 68.942 | 1.00 | 19.27 |
| ATOM | 1473 | C   | GLY | A | 795 | 93.846  | −72.786 | 70.191 | 1.00 | 19.35 |
| ATOM | 1474 | O   | GLY | A | 795 | 94.266  | −73.482 | 71.111 | 1.00 | 19.33 |
| ATOM | 1475 | N   | ASP | A | 796 | 92.678  | −72.154 | 70.231 | 1.00 | 19.35 |
| ATOM | 1476 | CA  | ASP | A | 796 | 91.757  | −72.296 | 71.347 | 1.00 | 19.47 |
| ATOM | 1477 | C   | ASP | A | 796 | 90.435  | −71.687 | 70.912 | 1.00 | 19.60 |
| ATOM | 1478 | O   | ASP | A | 796 | 90.384  | −70.535 | 70.479 | 1.00 | 19.36 |
| ATOM | 1479 | CB  | ASP | A | 796 | 92.271  | −71.577 | 72.599 | 1.00 | 19.40 |
| ATOM | 1480 | CG  | ASP | A | 796 | 91.432  | −71.886 | 73.850 | 1.00 | 19.63 |
| ATOM | 1481 | OD1 | ASP | A | 796 | 90.295  | −72.402 | 73.727 | 1.00 | 19.59 |
| ATOM | 1482 | OD2 | ASP | A | 796 | 91.907  | −71.593 | 74.964 | 1.00 | 19.63 |
| ATOM | 1483 | N   | PHE | A | 797 | 89.366  | −72.467 | 71.009 | 1.00 | 19.84 |
| ATOM | 1484 | CA  | PHE | A | 797 | 88.049  | −71.966 | 70.642 | 1.00 | 20.33 |
| ATOM | 1485 | C   | PHE | A | 797 | 87.583  | −70.878 | 71.617 | 1.00 | 20.57 |
| ATOM | 1486 | O   | PHE | A | 797 | 86.687  | −70.081 | 71.302 | 1.00 | 20.68 |
| ATOM | 1487 | CB  | PHE | A | 797 | 87.036  | −73.120 | 70.593 | 1.00 | 20.36 |
| ATOM | 1488 | CG  | PHE | A | 797 | 87.250  | −74.064 | 69.434 | 1.00 | 20.46 |
| ATOM | 1489 | CD1 | PHE | A | 797 | 88.087  | −75.166 | 69.556 | 1.00 | 20.37 |
| ATOM | 1490 | CD2 | PHE | A | 797 | 86.634  | −73.827 | 68.205 | 1.00 | 20.67 |
| ATOM | 1491 | CE1 | PHE | A | 797 | 88.311  | −76.021 | 68.476 | 1.00 | 20.56 |
| ATOM | 1492 | CE2 | PHE | A | 797 | 86.854  | −74.679 | 67.115 | 1.00 | 20.55 |
| ATOM | 1493 | CZ  | PHE | A | 797 | 87.692  | −75.774 | 67.253 | 1.00 | 20.43 |
| ATOM | 1494 | N   | GLY | A | 798 | 88.194  | −70.850 | 72.799 | 1.00 | 20.82 |
| ATOM | 1495 | CA  | GLY | A | 798 | 87.856  | −69.846 | 73.796 | 1.00 | 21.20 |
| ATOM | 1496 | C   | GLY | A | 798 | 86.379  | −69.732 | 74.133 | 1.00 | 21.52 |
| ATOM | 1497 | O   | GLY | A | 798 | 85.719  | −70.743 | 74.392 | 1.00 | 21.50 |
| ATOM | 1498 | N   | LEU | A | 799 | 85.857  | −68.502 | 74.123 | 1.00 | 21.83 |
| ATOM | 1499 | CA  | LEU | A | 799 | 84.452  | −68.266 | 74.449 | 1.00 | 22.19 |
| ATOM | 1500 | C   | LEU | A | 799 | 83.474  | −68.970 | 73.513 | 1.00 | 22.46 |
| ATOM | 1501 | O   | LEU | A | 799 | 82.257  | −68.962 | 73.748 | 1.00 | 22.59 |
| ATOM | 1502 | CB  | LEU | A | 799 | 84.155  | −66.757 | 74.493 | 1.00 | 22.32 |
| ATOM | 1503 | CG  | LEU | A | 799 | 84.372  | −65.872 | 73.262 | 1.00 | 22.46 |
| ATOM | 1504 | CD1 | LEU | A | 799 | 83.269  | −66.130 | 72.232 | 1.00 | 22.40 |
| ATOM | 1505 | CD2 | LEU | A | 799 | 84.363  | −64.399 | 73.695 | 1.00 | 22.48 |
| ATOM | 1506 | N   | ALA | A | 800 | 84.002  | −69.584 | 72.459 | 1.00 | 22.59 |
| ATOM | 1507 | CA  | ALA | A | 800 | 83.173  | −70.302 | 71.506 | 1.00 | 22.78 |
| ATOM | 1508 | C   | ALA | A | 800 | 83.117  | −71.786 | 71.856 | 1.00 | 22.93 |
| ATOM | 1509 | O   | ALA | A | 800 | 82.559  | −72.588 | 71.106 | 1.00 | 22.98 |
| ATOM | 1510 | CB  | ALA | A | 800 | 83.697  | −70.112 | 70.088 | 1.00 | 22.84 |
| ATOM | 1511 | N   | ARG | A | 801 | 83.710  | −72.164 | 72.983 | 1.00 | 23.12 |
| ATOM | 1512 | CA  | ARG | A | 801 | 83.643  | −73.562 | 73.389 | 1.00 | 23.31 |
| ATOM | 1513 | C   | ARG | A | 801 | 82.472  | −73.736 | 74.346 | 1.00 | 23.40 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1514 | O   | ARG | A | 801 | 82.228 | −72.887 | 75.205 | 1.00 | 23.46 |
| ATOM | 1515 | CB  | ARG | A | 801 | 84.929 | −74.033 | 74.080 | 1.00 | 23.33 |
| ATOM | 1516 | CG  | ARG | A | 801 | 84.791 | −75.484 | 74.584 | 1.00 | 23.38 |
| ATOM | 1517 | CD  | ARG | A | 801 | 86.085 | −76.076 | 75.082 | 1.00 | 23.36 |
| ATOM | 1518 | NE  | ARG | A | 801 | 87.116 | −76.124 | 74.046 | 1.00 | 23.38 |
| ATOM | 1519 | CZ  | ARG | A | 801 | 87.104 | −76.940 | 72.997 | 1.00 | 23.39 |
| ATOM | 1520 | NH1 | ARG | A | 801 | 86.104 | −77.801 | 72.823 | 1.00 | 23.35 |
| ATOM | 1521 | NH2 | ARG | A | 801 | 88.102 | −76.896 | 72.121 | 1.00 | 23.18 |
| ATOM | 1522 | N   | ASP | A | 802 | 81.759 | −74.846 | 74.190 | 1.00 | 23.50 |
| ATOM | 1523 | CA  | ASP | A | 802 | 80.597 | −75.165 | 75.014 | 1.00 | 23.65 |
| ATOM | 1524 | C   | ASP | A | 802 | 81.064 | −75.640 | 76.385 | 1.00 | 23.66 |
| ATOM | 1525 | O   | ASP | A | 802 | 80.713 | −76.726 | 76.847 | 1.00 | 23.66 |
| ATOM | 1526 | CB  | ASP | A | 802 | 79.783 | −76.252 | 74.309 | 1.00 | 23.82 |
| ATOM | 1527 | CG  | ASP | A | 802 | 78.481 | −76.559 | 75.011 | 1.00 | 23.93 |
| ATOM | 1528 | OD1 | ASP | A | 802 | 77.979 | −75.682 | 75.751 | 1.00 | 24.03 |
| ATOM | 1529 | OD2 | ASP | A | 802 | 77.958 | −77.678 | 74.804 | 1.00 | 24.09 |
| ATOM | 1530 | N   | ILE | A | 803 | 81.850 | −74.791 | 77.032 | 1.00 | 23.64 |
| ATOM | 1531 | CA  | ILE | A | 803 | 82.445 | −75.077 | 78.329 | 1.00 | 23.73 |
| ATOM | 1532 | C   | ILE | A | 803 | 81.489 | −75.469 | 79.466 | 1.00 | 23.67 |
| ATOM | 1533 | O   | ILE | A | 803 | 81.822 | −76.307 | 80.302 | 1.00 | 23.64 |
| ATOM | 1534 | CB  | ILE | A | 803 | 83.320 | −73.873 | 78.754 | 1.00 | 23.85 |
| ATOM | 1535 | CG1 | ILE | A | 803 | 84.379 | −74.310 | 79.757 | 1.00 | 24.03 |
| ATOM | 1536 | CG2 | ILE | A | 803 | 82.449 | −72.774 | 79.337 | 1.00 | 23.86 |
| ATOM | 1537 | CD1 | ILE | A | 803 | 85.300 | −73.178 | 80.183 | 1.00 | 24.15 |
| ATOM | 1538 | N   | MET | A | 804 | 80.301 | −74.874 | 79.496 | 1.00 | 23.63 |
| ATOM | 1539 | CA  | MET | A | 804 | 79.322 | −75.164 | 80.544 | 1.00 | 23.66 |
| ATOM | 1540 | C   | MET | A | 804 | 78.716 | −76.572 | 80.488 | 1.00 | 23.50 |
| ATOM | 1541 | O   | MET | A | 804 | 78.295 | −77.104 | 81.513 | 1.00 | 23.55 |
| ATOM | 1542 | CB  | MET | A | 804 | 78.185 | −74.135 | 80.486 | 1.00 | 23.83 |
| ATOM | 1543 | CG  | MET | A | 804 | 78.650 | −72.674 | 80.538 | 1.00 | 24.27 |
| ATOM | 1544 | SD  | MET | A | 804 | 79.564 | −72.293 | 82.046 | 1.00 | 24.77 |
| ATOM | 1545 | CE  | MET | A | 804 | 78.219 | −72.031 | 83.211 | 1.00 | 24.61 |
| ATOM | 1546 | N   | ASN | A | 805 | 78.663 | −77.165 | 79.298 | 1.00 | 23.33 |
| ATOM | 1547 | CA  | ASN | A | 805 | 78.074 | −78.495 | 79.117 | 1.00 | 23.27 |
| ATOM | 1548 | C   | ASN | A | 805 | 79.086 | −79.568 | 78.737 | 1.00 | 23.30 |
| ATOM | 1549 | O   | ASN | A | 805 | 78.712 | −80.657 | 78.290 | 1.00 | 23.14 |
| ATOM | 1550 | CB  | ASN | A | 805 | 76.991 | −78.435 | 78.039 | 1.00 | 23.20 |
| ATOM | 1551 | CG  | ASN | A | 805 | 75.955 | −77.379 | 78.331 | 1.00 | 23.10 |
| ATOM | 1552 | OD1 | ASN | A | 805 | 75.266 | −77.446 | 79.345 | 1.00 | 23.12 |
| ATOM | 1553 | ND2 | ASN | A | 805 | 75.851 | −76.386 | 77.456 | 1.00 | 23.00 |
| ATOM | 1554 | N   | ASP | A | 806 | 80.363 | −79.248 | 78.907 | 1.00 | 23.31 |
| ATOM | 1555 | CA  | ASP | A | 806 | 81.450 | −80.168 | 78.591 | 1.00 | 23.46 |
| ATOM | 1556 | C   | ASP | A | 806 | 81.994 | −80.725 | 79.914 | 1.00 | 23.64 |
| ATOM | 1557 | O   | ASP | A | 806 | 82.550 | −79.983 | 80.722 | 1.00 | 23.51 |
| ATOM | 1558 | CB  | ASP | A | 806 | 82.555 | −79.419 | 77.844 | 1.00 | 23.27 |
| ATOM | 1559 | CG  | ASP | A | 806 | 83.643 | −80.341 | 77.332 | 1.00 | 23.16 |
| ATOM | 1560 | OD1 | ASP | A | 806 | 83.983 | −81.315 | 78.035 | 1.00 | 23.08 |
| ATOM | 1561 | OD2 | ASP | A | 806 | 84.164 | −80.082 | 76.229 | 1.00 | 23.03 |
| ATOM | 1562 | N   | SER | A | 807 | 81.832 | −82.029 | 80.126 | 1.00 | 23.94 |
| ATOM | 1563 | CA  | SER | A | 807 | 82.287 | −82.663 | 81.363 | 1.00 | 24.37 |
| ATOM | 1564 | C   | SER | A | 807 | 83.807 | −82.699 | 81.552 | 1.00 | 24.47 |
| ATOM | 1565 | O   | SER | A | 807 | 84.288 | −83.165 | 82.591 | 1.00 | 24.50 |
| ATOM | 1566 | CB  | SER | A | 807 | 81.723 | −84.084 | 81.464 | 1.00 | 24.56 |
| ATOM | 1567 | OG  | SER | A | 807 | 82.149 | −84.883 | 80.370 | 1.00 | 25.16 |
| ATOM | 1568 | N   | ASN | A | 808 | 84.558 | −82.221 | 80.558 | 1.00 | 24.58 |
| ATOM | 1569 | CA  | ASN | A | 808 | 86.022 | −82.175 | 80.657 | 1.00 | 24.74 |
| ATOM | 1570 | C   | ASN | A | 808 | 86.436 | −80.912 | 81.415 | 1.00 | 24.96 |
| ATOM | 1571 | O   | ASN | A | 808 | 87.593 | −80.752 | 81.812 | 1.00 | 24.89 |
| ATOM | 1572 | CB  | ASN | A | 808 | 86.671 | −82.172 | 79.271 | 1.00 | 24.82 |
| ATOM | 1573 | CG  | ASN | A | 808 | 86.628 | −83.533 | 78.603 | 1.00 | 24.91 |
| ATOM | 1574 | OD1 | ASN | A | 808 | 86.957 | −84.542 | 79.215 | 1.00 | 25.03 |
| ATOM | 1575 | ND2 | ASN | A | 808 | 86.239 | −83.562 | 77.337 | 1.00 | 25.07 |
| ATOM | 1576 | N   | TYR | A | 809 | 85.483 | −80.004 | 81.598 | 1.00 | 25.07 |
| ATOM | 1577 | CA  | TYR | A | 809 | 85.750 | −78.773 | 82.324 | 1.00 | 25.23 |
| ATOM | 1578 | C   | TYR | A | 809 | 85.041 | −78.841 | 83.666 | 1.00 | 25.90 |
| ATOM | 1579 | O   | TYR | A | 809 | 83.821 | −79.022 | 83.728 | 1.00 | 25.85 |
| ATOM | 1580 | CB  | TYR | A | 809 | 85.283 | −77.563 | 81.518 | 1.00 | 24.53 |
| ATOM | 1581 | CG  | TYR | A | 809 | 86.099 | −77.357 | 80.263 | 1.00 | 23.89 |
| ATOM | 1582 | CD1 | TYR | A | 809 | 85.867 | −78.125 | 79.121 | 1.00 | 23.60 |
| ATOM | 1583 | CD2 | TYR | A | 809 | 87.126 | −76.417 | 80.227 | 1.00 | 23.57 |
| ATOM | 1584 | CE1 | TYR | A | 809 | 86.635 | −77.959 | 77.971 | 1.00 | 23.33 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1585 | CE2 | TYR | A | 809 | 87.904 | −76.242 | 79.085 | 1.00 | 23.40 |
| ATOM | 1586 | CZ  | TYR | A | 809 | 87.650 | −77.012 | 77.962 | 1.00 | 23.32 |
| ATOM | 1587 | OH  | TYR | A | 809 | 88.391 | −76.822 | 76.829 | 1.00 | 23.06 |
| ATOM | 1588 | N   | ILE | A | 810 | 85.825 | −78.700 | 84.732 | 1.00 | 26.67 |
| ATOM | 1589 | CA  | ILE | A | 810 | 85.337 | −78.780 | 86.108 | 1.00 | 27.41 |
| ATOM | 1590 | C   | ILE | A | 810 | 85.385 | −77.452 | 86.860 | 1.00 | 27.96 |
| ATOM | 1591 | O   | ILE | A | 810 | 86.352 | −76.706 | 86.760 | 1.00 | 27.88 |
| ATOM | 1592 | CB  | ILE | A | 810 | 86.170 | −79.818 | 86.897 | 1.00 | 27.49 |
| ATOM | 1593 | CG1 | ILE | A | 810 | 85.960 | −81.210 | 86.299 | 1.00 | 27.59 |
| ATOM | 1594 | CG2 | ILE | A | 810 | 85.810 | −79.783 | 88.375 | 1.00 | 27.59 |
| ATOM | 1595 | CD1 | ILE | A | 810 | 84.496 | −81.630 | 86.215 | 1.00 | 27.72 |
| ATOM | 1596 | N   | VAL | A | 811 | 84.338 | −77.162 | 87.630 | 1.00 | 28.72 |
| ATOM | 1597 | CA  | VAL | A | 811 | 84.310 | −75.922 | 88.393 | 1.00 | 29.44 |
| ATOM | 1598 | C   | VAL | A | 811 | 85.497 | −75.936 | 89.352 | 1.00 | 29.93 |
| ATOM | 1599 | O   | VAL | A | 811 | 85.689 | −76.883 | 90.110 | 1.00 | 30.03 |
| ATOM | 1600 | CB  | VAL | A | 811 | 83.006 | −75.770 | 89.216 | 1.00 | 29.52 |
| ATOM | 1601 | CG1 | VAL | A | 811 | 83.004 | −74.426 | 89.940 | 1.00 | 29.69 |
| ATOM | 1602 | CG2 | VAL | A | 811 | 81.799 | −75.863 | 88.307 | 1.00 | 29.69 |
| ATOM | 1603 | N   | LYS | A | 812 | 86.300 | −74.886 | 89.289 | 1.00 | 30.49 |
| ATOM | 1604 | CA  | LYS | A | 812 | 87.471 | −74.754 | 90.138 | 1.00 | 31.05 |
| ATOM | 1605 | C   | LYS | A | 812 | 87.481 | −73.294 | 90.544 | 1.00 | 31.28 |
| ATOM | 1606 | O   | LYS | A | 812 | 88.077 | −72.451 | 89.870 | 1.00 | 31.43 |
| ATOM | 1607 | CB  | LYS | A | 812 | 88.733 | −75.113 | 89.342 | 1.00 | 31.29 |
| ATOM | 1608 | CG  | LYS | A | 812 | 89.985 | −75.392 | 90.180 | 1.00 | 31.58 |
| ATOM | 1609 | CD  | LYS | A | 812 | 90.754 | −74.120 | 90.491 | 1.00 | 31.74 |
| ATOM | 1610 | CE  | LYS | A | 812 | 92.143 | −74.449 | 91.008 | 1.00 | 31.81 |
| ATOM | 1611 | NZ  | LYS | A | 812 | 92.914 | −73.210 | 91.242 | 1.00 | 31.95 |
| ATOM | 1612 | N   | GLY | A | 813 | 86.772 | −72.999 | 91.631 | 1.00 | 31.48 |
| ATOM | 1613 | CA  | GLY | A | 813 | 86.687 | −71.640 | 92.124 | 1.00 | 31.56 |
| ATOM | 1614 | C   | GLY | A | 813 | 85.979 | −70.679 | 91.184 | 1.00 | 31.62 |
| ATOM | 1615 | O   | GLY | A | 813 | 84.783 | −70.791 | 90.922 | 1.00 | 31.70 |
| ATOM | 1616 | N   | ASN | A | 814 | 86.741 | −69.725 | 90.671 | 1.00 | 31.60 |
| ATOM | 1617 | CA  | ASN | A | 814 | 86.222 | −68.706 | 89.774 | 1.00 | 31.52 |
| ATOM | 1618 | C   | ASN | A | 814 | 85.991 | −69.177 | 88.340 | 1.00 | 31.19 |
| ATOM | 1619 | O   | ASN | A | 814 | 85.569 | −68.382 | 87.496 | 1.00 | 31.30 |
| ATOM | 1620 | CB  | ASN | A | 814 | 87.195 | −67.524 | 89.760 | 1.00 | 31.90 |
| ATOM | 1621 | CG  | ASN | A | 814 | 88.586 | −67.915 | 89.255 | 1.00 | 32.17 |
| ATOM | 1622 | OD1 | ASN | A | 814 | 88.843 | −67.928 | 88.047 | 1.00 | 32.36 |
| ATOM | 1623 | ND2 | ASN | A | 814 | 89.484 | −68.244 | 90.183 | 1.00 | 32.36 |
| ATOM | 1624 | N   | ALA | A | 815 | 86.234 | −70.457 | 88.057 | 1.00 | 30.75 |
| ATOM | 1625 | CA  | ALA | A | 815 | 86.081 | −70.931 | 86.680 | 1.00 | 30.09 |
| ATOM | 1626 | C   | ALA | A | 815 | 85.813 | −72.414 | 86.438 | 1.00 | 29.57 |
| ATOM | 1627 | O   | ALA | A | 815 | 85.641 | −73.207 | 87.363 | 1.00 | 29.61 |
| ATOM | 1628 | CB  | ALA | A | 815 | 87.311 | −70.516 | 85.888 | 1.00 | 30.11 |
| ATOM | 1629 | N   | ARG | A | 816 | 85.774 | −72.762 | 85.153 | 1.00 | 28.90 |
| ATOM | 1630 | CA  | ARG | A | 816 | 85.567 | −74.131 | 84.687 | 1.00 | 28.10 |
| ATOM | 1631 | C   | ARG | A | 816 | 86.898 | −74.511 | 84.032 | 1.00 | 27.32 |
| ATOM | 1632 | O   | ARG | A | 816 | 87.248 | −73.973 | 82.988 | 1.00 | 27.13 |
| ATOM | 1633 | CB  | ARG | A | 816 | 84.451 | −74.161 | 83.646 | 1.00 | 28.45 |
| ATOM | 1634 | CG  | ARG | A | 816 | 83.138 | −73.580 | 84.132 | 1.00 | 28.97 |
| ATOM | 1635 | CD  | ARG | A | 816 | 82.076 | −74.647 | 84.251 | 1.00 | 29.34 |
| ATOM | 1636 | NE  | ARG | A | 816 | 80.958 | −74.178 | 85.063 | 1.00 | 29.85 |
| ATOM | 1637 | CZ  | ARG | A | 816 | 79.938 | −74.939 | 85.428 | 1.00 | 29.94 |
| ATOM | 1638 | NH1 | ARG | A | 816 | 78.963 | −74.434 | 86.174 | 1.00 | 30.24 |
| ATOM | 1639 | NH2 | ARG | A | 816 | 79.892 | −76.205 | 85.040 | 1.00 | 30.13 |
| ATOM | 1640 | N   | LEU | A | 817 | 87.633 | −75.439 | 84.638 | 1.00 | 26.46 |
| ATOM | 1641 | CA  | LEU | A | 817 | 88.946 | −75.816 | 84.114 | 1.00 | 25.57 |
| ATOM | 1642 | C   | LEU | A | 817 | 89.107 | −77.270 | 83.674 | 1.00 | 24.81 |
| ATOM | 1643 | O   | LEU | A | 817 | 88.487 | −78.176 | 84.237 | 1.00 | 24.90 |
| ATOM | 1644 | CB  | LEU | A | 817 | 90.020 | −75.496 | 85.158 | 1.00 | 25.61 |
| ATOM | 1645 | CG  | LEU | A | 817 | 90.074 | −74.084 | 85.746 | 1.00 | 25.66 |
| ATOM | 1646 | CD1 | LEU | A | 817 | 91.147 | −74.041 | 86.819 | 1.00 | 25.73 |
| ATOM | 1647 | CD2 | LEU | A | 817 | 90.369 | −73.055 | 84.653 | 1.00 | 25.66 |
| ATOM | 1648 | N   | PRO | A | 818 | 89.964 | −77.508 | 82.660 | 1.00 | 24.05 |
| ATOM | 1649 | CA  | PRO | A | 818 | 90.254 | −78.836 | 82.103 | 1.00 | 23.35 |
| ATOM | 1650 | C   | PRO | A | 818 | 91.250 | −79.555 | 83.021 | 1.00 | 22.76 |
| ATOM | 1651 | O   | PRO | A | 818 | 92.428 | −79.721 | 82.682 | 1.00 | 22.37 |
| ATOM | 1652 | CB  | PRO | A | 818 | 90.859 | −78.500 | 80.744 | 1.00 | 23.48 |
| ATOM | 1653 | CG  | PRO | A | 818 | 91.676 | −77.275 | 81.073 | 1.00 | 23.60 |
| ATOM | 1654 | CD  | PRO | A | 818 | 90.705 | −76.463 | 81.925 | 1.00 | 23.90 |
| ATOM | 1655 | N   | VAL | A | 819 | 90.761 | −79.979 | 84.181 | 1.00 | 22.17 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1656 | CA  | VAL | A | 819 | 91.598  | −80.624 | 85.192 | 1.00 | 21.70 |
|------|------|-----|-----|---|-----|---------|---------|--------|------|-------|
| ATOM | 1657 | C   | VAL | A | 819 | 92.444  | −81.827 | 84.786 | 1.00 | 21.38 |
| ATOM | 1658 | O   | VAL | A | 819 | 93.580  | −81.954 | 85.243 | 1.00 | 21.30 |
| ATOM | 1659 | CB  | VAL | A | 819 | 90.753  | −80.988 | 86.437 | 1.00 | 21.63 |
| ATOM | 1660 | CG1 | VAL | A | 819 | 91.624  | −81.644 | 87.497 | 1.00 | 21.64 |
| ATOM | 1661 | CG2 | VAL | A | 819 | 90.106  | −79.729 | 86.992 | 1.00 | 21.55 |
| ATOM | 1662 | N   | LYS | A | 820 | 91.925  | −82.711 | 83.940 | 1.00 | 21.01 |
| ATOM | 1663 | CA  | LYS | A | 820 | 92.731  | −83.864 | 83.546 | 1.00 | 20.73 |
| ATOM | 1664 | C   | LYS | A | 820 | 93.917  | −83.474 | 82.664 | 1.00 | 20.55 |
| ATOM | 1665 | O   | LYS | A | 820 | 94.797  | −84.292 | 82.412 | 1.00 | 20.44 |
| ATOM | 1666 | CB  | LYS | A | 820 | 91.883  | −84.911 | 82.828 | 1.00 | 20.72 |
| ATOM | 1667 | CG  | LYS | A | 820 | 90.953  | −85.693 | 83.735 | 1.00 | 20.71 |
| ATOM | 1668 | CD  | LYS | A | 820 | 90.347  | −86.868 | 82.988 | 1.00 | 20.79 |
| ATOM | 1669 | CE  | LYS | A | 820 | 89.503  | −87.714 | 83.919 | 1.00 | 20.97 |
| ATOM | 1670 | NZ  | LYS | A | 820 | 89.009  | −88.965 | 83.276 | 1.00 | 21.20 |
| ATOM | 1671 | N   | TRP | A | 821 | 93.946  | −82.224 | 82.204 | 1.00 | 20.34 |
| ATOM | 1672 | CA  | TRP | A | 821 | 95.047  | −81.750 | 81.359 | 1.00 | 20.35 |
| ATOM | 1673 | C   | TRP | A | 821 | 95.994  | −80.847 | 82.140 | 1.00 | 20.66 |
| ATOM | 1674 | O   | TRP | A | 821 | 97.022  | −80.416 | 81.628 | 1.00 | 20.57 |
| ATOM | 1675 | CB  | TRP | A | 821 | 94.503  | −80.963 | 80.159 | 1.00 | 19.67 |
| ATOM | 1676 | CG  | TRP | A | 821 | 94.057  | −81.822 | 79.023 | 1.00 | 18.97 |
| ATOM | 1677 | CD1 | TRP | A | 821 | 94.778  | −82.145 | 77.903 | 1.00 | 18.66 |
| ATOM | 1678 | CD2 | TRP | A | 821 | 92.801  | −82.502 | 78.904 | 1.00 | 18.56 |
| ATOM | 1679 | NE1 | TRP | A | 821 | 94.045  | −82.992 | 77.097 | 1.00 | 18.47 |
| ATOM | 1680 | CE2 | TRP | A | 821 | 92.830  | −83.225 | 77.688 | 1.00 | 18.52 |
| ATOM | 1681 | CE3 | TRP | A | 821 | 91.654  | −82.573 | 79.707 | 1.00 | 18.57 |
| ATOM | 1682 | CZ2 | TRP | A | 821 | 91.756  | −84.014 | 77.258 | 1.00 | 18.44 |
| ATOM | 1683 | CZ3 | TRP | A | 821 | 90.584  | −83.359 | 79.281 | 1.00 | 18.40 |
| ATOM | 1684 | CH2 | TRP | A | 821 | 90.646  | −84.069 | 78.066 | 1.00 | 18.39 |
| ATOM | 1685 | N   | MET | A | 822 | 95.650  | −80.580 | 83.392 | 1.00 | 21.13 |
| ATOM | 1686 | CA  | MET | A | 822 | 96.438  | −79.678 | 84.215 | 1.00 | 21.57 |
| ATOM | 1687 | C   | MET | A | 822 | 97.553  | −80.243 | 85.083 | 1.00 | 21.96 |
| ATOM | 1688 | O   | MET | A | 822 | 97.462  | −81.354 | 85.610 | 1.00 | 21.99 |
| ATOM | 1689 | CB  | MET | A | 822 | 95.488  | −78.855 | 85.078 | 1.00 | 21.57 |
| ATOM | 1690 | CG  | MET | A | 822 | 94.739  | −77.799 | 84.279 | 1.00 | 21.48 |
| ATOM | 1691 | SD  | MET | A | 822 | 93.329  | −77.131 | 85.159 | 1.00 | 21.51 |
| ATOM | 1692 | CE  | MET | A | 822 | 94.099  | −76.317 | 86.521 | 1.00 | 21.25 |
| ATOM | 1693 | N   | ALA | A | 823 | 98.602  | −79.437 | 85.229 | 1.00 | 22.40 |
| ATOM | 1694 | CA  | ALA | A | 823 | 99.760  | −79.783 | 86.039 | 1.00 | 22.99 |
| ATOM | 1695 | C   | ALA | A | 823 | 99.349  | −79.721 | 87.506 | 1.00 | 23.44 |
| ATOM | 1696 | O   | ALA | A | 823 | 98.488  | −78.925 | 87.876 | 1.00 | 23.40 |
| ATOM | 1697 | CB  | ALA | A | 823 | 100.893 | −78.795 | 85.777 | 1.00 | 22.76 |
| ATOM | 1698 | N   | PRO | A | 824 | 99.959  | −80.569 | 88.353 | 1.00 | 23.91 |
| ATOM | 1699 | CA  | PRO | A | 824 | 99.695  | −80.653 | 89.795 | 1.00 | 24.29 |
| ATOM | 1700 | C   | PRO | A | 824 | 99.797  | −79.300 | 90.502 | 1.00 | 24.66 |
| ATOM | 1701 | O   | PRO | A | 824 | 98.961  | −78.966 | 91.338 | 1.00 | 24.80 |
| ATOM | 1702 | CB  | PRO | A | 824 | 100.766 | −81.626 | 90.286 | 1.00 | 24.34 |
| ATOM | 1703 | CG  | PRO | A | 824 | 100.983 | −82.521 | 89.090 | 1.00 | 24.31 |
| ATOM | 1704 | CD  | PRO | A | 824 | 101.011 | −81.527 | 87.959 | 1.00 | 24.09 |
| ATOM | 1705 | N   | GLU | A | 825 | 100.820 | −78.521 | 90.168 | 1.00 | 24.98 |
| ATOM | 1706 | CA  | GLU | A | 825 | 101.005 | −77.224 | 90.812 | 1.00 | 25.39 |
| ATOM | 1707 | C   | GLU | A | 825 | 99.919  | −76.230 | 90.423 | 1.00 | 25.65 |
| ATOM | 1708 | O   | GLU | A | 825 | 99.681  | −75.245 | 91.137 | 1.00 | 25.75 |
| ATOM | 1709 | CB  | GLU | A | 825 | 102.393 | −76.643 | 90.496 | 1.00 | 25.38 |
| ATOM | 1710 | CG  | GLU | A | 825 | 102.597 | −76.175 | 89.058 | 1.00 | 25.46 |
| ATOM | 1711 | CD  | GLU | A | 825 | 103.056 | −77.277 | 88.109 | 1.00 | 25.46 |
| ATOM | 1712 | OE1 | GLU | A | 825 | 103.043 | −78.468 | 88.491 | 1.00 | 25.42 |
| ATOM | 1713 | OE2 | GLU | A | 825 | 103.429 | −76.937 | 86.967 | 1.00 | 25.54 |
| ATOM | 1714 | N   | SER | A | 826 | 99.255  | −76.480 | 89.296 | 1.00 | 25.73 |
| ATOM | 1715 | CA  | SER | A | 826 | 98.184  | −75.594 | 88.854 | 1.00 | 25.93 |
| ATOM | 1716 | C   | SER | A | 826 | 96.899  | −75.955 | 89.611 | 1.00 | 26.15 |
| ATOM | 1717 | O   | SER | A | 826 | 96.156  | −75.079 | 90.053 | 1.00 | 26.22 |
| ATOM | 1718 | CB  | SER | A | 826 | 97.962  | −75.730 | 87.337 | 1.00 | 25.76 |
| ATOM | 1719 | OG  | SER | A | 826 | 99.131  | −75.394 | 86.604 | 1.00 | 25.65 |
| ATOM | 1720 | N   | ILE | A | 827 | 96.654  | −77.252 | 89.765 | 1.00 | 26.36 |
| ATOM | 1721 | CA  | ILE | A | 827 | 95.471  | −77.731 | 90.460 | 1.00 | 26.73 |
| ATOM | 1722 | C   | ILE | A | 827 | 95.523  | −77.456 | 91.966 | 1.00 | 27.09 |
| ATOM | 1723 | O   | ILE | A | 827 | 94.507  | −77.124 | 92.579 | 1.00 | 27.07 |
| ATOM | 1724 | CB  | ILE | A | 827 | 95.292  | −79.254 | 90.265 | 1.00 | 26.66 |
| ATOM | 1725 | CG1 | ILE | A | 827 | 95.133  | −79.583 | 88.777 | 1.00 | 26.43 |
| ATOM | 1726 | CG2 | ILE | A | 827 | 94.080  | −79.737 | 91.050 | 1.00 | 26.75 |

TABLE 2-continued cFMS - Formula (Ia) compound co-crystal
resolution: 500.0-1.8 Å
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1727 | CD1 | ILE | A | 827 | 95.135 | −81.070 | 88.480 | 1.00 | 26.25 |
| ATOM | 1728 | N | PHE | A | 828 | 96.705 | −77.591 | 92.561 | 1.00 | 27.38 |
| ATOM | 1729 | CA | PHE | A | 828 | 96.840 | −77.376 | 93.998 | 1.00 | 27.75 |
| ATOM | 1730 | C | PHE | A | 828 | 97.227 | −75.961 | 94.414 | 1.00 | 27.83 |
| ATOM | 1731 | O | PHE | A | 828 | 96.680 | −75.425 | 95.378 | 1.00 | 28.01 |
| ATOM | 1732 | CB | PHE | A | 828 | 97.857 | −78.356 | 94.592 | 1.00 | 27.92 |
| ATOM | 1733 | CG | PHE | A | 828 | 97.393 | −79.782 | 94.610 | 1.00 | 28.18 |
| ATOM | 1734 | CD1 | PHE | A | 828 | 97.332 | −80.525 | 93.440 | 1.00 | 28.36 |
| ATOM | 1735 | CD2 | PHE | A | 828 | 97.028 | −80.391 | 95.810 | 1.00 | 28.32 |
| ATOM | 1736 | CE1 | PHE | A | 828 | 96.917 | −81.855 | 93.457 | 1.00 | 28.36 |
| ATOM | 1737 | CE2 | PHE | A | 828 | 96.610 | −81.724 | 95.839 | 1.00 | 28.44 |
| ATOM | 1738 | CZ | PHE | A | 828 | 96.557 | −82.456 | 94.656 | 1.00 | 28.42 |
| ATOM | 1739 | N | ASP | A | 829 | 98.162 | −75.354 | 93.696 | 1.00 | 27.86 |
| ATOM | 1740 | CA | ASP | A | 829 | 98.621 | −74.016 | 94.046 | 1.00 | 27.85 |
| ATOM | 1741 | C | ASP | A | 829 | 98.171 | −72.896 | 93.121 | 1.00 | 27.74 |
| ATOM | 1742 | O | ASP | A | 829 | 98.514 | −71.739 | 93.345 | 1.00 | 27.64 |
| ATOM | 1743 | CB | ASP | A | 829 | 100.146 | −74.007 | 94.133 | 1.00 | 28.13 |
| ATOM | 1744 | CG | ASP | A | 829 | 100.679 | −75.126 | 94.995 | 1.00 | 28.41 |
| ATOM | 1745 | OD1 | ASP | A | 829 | 100.111 | −75.347 | 96.086 | 1.00 | 28.64 |
| ATOM | 1746 | OD2 | ASP | A | 829 | 101.667 | −75.780 | 94.587 | 1.00 | 28.67 |
| ATOM | 1747 | N | CYS | A | 830 | 97.409 | −73.231 | 92.085 | 1.00 | 27.62 |
| ATOM | 1748 | CA | CYS | A | 830 | 96.938 | −72.225 | 91.137 | 1.00 | 27.52 |
| ATOM | 1749 | C | CYS | A | 830 | 98.114 | −71.516 | 90.483 | 1.00 | 27.20 |
| ATOM | 1750 | O | CYS | A | 830 | 98.038 | −70.326 | 90.169 | 1.00 | 27.19 |
| ATOM | 1751 | CB | CYS | A | 830 | 96.066 | −71.184 | 91.844 | 1.00 | 27.78 |
| ATOM | 1752 | SG | CYS | A | 830 | 94.703 | −71.881 | 92.753 | 1.00 | 28.60 |
| ATOM | 1753 | N | VAL | A | 831 | 99.209 | −72.242 | 90.297 | 1.00 | 26.85 |
| ATOM | 1754 | CA | VAL | A | 831 | 100.395 | −71.682 | 89.664 | 1.00 | 26.48 |
| ATOM | 1755 | C | VAL | A | 831 | 100.413 | −72.145 | 88.211 | 1.00 | 26.21 |
| ATOM | 1756 | O | VAL | A | 831 | 100.198 | −73.320 | 87.932 | 1.00 | 26.14 |
| ATOM | 1757 | CB | VAL | A | 831 | 101.693 | −72.161 | 90.369 | 1.00 | 26.59 |
| ATOM | 1758 | CG1 | VAL | A | 831 | 102.923 | −71.723 | 89.579 | 1.00 | 26.51 |
| ATOM | 1759 | CG2 | VAL | A | 831 | 101.746 | −71.601 | 91.784 | 1.00 | 26.46 |
| ATOM | 1760 | N | TYR | A | 832 | 100.666 | −71.218 | 87.296 | 1.00 | 25.92 |
| ATOM | 1761 | CA | TYR | A | 832 | 100.713 | −71.544 | 85.873 | 1.00 | 25.68 |
| ATOM | 1762 | C | TYR | A | 832 | 101.938 | −70.941 | 85.199 | 1.00 | 25.49 |
| ATOM | 1763 | O | TYR | A | 832 | 102.191 | −69.747 | 85.314 | 1.00 | 25.68 |
| ATOM | 1764 | CB | TYR | A | 832 | 99.461 | −71.029 | 85.167 | 1.00 | 25.63 |
| ATOM | 1765 | CG | TYR | A | 832 | 98.175 | −71.643 | 85.665 | 1.00 | 25.58 |
| ATOM | 1766 | CD1 | TYR | A | 832 | 97.510 | −71.122 | 86.775 | 1.00 | 25.56 |
| ATOM | 1767 | CD2 | TYR | A | 832 | 97.621 | −72.745 | 85.022 | 1.00 | 25.56 |
| ATOM | 1768 | CE1 | TYR | A | 832 | 96.315 | −71.686 | 87.229 | 1.00 | 25.56 |
| ATOM | 1769 | CE2 | TYR | A | 832 | 96.440 | −73.317 | 85.465 | 1.00 | 25.59 |
| ATOM | 1770 | CZ | TYR | A | 832 | 95.790 | −72.783 | 86.569 | 1.00 | 25.62 |
| ATOM | 1771 | OH | TYR | A | 832 | 94.618 | −73.357 | 87.000 | 1.00 | 25.71 |
| ATOM | 1772 | N | THR | A | 833 | 102.695 | −71.774 | 84.493 | 1.00 | 25.11 |
| ATOM | 1773 | CA | THR | A | 833 | 103.889 | −71.314 | 83.787 | 1.00 | 24.58 |
| ATOM | 1774 | C | THR | A | 833 | 103.951 | −72.043 | 82.450 | 1.00 | 24.32 |
| ATOM | 1775 | O | THR | A | 833 | 103.060 | −72.825 | 82.123 | 1.00 | 24.13 |
| ATOM | 1776 | CB | THR | A | 833 | 105.165 | −71.663 | 84.557 | 1.00 | 24.54 |
| ATOM | 1777 | OG1 | THR | A | 833 | 105.325 | −73.085 | 84.572 | 1.00 | 24.58 |
| ATOM | 1778 | CG2 | THR | A | 833 | 105.087 | −71.147 | 85.995 | 1.00 | 24.73 |
| ATOM | 1779 | N | VAL | A | 834 | 105.004 | −71.787 | 81.679 | 1.00 | 24.03 |
| ATOM | 1780 | CA | VAL | A | 834 | 105.168 | −72.463 | 80.400 | 1.00 | 23.70 |
| ATOM | 1781 | C | VAL | A | 834 | 105.318 | −73.949 | 80.699 | 1.00 | 23.47 |
| ATOM | 1782 | O | VAL | A | 834 | 104.824 | −74.791 | 79.946 | 1.00 | 23.31 |
| ATOM | 1783 | CB | VAL | A | 834 | 106.423 | −71.953 | 79.638 | 1.00 | 23.83 |
| ATOM | 1784 | CG1 | VAL | A | 834 | 106.800 | −72.932 | 78.524 | 1.00 | 23.83 |
| ATOM | 1785 | CG2 | VAL | A | 834 | 106.150 | −70.584 | 79.059 | 1.00 | 23.85 |
| ATOM | 1786 | N | GLN | A | 835 | 105.978 | −74.265 | 81.816 | 1.00 | 23.21 |
| ATOM | 1787 | CA | GLN | A | 835 | 106.182 | −75.661 | 82.213 | 1.00 | 23.01 |
| ATOM | 1788 | C | GLN | A | 835 | 104.842 | −76.301 | 82.497 | 1.00 | 22.49 |
| ATOM | 1789 | O | GLN | A | 835 | 104.687 | −77.523 | 82.435 | 1.00 | 22.31 |
| ATOM | 1790 | CB | GLN | A | 835 | 107.052 | −75.759 | 83.469 | 1.00 | 23.55 |
| ATOM | 1791 | CG | GLN | A | 835 | 108.511 | −75.476 | 83.232 | 1.00 | 24.46 |
| ATOM | 1792 | CD | GLN | A | 835 | 108.741 | −74.123 | 82.623 | 1.00 | 24.99 |
| ATOM | 1793 | OE1 | GLN | A | 835 | 109.467 | −73.991 | 81.633 | 1.00 | 25.63 |
| ATOM | 1794 | NE2 | GLN | A | 835 | 108.122 | −73.096 | 83.203 | 1.00 | 25.52 |
| ATOM | 1795 | N | SER | A | 836 | 103.881 | −75.453 | 82.830 | 1.00 | 21.95 |
| ATOM | 1796 | CA | SER | A | 836 | 102.531 | −75.897 | 83.124 | 1.00 | 21.49 |
| ATOM | 1797 | C | SER | A | 836 | 101.915 | −76.368 | 81.803 | 1.00 | 20.77 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1798 | O   | SER | A | 836 | 101.267 | −77.422 | 81.737 | 1.00 | 20.70 |
|------|------|-----|-----|---|-----|---------|---------|--------|------|-------|
| ATOM | 1799 | CB  | SER | A | 836 | 101.752 | −74.721 | 83.717 | 1.00 | 21.65 |
| ATOM | 1800 | OG  | SER | A | 836 | 100.504 | −75.138 | 84.174 | 1.00 | 22.80 |
| ATOM | 1801 | N   | ASP | A | 837 | 102.118 | −75.580 | 80.753 | 1.00 | 19.95 |
| ATOM | 1802 | CA  | ASP | A | 837 | 101.621 | −75.943 | 79.427 | 1.00 | 19.32 |
| ATOM | 1803 | C   | ASP | A | 837 | 102.356 | −77.181 | 78.911 | 1.00 | 19.02 |
| ATOM | 1804 | O   | ASP | A | 837 | 101.799 | −77.974 | 78.161 | 1.00 | 18.90 |
| ATOM | 1805 | CB  | ASP | A | 837 | 101.800 | −74.796 | 78.434 | 1.00 | 18.92 |
| ATOM | 1806 | CG  | ASP | A | 837 | 100.738 | −73.719 | 78.583 | 1.00 | 18.82 |
| ATOM | 1807 | OD1 | ASP | A | 837 | 99.645  | −74.010 | 79.126 | 1.00 | 18.53 |
| ATOM | 1808 | OD2 | ASP | A | 837 | 100.993 | −72.583 | 78.134 | 1.00 | 18.71 |
| ATOM | 1809 | N   | VAL | A | 838 | 103.618 | −77.332 | 79.292 | 1.00 | 18.76 |
| ATOM | 1810 | CA  | VAL | A | 838 | 104.382 | −78.503 | 78.874 | 1.00 | 18.51 |
| ATOM | 1811 | C   | VAL | A | 838 | 103.707 | −79.757 | 79.419 | 1.00 | 18.25 |
| ATOM | 1812 | O   | VAL | A | 838 | 103.571 | −80.763 | 78.711 | 1.00 | 18.14 |
| ATOM | 1813 | CB  | VAL | A | 838 | 105.838 | −78.433 | 79.374 | 1.00 | 18.51 |
| ATOM | 1814 | CG1 | VAL | A | 838 | 106.553 | −79.760 | 79.105 | 1.00 | 18.58 |
| ATOM | 1815 | CG2 | VAL | A | 838 | 106.560 | −77.307 | 78.662 | 1.00 | 18.66 |
| ATOM | 1816 | N   | TRP | A | 839 | 103.269 | −79.701 | 80.674 | 1.00 | 17.96 |
| ATOM | 1817 | CA  | TRP | A | 839 | 102.587 | −80.849 | 81.265 | 1.00 | 17.58 |
| ATOM | 1818 | C   | TRP | A | 839 | 101.362 | −81.174 | 80.418 | 1.00 | 17.29 |
| ATOM | 1819 | O   | TRP | A | 839 | 101.150 | −82.322 | 80.048 | 1.00 | 17.21 |
| ATOM | 1820 | CB  | TRP | A | 839 | 102.168 | −80.561 | 82.720 | 1.00 | 17.73 |
| ATOM | 1821 | CG  | TRP | A | 839 | 101.293 | −81.636 | 83.344 | 1.00 | 17.93 |
| ATOM | 1822 | CD1 | TRP | A | 839 | 99.995  | −81.936 | 83.015 | 1.00 | 17.92 |
| ATOM | 1823 | CD2 | TRP | A | 839 | 101.665 | −82.569 | 84.376 | 1.00 | 17.92 |
| ATOM | 1824 | NE1 | TRP | A | 839 | 99.547  | −82.987 | 83.769 | 1.00 | 17.95 |
| ATOM | 1825 | CE2 | TRP | A | 839 | 100.545 | −83.397 | 84.612 | 1.00 | 17.95 |
| ATOM | 1826 | CE3 | TRP | A | 839 | 102.832 | −82.784 | 85.118 | 1.00 | 17.95 |
| ATOM | 1827 | CZ2 | TRP | A | 839 | 100.557 | −84.430 | 85.559 | 1.00 | 18.01 |
| ATOM | 1828 | CZ3 | TRP | A | 839 | 102.848 | −83.813 | 86.065 | 1.00 | 17.92 |
| ATOM | 1829 | CH2 | TRP | A | 839 | 101.712 | −84.625 | 86.275 | 1.00 | 18.05 |
| ATOM | 1830 | N   | SER | A | 840 | 100.562 | −80.160 | 80.101 | 1.00 | 16.92 |
| ATOM | 1831 | CA  | SER | A | 840 | 99.362  | −80.368 | 79.304 | 1.00 | 16.67 |
| ATOM | 1832 | C   | SER | A | 840 | 99.751  | −80.933 | 77.936 | 1.00 | 16.49 |
| ATOM | 1833 | O   | SER | A | 840 | 99.070  | −81.807 | 77.402 | 1.00 | 16.40 |
| ATOM | 1834 | CB  | SER | A | 840 | 98.599  | −79.050 | 79.131 | 1.00 | 16.70 |
| ATOM | 1835 | OG  | SER | A | 840 | 98.259  | −78.491 | 80.388 | 1.00 | 16.79 |
| ATOM | 1836 | N   | TYR | A | 841 | 100.854 | −80.442 | 77.376 | 1.00 | 16.13 |
| ATOM | 1837 | CA  | TYR | A | 841 | 101.301 | −80.947 | 76.080 | 1.00 | 15.91 |
| ATOM | 1838 | C   | TYR | A | 841 | 101.559 | −82.451 | 76.188 | 1.00 | 15.75 |
| ATOM | 1839 | O   | TYR | A | 841 | 101.351 | −83.204 | 75.230 | 1.00 | 15.47 |
| ATOM | 1840 | CB  | TYR | A | 841 | 102.590 | −80.255 | 75.633 | 1.00 | 15.75 |
| ATOM | 1841 | CG  | TYR | A | 841 | 103.154 | −80.863 | 74.379 | 1.00 | 15.61 |
| ATOM | 1842 | CD1 | TYR | A | 841 | 102.667 | −80.498 | 73.130 | 1.00 | 15.63 |
| ATOM | 1843 | CD2 | TYR | A | 841 | 104.137 | −81.854 | 74.443 | 1.00 | 15.66 |
| ATOM | 1844 | CE1 | TYR | A | 841 | 103.140 | −81.107 | 71.971 | 1.00 | 15.60 |
| ATOM | 1845 | CE2 | TYR | A | 841 | 104.621 | −82.470 | 73.287 | 1.00 | 15.70 |
| ATOM | 1846 | CZ  | TYR | A | 841 | 104.117 | −82.092 | 72.060 | 1.00 | 15.63 |
| ATOM | 1847 | OH  | TYR | A | 841 | 104.577 | −82.698 | 70.918 | 1.00 | 15.72 |
| ATOM | 1848 | N   | GLY | A | 842 | 102.025 | −82.878 | 77.357 | 1.00 | 15.77 |
| ATOM | 1849 | CA  | GLY | A | 842 | 102.285 | −84.290 | 77.564 | 1.00 | 15.74 |
| ATOM | 1850 | C   | GLY | A | 842 | 100.974 | −85.062 | 77.494 | 1.00 | 15.86 |
| ATOM | 1851 | O   | GLY | A | 842 | 100.911 | −86.175 | 76.953 | 1.00 | 15.77 |
| ATOM | 1852 | N   | ILE | A | 843 | 99.916  | −84.473 | 78.049 | 1.00 | 15.91 |
| ATOM | 1853 | CA  | ILE | A | 843 | 98.614  | −85.128 | 78.027 | 1.00 | 15.81 |
| ATOM | 1854 | C   | ILE | A | 843 | 98.138  | −85.210 | 76.570 | 1.00 | 15.95 |
| ATOM | 1855 | O   | ILE | A | 843 | 97.628  | −86.238 | 76.140 | 1.00 | 15.72 |
| ATOM | 1856 | CB  | ILE | A | 843 | 97.572  | −84.358 | 78.879 | 1.00 | 15.84 |
| ATOM | 1857 | CG1 | ILE | A | 843 | 98.047  | −84.266 | 80.341 | 1.00 | 15.76 |
| ATOM | 1858 | CG2 | ILE | A | 843 | 96.201  | −85.079 | 78.806 | 1.00 | 15.76 |
| ATOM | 1859 | CD1 | ILE | A | 843 | 98.201  | −85.622 | 81.049 | 1.00 | 15.69 |
| ATOM | 1860 | N   | LEU | A | 844 | 98.326  | −84.120 | 75.828 | 1.00 | 16.23 |
| ATOM | 1861 | CA  | LEU | A | 844 | 97.939  | −84.026 | 74.417 | 1.00 | 16.54 |
| ATOM | 1862 | C   | LEU | A | 844 | 98.678  | −85.090 | 73.604 | 1.00 | 16.84 |
| ATOM | 1863 | O   | LEU | A | 844 | 98.096  | −85.745 | 72.731 | 1.00 | 16.98 |
| ATOM | 1864 | CB  | LEU | A | 844 | 98.273  | −82.619 | 73.879 | 1.00 | 16.67 |
| ATOM | 1865 | CG  | LEU | A | 844 | 97.968  | −82.246 | 72.420 | 1.00 | 16.87 |
| ATOM | 1866 | CD1 | LEU | A | 844 | 97.961  | −80.720 | 72.249 | 1.00 | 17.04 |
| ATOM | 1867 | CD2 | LEU | A | 844 | 98.996  | −82.876 | 71.507 | 1.00 | 16.97 |
| ATOM | 1868 | N   | LEU | A | 845 | 99.966  | −85.258 | 73.889 | 1.00 | 16.97 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1869 | CA  | LEU | A | 845 | 100.753 | −86.245 | 73.176 | 1.00 | 17.17 |
|------|------|-----|-----|---|-----|---------|---------|--------|------|-------|
| ATOM | 1870 | C   | LEU | A | 845 | 100.136 | −87.621 | 73.418 | 1.00 | 17.19 |
| ATOM | 1871 | O   | LEU | A | 845 | 100.049 | −88.435 | 72.496 | 1.00 | 17.02 |
| ATOM | 1872 | CB  | LEU | A | 845 | 102.208 | −86.203 | 73.647 | 1.00 | 17.45 |
| ATOM | 1873 | CG  | LEU | A | 845 | 103.271 | −86.890 | 72.785 | 1.00 | 17.81 |
| ATOM | 1874 | CD1 | LEU | A | 845 | 103.236 | −86.348 | 71.355 | 1.00 | 17.74 |
| ATOM | 1875 | CD2 | LEU | A | 845 | 104.637 | −86.641 | 73.400 | 1.00 | 17.88 |
| ATOM | 1876 | N   | TRP | A | 846 | 99.683  | −87.864 | 74.651 | 1.00 | 17.11 |
| ATOM | 1877 | CA  | TRP | A | 846 | 99.059  | −89.137 | 75.003 | 1.00 | 17.11 |
| ATOM | 1878 | C   | TRP | A | 846 | 97.765  | −89.319 | 74.208 | 1.00 | 17.20 |
| ATOM | 1879 | O   | TRP | A | 846 | 97.442  | −90.435 | 73.797 | 1.00 | 17.07 |
| ATOM | 1880 | CB  | TRP | A | 846 | 98.750  | −89.200 | 76.505 | 1.00 | 16.92 |
| ATOM | 1881 | CG  | TRP | A | 846 | 98.300  | −90.564 | 76.982 | 1.00 | 16.74 |
| ATOM | 1882 | CD1 | TRP | A | 846 | 99.100  | −91.593 | 77.404 | 1.00 | 16.65 |
| ATOM | 1883 | CD2 | TRP | A | 846 | 96.947  | −91.039 | 77.083 | 1.00 | 16.54 |
| ATOM | 1884 | NE1 | TRP | A | 846 | 98.329  | −92.673 | 77.765 | 1.00 | 16.65 |
| ATOM | 1885 | CE2 | TRP | A | 846 | 97.005  | −92.362 | 77.576 | 1.00 | 16.49 |
| ATOM | 1886 | CE3 | TRP | A | 846 | 95.694  | −90.474 | 76.806 | 1.00 | 16.51 |
| ATOM | 1887 | CZ2 | TRP | A | 846 | 95.858  | −93.131 | 77.800 | 1.00 | 16.37 |
| ATOM | 1888 | CZ3 | TRP | A | 846 | 94.540  | −91.247 | 77.030 | 1.00 | 16.50 |
| ATOM | 1889 | CH2 | TRP | A | 846 | 94.639  | −92.561 | 77.523 | 1.00 | 16.42 |
| ATOM | 1890 | N   | GLU | A | 847 | 97.022  | −88.231 | 73.996 | 1.00 | 17.31 |
| ATOM | 1891 | CA  | GLU | A | 847 | 95.784  | −88.303 | 73.215 | 1.00 | 17.63 |
| ATOM | 1892 | C   | GLU | A | 847 | 96.118  | −88.669 | 71.771 | 1.00 | 17.80 |
| ATOM | 1893 | O   | GLU | A | 847 | 95.403  | −89.447 | 71.123 | 1.00 | 17.91 |
| ATOM | 1894 | CB  | GLU | A | 847 | 95.053  | −86.960 | 73.186 | 1.00 | 17.70 |
| ATOM | 1895 | CG  | GLU | A | 847 | 94.542  | −86.434 | 74.513 | 1.00 | 17.87 |
| ATOM | 1896 | CD  | GLU | A | 847 | 93.764  | −85.159 | 74.315 | 1.00 | 17.98 |
| ATOM | 1897 | OE1 | GLU | A | 847 | 92.588  | −85.241 | 73.902 | 1.00 | 18.29 |
| ATOM | 1898 | OE2 | GLU | A | 847 | 94.335  | −84.071 | 74.545 | 1.00 | 18.16 |
| ATOM | 1899 | N   | ILE | A | 848 | 97.194  | −88.091 | 71.253 | 1.00 | 17.92 |
| ATOM | 1900 | CA  | ILE | A | 848 | 97.584  | −88.381 | 69.877 | 1.00 | 18.20 |
| ATOM | 1901 | C   | ILE | A | 848 | 97.941  | −89.852 | 69.714 | 1.00 | 18.43 |
| ATOM | 1902 | O   | ILE | A | 848 | 97.429  | −90.519 | 68.820 | 1.00 | 18.38 |
| ATOM | 1903 | CB  | ILE | A | 848 | 98.809  | −87.545 | 69.419 | 1.00 | 18.15 |
| ATOM | 1904 | CG1 | ILE | A | 848 | 98.431  | −86.065 | 69.279 | 1.00 | 17.85 |
| ATOM | 1905 | CG2 | ILE | A | 848 | 99.317  | −88.074 | 68.078 | 1.00 | 18.25 |
| ATOM | 1906 | CD1 | ILE | A | 848 | 99.622  | −85.144 | 68.994 | 1.00 | 17.82 |
| ATOM | 1907 | N   | PHE | A | 849 | 98.812  | −90.364 | 70.579 | 1.00 | 18.77 |
| ATOM | 1908 | CA  | PHE | A | 849 | 99.224  | −91.758 | 70.443 | 1.00 | 19.20 |
| ATOM | 1909 | C   | PHE | A | 849 | 98.287  | −92.839 | 70.980 | 1.00 | 19.49 |
| ATOM | 1910 | O   | PHE | A | 849 | 98.643  | −94.020 | 70.987 | 1.00 | 19.56 |
| ATOM | 1911 | CB  | PHE | A | 849 | 100.636 | −91.947 | 70.995 | 1.00 | 19.24 |
| ATOM | 1912 | CG  | PHE | A | 849 | 101.700 | −91.332 | 70.119 | 1.00 | 19.37 |
| ATOM | 1913 | CD1 | PHE | A | 849 | 102.026 | −89.988 | 70.237 | 1.00 | 19.40 |
| ATOM | 1914 | CD2 | PHE | A | 849 | 102.308 | −92.084 | 69.120 | 1.00 | 19.39 |
| ATOM | 1915 | CE1 | PHE | A | 849 | 102.942 | −89.394 | 69.369 | 1.00 | 19.47 |
| ATOM | 1916 | CE2 | PHE | A | 849 | 103.223 | −91.507 | 68.245 | 1.00 | 19.52 |
| ATOM | 1917 | CZ  | PHE | A | 849 | 103.540 | −90.160 | 68.367 | 1.00 | 19.48 |
| ATOM | 1918 | N   | SER | A | 850 | 97.097  | −92.435 | 71.414 | 1.00 | 19.86 |
| ATOM | 1919 | CA  | SER | A | 850 | 96.074  | −93.371 | 71.889 | 1.00 | 20.21 |
| ATOM | 1920 | C   | SER | A | 850 | 94.896  | −93.192 | 70.923 | 1.00 | 20.48 |
| ATOM | 1921 | O   | SER | A | 850 | 93.819  | −93.795 | 71.070 | 1.00 | 20.33 |
| ATOM | 1922 | CB  | SER | A | 850 | 95.633  | −93.023 | 73.318 | 1.00 | 20.19 |
| ATOM | 1923 | OG  | SER | A | 850 | 94.857  | −91.836 | 73.343 | 1.00 | 20.22 |
| ATOM | 1924 | N   | LEU | A | 851 | 95.131  | −92.349 | 69.926 | 1.00 | 20.69 |
| ATOM | 1925 | CA  | LEU | A | 851 | 94.148  | −92.020 | 68.905 | 1.00 | 21.02 |
| ATOM | 1926 | C   | LEU | A | 851 | 92.843  | −91.445 | 69.459 | 1.00 | 21.20 |
| ATOM | 1927 | O   | LEU | A | 851 | 91.759  | −91.829 | 69.035 | 1.00 | 21.16 |
| ATOM | 1928 | CB  | LEU | A | 851 | 93.856  | −93.245 | 68.009 | 1.00 | 21.07 |
| ATOM | 1929 | CG  | LEU | A | 851 | 95.032  | −93.801 | 67.183 | 1.00 | 21.07 |
| ATOM | 1930 | CD1 | LEU | A | 851 | 94.525  | −94.891 | 66.245 | 1.00 | 21.04 |
| ATOM | 1931 | CD2 | LEU | A | 851 | 95.686  | −92.691 | 66.375 | 1.00 | 20.96 |
| ATOM | 1932 | N   | GLY | A | 852 | 92.948  | −90.530 | 70.416 | 1.00 | 21.40 |
| ATOM | 1933 | CA  | GLY | A | 852 | 91.752  | −89.895 | 70.945 | 1.00 | 21.69 |
| ATOM | 1934 | C   | GLY | A | 852 | 91.066  | −90.452 | 72.176 | 1.00 | 21.95 |
| ATOM | 1935 | O   | GLY | A | 852 | 89.889  | −90.160 | 72.398 | 1.00 | 21.89 |
| ATOM | 1936 | N   | LEU | A | 853 | 91.760  | −91.262 | 72.965 | 1.00 | 22.19 |
| ATOM | 1937 | CA  | LEU | A | 853 | 91.161  | −91.783 | 74.186 | 1.00 | 22.50 |
| ATOM | 1938 | C   | LEU | A | 853 | 91.081  | −90.654 | 75.205 | 1.00 | 22.85 |
| ATOM | 1939 | O   | LEU | A | 853 | 91.890  | −89.722 | 75.179 | 1.00 | 22.77 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 1940 | CB  | LEU | A | 853 | 92.001 | −92.922 | 74.776 | 1.00 | 22.32 |
|------|------|-----|-----|---|-----|--------|---------|--------|------|-------|
| ATOM | 1941 | CG  | LEU | A | 853 | 91.968 | −94.277 | 74.062 | 1.00 | 22.28 |
| ATOM | 1942 | CD1 | LEU | A | 853 | 92.687 | −95.325 | 74.921 | 1.00 | 22.20 |
| ATOM | 1943 | CD2 | LEU | A | 853 | 90.520 | −94.695 | 73.823 | 1.00 | 22.18 |
| ATOM | 1944 | N   | ASN | A | 854 | 90.090 | −90.738 | 76.090 | 1.00 | 23.25 |
| ATOM | 1945 | CA  | ASN | A | 854 | 89.908 | −89.758 | 77.157 | 1.00 | 23.58 |
| ATOM | 1946 | C   | ASN | A | 854 | 91.006 | −90.028 | 78.179 | 1.00 | 23.67 |
| ATOM | 1947 | O   | ASN | A | 854 | 91.222 | −91.176 | 78.564 | 1.00 | 23.60 |
| ATOM | 1948 | CB  | ASN | A | 854 | 88.548 | −89.955 | 77.835 | 1.00 | 23.90 |
| ATOM | 1949 | CG  | ASN | A | 854 | 87.385 | −89.780 | 76.882 | 1.00 | 24.33 |
| ATOM | 1950 | OD1 | ASN | A | 854 | 87.151 | −88.687 | 76.360 | 1.00 | 24.68 |
| ATOM | 1951 | ND2 | ASN | A | 854 | 86.639 | −90.861 | 76.650 | 1.00 | 24.51 |
| ATOM | 1952 | N   | PRO | A | 855 | 91.718 | −88.982 | 78.629 | 1.00 | 23.81 |
| ATOM | 1953 | CA  | PRO | A | 855 | 92.793 | −89.163 | 79.614 | 1.00 | 24.10 |
| ATOM | 1954 | C   | PRO | A | 855 | 92.298 | −89.835 | 80.903 | 1.00 | 24.35 |
| ATOM | 1955 | O   | PRO | A | 855 | 91.160 | −89.630 | 81.312 | 1.00 | 24.37 |
| ATOM | 1956 | CB  | PRO | A | 855 | 93.292 | −87.734 | 79.846 | 1.00 | 23.96 |
| ATOM | 1957 | CG  | PRO | A | 855 | 93.081 | −87.097 | 78.497 | 1.00 | 23.90 |
| ATOM | 1958 | CD  | PRO | A | 855 | 91.691 | −87.596 | 78.132 | 1.00 | 23.84 |
| ATOM | 1959 | N   | TYR | A | 856 | 93.161 | −90.633 | 81.527 | 1.00 | 24.73 |
| ATOM | 1960 | CA  | TYR | A | 856 | 92.825 | −91.362 | 82.754 | 1.00 | 25.22 |
| ATOM | 1961 | C   | TYR | A | 856 | 91.493 | −92.092 | 82.577 | 1.00 | 25.61 |
| ATOM | 1962 | O   | TYR | A | 856 | 90.561 | −91.913 | 83.367 | 1.00 | 25.55 |
| ATOM | 1963 | CB  | TYR | A | 856 | 92.736 | −90.409 | 83.950 | 1.00 | 25.18 |
| ATOM | 1964 | CG  | TYR | A | 856 | 93.958 | −89.528 | 84.131 | 1.00 | 25.34 |
| ATOM | 1965 | CD1 | TYR | A | 856 | 94.003 | −88.248 | 83.583 | 1.00 | 25.39 |
| ATOM | 1966 | CD2 | TYR | A | 856 | 95.082 | −89.990 | 84.818 | 1.00 | 25.42 |
| ATOM | 1967 | CE1 | TYR | A | 856 | 95.143 | −87.445 | 83.711 | 1.00 | 25.59 |
| ATOM | 1968 | CE2 | TYR | A | 856 | 96.228 | −89.198 | 84.950 | 1.00 | 25.55 |
| ATOM | 1969 | CZ  | TYR | A | 856 | 96.246 | −87.930 | 84.393 | 1.00 | 25.55 |
| ATOM | 1970 | OH  | TYR | A | 856 | 97.368 | −87.146 | 84.503 | 1.00 | 25.91 |
| ATOM | 1971 | N   | PRO | A | 857 | 91.397 | −92.940 | 81.542 | 1.00 | 26.08 |
| ATOM | 1972 | CA  | PRO | A | 857 | 90.172 | −93.687 | 81.259 | 1.00 | 26.54 |
| ATOM | 1973 | C   | PRO | A | 857 | 89.537 | −94.375 | 82.457 | 1.00 | 26.96 |
| ATOM | 1974 | O   | PRO | A | 857 | 90.213 | −95.059 | 83.227 | 1.00 | 26.90 |
| ATOM | 1975 | CB  | PRO | A | 857 | 90.606 | −94.671 | 80.168 | 1.00 | 26.46 |
| ATOM | 1976 | CG  | PRO | A | 857 | 92.076 | −94.827 | 80.391 | 1.00 | 26.41 |
| ATOM | 1977 | CD  | PRO | A | 857 | 92.504 | −93.416 | 80.692 | 1.00 | 26.16 |
| ATOM | 1978 | N   | GLY | A | 858 | 88.229 | −94.168 | 82.606 | 1.00 | 27.44 |
| ATOM | 1979 | CA  | GLY | A | 858 | 87.492 | −94.778 | 83.697 | 1.00 | 28.02 |
| ATOM | 1980 | C   | GLY | A | 858 | 87.704 | −94.153 | 85.065 | 1.00 | 28.44 |
| ATOM | 1981 | O   | GLY | A | 858 | 87.077 | −94.578 | 86.034 | 1.00 | 28.45 |
| ATOM | 1982 | N   | ILE | A | 859 | 88.576 | −93.152 | 85.160 | 1.00 | 28.79 |
| ATOM | 1983 | CA  | ILE | A | 859 | 88.842 | −92.505 | 86.445 | 1.00 | 29.23 |
| ATOM | 1984 | C   | ILE | A | 859 | 88.115 | −91.168 | 86.568 | 1.00 | 29.60 |
| ATOM | 1985 | O   | ILE | A | 859 | 88.367 | −90.239 | 85.799 | 1.00 | 29.60 |
| ATOM | 1986 | CB  | ILE | A | 859 | 90.351 | −92.234 | 86.649 | 1.00 | 29.24 |
| ATOM | 1987 | CG1 | ILE | A | 859 | 91.148 | −93.534 | 86.539 | 1.00 | 29.09 |
| ATOM | 1988 | CG2 | ILE | A | 859 | 90.578 | −91.588 | 88.014 | 1.00 | 29.30 |
| ATOM | 1989 | CD1 | ILE | A | 859 | 92.655 | −93.340 | 86.664 | 1.00 | 29.10 |
| ATOM | 1990 | N   | LEU | A | 860 | 87.221 | −91.069 | 87.546 | 1.00 | 30.04 |
| ATOM | 1991 | CA  | LEU | A | 860 | 86.480 | −89.831 | 87.761 | 1.00 | 30.52 |
| ATOM | 1992 | C   | LEU | A | 860 | 87.332 | −88.817 | 88.510 | 1.00 | 30.76 |
| ATOM | 1993 | O   | LEU | A | 860 | 88.191 | −89.184 | 89.314 | 1.00 | 30.81 |
| ATOM | 1994 | CB  | LEU | A | 860 | 85.202 | −90.097 | 88.560 | 1.00 | 30.64 |
| ATOM | 1995 | CG  | LEU | A | 860 | 84.096 | −90.911 | 87.880 | 1.00 | 30.78 |
| ATOM | 1996 | CD1 | LEU | A | 860 | 82.852 | −90.898 | 88.764 | 1.00 | 30.84 |
| ATOM | 1997 | CD2 | LEU | A | 860 | 83.774 | −90.318 | 86.511 | 1.00 | 30.81 |
| ATOM | 1998 | N   | VAL | A | 861 | 87.088 | −87.541 | 88.234 | 1.00 | 31.12 |
| ATOM | 1999 | CA  | VAL | A | 861 | 87.810 | −86.461 | 88.884 | 1.00 | 31.64 |
| ATOM | 2000 | C   | VAL | A | 861 | 87.209 | −86.190 | 90.264 | 1.00 | 31.99 |
| ATOM | 2001 | O   | VAL | A | 861 | 86.122 | −85.628 | 90.383 | 1.00 | 32.05 |
| ATOM | 2002 | CB  | VAL | A | 861 | 87.744 | −85.156 | 88.052 | 1.00 | 31.58 |
| ATOM | 2003 | CG1 | VAL | A | 861 | 88.454 | −84.033 | 88.793 | 1.00 | 31.58 |
| ATOM | 2004 | CG2 | VAL | A | 861 | 88.385 | −85.367 | 86.691 | 1.00 | 31.59 |
| ATOM | 2005 | N   | ASN | A | 862 | 87.923 | −86.607 | 91.302 | 1.00 | 32.45 |
| ATOM | 2006 | CA  | ASN | A | 862 | 87.492 | −86.406 | 92.679 | 1.00 | 32.87 |
| ATOM | 2007 | C   | ASN | A | 862 | 88.738 | −86.383 | 93.542 | 1.00 | 33.08 |
| ATOM | 2008 | O   | ASN | A | 862 | 89.851 | −86.357 | 93.022 | 1.00 | 33.09 |
| ATOM | 2009 | CB  | ASN | A | 862 | 86.564 | −87.537 | 93.137 | 1.00 | 33.01 |
| ATOM | 2010 | CG  | ASN | A | 862 | 87.165 | −88.914 | 92.920 | 1.00 | 33.25 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2011 | OD1 | ASN | A | 862 | 88.354 | −89.141 | 93.175 | 1.00 | 33.30 |
|------|------|-----|-----|---|-----|--------|---------|--------|------|-------|
| ATOM | 2012 | ND2 | ASN | A | 862 | 86.339 | −89.850 | 92.457 | 1.00 | 33.36 |
| ATOM | 2013 | N   | SER | A | 863 | 88.552 | −86.405 | 94.857 | 1.00 | 33.37 |
| ATOM | 2014 | CA  | SER | A | 863 | 89.678 | −86.381 | 95.785 | 1.00 | 33.63 |
| ATOM | 2015 | C   | SER | A | 863 | 90.746 | −87.414 | 95.444 | 1.00 | 33.68 |
| ATOM | 2016 | O   | SER | A | 863 | 91.928 | −87.085 | 95.355 | 1.00 | 33.73 |
| ATOM | 2017 | CB  | SER | A | 863 | 89.189 | −86.614 | 97.219 | 1.00 | 33.70 |
| ATOM | 2018 | OG  | SER | A | 863 | 88.572 | −87.882 | 97.345 | 1.00 | 34.01 |
| ATOM | 2019 | N   | LYS | A | 864 | 90.334 | −88.662 | 95.247 | 1.00 | 33.78 |
| ATOM | 2020 | CA  | LYS | A | 864 | 91.285 | −89.719 | 94.930 | 1.00 | 33.85 |
| ATOM | 2021 | C   | LYS | A | 864 | 92.122 | −89.378 | 93.699 | 1.00 | 33.66 |
| ATOM | 2022 | O   | LYS | A | 864 | 93.346 | −89.538 | 93.711 | 1.00 | 33.72 |
| ATOM | 2023 | CB  | LYS | A | 864 | 90.551 | −91.047 | 94.729 | 1.00 | 34.18 |
| ATOM | 2024 | CG  | LYS | A | 864 | 89.744 | −91.462 | 95.955 | 1.00 | 34.67 |
| ATOM | 2025 | CD  | LYS | A | 864 | 89.156 | −92.860 | 95.842 | 1.00 | 35.03 |
| ATOM | 2026 | CE  | LYS | A | 864 | 88.464 | −93.237 | 97.156 | 1.00 | 35.25 |
| ATOM | 2027 | NZ  | LYS | A | 864 | 88.025 | −94.662 | 97.202 | 1.00 | 35.44 |
| ATOM | 2028 | N   | PHE | A | 865 | 91.469 | −88.898 | 92.645 | 1.00 | 33.39 |
| ATOM | 2029 | CA  | PHE | A | 865 | 92.184 | −88.536 | 91.426 | 1.00 | 33.10 |
| ATOM | 2030 | C   | PHE | A | 865 | 93.310 | −87.563 | 91.747 | 1.00 | 32.94 |
| ATOM | 2031 | O   | PHE | A | 865 | 94.453 | −87.764 | 91.332 | 1.00 | 32.87 |
| ATOM | 2032 | CB  | PHE | A | 865 | 91.247 | −87.886 | 90.409 | 1.00 | 33.10 |
| ATOM | 2033 | CG  | PHE | A | 865 | 91.967 | −87.310 | 89.219 | 1.00 | 33.03 |
| ATOM | 2034 | CD1 | PHE | A | 865 | 92.476 | −88.142 | 88.230 | 1.00 | 33.03 |
| ATOM | 2035 | CD2 | PHE | A | 865 | 92.197 | −85.939 | 89.125 | 1.00 | 33.07 |
| ATOM | 2036 | CE1 | PHE | A | 865 | 93.206 | −87.617 | 87.164 | 1.00 | 32.98 |
| ATOM | 2037 | CE2 | PHE | A | 865 | 92.929 | −85.404 | 88.058 | 1.00 | 33.09 |
| ATOM | 2038 | CZ  | PHE | A | 865 | 93.433 | −86.247 | 87.080 | 1.00 | 32.93 |
| ATOM | 2039 | N   | TYR | A | 866 | 92.977 | −86.505 | 92.481 | 1.00 | 32.78 |
| ATOM | 2040 | CA  | TYR | A | 866 | 93.960 | −85.499 | 92.868 | 1.00 | 32.69 |
| ATOM | 2041 | C   | TYR | A | 866 | 95.129 | −86.098 | 93.643 | 1.00 | 32.57 |
| ATOM | 2042 | O   | TYR | A | 866 | 96.276 | −85.723 | 93.422 | 1.00 | 32.57 |
| ATOM | 2043 | CB  | TYR | A | 866 | 93.297 | −84.400 | 93.699 | 1.00 | 32.73 |
| ATOM | 2044 | CG  | TYR | A | 866 | 92.307 | −83.572 | 92.913 | 1.00 | 32.76 |
| ATOM | 2045 | CD1 | TYR | A | 866 | 92.665 | −83.015 | 91.690 | 1.00 | 32.80 |
| ATOM | 2046 | CD2 | TYR | A | 866 | 91.016 | −83.340 | 93.391 | 1.00 | 32.79 |
| ATOM | 2047 | CE1 | TYR | A | 866 | 91.769 | −82.251 | 90.958 | 1.00 | 32.90 |
| ATOM | 2048 | CE2 | TYR | A | 866 | 90.106 | −82.571 | 92.663 | 1.00 | 32.74 |
| ATOM | 2049 | CZ  | TYR | A | 866 | 90.492 | −82.033 | 91.447 | 1.00 | 32.83 |
| ATOM | 2050 | OH  | TYR | A | 866 | 89.615 | −81.283 | 90.698 | 1.00 | 32.91 |
| ATOM | 2051 | N   | LYS | A | 867 | 94.840 | −87.027 | 94.551 | 1.00 | 32.53 |
| ATOM | 2052 | CA  | LYS | A | 867 | 95.899 | −87.663 | 95.329 | 1.00 | 32.40 |
| ATOM | 2053 | C   | LYS | A | 867 | 96.843 | −88.405 | 94.390 | 1.00 | 32.13 |
| ATOM | 2054 | O   | LYS | A | 867 | 98.067 | −88.290 | 94.501 | 1.00 | 32.12 |
| ATOM | 2055 | CB  | LYS | A | 867 | 95.323 | −88.660 | 96.335 | 1.00 | 32.65 |
| ATOM | 2056 | CG  | LYS | A | 867 | 96.416 | −89.371 | 97.138 | 1.00 | 33.14 |
| ATOM | 2057 | CD  | LYS | A | 867 | 95.890 | −90.552 | 97.941 | 1.00 | 33.37 |
| ATOM | 2058 | CE  | LYS | A | 867 | 97.046 | −91.327 | 98.576 | 1.00 | 33.57 |
| ATOM | 2059 | NZ  | LYS | A | 867 | 96.578 | −92.598 | 99.217 | 1.00 | 33.66 |
| ATOM | 2060 | N   | LEU | A | 868 | 96.260 | −89.173 | 93.474 | 1.00 | 31.83 |
| ATOM | 2061 | CA  | LEU | A | 868 | 97.031 | −89.942 | 92.504 | 1.00 | 31.55 |
| ATOM | 2062 | C   | LEU | A | 868 | 98.077 | −89.082 | 91.816 | 1.00 | 31.29 |
| ATOM | 2063 | O   | LEU | A | 868 | 99.268 | −89.380 | 91.868 | 1.00 | 31.23 |
| ATOM | 2064 | CB  | LEU | A | 868 | 96.109 | −90.541 | 91.438 | 1.00 | 31.64 |
| ATOM | 2065 | CG  | LEU | A | 868 | 95.220 | −91.742 | 91.779 | 1.00 | 31.73 |
| ATOM | 2066 | CD1 | LEU | A | 868 | 94.349 | −92.058 | 90.570 | 1.00 | 31.78 |
| ATOM | 2067 | CD2 | LEU | A | 868 | 96.068 | −92.952 | 92.148 | 1.00 | 31.70 |
| ATOM | 2068 | N   | VAL | A | 869 | 97.623 | −88.016 | 91.168 | 1.00 | 31.03 |
| ATOM | 2069 | CA  | VAL | A | 869 | 98.517 | −87.118 | 90.446 | 1.00 | 30.88 |
| ATOM | 2070 | C   | VAL | A | 869 | 99.574 | −86.533 | 91.365 | 1.00 | 30.65 |
| ATOM | 2071 | O   | VAL | A | 869 | 100.765 | −86.549 | 91.047 | 1.00 | 30.67 |
| ATOM | 2072 | CB  | VAL | A | 869 | 97.735 | −85.957 | 89.790 | 1.00 | 30.92 |
| ATOM | 2073 | CG1 | VAL | A | 869 | 98.684 | −85.058 | 89.020 | 1.00 | 30.93 |
| ATOM | 2074 | CG2 | VAL | A | 869 | 96.662 | −86.511 | 88.878 | 1.00 | 30.98 |
| ATOM | 2075 | N   | LYS | A | 870 | 99.130 | −86.018 | 92.505 | 1.00 | 30.35 |
| ATOM | 2076 | CA  | LYS | A | 870 | 100.035 | −85.424 | 93.476 | 1.00 | 30.04 |
| ATOM | 2077 | C   | LYS | A | 870 | 101.120 | −86.438 | 93.825 | 1.00 | 29.55 |
| ATOM | 2078 | O   | LYS | A | 870 | 102.294 | −86.088 | 93.926 | 1.00 | 29.54 |
| ATOM | 2079 | CB  | LYS | A | 870 | 99.268 | −85.031 | 94.742 | 1.00 | 30.40 |
| ATOM | 2080 | CG  | LYS | A | 870 | 100.075 | −84.193 | 95.721 | 1.00 | 30.97 |
| ATOM | 2081 | CD  | LYS | A | 870 | 100.424 | −82.845 | 95.102 | 1.00 | 31.42 |

TABLE 2-continued cFMS - Formula (Ia) compound co-crystal
resolution: 500.0-1.8 Å
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2082 | CE  | LYS | A | 870 | 101.182 | −81.947 | 96.077 | 1.00 | 31.64 |
|------|------|-----|-----|---|-----|---------|---------|--------|------|-------|
| ATOM | 2083 | NZ  | LYS | A | 870 | 101.515 | −80.634 | 95.446 | 1.00 | 31.98 |
| ATOM | 2084 | N   | ASP | A | 871 | 100.719 | −87.698 | 93.980 | 1.00 | 28.88 |
| ATOM | 2085 | CA  | ASP | A | 871 | 101.650 | −88.767 | 94.321 | 1.00 | 28.18 |
| ATOM | 2086 | C   | ASP | A | 871 | 102.532 | −89.254 | 93.169 | 1.00 | 27.60 |
| ATOM | 2087 | O   | ASP | A | 871 | 103.344 | −90.163 | 93.344 | 1.00 | 27.60 |
| ATOM | 2088 | CB  | ASP | A | 871 | 100.896 | −89.958 | 94.916 | 1.00 | 28.34 |
| ATOM | 2089 | CG  | ASP | A | 871 | 100.388 | −89.686 | 96.324 | 1.00 | 28.46 |
| ATOM | 2090 | OD1 | ASP | A | 871 | 100.899 | −88.753 | 96.974 | 1.00 | 28.53 |
| ATOM | 2091 | OD2 | ASP | A | 871 | 99.486  | −90.418 | 96.782 | 1.00 | 28.63 |
| ATOM | 2092 | N   | GLY | A | 872 | 102.369 | −88.669 | 91.991 | 1.00 | 26.79 |
| ATOM | 2093 | CA  | GLY | A | 872 | 103.207 | −89.071 | 90.876 | 1.00 | 25.81 |
| ATOM | 2094 | C   | GLY | A | 872 | 102.642 | −90.105 | 89.928 | 1.00 | 25.10 |
| ATOM | 2095 | O   | GLY | A | 872 | 103.384 | −90.673 | 89.126 | 1.00 | 24.89 |
| ATOM | 2096 | N   | TYR | A | 873 | 101.336 | −90.354 | 90.012 | 1.00 | 24.38 |
| ATOM | 2097 | CA  | TYR | A | 873 | 100.687 | −91.311 | 89.123 | 1.00 | 23.67 |
| ATOM | 2098 | C   | TYR | A | 873 | 100.790 | −90.811 | 87.685 | 1.00 | 23.28 |
| ATOM | 2099 | O   | TYR | A | 873 | 100.649 | −89.619 | 87.428 | 1.00 | 23.07 |
| ATOM | 2100 | CB  | TYR | A | 873 | 99.204  | −91.450 | 89.464 | 1.00 | 23.56 |
| ATOM | 2101 | CG  | TYR | A | 873 | 98.460  | −92.330 | 88.485 | 1.00 | 23.45 |
| ATOM | 2102 | CD1 | TYR | A | 873 | 98.474  | −93.720 | 88.613 | 1.00 | 23.45 |
| ATOM | 2103 | CD2 | TYR | A | 873 | 97.782  | −91.778 | 87.401 | 1.00 | 23.36 |
| ATOM | 2104 | CE1 | TYR | A | 873 | 97.828  | −94.541 | 87.683 | 1.00 | 23.48 |
| ATOM | 2105 | CE2 | TYR | A | 873 | 97.138  | −92.584 | 86.467 | 1.00 | 23.37 |
| ATOM | 2106 | CZ  | TYR | A | 873 | 97.160  | −93.965 | 86.611 | 1.00 | 23.39 |
| ATOM | 2107 | OH  | TYR | A | 873 | 96.493  | −94.761 | 85.703 | 1.00 | 23.29 |
| ATOM | 2108 | N   | GLN | A | 874 | 101.016 | −91.727 | 86.752 | 1.00 | 22.91 |
| ATOM | 2109 | CA  | GLN | A | 874 | 101.119 | −91.372 | 85.336 | 1.00 | 22.59 |
| ATOM | 2110 | C   | GLN | A | 874 | 100.367 | −92.386 | 84.487 | 1.00 | 22.33 |
| ATOM | 2111 | O   | GLN | A | 874 | 100.442 | −93.587 | 84.741 | 1.00 | 22.29 |
| ATOM | 2112 | CB  | GLN | A | 874 | 102.595 | −91.324 | 84.901 | 1.00 | 22.63 |
| ATOM | 2113 | CG  | GLN | A | 874 | 103.392 | −90.216 | 85.582 | 1.00 | 22.75 |
| ATOM | 2114 | CD  | GLN | A | 874 | 104.812 | −90.065 | 85.047 | 1.00 | 22.81 |
| ATOM | 2115 | OE1 | GLN | A | 874 | 105.567 | −89.215 | 85.511 | 1.00 | 23.18 |
| ATOM | 2116 | NE2 | GLN | A | 874 | 105.173 | −90.882 | 84.073 | 1.00 | 22.92 |
| ATOM | 2117 | N   | MET | A | 875 | 99.628  | −91.911 | 83.486 | 1.00 | 21.97 |
| ATOM | 2118 | CA  | MET | A | 875 | 98.910  | −92.828 | 82.608 | 1.00 | 21.54 |
| ATOM | 2119 | C   | MET | A | 875 | 99.911  | −93.807 | 82.010 | 1.00 | 21.51 |
| ATOM | 2120 | O   | MET | A | 875 | 101.098 | −93.501 | 81.884 | 1.00 | 21.56 |
| ATOM | 2121 | CB  | MET | A | 875 | 98.215  | −92.081 | 81.466 | 1.00 | 21.00 |
| ATOM | 2122 | CG  | MET | A | 875 | 96.949  | −91.353 | 81.864 | 1.00 | 20.49 |
| ATOM | 2123 | SD  | MET | A | 875 | 96.259  | −90.504 | 80.454 | 1.00 | 19.48 |
| ATOM | 2124 | CE  | MET | A | 875 | 97.185  | −88.947 | 80.549 | 1.00 | 19.66 |
| ATOM | 2125 | N   | ALA | A | 876 | 99.422  | −94.981 | 81.637 | 1.00 | 21.51 |
| ATOM | 2126 | CA  | ALA | A | 876 | 100.268 | −95.998 | 81.043 | 1.00 | 21.53 |
| ATOM | 2127 | C   | ALA | A | 876 | 100.574 | −95.616 | 79.597 | 1.00 | 21.56 |
| ATOM | 2128 | O   | ALA | A | 876 | 99.879  | −94.787 | 78.999 | 1.00 | 21.38 |
| ATOM | 2129 | CB  | ALA | A | 876 | 99.564  | −97.357 | 81.097 | 1.00 | 21.51 |
| ATOM | 2130 | N   | GLN | A | 877 | 101.632 | −96.215 | 79.061 | 1.00 | 21.67 |
| ATOM | 2131 | CA  | GLN | A | 877 | 102.064 | −95.998 | 77.684 | 1.00 | 21.77 |
| ATOM | 2132 | C   | GLN | A | 877 | 100.894 | −96.234 | 76.716 | 1.00 | 21.95 |
| ATOM | 2133 | O   | GLN | A | 877 | 100.245 | −97.289 | 76.752 | 1.00 | 21.92 |
| ATOM | 2134 | CB  | GLN | A | 877 | 103.208 | −96.971 | 77.368 | 1.00 | 21.77 |
| ATOM | 2135 | CG  | GLN | A | 877 | 103.813 | −96.841 | 75.977 | 1.00 | 21.64 |
| ATOM | 2136 | CD  | GLN | A | 877 | 104.932 | −97.844 | 75.741 | 1.00 | 21.80 |
| ATOM | 2137 | OE1 | GLN | A | 877 | 105.413 | −98.497 | 76.675 | 1.00 | 21.64 |
| ATOM | 2138 | NE2 | GLN | A | 877 | 105.356 | −97.965 | 74.493 | 1.00 | 21.78 |
| ATOM | 2139 | N   | PRO | A | 878 | 100.597 | −95.252 | 75.850 | 1.00 | 22.05 |
| ATOM | 2140 | CA  | PRO | A | 878 | 99.490  | −95.449 | 74.913 | 1.00 | 22.13 |
| ATOM | 2141 | C   | PRO | A | 878 | 99.821  | −96.471 | 73.816 | 1.00 | 22.26 |
| ATOM | 2142 | O   | PRO | A | 878 | 100.987 | −96.702 | 73.484 | 1.00 | 22.07 |
| ATOM | 2143 | CB  | PRO | A | 878 | 99.219  | −94.037 | 74.396 | 1.00 | 22.08 |
| ATOM | 2144 | CG  | PRO | A | 878 | 100.551 | −93.384 | 74.473 | 1.00 | 22.05 |
| ATOM | 2145 | CD  | PRO | A | 878 | 101.110 | −93.871 | 75.782 | 1.00 | 22.09 |
| ATOM | 2146 | N   | ALA | A | 879 | 98.775  | −97.084 | 73.271 | 1.00 | 22.44 |
| ATOM | 2147 | CA  | ALA | A | 879 | 98.910  | −98.129 | 72.262 | 1.00 | 22.58 |
| ATOM | 2148 | C   | ALA | A | 879 | 99.878  | −97.899 | 71.102 | 1.00 | 22.73 |
| ATOM | 2149 | O   | ALA | A | 879 | 100.713 | −98.754 | 70.809 | 1.00 | 22.64 |
| ATOM | 2150 | CB  | ALA | A | 879 | 97.530  | −98.482 | 71.716 | 1.00 | 22.73 |
| ATOM | 2151 | N   | PHE | A | 880 | 99.786  | −96.745 | 70.453 | 1.00 | 22.85 |
| ATOM | 2152 | CA  | PHE | A | 880 | 100.625 | −96.488 | 69.294 | 1.00 | 22.98 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2153 | C   | PHE | A | 880 | 101.909 | −95.731 | 69.566 | 1.00 | 23.15 |
|------|------|-----|-----|---|-----|---------|---------|--------|------|-------|
| ATOM | 2154 | O   | PHE | A | 880 | 102.640 | −95.379 | 68.641 | 1.00 | 23.15 |
| ATOM | 2155 | CB  | PHE | A | 880 | 99.772  | −95.791 | 68.235 | 1.00 | 23.04 |
| ATOM | 2156 | CG  | PHE | A | 880 | 98.552  | −96.588 | 67.857 | 1.00 | 23.09 |
| ATOM | 2157 | CD1 | PHE | A | 880 | 98.646  | −97.627 | 66.935 | 1.00 | 23.04 |
| ATOM | 2158 | CD2 | PHE | A | 880 | 97.338  | −96.376 | 68.508 | 1.00 | 23.14 |
| ATOM | 2159 | CE1 | PHE | A | 880 | 97.552  | −98.452 | 66.670 | 1.00 | 23.09 |
| ATOM | 2160 | CE2 | PHE | A | 880 | 96.231  | −97.196 | 68.256 | 1.00 | 23.12 |
| ATOM | 2161 | CZ  | PHE | A | 880 | 96.340  | −98.237 | 67.336 | 1.00 | 23.21 |
| ATOM | 2162 | N   | ALA | A | 881 | 102.211 | −95.517 | 70.840 | 1.00 | 23.27 |
| ATOM | 2163 | CA  | ALA | A | 881 | 103.424 | −94.798 | 71.192 | 1.00 | 23.53 |
| ATOM | 2164 | C   | ALA | A | 881 | 104.637 | −95.700 | 71.383 | 1.00 | 23.76 |
| ATOM | 2165 | O   | ALA | A | 881 | 104.602 | −96.664 | 72.156 | 1.00 | 23.69 |
| ATOM | 2166 | CB  | ALA | A | 881 | 103.203 | −93.978 | 72.459 | 1.00 | 23.52 |
| ATOM | 2167 | N   | PRO | A | 882 | 105.720 | −95.422 | 70.644 | 1.00 | 23.91 |
| ATOM | 2168 | CA  | PRO | A | 882 | 106.904 | −96.258 | 70.830 | 1.00 | 24.12 |
| ATOM | 2169 | C   | PRO | A | 882 | 107.441 | −95.835 | 72.198 | 1.00 | 24.22 |
| ATOM | 2170 | O   | PRO | A | 882 | 107.054 | −94.784 | 72.717 | 1.00 | 24.27 |
| ATOM | 2171 | CB  | PRO | A | 882 | 107.821 | −95.812 | 69.696 | 1.00 | 24.09 |
| ATOM | 2172 | CG  | PRO | A | 882 | 106.855 | −95.415 | 68.624 | 1.00 | 24.21 |
| ATOM | 2173 | CD  | PRO | A | 882 | 105.821 | −94.634 | 69.405 | 1.00 | 24.04 |
| ATOM | 2174 | N   | LYS | A | 883 | 108.323 | −96.641 | 72.776 | 1.00 | 24.33 |
| ATOM | 2175 | CA  | LYS | A | 883 | 108.909 | −96.336 | 74.071 | 1.00 | 24.37 |
| ATOM | 2176 | C   | LYS | A | 883 | 109.508 | −94.932 | 74.118 | 1.00 | 24.11 |
| ATOM | 2177 | O   | LYS | A | 883 | 109.315 | −94.204 | 75.088 | 1.00 | 24.06 |
| ATOM | 2178 | CB  | LYS | A | 883 | 109.997 | −97.369 | 74.398 | 1.00 | 24.87 |
| ATOM | 2179 | CG  | LYS | A | 883 | 110.802 | −97.090 | 75.661 | 1.00 | 25.38 |
| ATOM | 2180 | CD  | LYS | A | 883 | 109.917 | −97.062 | 76.904 | 1.00 | 25.81 |
| ATOM | 2181 | CE  | LYS | A | 883 | 110.736 | −97.159 | 78.197 | 1.00 | 26.11 |
| ATOM | 2182 | NZ  | LYS | A | 883 | 111.720 | −96.041 | 78.381 | 1.00 | 26.41 |
| ATOM | 2183 | N   | ASN | A | 884 | 110.231 | −94.548 | 73.071 | 1.00 | 23.79 |
| ATOM | 2184 | CA  | ASN | A | 884 | 110.855 | −93.231 | 73.055 | 1.00 | 23.47 |
| ATOM | 2185 | C   | ASN | A | 884 | 109.859 | −92.078 | 73.058 | 1.00 | 23.15 |
| ATOM | 2186 | O   | ASN | A | 884 | 110.179 | −90.992 | 73.543 | 1.00 | 23.21 |
| ATOM | 2187 | CB  | ASN | A | 884 | 111.804 | −93.091 | 71.859 | 1.00 | 23.61 |
| ATOM | 2188 | CG  | ASN | A | 884 | 113.056 | −93.933 | 72.009 | 1.00 | 23.79 |
| ATOM | 2189 | OD1 | ASN | A | 884 | 113.320 | −94.490 | 73.078 | 1.00 | 23.88 |
| ATOM | 2190 | ND2 | ASN | A | 884 | 113.842 | −94.025 | 70.938 | 1.00 | 23.72 |
| ATOM | 2191 | N   | ILE | A | 885 | 108.658 | −92.299 | 72.531 | 1.00 | 22.59 |
| ATOM | 2192 | CA  | ILE | A | 885 | 107.653 | −91.235 | 72.513 | 1.00 | 22.13 |
| ATOM | 2193 | C   | ILE | A | 885 | 106.978 | −91.171 | 73.889 | 1.00 | 21.79 |
| ATOM | 2194 | O   | ILE | A | 885 | 106.548 | −90.103 | 74.332 | 1.00 | 21.66 |
| ATOM | 2195 | CB  | ILE | A | 885 | 106.603 | −91.462 | 71.387 | 1.00 | 22.22 |
| ATOM | 2196 | CG1 | ILE | A | 885 | 107.298 | −91.425 | 70.016 | 1.00 | 22.22 |
| ATOM | 2197 | CG2 | ILE | A | 885 | 105.512 | −90.396 | 71.439 | 1.00 | 22.18 |
| ATOM | 2198 | CD1 | ILE | A | 885 | 108.090 | −90.146 | 69.753 | 1.00 | 22.35 |
| ATOM | 2199 | N   | TYR | A | 886 | 106.919 | −92.310 | 74.573 | 1.00 | 21.31 |
| ATOM | 2200 | CA  | TYR | A | 886 | 106.331 | −92.362 | 75.907 | 1.00 | 20.90 |
| ATOM | 2201 | C   | TYR | A | 886 | 107.264 | −91.631 | 76.872 | 1.00 | 20.71 |
| ATOM | 2202 | O   | TYR | A | 886 | 106.811 | −91.055 | 77.853 | 1.00 | 20.63 |
| ATOM | 2203 | CB  | TYR | A | 886 | 106.130 | −93.815 | 76.361 | 1.00 | 20.74 |
| ATOM | 2204 | CG  | TYR | A | 886 | 105.467 | −93.958 | 77.722 | 1.00 | 20.49 |
| ATOM | 2205 | CD1 | TYR | A | 886 | 104.283 | −93.273 | 78.023 | 1.00 | 20.44 |
| ATOM | 2206 | CD2 | TYR | A | 886 | 106.019 | −94.779 | 78.702 | 1.00 | 20.34 |
| ATOM | 2207 | CE1 | TYR | A | 886 | 103.669 | −93.404 | 79.269 | 1.00 | 20.32 |
| ATOM | 2208 | CE2 | TYR | A | 886 | 105.414 | −94.919 | 79.955 | 1.00 | 20.45 |
| ATOM | 2209 | CZ  | TYR | A | 886 | 104.236 | −94.230 | 80.231 | 1.00 | 20.40 |
| ATOM | 2210 | OH  | TYR | A | 886 | 103.620 | −94.386 | 81.457 | 1.00 | 20.39 |
| ATOM | 2211 | N   | SER | A | 887 | 108.568 | −91.658 | 76.583 | 1.00 | 20.36 |
| ATOM | 2212 | CA  | SER | A | 887 | 109.555 | −90.976 | 77.415 | 1.00 | 20.07 |
| ATOM | 2213 | C   | SER | A | 887 | 109.370 | −89.468 | 77.366 | 1.00 | 19.77 |
| ATOM | 2214 | O   | SER | A | 887 | 109.770 | −88.761 | 78.295 | 1.00 | 19.69 |
| ATOM | 2215 | CB  | SER | A | 887 | 110.979 | −91.313 | 76.970 | 1.00 | 20.21 |
| ATOM | 2216 | OG  | SER | A | 887 | 111.309 | −92.641 | 77.332 | 1.00 | 20.57 |
| ATOM | 2217 | N   | ILE | A | 888 | 108.802 | −88.970 | 76.270 | 1.00 | 19.33 |
| ATOM | 2218 | CA  | ILE | A | 888 | 108.547 | −87.536 | 76.159 | 1.00 | 18.95 |
| ATOM | 2219 | C   | ILE | A | 888 | 107.416 | −87.205 | 77.136 | 1.00 | 18.74 |
| ATOM | 2220 | O   | ILE | A | 888 | 107.489 | −86.220 | 77.875 | 1.00 | 18.70 |
| ATOM | 2221 | CB  | ILE | A | 888 | 108.123 | −87.139 | 74.724 | 1.00 | 18.86 |
| ATOM | 2222 | CG1 | ILE | A | 888 | 109.254 | −87.467 | 73.742 | 1.00 | 18.93 |
| ATOM | 2223 | CG2 | ILE | A | 888 | 107.805 | −85.635 | 74.658 | 1.00 | 18.93 |

TABLE 2-continued cFMS - Formula (Ia) compound co-crystal
resolution: 500.0-1.8 Å
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2224 | CD1 | ILE | A | 888 | 108.882 | −87.276 | 72.285 | 1.00 | 18.95 |
|------|------|-----|-----|---|-----|---------|---------|--------|------|-------|
| ATOM | 2225 | N   | MET | A | 889 | 106.373 | −88.036 | 77.138 | 1.00 | 18.45 |
| ATOM | 2226 | CA  | MET | A | 889 | 105.235 | −87.836 | 78.032 | 1.00 | 18.23 |
| ATOM | 2227 | C   | MET | A | 889 | 105.678 | −87.844 | 79.496 | 1.00 | 18.15 |
| ATOM | 2228 | O   | MET | A | 889 | 105.304 | −86.968 | 80.276 | 1.00 | 18.09 |
| ATOM | 2229 | CB  | MET | A | 889 | 104.188 | −88.937 | 77.814 | 1.00 | 18.16 |
| ATOM | 2230 | CG  | MET | A | 889 | 103.565 | −88.931 | 76.434 | 1.00 | 18.13 |
| ATOM | 2231 | SD  | MET | A | 889 | 102.506 | −90.364 | 76.123 | 1.00 | 18.45 |
| ATOM | 2232 | CE  | MET | A | 889 | 102.684 | −90.510 | 74.362 | 1.00 | 18.11 |
| ATOM | 2233 | N   | GLN | A | 890 | 106.475 | −88.840 | 79.865 | 1.00 | 17.94 |
| ATOM | 2234 | CA  | GLN | A | 890 | 106.962 | −88.943 | 81.231 | 1.00 | 17.88 |
| ATOM | 2235 | C   | GLN | A | 890 | 107.759 | −87.700 | 81.616 | 1.00 | 17.71 |
| ATOM | 2236 | O   | GLN | A | 890 | 107.658 | −87.217 | 82.739 | 1.00 | 17.61 |
| ATOM | 2237 | CB  | GLN | A | 890 | 107.830 | −90.200 | 81.387 | 1.00 | 18.02 |
| ATOM | 2238 | CG  | GLN | A | 890 | 107.055 | −91.506 | 81.202 | 1.00 | 18.41 |
| ATOM | 2239 | CD  | GLN | A | 890 | 107.954 | −92.725 | 81.267 | 1.00 | 18.74 |
| ATOM | 2240 | OE1 | GLN | A | 890 | 108.859 | −92.887 | 80.444 | 1.00 | 19.12 |
| ATOM | 2241 | NE2 | GLN | A | 890 | 107.718 | −93.585 | 82.247 | 1.00 | 18.79 |
| ATOM | 2242 | N   | ALA | A | 891 | 108.551 | −87.189 | 80.680 | 1.00 | 17.69 |
| ATOM | 2243 | CA  | ALA | A | 891 | 109.357 | −85.993 | 80.930 | 1.00 | 17.67 |
| ATOM | 2244 | C   | ALA | A | 891 | 108.456 | −84.771 | 81.162 | 1.00 | 17.72 |
| ATOM | 2245 | O   | ALA | A | 891 | 108.716 | −83.953 | 82.050 | 1.00 | 17.75 |
| ATOM | 2246 | CB  | ALA | A | 891 | 110.291 | −85.738 | 79.755 | 1.00 | 17.60 |
| ATOM | 2247 | N   | CYS | A | 892 | 107.407 | −84.642 | 80.358 | 1.00 | 17.82 |
| ATOM | 2248 | CA  | CYS | A | 892 | 106.471 | −83.527 | 80.514 | 1.00 | 17.87 |
| ATOM | 2249 | C   | CYS | A | 892 | 105.707 | −83.666 | 81.841 | 1.00 | 17.96 |
| ATOM | 2250 | O   | CYS | A | 892 | 105.198 | −82.681 | 82.378 | 1.00 | 17.83 |
| ATOM | 2251 | CB  | CYS | A | 892 | 105.451 | −83.500 | 79.368 | 1.00 | 17.94 |
| ATOM | 2252 | SG  | CYS | A | 892 | 106.091 | −83.200 | 77.699 | 1.00 | 17.70 |
| ATOM | 2253 | N   | TRP | A | 893 | 105.635 | −84.887 | 82.363 | 1.00 | 18.05 |
| ATOM | 2254 | CA  | TRP | A | 893 | 104.916 | −85.132 | 83.602 | 1.00 | 18.21 |
| ATOM | 2255 | C   | TRP | A | 893 | 105.788 | −85.149 | 84.856 | 1.00 | 18.64 |
| ATOM | 2256 | O   | TRP | A | 893 | 105.380 | −85.667 | 85.895 | 1.00 | 18.66 |
| ATOM | 2257 | CB  | TRP | A | 893 | 104.098 | −86.432 | 83.494 | 1.00 | 17.81 |
| ATOM | 2258 | CG  | TRP | A | 893 | 103.084 | −86.416 | 82.359 | 1.00 | 17.21 |
| ATOM | 2259 | CD1 | TRP | A | 893 | 102.465 | −85.321 | 81.833 | 1.00 | 17.07 |
| ATOM | 2260 | CD2 | TRP | A | 893 | 102.545 | −87.552 | 81.660 | 1.00 | 16.95 |
| ATOM | 2261 | NE1 | TRP | A | 893 | 101.577 | −85.698 | 80.855 | 1.00 | 16.96 |
| ATOM | 2262 | CE2 | TRP | A | 893 | 101.604 | −87.061 | 80.729 | 1.00 | 16.89 |
| ATOM | 2263 | CE3 | TRP | A | 893 | 102.764 | −88.933 | 81.735 | 1.00 | 16.75 |
| ATOM | 2264 | CZ2 | TRP | A | 893 | 100.877 | −87.904 | 79.875 | 1.00 | 16.68 |
| ATOM | 2265 | CZ3 | TRP | A | 893 | 102.043 | −89.772 | 80.889 | 1.00 | 16.80 |
| ATOM | 2266 | CH2 | TRP | A | 893 | 101.108 | −89.250 | 79.969 | 1.00 | 16.69 |
| ATOM | 2267 | N   | ALA | A | 894 | 106.982 | −84.566 | 84.774 | 1.00 | 19.09 |
| ATOM | 2268 | CA  | ALA | A | 894 | 107.847 | −84.510 | 85.953 | 1.00 | 19.69 |
| ATOM | 2269 | C   | ALA | A | 894 | 107.125 | −83.661 | 86.995 | 1.00 | 20.05 |
| ATOM | 2270 | O   | ALA | A | 894 | 106.596 | −82.595 | 86.673 | 1.00 | 20.02 |
| ATOM | 2271 | CB  | ALA | A | 894 | 109.189 | −83.878 | 85.598 | 1.00 | 19.59 |
| ATOM | 2272 | N   | LEU | A | 895 | 107.090 | −84.126 | 88.240 | 1.00 | 20.71 |
| ATOM | 2273 | CA  | LEU | A | 895 | 106.414 | −83.369 | 89.290 | 1.00 | 21.27 |
| ATOM | 2274 | C   | LEU | A | 895 | 107.086 | −82.016 | 89.478 | 1.00 | 21.66 |
| ATOM | 2275 | O   | LEU | A | 895 | 106.422 | −81.001 | 89.664 | 1.00 | 21.82 |
| ATOM | 2276 | CB  | LEU | A | 895 | 106.418 | −84.157 | 90.605 | 1.00 | 21.38 |
| ATOM | 2277 | CG  | LEU | A | 895 | 105.573 | −85.433 | 90.596 | 1.00 | 21.51 |
| ATOM | 2278 | CD1 | LEU | A | 895 | 105.815 | −86.229 | 91.881 | 1.00 | 21.68 |
| ATOM | 2279 | CD2 | LEU | A | 895 | 104.104 | −85.065 | 90.451 | 1.00 | 21.66 |
| ATOM | 2280 | N   | GLU | A | 896 | 108.411 | −82.011 | 89.410 | 1.00 | 22.17 |
| ATOM | 2281 | CA  | GLU | A | 896 | 109.192 | −80.786 | 89.554 | 1.00 | 22.59 |
| ATOM | 2282 | C   | GLU | A | 896 | 109.121 | −80.066 | 88.203 | 1.00 | 22.53 |
| ATOM | 2283 | O   | GLU | A | 896 | 109.698 | −80.529 | 87.221 | 1.00 | 22.61 |
| ATOM | 2284 | CB  | GLU | A | 896 | 110.640 | −81.155 | 89.894 | 1.00 | 23.19 |
| ATOM | 2285 | CG  | GLU | A | 896 | 111.499 | −80.012 | 90.428 | 1.00 | 24.23 |
| ATOM | 2286 | CD  | GLU | A | 896 | 110.932 | −79.406 | 91.699 | 1.00 | 24.77 |
| ATOM | 2287 | OE1 | GLU | A | 896 | 110.206 | −78.393 | 91.611 | 1.00 | 24.96 |
| ATOM | 2288 | OE2 | GLU | A | 896 | 111.206 | −79.957 | 92.792 | 1.00 | 25.59 |
| ATOM | 2289 | N   | PRO | A | 897 | 108.396 | −78.932 | 88.133 | 1.00 | 22.41 |
| ATOM | 2290 | CA  | PRO | A | 897 | 108.251 | −78.161 | 86.894 | 1.00 | 22.32 |
| ATOM | 2291 | C   | PRO | A | 897 | 109.571 | −77.890 | 86.165 | 1.00 | 22.19 |
| ATOM | 2292 | O   | PRO | A | 897 | 109.653 | −78.070 | 84.951 | 1.00 | 22.05 |
| ATOM | 2293 | CB  | PRO | A | 897 | 107.581 | −76.874 | 87.366 | 1.00 | 22.31 |
| ATOM | 2294 | CG  | PRO | A | 897 | 106.742 | −77.344 | 88.505 | 1.00 | 22.28 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2295 | CD  | PRO | A | 897 | 107.682 | −78.271 | 89.240 | 1.00 | 22.41 |
|------|------|-----|-----|---|-----|---------|---------|--------|------|-------|
| ATOM | 2296 | N   | THR | A | 898 | 110.589 | −77.455 | 86.911 | 1.00 | 22.12 |
| ATOM | 2297 | CA  | THR | A | 898 | 111.896 | −77.152 | 86.325 | 1.00 | 22.17 |
| ATOM | 2298 | C   | THR | A | 898 | 112.592 | −78.383 | 85.764 | 1.00 | 22.04 |
| ATOM | 2299 | O   | THR | A | 898 | 113.626 | −78.269 | 85.106 | 1.00 | 22.05 |
| ATOM | 2300 | CB  | THR | A | 898 | 112.852 | −76.485 | 87.348 | 1.00 | 22.19 |
| ATOM | 2301 | OG1 | THR | A | 898 | 113.055 | −77.365 | 88.462 | 1.00 | 22.26 |
| ATOM | 2302 | CG2 | THR | A | 898 | 112.277 | −75.159 | 87.832 | 1.00 | 22.30 |
| ATOM | 2303 | N   | HIS | A | 899 | 112.042 | −79.561 | 86.030 | 1.00 | 21.98 |
| ATOM | 2304 | CA  | HIS | A | 899 | 112.637 | −80.780 | 85.499 | 1.00 | 21.91 |
| ATOM | 2305 | C   | HIS | A | 899 | 111.966 | −81.201 | 84.193 | 1.00 | 21.60 |
| ATOM | 2306 | O   | HIS | A | 899 | 112.332 | −82.211 | 83.600 | 1.00 | 21.57 |
| ATOM | 2307 | CB  | HIS | A | 899 | 112.559 | −81.915 | 86.514 | 1.00 | 22.16 |
| ATOM | 2308 | CG  | HIS | A | 899 | 113.549 | −81.791 | 87.630 | 1.00 | 22.50 |
| ATOM | 2309 | ND1 | HIS | A | 899 | 113.834 | −82.830 | 88.489 | 1.00 | 22.74 |
| ATOM | 2310 | CD2 | HIS | A | 899 | 114.313 | −80.747 | 88.033 | 1.00 | 22.55 |
| ATOM | 2311 | CE1 | HIS | A | 899 | 114.731 | −82.430 | 89.375 | 1.00 | 22.82 |
| ATOM | 2312 | NE2 | HIS | A | 899 | 115.037 | −81.170 | 89.119 | 1.00 | 22.79 |
| ATOM | 2313 | N   | ARG | A | 900 | 110.976 | −80.428 | 83.755 | 1.00 | 21.20 |
| ATOM | 2314 | CA  | ARG | A | 900 | 110.291 | −80.727 | 82.502 | 1.00 | 20.91 |
| ATOM | 2315 | C   | ARG | A | 900 | 111.087 | −80.096 | 81.368 | 1.00 | 20.74 |
| ATOM | 2316 | O   | ARG | A | 900 | 111.833 | −79.141 | 81.582 | 1.00 | 20.75 |
| ATOM | 2317 | CB  | ARG | A | 900 | 108.864 | −80.161 | 82.509 | 1.00 | 20.57 |
| ATOM | 2318 | CG  | ARG | A | 900 | 107.979 | −80.787 | 83.564 | 1.00 | 20.04 |
| ATOM | 2319 | CD  | ARG | A | 900 | 106.653 | −80.064 | 83.717 | 1.00 | 19.75 |
| ATOM | 2320 | NE  | ARG | A | 900 | 106.012 | −80.458 | 84.965 | 1.00 | 19.42 |
| ATOM | 2321 | CZ  | ARG | A | 900 | 105.119 | −79.722 | 85.620 | 1.00 | 19.48 |
| ATOM | 2322 | NH1 | ARG | A | 900 | 104.740 | −78.538 | 85.145 | 1.00 | 19.31 |
| ATOM | 2323 | NH2 | ARG | A | 900 | 104.641 | −80.151 | 86.779 | 1.00 | 19.38 |
| ATOM | 2324 | N   | PRO | A | 901 | 110.950 | −80.629 | 80.148 | 1.00 | 20.66 |
| ATOM | 2325 | CA  | PRO | A | 901 | 111.688 | −80.057 | 79.022 | 1.00 | 20.84 |
| ATOM | 2326 | C   | PRO | A | 901 | 111.013 | −78.789 | 78.529 | 1.00 | 20.78 |
| ATOM | 2327 | O   | PRO | A | 901 | 109.908 | −78.447 | 78.963 | 1.00 | 20.66 |
| ATOM | 2328 | CB  | PRO | A | 901 | 111.631 | −81.167 | 77.978 | 1.00 | 20.82 |
| ATOM | 2329 | CG  | PRO | A | 901 | 110.274 | −81.767 | 78.231 | 1.00 | 20.83 |
| ATOM | 2330 | CD  | PRO | A | 901 | 110.243 | −81.858 | 79.744 | 1.00 | 20.69 |
| ATOM | 2331 | N   | THR | A | 902 | 111.687 | −78.089 | 77.630 | 1.00 | 20.78 |
| ATOM | 2332 | CA  | THR | A | 902 | 111.138 | −76.878 | 77.036 | 1.00 | 21.02 |
| ATOM | 2333 | C   | THR | A | 902 | 110.505 | −77.372 | 75.738 | 1.00 | 20.92 |
| ATOM | 2334 | O   | THR | A | 902 | 110.794 | −78.484 | 75.291 | 1.00 | 20.82 |
| ATOM | 2335 | CB  | THR | A | 902 | 112.244 | −75.855 | 76.695 | 1.00 | 21.04 |
| ATOM | 2336 | OG1 | THR | A | 902 | 113.100 | −76.405 | 75.689 | 1.00 | 21.30 |
| ATOM | 2337 | CG2 | THR | A | 902 | 113.070 | −75.531 | 77.922 | 1.00 | 21.03 |
| ATOM | 2338 | N   | PHE | A | 903 | 109.633 | −76.572 | 75.143 | 1.00 | 20.96 |
| ATOM | 2339 | CA  | PHE | A | 903 | 108.998 | −76.972 | 73.898 | 1.00 | 21.21 |
| ATOM | 2340 | C   | PHE | A | 903 | 110.025 | −77.083 | 72.779 | 1.00 | 21.58 |
| ATOM | 2341 | O   | PHE | A | 903 | 109.899 | −77.927 | 71.890 | 1.00 | 21.56 |
| ATOM | 2342 | CB  | PHE | A | 903 | 107.903 | −75.979 | 73.518 | 1.00 | 20.90 |
| ATOM | 2343 | CG  | PHE | A | 903 | 106.636 | −76.154 | 74.311 | 1.00 | 20.63 |
| ATOM | 2344 | CD1 | PHE | A | 903 | 105.935 | −77.358 | 74.263 | 1.00 | 20.55 |
| ATOM | 2345 | CD2 | PHE | A | 903 | 106.142 | −75.123 | 75.105 | 1.00 | 20.58 |
| ATOM | 2346 | CE1 | PHE | A | 903 | 104.757 | −77.531 | 74.993 | 1.00 | 20.42 |
| ATOM | 2347 | CE2 | PHE | A | 903 | 104.967 | −75.284 | 75.840 | 1.00 | 20.49 |
| ATOM | 2348 | CZ  | PHE | A | 903 | 104.273 | −76.491 | 75.783 | 1.00 | 20.45 |
| ATOM | 2349 | N   | GLN | A | 904 | 111.038 | −76.225 | 72.815 | 1.00 | 22.00 |
| ATOM | 2350 | CA  | GLN | A | 904 | 112.075 | −76.282 | 71.795 | 1.00 | 22.56 |
| ATOM | 2351 | C   | GLN | A | 904 | 112.796 | −77.621 | 71.899 | 1.00 | 22.63 |
| ATOM | 2352 | O   | GLN | A | 904 | 113.086 | −78.261 | 70.889 | 1.00 | 22.67 |
| ATOM | 2353 | CB  | GLN | A | 904 | 113.067 | −75.132 | 71.972 | 1.00 | 22.93 |
| ATOM | 2354 | CG  | GLN | A | 904 | 114.103 | −75.054 | 70.859 | 1.00 | 23.84 |
| ATOM | 2355 | CD  | GLN | A | 904 | 113.474 | −75.114 | 69.470 | 1.00 | 24.26 |
| ATOM | 2356 | OE1 | GLN | A | 904 | 112.634 | −74.278 | 69.110 | 1.00 | 24.68 |
| ATOM | 2357 | NE2 | GLN | A | 904 | 113.879 | −76.106 | 68.683 | 1.00 | 24.60 |
| ATOM | 2358 | N   | GLN | A | 905 | 113.075 | −78.053 | 73.124 | 1.00 | 22.82 |
| ATOM | 2359 | CA  | GLN | A | 905 | 113.760 | −79.321 | 73.335 | 1.00 | 22.99 |
| ATOM | 2360 | C   | GLN | A | 905 | 112.903 | −80.503 | 72.895 | 1.00 | 23.21 |
| ATOM | 2361 | O   | GLN | A | 905 | 113.428 | −81.512 | 72.424 | 1.00 | 23.11 |
| ATOM | 2362 | CB  | GLN | A | 905 | 114.155 | −79.471 | 74.798 | 1.00 | 23.04 |
| ATOM | 2363 | CG  | GLN | A | 905 | 115.223 | −78.484 | 75.232 | 1.00 | 23.19 |
| ATOM | 2364 | CD  | GLN | A | 905 | 115.420 | −78.484 | 76.730 | 1.00 | 23.22 |
| ATOM | 2365 | OE1 | GLN | A | 905 | 114.542 | −78.920 | 77.472 | 1.00 | 23.47 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2366 | NE2 | GLN | A | 905 | 116.563 | −77.973 | 77.186 | 1.00 | 23.20 |
| ATOM | 2367 | N | ILE | A | 906 | 111.587 | −80.374 | 73.052 | 1.00 | 23.34 |
| ATOM | 2368 | CA | ILE | A | 906 | 110.667 | −81.422 | 72.636 | 1.00 | 23.70 |
| ATOM | 2369 | C | ILE | A | 906 | 110.684 | −81.479 | 71.106 | 1.00 | 24.23 |
| ATOM | 2370 | O | ILE | A | 906 | 110.596 | −82.552 | 70.512 | 1.00 | 24.22 |
| ATOM | 2371 | CB | ILE | A | 906 | 109.214 | −81.121 | 73.106 | 1.00 | 23.45 |
| ATOM | 2372 | CG1 | ILE | A | 906 | 109.108 | −81.256 | 74.629 | 1.00 | 23.27 |
| ATOM | 2373 | CG2 | ILE | A | 906 | 108.236 | −82.045 | 72.403 | 1.00 | 23.22 |
| ATOM | 2374 | CD1 | ILE | A | 906 | 107.763 | −80.801 | 75.198 | 1.00 | 22.92 |
| ATOM | 2375 | N | CYS | A | 907 | 110.783 | −80.317 | 70.470 | 1.00 | 24.89 |
| ATOM | 2376 | CA | CYS | A | 907 | 110.808 | −80.263 | 69.009 | 1.00 | 25.72 |
| ATOM | 2377 | C | CYS | A | 907 | 112.052 | −80.975 | 68.478 | 1.00 | 26.30 |
| ATOM | 2378 | O | CYS | A | 907 | 111.976 | −81.784 | 67.550 | 1.00 | 26.45 |
| ATOM | 2379 | CB | CYS | A | 907 | 110.813 | −78.810 | 68.516 | 1.00 | 25.67 |
| ATOM | 2380 | SG | CYS | A | 907 | 109.247 | −77.898 | 68.624 | 1.00 | 25.92 |
| ATOM | 2381 | N | SER | A | 908 | 113.199 | −80.669 | 69.072 | 1.00 | 27.06 |
| ATOM | 2382 | CA | SER | A | 908 | 114.459 | −81.268 | 68.653 | 1.00 | 27.82 |
| ATOM | 2383 | C | SER | A | 908 | 114.427 | −82.791 | 68.707 | 1.00 | 28.26 |
| ATOM | 2384 | O | SER | A | 908 | 114.785 | −83.455 | 67.737 | 1.00 | 28.18 |
| ATOM | 2385 | CB | SER | A | 908 | 115.603 | −80.743 | 69.517 | 1.00 | 27.88 |
| ATOM | 2386 | OG | SER | A | 908 | 115.720 | −79.339 | 69.375 | 1.00 | 28.33 |
| ATOM | 2387 | N | PHE | A | 909 | 113.998 | −83.339 | 69.840 | 1.00 | 28.84 |
| ATOM | 2388 | CA | PHE | A | 909 | 113.926 | −84.788 | 70.003 | 1.00 | 29.53 |
| ATOM | 2389 | C | PHE | A | 909 | 112.964 | −85.399 | 68.987 | 1.00 | 30.09 |
| ATOM | 2390 | O | PHE | A | 909 | 113.268 | −86.423 | 68.372 | 1.00 | 30.13 |
| ATOM | 2391 | CB | PHE | A | 909 | 113.472 | −85.142 | 71.422 | 1.00 | 29.32 |
| ATOM | 2392 | CG | PHE | A | 909 | 113.515 | −86.616 | 71.727 | 1.00 | 29.22 |
| ATOM | 2393 | CD1 | PHE | A | 909 | 114.729 | −87.297 | 71.773 | 1.00 | 29.15 |
| ATOM | 2394 | CD2 | PHE | A | 909 | 112.341 | −87.321 | 71.985 | 1.00 | 29.12 |
| ATOM | 2395 | CE1 | PHE | A | 909 | 114.776 | −88.654 | 72.073 | 1.00 | 29.07 |
| ATOM | 2396 | CE2 | PHE | A | 909 | 112.377 | −88.680 | 72.286 | 1.00 | 29.04 |
| ATOM | 2397 | CZ | PHE | A | 909 | 113.596 | −89.348 | 72.330 | 1.00 | 29.07 |
| ATOM | 2398 | N | LEU | A | 910 | 111.803 | −84.771 | 68.818 | 1.00 | 30.82 |
| ATOM | 2399 | CA | LEU | A | 910 | 110.804 | −85.254 | 67.868 | 1.00 | 31.67 |
| ATOM | 2400 | C | LEU | A | 910 | 111.362 | −85.247 | 66.452 | 1.00 | 32.45 |
| ATOM | 2401 | O | LEU | A | 910 | 110.975 | −86.071 | 65.623 | 1.00 | 32.47 |
| ATOM | 2402 | CB | LEU | A | 910 | 109.542 | −84.384 | 67.915 | 1.00 | 31.31 |
| ATOM | 2403 | CG | LEU | A | 910 | 108.583 | −84.578 | 69.091 | 1.00 | 31.17 |
| ATOM | 2404 | CD1 | LEU | A | 910 | 107.468 | −83.541 | 69.002 | 1.00 | 30.98 |
| ATOM | 2405 | CD2 | LEU | A | 910 | 108.006 | −85.995 | 69.069 | 1.00 | 30.94 |
| ATOM | 2406 | N | GLN | A | 911 | 112.264 | −84.309 | 66.181 | 1.00 | 33.43 |
| ATOM | 2407 | CA | GLN | A | 911 | 112.888 | −84.192 | 64.865 | 1.00 | 34.52 |
| ATOM | 2408 | C | GLN | A | 911 | 113.793 | −85.391 | 64.619 | 1.00 | 35.11 |
| ATOM | 2409 | O | GLN | A | 911 | 113.814 | −85.947 | 63.524 | 1.00 | 35.18 |
| ATOM | 2410 | CB | GLN | A | 911 | 113.707 | −82.906 | 64.783 | 1.00 | 34.80 |
| ATOM | 2411 | CG | GLN | A | 911 | 114.190 | −82.557 | 63.380 | 1.00 | 35.39 |
| ATOM | 2412 | CD | GLN | A | 911 | 114.825 | −81.171 | 63.311 | 1.00 | 35.71 |
| ATOM | 2413 | OE1 | GLN | A | 911 | 115.114 | −80.659 | 62.223 | 1.00 | 36.02 |
| ATOM | 2414 | NE2 | GLN | A | 911 | 115.047 | −80.559 | 64.473 | 1.00 | 35.86 |
| ATOM | 2415 | N | GLU | A | 912 | 114.524 | −85.794 | 65.653 | 1.00 | 35.86 |
| ATOM | 2416 | CA | GLU | A | 912 | 115.428 | −86.932 | 65.562 | 1.00 | 36.66 |
| ATOM | 2417 | C | GLU | A | 912 | 114.666 | −88.250 | 65.423 | 1.00 | 37.15 |
| ATOM | 2418 | O | GLU | A | 912 | 115.113 | −89.161 | 64.728 | 1.00 | 37.16 |
| ATOM | 2419 | CB | GLU | A | 912 | 116.330 | −86.988 | 66.799 | 1.00 | 36.80 |
| ATOM | 2420 | CG | GLU | A | 912 | 116.947 | −85.655 | 67.162 | 1.00 | 37.12 |
| ATOM | 2421 | CD | GLU | A | 912 | 117.928 | −85.755 | 68.303 | 1.00 | 37.35 |
| ATOM | 2422 | OE1 | GLU | A | 912 | 117.640 | −86.487 | 69.273 | 1.00 | 37.59 |
| ATOM | 2423 | OE2 | GLU | A | 912 | 118.987 | −85.091 | 68.237 | 1.00 | 37.52 |
| ATOM | 2424 | N | GLN | A | 913 | 113.517 | −88.357 | 66.084 | 1.00 | 37.74 |
| ATOM | 2425 | CA | GLN | A | 913 | 112.729 | −89.584 | 66.009 | 1.00 | 38.42 |
| ATOM | 2426 | C | GLN | A | 913 | 112.096 | −89.729 | 64.629 | 1.00 | 38.99 |
| ATOM | 2427 | O | GLN | A | 913 | 111.978 | −90.834 | 64.102 | 1.00 | 39.02 |
| ATOM | 2428 | CB | GLN | A | 913 | 111.647 | −89.594 | 67.099 | 1.00 | 38.29 |
| ATOM | 2429 | CG | GLN | A | 913 | 112.201 | −89.568 | 68.523 | 1.00 | 38.16 |
| ATOM | 2430 | CD | GLN | A | 913 | 113.025 | −90.800 | 68.869 | 1.00 | 38.15 |
| ATOM | 2431 | OE1 | GLN | A | 913 | 112.494 | −91.903 | 69.001 | 1.00 | 38.07 |
| ATOM | 2432 | NE2 | GLN | A | 913 | 114.334 | −90.614 | 69.017 | 1.00 | 38.13 |
| ATOM | 2433 | N | ALA | A | 914 | 111.701 | −88.606 | 64.042 | 1.00 | 39.69 |
| ATOM | 2434 | CA | ALA | A | 914 | 111.097 | −88.612 | 62.717 | 1.00 | 40.49 |
| ATOM | 2435 | C | ALA | A | 914 | 112.120 | −89.030 | 61.661 | 1.00 | 41.07 |
| ATOM | 2436 | O | ALA | A | 914 | 111.808 | −89.807 | 60.756 | 1.00 | 41.13 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2437 | CB | ALA | A | 914 | 110.547 | −87.230 | 62.390 | 1.00 | 40.44 |
| ATOM | 2438 | N | GLN | A | 915 | 113.338 | −88.511 | 61.777 | 1.00 | 41.81 |
| ATOM | 2439 | CA | GLN | A | 915 | 114.395 | −88.838 | 60.825 | 1.00 | 42.59 |
| ATOM | 2440 | C | GLN | A | 915 | 114.746 | −90.313 | 60.929 | 1.00 | 43.08 |
| ATOM | 2441 | O | GLN | A | 915 | 115.004 | −90.975 | 59.922 | 1.00 | 43.10 |
| ATOM | 2442 | CB | GLN | A | 915 | 115.644 | −87.995 | 61.092 | 1.00 | 42.69 |
| ATOM | 2443 | CG | GLN | A | 915 | 115.396 | −86.498 | 61.101 | 1.00 | 42.98 |
| ATOM | 2444 | CD | GLN | A | 915 | 116.683 | −85.691 | 61.083 | 1.00 | 43.23 |
| ATOM | 2445 | OE1 | GLN | A | 915 | 116.707 | −84.526 | 61.494 | 1.00 | 43.39 |
| ATOM | 2446 | NE2 | GLN | A | 915 | 117.759 | −86.302 | 60.592 | 1.00 | 43.27 |
| ATOM | 2447 | N | GLU | A | 916 | 114.754 | −90.825 | 62.154 | 1.00 | 43.66 |
| ATOM | 2448 | CA | GLU | A | 916 | 115.062 | −92.226 | 62.384 | 1.00 | 44.31 |
| ATOM | 2449 | C | GLU | A | 916 | 113.979 | −93.091 | 61.747 | 1.00 | 44.73 |
| ATOM | 2450 | O | GLU | A | 916 | 114.256 | −94.175 | 61.232 | 1.00 | 44.81 |
| ATOM | 2451 | CB | GLU | A | 916 | 115.142 | −92.504 | 63.886 | 1.00 | 44.36 |
| ATOM | 2452 | CG | GLU | A | 916 | 115.302 | −93.971 | 64.253 | 1.00 | 44.48 |
| ATOM | 2453 | CD | GLU | A | 916 | 116.492 | −94.622 | 63.573 | 1.00 | 44.56 |
| ATOM | 2454 | OE1 | GLU | A | 916 | 117.591 | −94.026 | 63.586 | 1.00 | 44.55 |
| ATOM | 2455 | OE2 | GLU | A | 916 | 116.326 | −95.738 | 63.034 | 1.00 | 44.61 |
| ATOM | 2456 | N | ASP | A | 917 | 112.742 | −92.603 | 61.779 | 1.00 | 45.22 |
| ATOM | 2457 | CA | ASP | A | 917 | 111.623 | −93.339 | 61.204 | 1.00 | 45.71 |
| ATOM | 2458 | C | ASP | A | 917 | 111.718 | −93.383 | 59.681 | 1.00 | 46.10 |
| ATOM | 2459 | O | ASP | A | 917 | 111.424 | −94.407 | 59.064 | 1.00 | 46.11 |
| ATOM | 2460 | CB | ASP | A | 917 | 110.300 | −92.697 | 61.618 | 1.00 | 45.71 |
| ATOM | 2461 | CG | ASP | A | 917 | 109.101 | −93.403 | 61.020 | 1.00 | 45.71 |
| ATOM | 2462 | OD1 | ASP | A | 917 | 108.907 | −94.600 | 61.320 | 1.00 | 45.64 |
| ATOM | 2463 | OD2 | ASP | A | 917 | 108.358 | −92.760 | 60.247 | 1.00 | 45.74 |
| ATOM | 2464 | N | ARG | A | 918 | 112.124 | −92.268 | 59.080 | 1.00 | 46.59 |
| ATOM | 2465 | CA | ARG | A | 918 | 112.259 | −92.188 | 57.629 | 1.00 | 47.08 |
| ATOM | 2466 | C | ARG | A | 918 | 113.424 | −93.037 | 57.130 | 1.00 | 47.31 |
| ATOM | 2467 | O | ARG | A | 918 | 113.389 | −93.553 | 56.011 | 1.00 | 47.38 |
| ATOM | 2468 | CB | ARG | A | 918 | 112.455 | −90.734 | 57.191 | 1.00 | 47.28 |
| ATOM | 2469 | CG | ARG | A | 918 | 111.186 | −89.904 | 57.217 | 1.00 | 47.61 |
| ATOM | 2470 | CD | ARG | A | 918 | 111.465 | −88.451 | 56.854 | 1.00 | 47.87 |
| ATOM | 2471 | NE | ARG | A | 918 | 112.334 | −87.803 | 57.834 | 1.00 | 48.09 |
| ATOM | 2472 | CZ | ARG | A | 918 | 112.699 | −86.527 | 57.781 | 1.00 | 48.15 |
| ATOM | 2473 | NH1 | ARG | A | 918 | 113.492 | −86.023 | 58.717 | 1.00 | 48.19 |
| ATOM | 2474 | NH2 | ARG | A | 918 | 112.273 | −85.754 | 56.790 | 1.00 | 48.24 |
| ATOM | 2475 | N | ARG | A | 919 | 114.456 | −93.177 | 57.954 | 1.00 | 47.55 |
| ATOM | 2476 | CA | ARG | A | 919 | 115.612 | −93.982 | 57.578 | 1.00 | 47.80 |
| ATOM | 2477 | C | ARG | A | 919 | 115.173 | −95.378 | 57.155 | 1.00 | 47.84 |
| ATOM | 2478 | O | ARG | A | 919 | 115.439 | −95.752 | 55.993 | 1.00 | 47.91 |
| ATOM | 2479 | CB | ARG | A | 919 | 116.590 | −94.096 | 58.747 | 1.00 | 47.98 |
| ATOM | 2480 | CG | ARG | A | 919 | 117.532 | −92.919 | 58.884 | 1.00 | 48.20 |
| ATOM | 2481 | CD | ARG | A | 919 | 118.492 | −93.142 | 60.034 | 1.00 | 48.44 |
| ATOM | 2482 | NE | ARG | A | 919 | 119.059 | −94.490 | 60.023 | 1.00 | 48.59 |
| ATOM | 2483 | CZ | ARG | A | 919 | 119.984 | −94.915 | 60.878 | 1.00 | 48.65 |
| ATOM | 2484 | NH1 | ARG | A | 919 | 120.447 | −94.094 | 61.810 | 1.00 | 48.66 |
| ATOM | 2485 | NH2 | ARG | A | 919 | 120.441 | −96.158 | 60.804 | 1.00 | 48.62 |
| ATOM | 2486 | OXT | ARG | A | 919 | 114.564 | −96.077 | 57.993 | 1.00 | 47.88 |
| ATOM | 2487 | N1 | LIG | B | 1 | 87.953 | −75.024 | 60.820 | 1.00 | 20.15 |
| ATOM | 2488 | C2 | LIG | B | 1 | 87.885 | −74.029 | 61.721 | 1.00 | 20.25 |
| ATOM | 2489 | N3 | LIG | B | 1 | 88.796 | −72.973 | 61.568 | 1.00 | 20.17 |
| ATOM | 2490 | C4 | LIG | B | 1 | 88.772 | −71.935 | 62.512 | 1.00 | 20.14 |
| ATOM | 2491 | C5 | LIG | B | 1 | 87.819 | −71.881 | 63.655 | 1.00 | 20.01 |
| ATOM | 2492 | C6 | LIG | B | 1 | 86.950 | −73.036 | 63.730 | 1.00 | 20.08 |
| ATOM | 2493 | N7 | LIG | B | 1 | 86.947 | −74.069 | 62.784 | 1.00 | 20.07 |
| ATOM | 2494 | C8 | LIG | B | 1 | 87.735 | −70.809 | 64.743 | 1.00 | 19.91 |
| ATOM | 2495 | C9 | LIG | B | 1 | 89.001 | −70.565 | 65.559 | 1.00 | 19.70 |
| ATOM | 2496 | C10 | LIG | B | 1 | 89.665 | −71.664 | 66.309 | 1.00 | 19.56 |
| ATOM | 2497 | C11 | LIG | B | 1 | 90.897 | −71.465 | 67.076 | 1.00 | 19.50 |
| ATOM | 2498 | C12 | LIG | B | 1 | 91.477 | −70.107 | 67.094 | 1.00 | 19.54 |
| ATOM | 2499 | C13 | LIG | B | 1 | 90.816 | −68.987 | 66.332 | 1.00 | 19.52 |
| ATOM | 2500 | C14 | LIG | B | 1 | 89.580 | −69.220 | 65.569 | 1.00 | 19.75 |
| ATOM | 2501 | O15 | LIG | B | 1 | 92.664 | −70.048 | 67.811 | 1.00 | 19.38 |
| ATOM | 2502 | C16 | LIG | B | 1 | 93.340 | −68.781 | 67.917 | 1.00 | 19.33 |
| ATOM | 2503 | C17 | LIG | B | 1 | 94.338 | −68.904 | 68.982 | 1.00 | 19.35 |
| ATOM | 2504 | C18 | LIG | B | 1 | 95.768 | −69.129 | 68.648 | 1.00 | 19.38 |
| ATOM | 2505 | C19 | LIG | B | 1 | 96.766 | −69.164 | 69.733 | 1.00 | 19.46 |
| ATOM | 2506 | C20 | LIG | B | 1 | 96.337 | −69.000 | 71.157 | 1.00 | 19.47 |
| ATOM | 2507 | C21 | LIG | B | 1 | 94.883 | −68.822 | 71.455 | 1.00 | 19.39 |

TABLE 2-continued cFMS - Formula (Ia) compound co-crystal
resolution: 500.0-1.8 Å
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2508 | C22 | LIG | B | 1 | 93.893 | −68.798 | 70.383 | 1.00 | 19.38 |
|------|------|-----|-----|---|---|--------|---------|--------|------|-------|
| ATOM | 2509 | O23 | LIG | B | 1 | 97.383 | −69.025 | 72.077 | 1.00 | 19.59 |
| ATOM | 2510 | C24 | LIG | B | 1 | 97.118 | −68.685 | 73.457 | 1.00 | 19.63 |
| ATOM | 2511 | O25 | LIG | B | 1 | 91.607 | −72.492 | 67.759 | 1.00 | 19.43 |
| ATOM | 2512 | C26 | LIG | B | 1 | 91.023 | −73.771 | 68.011 | 1.00 | 19.52 |
| ATOM | 2513 | N27 | LIG | B | 1 | 89.728 | −70.994 | 62.376 | 1.00 | 20.22 |
| ATOM | 2514 | O | HOH | C | 1 | 78.820 | −73.654 | 77.373 | 1.00 | 19.24 |
| ATOM | 2515 | O | HOH | C | 2 | 91.210 | −82.862 | 73.817 | 1.00 | 18.08 |
| ATOM | 2516 | O | HOH | C | 3 | 97.094 | −84.418 | 84.144 | 1.00 | 17.67 |
| ATOM | 2517 | O | HOH | C | 4 | 99.687 | −89.028 | 83.021 | 1.00 | 17.29 |
| ATOM | 2518 | O | HOH | C | 5 | 88.703 | −83.415 | 74.883 | 1.00 | 17.82 |
| ATOM | 2519 | O | HOH | C | 6 | 93.701 | −78.401 | 78.558 | 1.00 | 18.89 |
| ATOM | 2520 | O | HOH | C | 7 | 93.430 | −71.398 | 88.869 | 1.00 | 25.82 |
| ATOM | 2521 | O | HOH | C | 8 | 89.183 | −82.752 | 82.892 | 1.00 | 17.91 |
| ATOM | 2522 | O | HOH | C | 9 | 88.190 | −83.098 | 62.548 | 1.00 | 22.13 |
| ATOM | 2523 | O | HOH | C | 10 | 101.769 | −87.363 | 88.435 | 1.00 | 24.55 |
| ATOM | 2524 | O | HOH | C | 11 | 92.925 | −71.283 | 78.765 | 1.00 | 20.63 |
| ATOM | 2525 | O | HOH | C | 12 | 97.542 | −75.898 | 79.029 | 1.00 | 19.25 |
| ATOM | 2526 | O | HOH | C | 13 | 89.564 | −93.244 | 69.962 | 1.00 | 19.39 |
| ATOM | 2527 | O | HOH | C | 14 | 95.267 | −77.146 | 80.900 | 1.00 | 19.72 |
| ATOM | 2528 | O | HOH | C | 16 | 115.127 | −59.707 | 82.667 | 1.00 | 26.66 |
| ATOM | 2529 | O | HOH | C | 17 | 88.724 | −85.874 | 75.790 | 1.00 | 20.06 |
| ATOM | 2530 | O | HOH | C | 18 | 111.839 | −89.182 | 79.925 | 1.00 | 24.03 |
| ATOM | 2531 | O | HOH | C | 19 | 74.485 | −77.517 | 81.905 | 1.00 | 19.81 |
| ATOM | 2532 | O | HOH | C | 20 | 75.526 | −77.434 | 74.151 | 1.00 | 22.32 |
| ATOM | 2533 | O | HOH | C | 21 | 104.311 | −87.465 | 87.677 | 1.00 | 20.04 |
| ATOM | 2534 | O | HOH | C | 22 | 106.400 | −88.766 | 88.822 | 1.00 | 28.97 |
| ATOM | 2535 | O | HOH | C | 23 | 111.159 | −96.623 | 71.329 | 1.00 | 29.08 |
| ATOM | 2536 | O | HOH | C | 24 | 109.645 | −59.975 | 81.044 | 1.00 | 22.04 |
| ATOM | 2537 | O | HOH | C | 25 | 92.057 | −73.069 | 81.085 | 1.00 | 19.19 |
| ATOM | 2538 | O | HOH | C | 26 | 93.976 | −74.326 | 83.136 | 1.00 | 25.74 |
| ATOM | 2539 | O | HOH | C | 27 | 109.275 | −73.911 | 76.137 | 1.00 | 21.83 |
| ATOM | 2540 | O | HOH | C | 28 | 89.927 | −67.909 | 69.279 | 1.00 | 22.86 |
| ATOM | 2541 | O | HOH | C | 29 | 90.752 | −68.407 | 77.433 | 1.00 | 21.17 |
| ATOM | 2542 | O | HOH | C | 30 | 92.171 | −74.817 | 55.187 | 1.00 | 25.32 |
| ATOM | 2543 | O | HOH | C | 31 | 88.720 | −74.104 | 75.095 | 1.00 | 30.17 |
| ATOM | 2544 | O | HOH | C | 32 | 98.195 | −76.828 | 84.252 | 1.00 | 31.02 |
| ATOM | 2545 | O | HOH | C | 33 | 107.829 | −91.419 | 85.161 | 1.00 | 31.57 |
| ATOM | 2546 | O | HOH | C | 34 | 81.832 | −77.650 | 82.629 | 1.00 | 29.52 |
| ATOM | 2547 | O | HOH | C | 35 | 99.032 | −74.222 | 81.685 | 1.00 | 29.79 |
| ATOM | 2548 | O | HOH | C | 36 | 76.518 | −76.360 | 83.555 | 1.00 | 31.49 |
| ATOM | 2549 | O | HOH | C | 37 | 115.252 | −74.894 | 75.298 | 1.00 | 24.36 |
| ATOM | 2550 | O | HOH | C | 38 | 105.897 | −69.850 | 61.080 | 1.00 | 34.95 |
| ATOM | 2551 | O | HOH | C | 39 | 71.283 | −64.605 | 71.637 | 1.00 | 31.76 |
| ATOM | 2552 | O | HOH | C | 40 | 110.322 | −71.301 | 72.626 | 1.00 | 24.81 |
| ATOM | 2553 | O | HOH | C | 41 | 104.302 | −79.769 | 90.650 | 1.00 | 25.20 |
| ATOM | 2554 | O | HOH | C | 42 | 80.196 | −59.912 | 68.541 | 1.00 | 25.49 |
| ATOM | 2555 | O | HOH | C | 43 | 87.943 | −66.500 | 64.398 | 1.00 | 27.99 |
| ATOM | 2556 | O | HOH | C | 44 | 82.147 | −77.364 | 65.927 | 1.00 | 25.90 |
| ATOM | 2557 | O | HOH | C | 45 | 78.891 | −83.123 | 77.099 | 1.00 | 28.03 |
| ATOM | 2558 | O | HOH | C | 46 | 95.767 | −83.158 | 85.978 | 1.00 | 23.90 |
| ATOM | 2559 | O | HOH | C | 47 | 104.844 | −74.180 | 86.734 | 1.00 | 32.08 |
| ATOM | 2560 | O | HOH | C | 48 | 99.733 | −70.306 | 58.451 | 1.00 | 23.83 |
| ATOM | 2561 | O | HOH | C | 49 | 104.245 | −77.356 | 59.877 | 1.00 | 27.25 |
| ATOM | 2562 | O | HOH | C | 50 | 95.813 | −65.894 | 66.634 | 1.00 | 24.21 |
| ATOM | 2563 | O | HOH | C | 51 | 111.093 | −66.179 | 78.386 | 1.00 | 29.25 |
| ATOM | 2564 | O | HOH | C | 52 | 76.034 | −61.107 | 76.239 | 1.00 | 44.40 |
| ATOM | 2565 | O | HOH | C | 53 | 105.325 | −60.952 | 74.570 | 1.00 | 24.86 |
| ATOM | 2566 | O | HOH | C | 54 | 92.430 | −70.004 | 90.824 | 1.00 | 42.70 |
| ATOM | 2567 | O | HOH | C | 55 | 90.502 | −71.063 | 77.293 | 1.00 | 27.98 |
| ATOM | 2568 | O | HOH | C | 56 | 103.073 | −98.089 | 80.718 | 1.00 | 19.56 |
| ATOM | 2569 | O | HOH | C | 57 | 110.972 | −73.593 | 74.021 | 1.00 | 24.24 |
| ATOM | 2570 | O | HOH | C | 58 | 90.900 | −87.316 | 74.421 | 1.00 | 17.46 |
| ATOM | 2571 | O | HOH | C | 59 | 105.194 | −93.530 | 83.669 | 1.00 | 27.43 |
| ATOM | 2572 | O | HOH | C | 60 | 80.659 | −83.692 | 78.565 | 1.00 | 29.19 |
| ATOM | 2573 | O | HOH | C | 61 | 87.066 | −79.132 | 69.692 | 1.00 | 20.92 |
| ATOM | 2574 | O | HOH | C | 62 | 78.433 | −78.956 | 72.588 | 1.00 | 37.79 |
| ATOM | 2575 | O | HOH | C | 63 | 84.753 | −88.446 | 65.375 | 1.00 | 38.57 |
| ATOM | 2576 | O | HOH | C | 64 | 106.231 | −81.734 | 60.864 | 1.00 | 36.73 |
| ATOM | 2577 | O | HOH | C | 65 | 75.494 | −69.442 | 59.557 | 1.00 | 38.26 |
| ATOM | 2578 | O | HOH | C | 66 | 95.374 | −72.520 | 56.932 | 1.00 | 32.84 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2579 | O | HOH | C | 67  | 98.574  | −92.243 | 95.345 | 1.00 | 40.41 |
|------|------|---|-----|---|-----|---------|---------|--------|------|-------|
| ATOM | 2580 | O | HOH | C | 68  | 108.402 | −86.651 | 89.048 | 1.00 | 37.14 |
| ATOM | 2581 | O | HOH | C | 69  | 94.944  | −81.070 | 51.812 | 1.00 | 33.47 |
| ATOM | 2582 | O | HOH | C | 70  | 99.145  | −60.402 | 81.632 | 1.00 | 45.72 |
| ATOM | 2583 | O | HOH | C | 71  | 98.020  | −60.834 | 79.213 | 1.00 | 51.68 |
| ATOM | 2584 | O | HOH | C | 72  | 111.845 | −71.353 | 70.232 | 1.00 | 48.86 |
| ATOM | 2585 | O | HOH | C | 73  | 109.611 | −76.073 | 80.276 | 1.00 | 41.97 |
| ATOM | 2586 | O | HOH | C | 74  | 110.221 | −84.279 | 89.188 | 1.00 | 33.27 |
| ATOM | 2587 | O | HOH | C | 75  | 107.372 | −99.771 | 73.649 | 1.00 | 27.08 |
| ATOM | 2588 | O | HOH | C | 77  | 111.176 | −95.743 | 68.722 | 1.00 | 35.72 |
| ATOM | 2589 | O | HOH | C | 78  | 110.354 | −93.132 | 68.043 | 1.00 | 31.35 |
| ATOM | 2590 | O | HOH | C | 79  | 100.225 | −99.680 | 77.985 | 1.00 | 22.42 |
| ATOM | 2591 | O | HOH | C | 80  | 103.380 | −71.794 | 76.658 | 1.00 | 30.43 |
| ATOM | 2592 | O | HOH | C | 81  | 96.886  | −68.134 | 88.963 | 1.00 | 44.12 |
| ATOM | 2593 | O | HOH | C | 82  | 108.757 | −66.515 | 83.534 | 1.00 | 44.85 |
| ATOM | 2594 | O | HOH | C | 83  | 108.511 | −57.676 | 81.951 | 1.00 | 31.79 |
| ATOM | 2595 | O | HOH | C | 84  | 109.663 | −54.835 | 82.871 | 1.00 | 36.09 |
| ATOM | 2596 | O | HOH | C | 85  | 118.008 | −64.497 | 76.818 | 1.00 | 45.87 |
| ATOM | 2597 | O | HOH | C | 86  | 113.000 | −68.153 | 79.745 | 1.00 | 44.28 |
| ATOM | 2598 | O | HOH | C | 87  | 112.086 | −61.307 | 73.799 | 1.00 | 28.84 |
| ATOM | 2599 | O | HOH | C | 88  | 109.480 | −62.526 | 72.724 | 1.00 | 35.79 |
| ATOM | 2600 | O | HOH | C | 89  | 113.686 | −62.398 | 80.305 | 1.00 | 33.64 |
| ATOM | 2601 | O | HOH | C | 90  | 107.287 | −57.712 | 74.604 | 1.00 | 35.50 |
| ATOM | 2602 | O | HOH | C | 91  | 105.146 | −58.297 | 75.578 | 1.00 | 35.93 |
| ATOM | 2603 | O | HOH | C | 92  | 101.656 | −52.573 | 78.355 | 1.00 | 40.41 |
| ATOM | 2604 | O | HOH | C | 93  | 90.794  | −50.511 | 72.030 | 1.00 | 47.23 |
| ATOM | 2605 | O | HOH | C | 94  | 91.548  | −49.206 | 69.473 | 1.00 | 51.71 |
| ATOM | 2606 | O | HOH | C | 95  | 95.177  | −48.246 | 66.523 | 1.00 | 36.93 |
| ATOM | 2607 | O | HOH | C | 96  | 96.500  | −54.314 | 72.533 | 1.00 | 33.08 |
| ATOM | 2608 | O | HOH | C | 97  | 95.131  | −55.501 | 68.416 | 1.00 | 27.23 |
| ATOM | 2609 | O | HOH | C | 98  | 96.469  | −56.170 | 70.574 | 1.00 | 40.76 |
| ATOM | 2610 | O | HOH | C | 99  | 88.083  | −50.728 | 67.931 | 1.00 | 34.77 |
| ATOM | 2611 | O | HOH | C | 100 | 93.405  | −52.075 | 58.481 | 1.00 | 46.47 |
| ATOM | 2612 | O | HOH | C | 101 | 94.383  | −56.688 | 58.741 | 1.00 | 50.76 |
| ATOM | 2613 | O | HOH | C | 102 | 79.900  | −72.040 | 54.133 | 1.00 | 30.00 |
| ATOM | 2614 | O | HOH | C | 103 | 81.364  | −76.289 | 68.114 | 1.00 | 27.22 |
| ATOM | 2615 | O | HOH | C | 104 | 75.303  | −70.538 | 75.043 | 1.00 | 35.54 |
| ATOM | 2616 | O | HOH | C | 105 | 88.865  | −66.057 | 67.079 | 1.00 | 27.43 |
| ATOM | 2617 | O | HOH | C | 106 | 77.619  | −60.699 | 67.849 | 1.00 | 21.97 |
| ATOM | 2618 | O | HOH | C | 107 | 80.479  | −57.883 | 70.502 | 1.00 | 33.14 |
| ATOM | 2619 | O | HOH | C | 108 | 77.184  | −60.931 | 65.120 | 1.00 | 41.97 |
| ATOM | 2620 | O | HOH | C | 109 | 83.263  | −57.212 | 71.749 | 1.00 | 31.99 |
| ATOM | 2621 | O | HOH | C | 110 | 100.861 | −56.339 | 70.926 | 1.00 | 38.51 |
| ATOM | 2622 | O | HOH | C | 111 | 98.698  | −55.770 | 69.139 | 1.00 | 36.72 |
| ATOM | 2623 | O | HOH | C | 112 | 97.835  | −64.788 | 64.719 | 1.00 | 39.74 |
| ATOM | 2624 | O | HOH | C | 113 | 88.859  | −64.544 | 69.263 | 1.00 | 27.71 |
| ATOM | 2625 | O | HOH | C | 114 | 105.882 | −94.301 | 59.848 | 1.00 | 28.24 |
| ATOM | 2626 | O | HOH | C | 115 | 116.953 | −82.093 | 66.009 | 1.00 | 36.17 |
| ATOM | 2627 | O | HOH | C | 116 | 109.710 | −80.655 | 65.733 | 1.00 | 46.19 |
| ATOM | 2628 | O | HOH | C | 117 | 113.837 | −72.757 | 74.801 | 1.00 | 32.06 |
| ATOM | 2629 | O | HOH | C | 118 | 115.166 | −77.957 | 79.871 | 1.00 | 37.33 |
| ATOM | 2630 | O | HOH | C | 119 | 114.428 | −75.677 | 81.136 | 1.00 | 45.18 |
| ATOM | 2631 | O | HOH | C | 120 | 111.060 | −77.224 | 89.885 | 1.00 | 33.54 |
| ATOM | 2632 | O | HOH | C | 121 | 109.976 | −74.871 | 90.692 | 1.00 | 39.60 |
| ATOM | 2633 | O | HOH | C | 122 | 105.708 | −77.624 | 92.175 | 1.00 | 31.05 |
| ATOM | 2634 | O | HOH | C | 123 | 105.644 | −74.721 | 91.291 | 1.00 | 40.28 |
| ATOM | 2635 | O | HOH | C | 124 | 102.815 | −80.479 | 92.856 | 1.00 | 40.66 |
| ATOM | 2636 | O | HOH | C | 125 | 88.697  | −84.103 | 58.822 | 1.00 | 30.65 |
| ATOM | 2637 | O | HOH | C | 126 | 90.415  | −85.397 | 56.884 | 1.00 | 36.44 |
| ATOM | 2638 | O | HOH | C | 127 | 96.947  | −84.499 | 53.567 | 1.00 | 34.18 |
| ATOM | 2639 | O | HOH | C | 128 | 91.899  | −68.874 | 55.574 | 1.00 | 44.79 |
| ATOM | 2640 | O | HOH | C | 129 | 87.103  | −93.604 | 68.048 | 1.00 | 32.28 |
| ATOM | 2641 | O | HOH | C | 130 | 103.631 | −96.880 | 61.928 | 1.00 | 32.04 |
| ATOM | 2642 | O | HOH | C | 131 | 100.840 | −96.600 | 64.145 | 1.00 | 44.14 |
| ATOM | 2643 | O | HOH | C | 132 | 100.694 | −86.152 | 59.735 | 1.00 | 45.40 |
| ATOM | 2644 | O | HOH | C | 133 | 100.472 | −83.398 | 59.470 | 1.00 | 40.35 |
| ATOM | 2645 | O | HOH | C | 134 | 98.032  | −87.291 | 58.618 | 1.00 | 40.61 |
| ATOM | 2646 | O | HOH | C | 135 | 108.245 | −68.079 | 78.043 | 1.00 | 35.34 |
| ATOM | 2647 | O | HOH | C | 136 | 86.462  | −82.768 | 73.322 | 1.00 | 24.71 |
| ATOM | 2648 | O | HOH | C | 137 | 86.128  | −81.698 | 75.616 | 1.00 | 29.61 |
| ATOM | 2649 | O | HOH | C | 138 | 92.379  | −95.831 | 70.646 | 1.00 | 38.11 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| ATOM | 2650 | O | HOH | C | 139 | 87.910 | −92.262 | 72.101 | 1.00 | 31.36 |
|---|---|---|---|---|---|---|---|---|---|---|
| ATOM | 2651 | O | HOH | C | 140 | 88.170 | −87.156 | 78.234 | 1.00 | 23.99 |
| ATOM | 2652 | O | HOH | C | 141 | 88.777 | −93.633 | 76.636 | 1.00 | 26.56 |
| ATOM | 2653 | O | HOH | C | 142 | 94.995 | −94.007 | 83.614 | 1.00 | 21.45 |
| ATOM | 2654 | O | HOH | C | 143 | 92.734 | −95.597 | 83.791 | 1.00 | 26.22 |
| ATOM | 2655 | O | HOH | C | 144 | 88.907 | −91.128 | 91.122 | 1.00 | 33.19 |
| ATOM | 2656 | O | HOH | C | 145 | 87.053 | −93.455 | 89.140 | 1.00 | 35.14 |
| ATOM | 2657 | O | HOH | C | 146 | 79.694 | −78.643 | 85.453 | 1.00 | 41.37 |
| ATOM | 2658 | O | HOH | C | 147 | 79.282 | −79.540 | 82.363 | 1.00 | 43.66 |
| ATOM | 2659 | O | HOH | C | 148 | 86.267 | −70.614 | 83.215 | 1.00 | 43.27 |
| ATOM | 2660 | O | HOH | C | 149 | 82.302 | −79.158 | 87.974 | 1.00 | 36.44 |
| ATOM | 2661 | O | HOH | C | 150 | 87.429 | −70.422 | 80.810 | 1.00 | 41.76 |
| ATOM | 2662 | O | HOH | C | 151 | 89.321 | −73.406 | 80.701 | 1.00 | 28.86 |
| ATOM | 2663 | O | HOH | C | 152 | 95.403 | −62.183 | 79.696 | 1.00 | 42.83 |
| ATOM | 2664 | O | HOH | C | 153 | 111.325 | −64.602 | 85.894 | 1.00 | 44.96 |
| ATOM | 2665 | O | HOH | C | 154 | 107.804 | −61.144 | 74.071 | 1.00 | 35.04 |
| ATOM | 2666 | O | HOH | C | 155 | 99.389 | −54.262 | 72.384 | 1.00 | 47.89 |
| ATOM | 2667 | O | HOH | C | 156 | 97.587 | −51.070 | 70.147 | 1.00 | 48.44 |
| ATOM | 2668 | O | HOH | C | 157 | 98.876 | −55.986 | 66.495 | 1.00 | 34.72 |
| ATOM | 2669 | O | HOH | C | 158 | 93.523 | −56.478 | 56.114 | 1.00 | 48.54 |
| ATOM | 2670 | O | HOH | C | 159 | 91.467 | −54.818 | 54.293 | 1.00 | 46.12 |
| ATOM | 2671 | O | HOH | C | 160 | 83.992 | −73.951 | 65.639 | 1.00 | 40.15 |
| ATOM | 2672 | O | HOH | C | 161 | 80.079 | −76.994 | 70.717 | 1.00 | 30.00 |
| ATOM | 2673 | O | HOH | C | 162 | 83.191 | −74.225 | 68.739 | 1.00 | 46.68 |
| ATOM | 2674 | O | HOH | C | 163 | 82.497 | −76.889 | 72.311 | 1.00 | 25.98 |
| ATOM | 2675 | O | HOH | C | 164 | 83.446 | −78.707 | 74.033 | 1.00 | 35.86 |
| ATOM | 2676 | O | HOH | C | 165 | 80.056 | −79.909 | 74.373 | 1.00 | 39.56 |
| ATOM | 2677 | O | HOH | C | 166 | 86.743 | −72.343 | 76.517 | 1.00 | 36.47 |
| ATOM | 2678 | O | HOH | C | 167 | 80.339 | −82.333 | 75.077 | 1.00 | 41.28 |
| ATOM | 2679 | O | HOH | C | 168 | 87.010 | −84.787 | 83.172 | 1.00 | 44.38 |
| ATOM | 2680 | O | HOH | C | 169 | 88.212 | −88.605 | 80.498 | 1.00 | 47.00 |
| ATOM | 2681 | O | HOH | C | 170 | 100.640 | −68.818 | 88.278 | 1.00 | 34.41 |
| ATOM | 2682 | O | HOH | C | 171 | 105.919 | −73.455 | 88.943 | 1.00 | 28.12 |
| ATOM | 2683 | O | HOH | C | 172 | 106.350 | −70.649 | 89.289 | 1.00 | 34.78 |
| ATOM | 2684 | O | HOH | C | 173 | 107.174 | −68.153 | 84.755 | 1.00 | 29.49 |
| ATOM | 2685 | O | HOH | C | 174 | 108.020 | −69.198 | 86.885 | 1.00 | 45.65 |
| ATOM | 2686 | O | HOH | C | 175 | 107.090 | −70.063 | 82.584 | 1.00 | 35.05 |
| ATOM | 2687 | O | HOH | C | 176 | 89.839 | −95.990 | 70.513 | 1.00 | 31.66 |
| ATOM | 2688 | O | HOH | C | 177 | 86.245 | −96.029 | 68.213 | 1.00 | 39.26 |
| ATOM | 2689 | O | HOH | C | 178 | 85.197 | −91.572 | 71.558 | 1.00 | 45.57 |
| ATOM | 2690 | O | HOH | C | 179 | 87.336 | −89.700 | 96.243 | 1.00 | 45.40 |
| ATOM | 2691 | O | HOH | C | 180 | 102.077 | −94.453 | 87.471 | 1.00 | 35.13 |
| ATOM | 2692 | O | HOH | C | 181 | 100.020 | −96.719 | 84.747 | 1.00 | 47.89 |
| ATOM | 2693 | O | HOH | C | 182 | 105.473 | −92.228 | 87.820 | 1.00 | 51.24 |
| ATOM | 2694 | O | HOH | C | 183 | 102.331 | −100.426 | 79.359 | 1.00 | 33.37 |
| ATOM | 2695 | O | HOH | C | 184 | 104.620 | −101.066 | 77.764 | 1.00 | 37.03 |
| ATOM | 2696 | O | HOH | C | 185 | 105.284 | −98.924 | 68.539 | 1.00 | 43.33 |
| ATOM | 2697 | O | HOH | C | 186 | 107.945 | −99.447 | 69.059 | 1.00 | 36.89 |
| ATOM | 2698 | O | HOH | C | 187 | 110.153 | −97.990 | 67.782 | 1.00 | 40.97 |
| ATOM | 2699 | O | HOH | C | 188 | 112.537 | −94.623 | 75.999 | 1.00 | 42.32 |
| ATOM | 2700 | O | HOH | C | 189 | 109.223 | −94.650 | 78.613 | 1.00 | 39.46 |
| ATOM | 2701 | O | HOH | C | 190 | 108.658 | −88.240 | 84.873 | 1.00 | 31.55 |
| ATOM | 2702 | O | HOH | C | 191 | 112.425 | −85.594 | 87.586 | 1.00 | 54.08 |
| ATOM | 2703 | O | HOH | C | 192 | 117.159 | −79.661 | 89.698 | 1.00 | 42.46 |
| ATOM | 2704 | O | HOH | C | 193 | 116.589 | −77.662 | 71.428 | 1.00 | 40.35 |
| ATOM | 2705 | O | HOH | C | 194 | 116.739 | −75.758 | 73.205 | 1.00 | 37.78 |
| ATOM | 2706 | O | HOH | C | 195 | 117.711 | −89.479 | 64.063 | 1.00 | 41.29 |
| ATOM | 2707 | O | HOH | C | 196 | 111.481 | −93.079 | 65.463 | 1.00 | 40.51 |
| ATOM | 2708 | O | HOH | C | 197 | 114.236 | −95.689 | 67.751 | 1.00 | 41.02 |
| ATOM | 2709 | O | HOH | C | 198 | 108.489 | −73.770 | 85.657 | 1.00 | 48.76 |
| ATOM | 2710 | O | HOH | C | 199 | 115.323 | −96.534 | 70.607 | 1.00 | 51.48 |
| ATOM | 2711 | O | HOH | C | 200 | 107.669 | −90.114 | 91.655 | 1.00 | 49.65 |
| ATOM | 2712 | O | HOH | C | 201 | 86.244 | −95.303 | 80.834 | 1.00 | 48.45 |
| ATOM | 2713 | O | HOH | C | 202 | 87.199 | −94.002 | 74.386 | 1.00 | 50.03 |
| ATOM | 2714 | O | HOH | C | 203 | 94.291 | −64.806 | 81.761 | 1.00 | 40.32 |
| ATOM | 2715 | O | HOH | C | 204 | 93.056 | −60.983 | 79.186 | 1.00 | 42.78 |
| ATOM | 2716 | O | HOH | C | 205 | 111.749 | −59.184 | 72.239 | 1.00 | 43.92 |
| ATOM | 2717 | O | HOH | C | 206 | 100.244 | −53.665 | 69.274 | 1.00 | 50.16 |
| ATOM | 2718 | O | HOH | C | 207 | 88.978 | −46.187 | 67.628 | 1.00 | 43.97 |
| ATOM | 2719 | O | HOH | C | 208 | 89.165 | −51.930 | 56.991 | 1.00 | 46.41 |
| ATOM | 2720 | O | HOH | C | 209 | 76.923 | −64.275 | 74.150 | 1.00 | 44.26 |

TABLE 2-continued cFMS - Formula (Ia) compound co-crystal
resolution: 500.0-1.8 A
sg = R3 a = 80.404 b = 80.404 c = 144.968 alpha = 90 beta = 90 gamma = 120
final_r = 0.2070 free_r = 0.2467
rmsd bonds = 0.009739 rmsd angles = 1.33150
data completeness 96.6%
data collect at IMCA, −180 C, processed with HKL2000, solved with CNX

| | | | | | | | | | |
|---|---|---|---|---|---|---|---|---|---|
| ATOM | 2721 | O | HOH | C | 210 | 83.188 | −54.427 | 72.476 | 1.00 | 40.37 |
| ATOM | 2722 | O | HOH | C | 211 | 80.860 | −53.610 | 71.161 | 1.00 | 39.81 |
| ATOM | 2723 | O | HOH | C | 212 | 105.365 | −63.541 | 63.504 | 1.00 | 40.80 |
| ATOM | 2724 | O | HOH | C | 213 | 105.984 | −62.164 | 65.900 | 1.00 | 41.33 |
| ATOM | 2725 | O | HOH | C | 214 | 108.031 | −71.867 | 60.656 | 1.00 | 45.06 |
| ATOM | 2726 | O | HOH | C | 215 | 104.730 | −68.665 | 58.732 | 1.00 | 48.93 |
| ATOM | 2727 | O | HOH | C | 216 | 118.493 | −89.935 | 67.772 | 1.00 | 45.65 |
| ATOM | 2728 | O | HOH | C | 217 | 108.073 | −84.824 | 62.444 | 1.00 | 41.90 |
| ATOM | 2729 | O | HOH | C | 218 | 115.472 | −82.184 | 74.611 | 1.00 | 65.71 |
| ATOM | 2730 | O | HOH | C | 219 | 107.548 | −80.478 | 93.056 | 1.00 | 48.08 |
| ATOM | 2731 | O | HOH | C | 220 | 106.570 | −82.666 | 93.866 | 1.00 | 43.56 |
| ATOM | 2732 | O | HOH | C | 221 | 107.641 | −90.970 | 87.806 | 1.00 | 43.09 |
| ATOM | 2733 | O | HOH | C | 222 | 113.394 | −97.448 | 72.465 | 1.00 | 32.61 |
| ATOM | 2734 | O | HOH | C | 223 | 106.081 | −92.234 | 91.740 | 1.00 | 40.74 |
| ATOM | 2735 | O | HOH | C | 224 | 103.608 | −83.622 | 94.802 | 1.00 | 43.45 |
| ATOM | 2736 | O | HOH | C | 225 | 85.542 | −77.303 | 58.419 | 1.00 | 38.63 |
| ATOM | 2737 | O | HOH | C | 226 | 85.801 | −79.398 | 64.985 | 1.00 | 55.72 |
| ATOM | 2738 | O | HOH | C | 227 | 86.686 | −82.171 | 69.803 | 1.00 | 42.56 |
| ATOM | 2739 | O | HOH | C | 228 | 83.126 | −80.686 | 71.440 | 1.00 | 45.41 |
| ATOM | 2740 | O | HOH | C | 229 | 85.551 | −85.887 | 69.448 | 1.00 | 44.24 |
| ATOM | 2741 | O | HOH | C | 230 | 84.479 | −84.563 | 73.497 | 1.00 | 36.75 |
| ATOM | 2742 | O | HOH | C | 231 | 106.142 | −97.152 | 61.057 | 1.00 | 47.55 |
| ATOM | 2743 | O | HOH | C | 232 | 108.447 | −72.745 | 67.074 | 1.00 | 31.95 |
| ATOM | 2744 | O | HOH | C | 233 | 109.274 | −70.180 | 67.814 | 1.00 | 43.76 |
| ATOM | 2745 | O | HOH | C | 234 | 109.118 | −69.937 | 64.527 | 1.00 | 47.64 |
| ATOM | 2746 | O | HOH | C | 235 | 111.778 | −69.345 | 74.102 | 1.00 | 35.18 |
| ATOM | 2747 | O | HOH | C | 236 | 88.662 | −72.605 | 78.381 | 1.00 | 41.54 |
| ATOM | 2748 | O | HOH | C | 237 | 94.288 | −68.038 | 89.654 | 1.00 | 46.35 |
| ATOM | 2749 | O | HOH | C | 238 | 83.710 | −63.722 | 81.962 | 1.00 | 40.37 |
| ATOM | 2750 | O | HOH | C | 239 | 108.330 | −67.803 | 80.449 | 1.00 | 37.00 |
| ATOM | 2751 | O | HOH | C | 240 | 119.325 | −66.490 | 75.483 | 1.00 | 42.29 |
| ATOM | 2752 | O | HOH | C | 241 | 113.515 | −63.136 | 72.433 | 1.00 | 43.49 |
| ATOM | 2753 | O | HOH | C | 242 | 109.594 | −59.379 | 73.468 | 1.00 | 39.75 |
| ATOM | 2754 | O | HOH | C | 243 | 90.951 | −55.822 | 76.333 | 1.00 | 44.26 |
| ATOM | 2755 | O | HOH | C | 244 | 87.061 | −50.366 | 58.145 | 1.00 | 43.01 |
| ATOM | 2756 | O | HOH | C | 245 | 84.786 | −60.046 | 51.622 | 1.00 | 33.53 |
| ATOM | 2757 | O | HOH | C | 246 | 80.488 | −77.016 | 59.865 | 1.00 | 29.43 |
| ATOM | 2758 | O | HOH | C | 247 | 76.165 | −56.649 | 81.565 | 1.00 | 38.01 |
| ATOM | 2759 | O | HOH | C | 248 | 85.163 | −52.841 | 70.845 | 1.00 | 37.13 |
| ATOM | 2760 | O | HOH | C | 249 | 81.016 | −53.253 | 68.420 | 1.00 | 42.06 |
| ATOM | 2761 | O | HOH | C | 250 | 79.222 | −55.726 | 70.403 | 1.00 | 39.42 |
| ATOM | 2762 | O | HOH | C | 251 | 103.336 | −61.264 | 63.121 | 1.00 | 37.27 |
| ATOM | 2763 | O | HOH | C | 252 | 106.162 | −65.055 | 60.097 | 1.00 | 41.20 |
| ATOM | 2764 | O | HOH | C | 253 | 106.400 | −67.250 | 62.639 | 1.00 | 37.38 |
| ATOM | 2765 | O | HOH | C | 254 | 100.113 | −73.798 | 57.938 | 1.00 | 37.83 |
| ATOM | 2766 | O | HOH | C | 255 | 108.871 | −72.425 | 63.401 | 1.00 | 44.07 |
| ATOM | 2767 | O | HOH | C | 256 | 90.412 | −73.463 | 52.583 | 1.00 | 39.94 |
| ATOM | 2768 | O | HOH | C | 257 | 84.800 | −91.037 | 65.780 | 1.00 | 44.81 |
| ATOM | 2769 | O | HOH | C | 258 | 94.924 | −94.470 | 62.475 | 1.00 | 34.35 |
| ATOM | 2770 | O | HOH | C | 259 | 97.369 | −95.560 | 64.039 | 1.00 | 40.90 |
| ATOM | 2771 | O | HOH | C | 260 | 109.696 | −65.795 | 68.485 | 1.00 | 37.06 |
| ATOM | 2772 | O | HOH | C | 261 | 110.693 | −68.163 | 76.371 | 1.00 | 41.43 |
| ATOM | 2773 | O | HOH | C | 262 | 98.419 | −72.575 | 56.636 | 1.00 | 39.73 |
| ATOM | 2774 | O | HOH | C | 263 | 93.806 | −67.354 | 55.165 | 1.00 | 37.51 |
| ATOM | 2775 | O | HOH | C | 264 | 118.300 | −87.590 | 71.950 | 1.00 | 40.52 |
| ATOM | 2776 | O | HOH | C | 265 | 112.255 | −76.653 | 82.170 | 1.00 | 33.98 |
| ATOM | 2777 | O | HOH | C | 266 | 102.339 | −99.592 | 68.160 | 1.00 | 42.20 |
| ATOM | 2778 | O | HOH | C | 267 | 100.139 | −92.592 | 92.839 | 1.00 | 41.71 |
| ATOM | 2779 | O | HOH | C | 268 | 85.770 | −86.081 | 75.298 | 1.00 | 43.00 |
| ATOM | 2780 | O | HOH | C | 269 | 100.537 | −72.051 | 81.519 | 1.00 | 39.66 |
| ATOM | 2781 | O | HOH | C | 270 | 87.364 | −80.829 | 91.647 | 1.00 | 33.99 |
| ATOM | 2782 | O | HOH | C | 271 | 91.802 | −68.909 | 88.818 | 1.00 | 42.25 |
| ATOM | 2783 | O | HOH | C | 272 | 94.063 | −68.824 | 87.400 | 1.00 | 44.78 |
| ATOM | 2784 | O | HOH | C | 273 | 87.264 | −64.128 | 49.727 | 1.00 | 41.75 |
| ATOM | 2785 | O | HOH | C | 274 | 84.187 | −75.560 | 70.350 | 1.00 | 22.00 |
| ATOM | 2786 | O | HOH | C | 275 | 95.221 | −73.133 | 96.184 | 1.00 | 31.75 |
| ATOM | 2787 | O | HOH | C | 276 | 91.373 | −72.038 | 93.361 | 1.00 | 35.12 |
| END | | | | | | | | | | |

REFERENCES

Alonso, G., Koegl, M., Mazurenko, N. and Courtneidge, S. A. (1995). Sequence requirements for binding of Src family tyrosine kinases to activated growth factor receptors. *J. Biol. Chem.* 270, 9840-9848.

Becker, S. Warren, M., & Haskill, S. (1987). Colony-stimulating factor-induced monocyte survival and differentiation into macrophages in serum-free cultures. J. Immunol. 139, 3703-3709.

Bergamini, A., Perno, C. F., Dini, L., Falasca, L., Milanese, G., Calio, R., & Rocchi, G. (1994). Macrophage colony stimulating factor enhances the susceptibility of macrophages to infection by human immunodeficiency virus and reduced the activity of compounds that inhibit virus binding. Blood 84, 3405-3412.

Bischof, R. J., Zafiropoulos, D., Hamilton, J. A., & Campbell, I. K. 2000. Exacerbation of acute inflammatory arthritis by the colony-stimulating factors CSF-1 and granulocyte macrophage (GM-CSF): evidence of macrophage infiltration and local proliferation. Clin. Exp. Immunol. 119, 361-367.

Bourette, R. P., Myles, G. M., Carlberg, K., Chen, A. R. and Rohrschneider, L. R. (1995). Cell Growth Differ. 6, 631-645.

Boyce, B. F., Hughes, D. E., Wright, K. R., Xing, L., & Dai, A. (1999). Recent advances in bone biology provide insight into the pathogenesis of bone diseases. Laboratory Investigation 79, 83-94.

Campbell, I. K., Rich, M. J., Bischof, R. J. & Hamilton, J. A. (2000). The colony stimulating factors and collagen-induced arthritis: exacerbation of disease by M-CSF and G-CSF and requirement for endogenous M-CSF. J. Leukocyte Biol. 68, 144-150.

Carlberg, K., Tapley, P., Haystead, C. & Rohrschneider, L. (1991). The role of kinase activity and the kinase insert region in ligand-induced internalization and degradation of the c-fms protein. *Eur. Mol. Biol. Org. J.* 10, 877-831.

Cenci, S., Weitzmann, M. N., Gentile, M. A., Aisa, M. C. & Pacifici, R. (2000). M-CSF neutralization and Egr-1 Prevent ovariectomy-induced bone loss. J. Clin. Invest. 105, 1279-1287.

Coussens, L., Van Beveren, C., Smith, D., Chen, E., Mitchell, R. L., Isacke, C. M., Verma, I. M., & Ullrich, A. (1986). Structural alteration of viral homologue of receptor proto-oncogene fms at the carboxyl terminus. Nature 320, 277-280.

Cox, S., Radzio-Andzelm, E. & Taylor, S. S. (1994). Domain movements in protein kinases. *Curr. Opin. Struct. Biol.* 4, 893-901.

Elliott, M., Vadas, M., Eglinton, J., Park, L., To, L. Clel;nad, L, Clark, S. & Lopez, A. (1989). Recombinant human interleukin-3 and granulocyte-macrophage colony-stimulating factor show common biological effects and binding characteristics on human monocytes. Blood 74, 2349-2359.

Gallo, P., DeRossi, A., Sivieri, S., Chieco-Bianchi, L., & Tavolata, B. (1994). M-CSF production by HIV-1 and its intrathecal synthesis. J. Neuroimmunol. 51, 193-198.

Hanks, S. J., Quinn, A. M., & Hunter, T. (1988). The protein kinase family: conserved features and deduced phylogeny of the catalytic domains. Science 241, 42-52.

Haran-Ghera, N., Krautghamer, R., Lapidot, T., Peled, A., Dominguez, M. G., & Stanley, E. R. (1997). Increased circulating colony-stimulating factor-1 (CSF-1) in SJL/J mice with radiation-induced acute myeloid leukemia (AML) is associated with autocrine regulation of AML cells by CSF-1. Blood 89, 2537-2545.

Heidaran, et al, & Aaronson, S. A. (1991). Deletion or substitution within the platelet-derived growth factor receptor kinase insert domain: Effects on functional coupling with intracellular signaling pathways. *Mol. Cell. Biol.* 11, 134-142.

Hubbard, S. R., Wei, L., Ellis, L. & Hendrickson, W. A. (1994). Crystal structure of the tyrosine kinase domain of the human insulin receptor. Nature 372, 746-754.

Hubbard, S. R. (1997). Crystal structure of the activated insulin receptor tyrosine kinase in complex with peptide substrate and ATP analog. *Embo J.* 16, 5572-5581.

Johnson, L. N., Noble, M. E. M & Owen, D. J. (1996). Active and inactive protein kinases: structural basis for regulation. *Cell* 85, 149-158.

Joos, H., Trouliaris, S., Helftenbein, G., Niemann, H. & Tamura, T. (1996), Tyrosine phosphorylation of the juxtamembrane domain of the v-Fms oncogene product is required for its association with a 55 kDa protein. *J. Biol. Chem.* 271, 24476-24481.

Kacinski, B. M. (1997). CSF-1 and its receptor in breast carcinoma and neoplasm of the female reproductive system. Mol. Repro. Dev. 46, 71-74.

Kalter, D. C., Nakamura, M, Turpin, J. A., Baca, L. M., Hoover, D. L., Diefenbach, C., Ralph, P., Gendelman, H. E., & Meltzer, M. S. (1991). Enhanced HIV replication in macrophage colony stimulating factor treated monocytes. J. Immunol. 146, 298-306.

Kanagasundaram, V., Jaworowski, A., Byrne, R., & Hamilton, J. A. (1999). Separation and characterization of the activated pool of colony stimulating factor 1 receptor forming distinct multimeric complexes with signalling molecules in macrophages. Molec. Cell Biol. 19, 4079-4092.

Kelley, T. W., Graham, M. M., Doseff, A. I., Pomerantz, R. W., Lau, S. M., Ostrowski, M. C., Franke, T. F., & Marsh, C. B. (1999). Macrophage colony-stimulating factor promotes cell survival through Akt/Protein Kinase B. J. Biol. Chem. 274, 26393-26398.

Knighton, D. R., et al., & Sowadski, J. M. (1991). Crystal structure of the catalytic subunit of cyclic adenosine monophosphate-dependent protein kinase. Science 253, 407-413.

Kutza, J., Crim, L., Feldman, S., Hayes, M. P., Gruber, M., Beeler, J., & Clouse, K. A. (2000). Macrophage colony-stimulating factor antagonists inhibit replication of HIV-1 in human macrophages. J. Immunol. 2000 164, 4955-4960.

McTigue, M. A., et al, & Appelt, K. (1999). Crystal structure of the kinase domain of human vascular endothelial growth factor receptor 2: a key enzyme in angiogenesis. *Structure* 7, 319-330.

Metcalf, D. (1986). The molecular biology and functions of the granulocyte-macrophage colony-stimulating factors. Blood 67, 257-267.

Mohammadi, M., Schlessinger, J. & Hubbard, S. R. (1996). Structure of the FGF receptor tyrosine kinase domain reveals a novel autoinhibitory mechanism. *Cell* 86, 577-87.

Murphy, Jr., G. M., Zhao, F., Yang, L., & Cordell, B. (2000). Expression of macrophage colony-stimulating factor receptor is increased in the $A\beta PP^{V717F}$ transgenic mouse model of Alzheimer's Disease. Amer. J. Pathology 157, 895-904.

Myles, G. M, Brandt, C. S., Carlsberg, K. & Rohrschneider, L. R. (1994). Tyrosine 559 in the c-Fms juxtamembrane domain is essential for kinase activity and macrophage colony-stimulating factor-dependent internalization. *Mol. Cell. Biol.* 14, 4843-4854.

Reedijk, M., Liu, X., van der Geer, P., Letwin, K., Waterfield, M. D., Hunter, T., & Pawson, T. (1992). Tyr 721 regulates specific binding of the CSF-1 receptor kinase insert to PI 3'-kinase SH2 domains: a model for SH2-mediated receptor-target interactions. EMBO J. 11, 1365-1372.

Roussel, M. F., Shurtleff, S. A., Downing, J. R. and Sherr, C. J. (1990). Proc. Natl. Acad. Sci. USA 87, 6738-6742.

Schindler, T.; Bornmann, W., Pellicena, P., Miller, W. T., Clarkson, B., Kuriyan, J. (2000). Structural Mechanism for Sti-571 Inhibition of Abelson Tyrosine Kinase. *Science* 289, 1857-9.

Sengupta, A., Liu, W.-K., Yeung, Y. G., Yeung, D. C. Y., Frackelton, Jr., A. R., & Stanley, E. R. (1988). Identification and subcellular localization of proteins that are rapidly phosphorylated in tyrosine in response to colony-stimulating factor-1. Proc. Natl. Sci. USA 85, 8062-8066.

Sherr, C. J. (1988). The fms oncogene. Biochim. Biophys. Acta 948, 225-243.

Sherr, C. J. (1991). Mitogenic response to colony-stimulating factor 1. Trends Genet. 7, 398-402.

Shewchuk, L. M., et al, & Moore, J. T. (2000). Structure of the Tie2 RTK Domain: Self-Inhibitoion by the Nucleotide Binding Loop, Activation Loop and C-Terminal Tail. *Structure* 8, 1105-1113.

Taylor, G. R., Reedijk, M., Rothwell, V., Rohrschneider, L., and Pawson, T. (1989). The unique insert of cellular and viral fms protein tyrosine kinase domains is dispensible for enzymatic and transforming activities. *EMBO J.* 8, 2029-2037.

Tushinski, R., Oliver, I., Guilbert, L., Tynan, P., Warner, J, & Stanley, E. (1982). Survival of mononuclear phagocytes depends on lineage-specific growth factor that the differentiated cells selectively destroy. Cell 28, 71-81.

Valledor, A. F., Comalada, M., Xaus, J. & Celada, A. (2000). The differential time-course of extracellular-regulated kinase activity correlates with the macrophage response toward proliferation or activation. J. Biol. Chem. 275 (10), 7403-7409.

Van der Geer, P. and Hunter, T. (1991). Mol. Cel. Biol. 11, 4698-4709.

Wang, Z., Myles, G. M., Brandt, C. S., Lioubin, M. N., & Rohrschneider, L. (1993). Identification of the ligand-binding regions in the macrophage colony-stimulating factor extracellular domain. Mol. Cell. Biol. 13, 5348-5359.

Wiktor-Jedrzejczak, W., Bartocci, A., Ferrante, A. W., Jr., Ahmed-Ansari, A., Sell, K. W., Pollard, J. W., & Stanley, E. R. (1991). Total absence of colony stimulating factor-1 in the macrophage deficient osteopetrotic (op/op) mouse. Proc. Natl. Acad. Sci. USA 87, 4828-4832.

Yang, Y. & Hamilton, J. A. (2001). Dependence of Interleukin-1-induced arthritis on granulocyte—macrophage colony-stimulating factor. Arthritis & Rheum. 44, 111-119.

Yano, S., Nishioka, Y., Nokihara, H., Sone, S. (1997). Macrophage colony stimulating factor gene transduction into human lung cancer cells differentially regulates metastasis formation in various organ microenvironments of natural killer cell-depleted SCID mice. Cancer Res. 57, 784-790.

Yeung, Y. G., Wang, Y., Einstein, D. B., Lee, P. S., & Stanley, E. R. (1998). Colony stimulating factor-1 stimulates the formation of multimeric cytosolic complexes of signaling proteins and cytoskeletal components in macrophages. J. Biol. Chem. 273, 17128-17137.

Yoshida, H., Hayashi, S-I., Kunisada, I., Ogawam, M., Nishikawa., S., Okamura, H., Sudo, T. Schultz. L. D., & Nishikawa, S-I. (1990). The murine mutation "osteoporosis" is a mutation in the coding region of the macrophage colony stimulating factor (Csf m) gene. Nature 345, 442-444.

Young, D. A., Lowe, L. D., & Clark, S. C. (1990). Comparison of the effects of IL3-, granulocyte-macrophage colony-stimulating factor in supporting monocyte differentiation in culture. J. Immunol. 145, 607-615.

---

We claim:

1. A compound selected from the group consisting of:

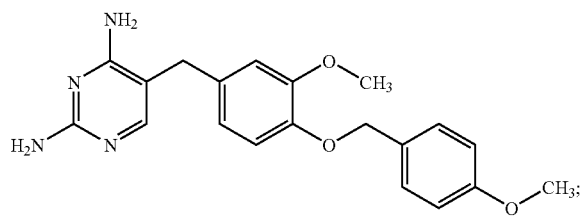

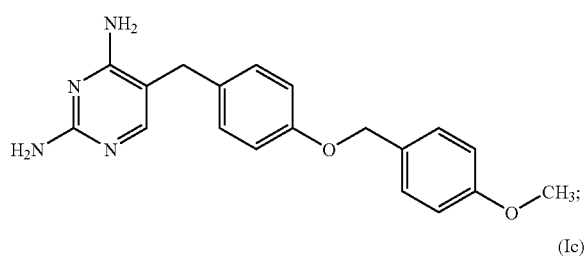

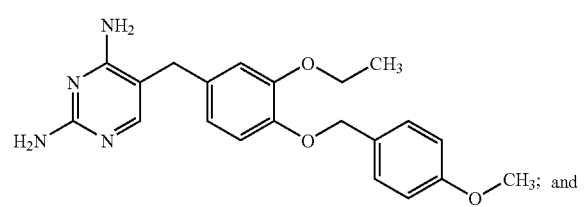

salts thereof.

2. The compound of claim 1 or salt thereof, wherein said compound has Formula (Id):

3. A pharmaceutical composition comprising a therapeutically effective amount of a compound as claimed in claim 1, or a salt thereof and one or more of pharmaceutically acceptable carriers, diluents and excipients.

4. A pharmaceutical composition comprising a therapeutically effective amount of a compound as claimed in claim 2, or a salt thereof and one or more of pharmaceutically acceptable carriers, diluents and excipients.

* * * * *

SEQUENCE LISTING

```
<160> NUMBER OF SEQ ID NOS: 8

<210> SEQ ID NO 1
<211> LENGTH: 343
<212> TYPE: PRT
<213> ORGANISM: Artificial Sequence
<220> FEATURE:
<223> OTHER INFORMATION: MODEL SEQUENCES BASED ON FGFR1 AND CFMS1

<400> SEQUENCE: 1

Met Lys Lys Gly His His His His His Gly Gln Lys Pro Lys Tyr
1               5                   10                  15

Gln Val Arg Trp Lys Ile Ile Glu Ser Tyr Glu Gly Asn Ser Tyr Thr
            20                  25                  30

Phe Ile Asp Pro Thr Gln Leu Pro Tyr Asn Glu Lys Trp Glu Phe Pro
        35                  40                  45

Arg Asn Asn Leu Gln Phe Gly Lys Thr Leu Gly Ala Gly Ala Phe Gly
    50                  55                  60

Lys Val Val Glu Ala Thr Ala Phe Gly Leu Gly Lys Glu Asp Ala Val
65                  70                  75                  80

Leu Lys Val Ala Val Lys Met Leu Lys Ser Thr Ala His Ala Asp Glu
                85                  90                  95
```

-continued

```
Lys Glu Ala Leu Met Ser Glu Leu Lys Ile Met Ser His Leu Gly Gln
            100                 105                 110

His Glu Asn Ile Val Asn Leu Leu Gly Ala Cys Thr His Gly Gly Pro
        115                 120                 125

Val Leu Val Ile Thr Glu Tyr Cys Cys Tyr Gly Asp Leu Leu Asn Phe
    130                 135                 140

Leu Arg Arg Lys Ala Glu Ala Met Leu Gly Pro Ser Leu Ala Pro Gly
145                 150                 155                 160

Gln Asp Pro Glu Gly Leu Asp Lys Glu Asp Gly Arg Pro Leu Glu Leu
                165                 170                 175

Arg Asp Leu Leu His Phe Ser Ser Gln Val Ala Gln Gly Met Ala Phe
            180                 185                 190

Leu Ala Ser Lys Asn Cys Ile His Arg Asp Val Ala Ala Arg Asn Val
        195                 200                 205

Leu Leu Thr Asn Gly His Val Ala Lys Ile Gly Asp Phe Gly Leu Ala
    210                 215                 220

Arg Asp Ile Met Asn Asp Ser Asn Tyr Ile Val Lys Gly Asn Ala Arg
225                 230                 235                 240

Leu Pro Val Lys Trp Met Ala Pro Glu Ser Ile Phe Asp Cys Val Tyr
                245                 250                 255

Thr Val Gln Ser Asp Val Trp Ser Tyr Gly Ile Leu Leu Trp Glu Ile
            260                 265                 270

Phe Ser Leu Gly Leu Asn Pro Tyr Pro Gly Ile Leu Val Asn Ser Lys
        275                 280                 285

Phe Tyr Lys Leu Val Lys Asp Gly Tyr Gln Met Ala Gln Pro Ala Phe
    290                 295                 300

Ala Pro Lys Asn Ile Tyr Ser Ile Met Gln Ala Cys Trp Ala Leu Glu
305                 310                 315                 320

Pro Thr His Arg Pro Thr Phe Gln Gln Ile Cys Ser Phe Leu Gln Glu
                325                 330                 335

Gln Ala Gln Glu Asp Arg Arg
            340

<210> SEQ ID NO 2
<211> LENGTH: 329
<212> TYPE: PRT
<213> ORGANISM: Artificial Sequence
<220> FEATURE:
<223> OTHER INFORMATION: MODEL SEQUENCES BASED ON FGFR1 AND CFMS1

<400> SEQUENCE: 2

Met Lys Lys Gly His His His His His Gly Gln Lys Pro Lys Tyr
 1                5                  10                  15

Gln Val Arg Trp Lys Ile Ile Glu Ser Tyr Glu Gly Asn Ser Tyr Thr
                20                  25                  30

Phe Ile Asp Pro Thr Gln Leu Pro Tyr Asn Glu Lys Trp Glu Phe Pro
            35                  40                  45

Arg Asn Asn Leu Gln Phe Gly Lys Thr Leu Gly Ala Gly Ala Phe Gly
        50                  55                  60

Lys Val Val Glu Ala Thr Ala Phe Gly Leu Gly Lys Glu Asp Ala Val
65                  70                  75                  80

Leu Lys Val Ala Val Lys Met Leu Lys Ser Thr Ala His Ala Asp Glu
                85                  90                  95

Lys Glu Ala Leu Met Ser Glu Leu Lys Ile Met Ser His Leu Gly Gln
                100                 105                 110
```

```
His Glu Asn Ile Val Asn Leu Leu Gly Ala Cys Thr His Gly Gly Pro
        115                 120                 125

Val Leu Val Ile Thr Glu Tyr Cys Cys Tyr Gly Asp Leu Leu Asn Phe
    130                 135                 140

Leu Arg Arg Lys Ala Glu Ala Leu Asp Lys Glu Asp Gly Arg Pro Leu
145                 150                 155                 160

Glu Leu Arg Asp Leu Leu His Phe Ser Ser Gln Val Ala Gln Gly Met
                165                 170                 175

Ala Phe Leu Ala Ser Lys Asn Cys Ile His Arg Asp Val Ala Ala Arg
            180                 185                 190

Asn Val Leu Leu Thr Asn Gly His Val Ala Lys Ile Gly Asp Phe Gly
        195                 200                 205

Leu Ala Arg Asp Ile Met Asn Asp Ser Asn Tyr Ile Val Lys Gly Asn
    210                 215                 220

Ala Arg Leu Pro Val Lys Trp Met Ala Pro Glu Ser Ile Phe Asp Cys
225                 230                 235                 240

Val Tyr Thr Val Gln Ser Asp Val Trp Ser Tyr Gly Ile Leu Leu Trp
                245                 250                 255

Glu Ile Phe Ser Leu Gly Leu Asn Pro Tyr Pro Gly Ile Leu Val Asn
            260                 265                 270

Ser Lys Phe Tyr Lys Leu Val Lys Asp Gly Tyr Gln Met Ala Gln Pro
        275                 280                 285

Ala Phe Ala Pro Lys Asn Ile Tyr Ser Ile Met Gln Ala Cys Trp Ala
    290                 295                 300

Leu Glu Pro Thr His Arg Pro Thr Phe Gln Gln Ile Cys Ser Phe Leu
305                 310                 315                 320

Gln Glu Gln Ala Gln Glu Asp Arg Arg
                325

<210> SEQ ID NO 3
<211> LENGTH: 1035
<212> TYPE: DNA
<213> ORGANISM: Artificial Sequence
<220> FEATURE:
<223> OTHER INFORMATION: MODEL SEQUENCES BASED ON FGFR1 AND CFMS1

<400> SEQUENCE: 3
atgaaaaaag gtcatcatca tcatcatcat ggtcagaagc ccaagtacca ggtccgctgg      60
aagatcatcg agagctatga gggcaacagt tatactttca tcgacccac gcagctgcct     120 tacaacgaga gtgggagtt ccccggaac aacctgcagt ttggtaagac cctcggagct      180
ggagcctttg gaaggtggt ggaggccacg gcctttggtc tgggcaagga ggatgctgtc     240
ctgaaggtgg ctgtgaagat gctgaagtcc acggcccatg ctgatgagaa ggaggccctc     300
atgtccgagc tgaagatcat gagccacctg ggccagcacg agaacatcgt caaccttctg     360
ggagcctgta cccatggagg ccctgtactg gtcatcacgg agtactgttg ctatggcgac     420
ctgctcaact ttctgcgaag gaaggctgag gccatgctgg acccagcct ggccccggc      480 caggaccccg agggactgga caaggaggat ggacggcccc tggagctccg ggacctgctt     540
cacttctcca gccaagtagc ccagggcatg gccttcctcg cttccaagaa ttgcatccac     600
cgggacgtgg cagcgcgtaa cgtgctgttg accaatggtc atgtggccaa gattggggac     660
ttcgggctgg ctagggacat catgaatgac tccaactaca ttgtcaaggg caatgcccgc     720
ctgcctgtga agtggatggc cccagagagc atctttgact gtgtctacac ggttcagagc     780
gacgtctggt cctatggcat cctcctctgg gagatcttct cacttgggct gaatccctac     840
```

-continued

```
cctggcatcc tggtgaacag caagttctat aaactggtga aggatggata ccaaatggcc      900
cagcctgcat ttgccccaaa gaatatatac agcatcatgc aggcctgctg ggccttggag      960
cccacccaca gacccacctt ccagcagatc tgctccttcc ttcaggagca ggcccaagag     1020
gacaggagat aataa                                                      1035

<210> SEQ ID NO 4
<211> LENGTH: 993
<212> TYPE: DNA
<213> ORGANISM: Artificial Sequence
<220> FEATURE:
<223> OTHER INFORMATION: MODEL SEQUENCES BASED ON FGFR1 AND CFMS1

<400> SEQUENCE: 4
atgaaaaaag gtcatcatca tcatcatcat ggtcagaagc ccaagtacca ggtccgctgg       60
aagatcatcg agagctatga gggcaacagt tatactttca tcgacccccac gcagctgcct     120 tacaacgaga agtgggagtt cccccggaac aacctgcagt tggtaagac cctcggagct      180 ggagcctttg gaaggtggt ggaggccacg gcctttggtc tgggcaagga ggatgctgtc      240
ctgaaggtgg ctgtgaagat gctgaagtcc acggcccatg ctgatgagaa ggaggccctc     300
atgtccgagc tgaagatcat gagccacctg ggccagcacg agaacatcgt caaccttctg     360
ggagcctgta cccatggagg ccctgtactg gtcatcacgg agtactgttg ctatggcgac     420
ctgctcaact ttctgcgaag gaaggctgag gccctggaca aggaggatgg acggcccctg     480
gagctccggg acctgcttca cttctccagc caagtagccc agggcatggc cttcctcgct     540
tccaagaatt gcatccaccg ggacgtggca gcgcgtaacg tgctgttgac caatggtcat     600
gtggccaaga ttggggactt cgggctggct agggacatca tgaatgactc caactacatt     660
gtcaagggca atgcccgcct gcctgtgaag tggatggccc agagagcat ctttgactgt      720 gtctacacgt tcagagcga cgtctggtcc tatggcatcc tcctctggga gatcttctca     780
cttgggctga atccctaccc tggcatcctg gtgaacagca gttctataa actggtgaag    840 gatggatacc aaatggccca gcctgcattt gccccaaaga atatatacag catcatgcag    900
gcctgctggg ccttggagcc cacccacaga cccaccttcc agcagatctg ctccttcctt    960
caggagcagg cccaagagga caggagataa taa                                 993

<210> SEQ ID NO 5
<211> LENGTH: 11
<212> TYPE: PRT
<213> ORGANISM: Artificial Sequence
<220> FEATURE:
<223> OTHER INFORMATION: 6 x HIS TAG

<400> SEQUENCE: 5

Met Lys Lys Gly His His His His His His Gly
  1               5                  10

<210> SEQ ID NO 6
<211> LENGTH: 27
<212> TYPE: DNA
<213> ORGANISM: Artificial Sequence
<220> FEATURE:
<223> OTHER INFORMATION: PRIMER FOR SITE DIRECTED MUTAGENESIS

<400> SEQUENCE: 6
ggacccagcc tggcccccgg ccaggac                                         27
```

```
<210> SEQ ID NO 7
<211> LENGTH: 27
<212> TYPE: DNA
<213> ORGANISM: Artificial Sequence
<220> FEATURE:
<223> OTHER INFORMATION: PRIMER FOR SITE DIRECTED MUTAGENESIS

<400> SEQUENCE: 7
gtccgcaggg acgctggctt ctccagc                                    27

<210> SEQ ID NO 8
<211> LENGTH: 27
<212> TYPE: DNA
<213> ORGANISM: Artificial Sequence
<220> FEATURE:
<223> OTHER INFORMATION: PRIMER FOR SITE DIRECTED MUTAGENESIS

<400> SEQUENCE: 8
gtctccactt ctgcaaatga ctccttc                                    27
```